(12) United States Patent
Uehling et al.

(10) Patent No.: US 7,812,022 B2
(45) Date of Patent: Oct. 12, 2010

(54) 2-PYRIMIDINYL PYRAZOLOPYRIDINE ERBB KINASE INHIBITORS

(75) Inventors: David Edward Uehling, Durham, NC (US); Kirk Lawrence Stevens, Durham, NC (US); Scott Howard Dickerson, Durham, NC (US); Alex Gregory Waterson, Durham, NC (US); Philip Anthony Harris, Durham, NC (US); Douglas McCord Sammond, Durham, NC (US); Robert Dale Hubbard, Lindenhurst, IL (US); Holly Kathleen Emerson, Durham, NC (US); Joseph W. Wilson, Durham, NC (US)

(73) Assignee: GlaxoSmithKline LLC, Philadelphia, PA (US)

( * ) Notice: Subject to any disclaimer, the term of this patent is extended or adjusted under 35 U.S.C. 154(b) by 775 days.

(21) Appl. No.: 11/721,504

(22) PCT Filed: Dec. 6, 2005

(86) PCT No.: PCT/US2005/044166

§ 371 (c)(1),
(2), (4) Date: Jun. 12, 2007

(87) PCT Pub. No.: WO2006/068826

PCT Pub. Date: Jun. 29, 2006

(65) Prior Publication Data

US 2008/0051395 A1    Feb. 28, 2008

Related U.S. Application Data

(60) Provisional application No. 60/637,928, filed on Dec. 21, 2004, provisional application No. 60/709,079, filed on Aug. 17, 2005.

(51) Int. Cl.
 *C07D 471/04* (2006.01)
 *A61K 31/437* (2006.01)

(52) U.S. Cl. .............................. 514/235.8; 514/252.14; 514/275; 544/122; 544/295; 544/331

(58) Field of Classification Search ................ 544/122, 544/295, 331; 514/235.8, 252.14, 275
See application file for complete search history.

(56) References Cited

U.S. PATENT DOCUMENTS

| | | | |
|---|---|---|---|
| 6,727,256 | B1 | 4/2004 | Carter et al. |
| 6,855,719 | B1 | 2/2005 | Thomas et al. |
| 6,919,352 | B2 | 7/2005 | Chamberlain et al. |
| 6,962,914 | B2 | 11/2005 | Gudmundsson et al. |
| 7,141,569 | B2 | 11/2006 | Cheung et al. |
| 7,153,863 | B2 | 12/2006 | Gudmundsson et al. |
| 2004/0053942 | A1 | 3/2004 | Alberti et al. |

FOREIGN PATENT DOCUMENTS

| | | |
|---|---|---|
| WO | 9935146 | 7/1999 |
| WO | 0216359 | 2/2002 |
| WO | 2004/021988 A2 | 3/2004 |
| WO | 2005/068452 A2 | 7/2005 |
| WO | 2006068826 | 6/2006 |

OTHER PUBLICATIONS

Traxler, Protein Tyrosine Kinase Inhibitors in Cancer Treatment, Expert Opinion on Therapeutic Patents, 7(6):571-588, 1997.*
Simone, Oncology: Introduction, Cecil Textbook of Medicine, 20th Edition, vol. 1, pp. 1004-1010, 1996.*
R. Hubbard, et al.,; Pyrazolo[3,4-d]pyrimidines as potent inhibitors of the insulin-like growth factor receptor (IGF-1R); Bioorganic & Med Chem Lttrs; Jul. 25, 2007; 17: 5406-5409.

* cited by examiner

*Primary Examiner*—Deepak Rao
(74) *Attorney, Agent, or Firm*—J. Scott Young

(57) ABSTRACT

The present invention provides 2-pyrimidinyl pyrazolopyridine compounds, compositions containing the same, as well as processes for the preparation and their use as pharmaceutical agents.

15 Claims, No Drawings

2-PYRIMIDINYL PYRAZOLOPYRIDINE ERBB KINASE INHIBITORS

CROSS REFERENCE TO RELATED APPLICATIONS

This application is a 371 Application of PCT/US2005/044166, filed 6 Dec. 2005, which claims priority to U.S. Application Ser. Nos. 60/637,928, filed 21 Dec. 2004 and 60/709,079, filed 17 Aug. 2005.

FIELD OF THE INVENTION

The present invention relates to pyrimidine derivatives, compositions and medicaments containing the same, as well as processes for the preparation and use of such compounds, compositions and medicaments. Such pyrimidine derivatives are useful in the treatment of diseases associated with inappropriate ErbB family kinase activity.

BACKGROUND OF THE INVENTION

An important large family of enzymes is the protein kinase enzyme family. Currently, there are about 500 different known protein kinases. Protein kinases serve to catalyze the phosphorylation of an amino acid side chain in various proteins by the transfer of the γ-phosphate of the ATP-Mg2+ complex to said amino acid side chain. These enzymes control the majority of the signaling processes inside cells, thereby governing cell function, growth, differentiation and destruction (apoptosis) through reversible phosphorylation of the hydroxyl groups of serine, threonine and tyrosine residues in proteins. Studies have shown that protein kinases are key regulators of many cell functions, including signal transduction, transcriptional regulation, cell motility, and cell division. Several oncogenes have also been shown to encode protein kinases, suggesting that kinases play a role in oncogenesis. These processes are highly regulated, often by complex intermeshed pathways where each kinase will itself be regulated by one or more kinases. Consequently, aberrant or inappropriate protein kinase activity can contribute to the rise of disease states associated with such aberrant kinase activity. Due to their physiological relevance, variety and ubiquitousness, protein kinases have become one of the most important and widely studied family of enzymes in biochemical and medical research.

One type of protein kinases is protein tyrosine kinases (PTK). Aberrant PTK activity has been implicated in a variety of disorders including psoriasis, rheumatoid arthritis, bronchitis, as well as cancer. Development of effective treatments for such disorders is a constant and ongoing enterprise in the medical field. The ErbB family of PTKs, which includes c-ErbB-2, EGFR, and ErbB-4, is one group of PTKs that has attracted interest as a therapeutic target. Currently, of special interest, is the role of ErbB family PTKs in hyperproliferative disorders, particularly human malignancies. Elevated EGFR activity has, for example, been implicated in non-small cell lung, bladder, and head and neck cancers. Furthermore, increased c-ErbB-2 activity has been implicated in breast, ovarian, gastric and pancreatic cancers. Consequently, inhibition of ErbB family PTKs should provide a treatment for disorders characterized by aberrant ErbB family PTK activity. The biological role of ErbB family PTKs and their implication in various disease states is discussed, for instance in U.S. Pat. No. 5,773,476; International Patent Application WO 99/35146; M. C. Hung et al, Seminars in Oncology, 26: 4, Suppl. 12 (August) 1999, 51-59; Ullrich et al, Cell, 61: 203-212, Apr. 20, 1990; Modjtahedi et al, Int'l. J. of Oncology, 13: 335-342, 1998; and J. R. Woodburn, Pharmacol. Ther., 82: 2-3, 241-250, 1999.

The present inventors have discovered novel pyrimidine compounds, which are inhibitors of ErbB family kinase activity. Such derivatives are useful in the treatment of disorders associated with inappropriate ErbB family kinase activity.

SUMMARY OF THE INVENTION

In a first aspect of the present invention, there is provided a compound of formula (I):

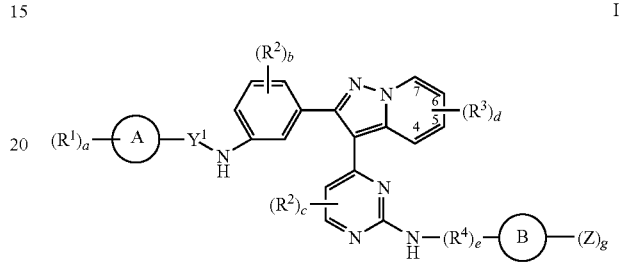

wherein:

a is 0, 1, 2 or 3;

each $R^1$ is the same or different and is independently selected from halo, alkyl, alkenyl, alkynyl, cycloalkyl, cycloalkenyl, Ay, Het, —$OR^6$, —$R^4OR^6$, —$OC(O)R^6$, —$C(O)R^6$, —$R^4C(O)R^6$, —$C(O)NR^6R^7$, —$R^4C(O)NR^6R^7$, —$CO_2R^6$, —$C(S)R^6$, —$C(S)NR^6R^7$, —$S(O)_fR^6$, —$R^4S(O)_fR^6$, —$S(O)_2NR^6R^7$, —$NR^6R^7$, —$R^4NR^6R^7$, —$N(R^6)$—$R^4R^7$, —$N(R^6)$—$R^4$—$OR^7$, —$N(R^6)$—$R^4$—$S(O)_fR^7$, —$N(R^6)$—$R^4$—CN, —$C(NH)NR^6R^7$, —$N(R^6)C(O)R^6$, —$N(R^6)S(O)_2R^6$, —$N(R^6)$—$C(O)$—$NR^6R^7$, —$N(R^6)$—$S(O)_2$—$NR^6R^7$, —CN, and —$NO_2$;

f is 0, 1 or 2;

Ay is aryl optionally substituted 1, 2 or 3 times with a substituent selected from halo, $C_{1-3}$alkyl, $C_{1-3}$alkoxy, $NH_2$, $N(H)C_{1-3}$alkyl, $N(C_{1-3}alkyl)_2$, CN and $NO_2$;

Het is a 5-6 membered heterocycle or heteroaryl having 1 or 2 heteroatoms selected from N, O and S and optionally substituted 1, 2 or 3 times with a substituent selected from halo, $C_{1-3}$alkyl, $C_{1-3}$alkoxy, hydroxyl, oxo, $NH_2$, $N(H)C_{1-3}$alkyl, $N(C_{1-3}alkyl)_2$, CN and $NO_2$;

Ring A is selected from aryl, heterocycle and heteroaryl;

$Y^1$ is —C(O)—, —N(H)C(O)—, —C(S)— or —N(H)C(S)—;

b and c are the same or different and are each independently is 0, 1 or 2;

each $R^2$ is the same or different and is independently selected from halo, alkyl, —$OR^6$, —$S(O)_fR^6$, —$NR^6R^7$, —CN and —$NO_2$;

d is 0, 1 or 2;

each $R^3$ is the same or different and is independently selected from halo, alkyl, alkenyl, alkynyl, cycloalkyl, cycloalkenyl, Ay, Het, —$OR^6$, —$R^4OR^6$, —OAy, —$R^4$OAy, —OC(O)$R^6$, —COR$^6$, —$R^4C(O)R^6$, —C(O)Ay, —C(O)$NR^6R^7$, —$R^4C(O)NR^6R^7$, —C(O)N(H)Ay, —C(O)N(H)Het, —$CO_2R^6$, —$CO_2$Ay, —C(S)$R^6$, —C(S)$NR^6R^7$, —$S(O)_fR^6$, —$R^4S(O)_fR^6$, —$S(O)_f$Ay, —$S(O)_2NR^6R^7$, —$NR^6R^7$, —$R^4NR^6R^7$, —N(H)Ay, —$R^4N(H)$Ay, —N(H)Het, —N(H)$R^4$Het, —$N(R^6)$—$R^4R^7$, —$N(R^6)$—$R^4$—$OR^7$, —$N(R^6)$—$R^4$—$S(O)_fR^7$, —$N(R^6)$—$R^4$—CN, —C(NH)

$NR^6R^7$, —N(H)C(O)$R^6$, —N(H)C(O)Ay, —N(H)SO$_2$$R^6$, —N($R^6$)—C(O)—N$R^6$$R^7$, —N($R^6$)—S(O)$_2$—N$R^6$$R^7$, —CN and —NO$_2$;

e is 0 or 1;

each $R^4$ is the same or different and is independently $C_{1-4}$alkylene or $C_{3-4}$alkenylene;

Ring B is selected from aryl and heteroaryl;

g is 0, 1, 2, 3 or 4;

each Z is the same or different and is independently a moiety of formula II:

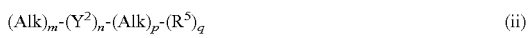

wherein:

m, n and p are the same or different and are each independently 0 or 1;

each Alk is the same or different and is independently selected from $C_{1-4}$alkylene and $C_{3-4}$alkenylene;

$Y^2$ is —O—, —C(O)—, —S(O)$_f$—, —N(H)— or —N(Alk)-;

q is 1 or 2;

each $R^5$ is the same or different and is independently selected from H, halo, alkyl, alkenyl, cycloalkyl, cycloalkenyl, Ay, Het, oxo, —O$R^6$, —OAy, —C(O)$R^6$, —OC(O)$R^6$, —C(O)Ay, —OC(O)Ay, —C(O)N$R^6$$R^7$, —CO$_2$$R^6$, —CO$_2$Ay, —S(O)$_f$$R^6$, —S(O)$_f$Ay, —S(O)$_2$N$R^6$$R^7$, —C(S)$R^6$, —C(S)N$R^6$$R^7$, —C(S)N(H)Ay, —N$R^6$$R^7$, —N(H)Ay, —N(H)Het, —N($R^6$)—$R^4$$R^7$, —N($R^6$)—$R^4$—O$R^7$, —N($R^6$)—$R^4$—S(O)$_f$$R^7$, —N($R^6$)—$R^4$—CN, —NHC(O)$R^6$, —N(H)S(O)$_2$$R^6$, —C(NH)N$R^6$$R^7$, —N($R^6$)—C(O)—N$R^6$$R^7$, —N($R^6$)—S(O)$_2$—N$R^6$$R^7$, —N($R^6$)—C(O)—$R^4$N$R^6$$R^7$, —N($R^6$)—S(O)$_2$—$R^4$N$R^6$$R^7$, —CN and —NO$_2$; and each $R^6$ and $R^7$ are the same or different and are each independently selected from H, alkyl, alkenyl, alkynyl, $C_{3-6}$cycloalkyl and $C_{3-6}$cycloalkenyl;

or a pharmaceutically acceptable salt or solvate thereof.

In a second aspect of the present invention, there is provided a pharmaceutical composition comprising a compound of formula (I) or a pharmaceutically acceptable salt or solvate thereof. In one embodiment, the pharmaceutical composition further comprises one or more of pharmaceutically acceptable carriers, diluents and excipients.

In a third aspect of the present invention, there is provided a method for treating a condition mediated by inappropriate activity of at least one ErbB family kinase in a mammal in need thereof, comprising: administering to the mammal a therapeutically effective amount of a compound of formula (I) or a pharmaceutically acceptable salt or solvate thereof.

In a fourth aspect of the present invention, there is provided a method for treating a condition mediated by inappropriate activity of at least two ErbB family kinases in a mammal in need thereof, comprising: administering to the mammal a therapeutically effective amount of a compound of formula (I) or a pharmaceutically acceptable salt or solvate thereof.

In a fifth aspect of the present invention, there is provided a method for treating a susceptible neoplasm in a mammal in need thereof, comprising: administering to the mammal, a therapeutically effective amount of a compound of formula (I) or a pharmaceutically acceptable salt or solvate thereof. Susceptible neoplasms include breast cancer, colon cancer, non-small cell lung cancer, prostate cancer, bladder cancer, ovarian cancer, gastric cancer, pancreatic cancer, carcinoma of the head and neck, esophageal carcinoma, melanoma and renal carcinoma.

In a sixth aspect of the present invention, there is provided a process for preparing a compound of formula (I). The process comprises the steps of:

a) reacting a compound of formula (VII):

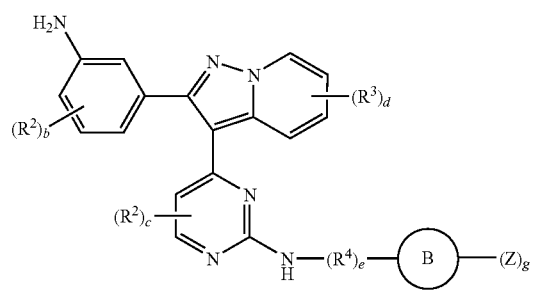

VII with a compound of formula (VIII):

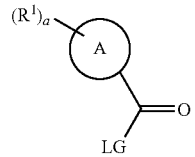

VIII wherein LG is a leaving group;

or a compound of formula (X):

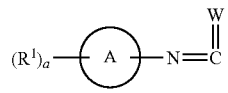

X wherein W is O or S;

to prepare a compound of formula (I);

b) optionally converting the compound of formula (I) to a pharmaceutically acceptable salt or solvate thereof; and c) optionally converting the compound of formula (I) or a pharmaceutically acceptable salt or solvate thereof to a different compound of formula (I) or a pharmaceutically acceptable salt or solvate thereof.

In a seventh aspect of the present invention, there is provided a compound of formula (I), or a pharmaceutically acceptable salt or solvate thereof for use in therapy.

In an eighth aspect of the present invention, there is provided the use of a compound of formula (I), or a pharmaceutically acceptable salt or solvate thereof in the preparation of a medicament for use in the treatment of a condition mediated by inappropriate activity of at least one ErbB family kinase in a mammal.

In a ninth aspect of the present invention, there is provided the use of a compound of formula (I), or a pharmaceutically acceptable salt or solvate thereof in the preparation of a medicament for use in the treatment of a condition mediated by inappropriate activity of at least two ErbB family kinases in a mammal.

In a tenth aspect of the present invention, there is provided the use of a compound of formula (I), or a pharmaceutically acceptable salt or solvate thereof in the preparation of a medicament for use in the treatment of a susceptible neoplasm in a mammal.

DETAILED DESCRIPTION OF THE INVENTION

As used herein the term "ErbB family kinase" refers to those ErbB kinases and includes within its scope EGFR (also known as ErbB-1), ErbB-2, and ErbB-4.

As used herein, "a compound of the invention" or "a compound of formula (I)" means a compound of formula (I) or a pharmaceutically acceptable salt or solvate thereof. Similarly, with respect to isolatable intermediates such as for example, compounds of formula (IV), (V), (VI), (VII), (XVI), (XVII), (XVIII) and (XIX) the phrase "a compound of formula (number)" means a compound having that formula and pharmaceutically acceptable salts and solvates thereof.

As used herein, the terms "alkyl" (and "alkylene") refer to straight or branched hydrocarbon chains containing from 1 to 8 carbon atoms, unless a different number of atoms is specified. Examples of "alkyl" as used herein include, but are not limited to, methyl, ethyl, n-propyl, n-butyl, n-pentyl, isobutyl, isopropyl, and tert-butyl. Examples of "alkylene" as used herein include, but are not limited to, methylene, ethylene, propylene, butylene, and isobutylene. "Alkyl" also includes substituted alkyl. The alkyl (and alkylene) groups may be optionally substituted one or more times with a halogen or hydroxyl. Thus, the term "alkyl" includes for example, trifluoromethyl and trifluoroethyl, among other halogenated alkyls, and hydroxymethyl and other hydroxylated alkyls.

As used herein, the term "alkenyl" (and "alkylene") refers to straight or branched hydrocarbon chains containing from 2 to 8 carbon atoms, unless a different number of atoms is specified, and at least one and up to three carbon-carbon double bonds. Examples of "alkenyl" as used herein include, but are not limited to ethenyl and propenyl. Examples of "alkenylene" as used herein include, but are not limited to, ethenylene, propenylene and butenylene. "Alkenyl" (and "alkenylene") also includes substituted alkenyl. The alkenyl groups may optionally be substituted one or more times with a halogen or hydroxyl.

As used herein, the term "alkynyl" refers to straight or branched hydrocarbon chains containing from 2 to 8 carbon atoms, unless a different number of atoms is specified, and at least one and up to three carbon-carbon triple bonds. Examples of "alkynyl" as used herein include, but are not limited to ethynyl and propynyl. "Alkynyl" also includes substituted alkynyl. The alkynyl groups may optionally be substituted one or more times with a halogen or hydroxyl.

As used herein, the term "cycloalkyl" refers to a saturated monocyclic carbocyclic ring having from 3 to 8 carbon atoms, unless a different number of atoms is specified. "Cycloalkyl" includes by way of example cyclopropyl, cyclobutyl, cyclopentyl, cyclohexyl, cycloheptyl and cyclooctyl. "Cycloalkyl" also includes substituted cycloalkyl. The cycloalkyl may optionally be substituted on any available carbon with one or more substituents selected from the group consisting of halo, $C_{1-3}$alkyl (including haloalkyl, e.g., perfluoroalkyl), —OH and oxo. Preferred cycloalkyl groups include $C_{3-6}$cycloalkyl and substituted $C_{3-6}$cycloalkyl.

As used herein, the term "cycloalkenyl" refers to a non-aromatic monocyclic carbocyclic ring having from 3 to 8 carbon atoms, unless a different number of atoms is specified, and up to 3 carbon-carbon double bonds. "Cycloalkenyl" includes by way of example cyclobutenyl, cyclopentenyl and cyclohexenyl. "Cycloalkenyl" also includes substituted cycloalkenyl. The cycloalkenyl may optionally be substituted on any available carbon with one or more substituents selected from the group consisting of halo, $C_{1-3}$alkyl (including haloalkyl, e.g., perfluoroalkyl), —OH and oxo.

The term "halo" or "halogen" refers to fluoro, chloro, bromo and iodo.

The term "oxo" as used herein refers to the group =O attached directly to a carbon atom of a hydrocarbon ring (i.e., cycloalkenyl, aryl, heterocycle or heteroaryl ring) as well as —N-oxides, sulfones and sulfoxides wherein the N or S are atoms of a heterocyclic or heteroaryl ring.

As used herein, the term "alkoxy" refers to the group —O-alkyl, where alkyl is as defined above. Examples of "alkoxy" as used herein include, but are not limited to, methoxy, ethoxy, n-propoxy, isopropoxy, n-butoxy, and t-butoxy. "Alkoxy" also includes substituted alkoxy. The alkoxy groups may be optionally substituted one or more times with a halogen.

The term "aryl" refers to monocyclic carbocyclic groups and fused bicyclic carbocyclic groups having from 6 to 10 carbon atoms, unless a different number of atoms is specified, and having at least one aromatic ring. Examples of particular aryl groups include but are not limited to phenyl, indenyl and naphthyl. One particular aryl group according to the invention is phenyl.

The terms "heterocycle" and "heterocyclic" refer to monocyclic saturated or unsaturated non-aromatic groups and fused bicyclic saturated or unsaturated non-aromatic groups, having from 5 to 10 members (unless a different number of members is specified) and containing 1, 2, 3 or 4 heteroatoms selected from N, O and S, unless a different number of heteroatoms is specified. Examples of particular heterocyclic groups include but are not limited to tetrahydrofuran, dihydropyran, tetrahydropyran, pyran, thietane, 1,4-dioxane, 1,3-dioxane, 1,3-dioxalane, piperidine, piperazine, pyrrolidine, morpholine, thiomorpholine, thiazolidine, oxazolidine, tetrahydrothiopyran, tetrahydrothiophene, and the like.

The term "heteroaryl" refers to aromatic monocyclic groups and fused bicyclic groups wherein at least one ring is aromatic, having from 5 to 10 members (unless a different number of members is specified) and containing 1, 2, 3, or 4 heteroatoms selected from N, O and S, unless a different number of heteroatoms is specified. "Heteroaryl" also includes heteroaryl groups substituted by oxo, e.g., N-oxides, sulfur oxides and dioxides. Examples of particular heteroaryl groups include but are not limited to furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, tetrahydropyrimidine, triazine, quinoline, tetrahydroquinoline, isoquinoline, tetrahydroisoquinoline, benzofuran, benzothiophene, indole, indazole, benzodioxane, benzodioxin, benzodithiane, benzopiperidine and benzopiperzine.

The term "members" (and variants thereof e.g., "membered") in the context of heterocyclic and heteroaryl groups refers to the total atoms, carbon and heteroatoms N, O and/or S, which form the ring. Thus, an example of a 6-membered heterocyclic ring is piperidine and an example of a 6-membered heteroaryl ring is pyridine.

The present invention provides compounds of formula (I):

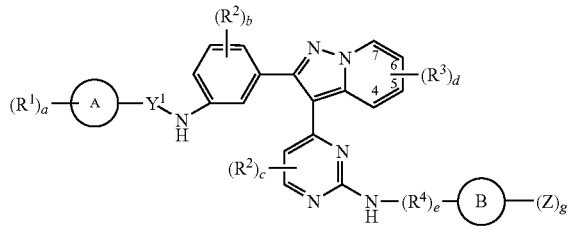

wherein:
a is 0, 1, 2 or 3;
each $R^1$ is the same or different and is independently selected from halo, alkyl, alkenyl, alkynyl, cycloalkyl, cycloalkenyl, Ay, Het, —$OR^6$, —$R^4OR^6$, —OC(O)$R^6$, —C(O)$R^6$, —$R^4$C(O)$R^6$, —C(O)$NR^6R^7$, —$R^4$C(O)$NR^6R^7$, —$CO_2R^6$, —C(S)$R^6$, —C(S)$NR^6R^7$, —S(O)$_fR^6$, —$R^4$S(O)$_fR^6$, —S(O)$_2NR^6R^7$, —$NR^6R^7$, —$R^4NR^6R^7$, —N($R^6$)—$R^4R^7$, —N($R^6$)—$R^4$—$OR^7$, —N($R^6$)—$R^4$—S(O)$_fR^7$, —N($R^6$)—$R^4$—CN, —C(NH)$NR^6R^7$, —N($R^6$)C(O)$R^6$, —N($R^6$)S(O)$_2R^6$, —N($R^6$)—C(O)—$NR^6R^7$, —N($R^6$)—S(O)$_2$—$NR^6R^7$, —CN, and —$NO_2$;
f is 0, 1 or 2;
Ay is aryl optionally substituted 1, 2 or 3 times with a substituent selected from halo, $C_{1-3}$alkyl, $C_{1-3}$alkoxy, $NH_2$, N(H)$C_{1-3}$alkyl, N($C_{1-3}$alkyl)$_2$, CN and $NO_2$;
Het is a 5-6 membered heterocycle or heteroaryl optionally substituted 1, 2 or 3 times with a substituent selected from halo, $C_{1-3}$alkyl, $C_{1-3}$alkoxy, hydroxyl, oxo, $NH_2$, N(H)$C_{1-3}$alkyl, N($C_{1-3}$alkyl)$_2$, CN and $NO_2$;
Ring A is selected from aryl, heterocycle and heteroaryl;
$Y^1$ is —C(O)—, —N(H)C(O)—, —C(S)— or —N(H)C(S)—;
b and c are the same or different and are each independently is 0, 1 or 2;
each $R^2$ is the same or different and is independently selected from halo, alkyl, —$OR^6$, —S(O)$_fR^6$, —$NR^6R^7$, —CN and —$NO_2$;
d is 0, 1 or 2;
each $R^3$ is the same or different and is independently selected from halo, alkyl, alkenyl, alkynyl, cycloalkyl, cycloalkenyl, Ay, Het, —$OR^6$, —$R^4OR^6$, —OAy, —$R^4$OAy, —OC(O)$R^6$, —COR$^6$, —$R^4$C(O)$R^6$, —C(O)Ay, —C(O)$NR^6R^7$, —$R^4$C(O)$NR^6R^7$, —C(O)N(H)Ay, —C(O)N(H)Het, —$CO_2R^6$, —$CO_2$Ay, —C(S)$R^6$, —C(S)$NR^6R^7$, —S(O)$_fR^6$, —$R^4$S(O)$_fR^6$, —S(O)$_f$Ay, —S(O)$_2NR^6R^7$, —$NR^6R^7$, —$R^4NR^6R^7$, —N(H)Ay, —$R^4$N(H)Ay, —N(H)$R^4$Het, —N($R^6$)—$R^4R^7$, —N($R^6$)—$R^4$—$OR^7$, —N($R^6$)—$R^4$—S(O)$_fR^7$, —N($R^6$)—$R^4$—CN, —C(NH)$NR^6R^7$, —N(H)C(O)$R^6$, —N(H)C(O)Ay, —N(H)$SO_2R^6$, —N($R^6$)—C(O)—$NR^6R^7$, —N($R^6$)—S(O)$_2$—$NR^6R^7$, —CN and —$NO_2$;
e is 0 or 1;
each $R^4$ is the same or different and is independently $C_{1-4}$alkylene or $C_{3-4}$alkenylene;
Ring B is selected from aryl and heteroaryl;
g is 0, 1, 2, 3 or 4;
each Z is the same or different and is independently a moiety of formula II:

$$(\text{Alk})_m\text{-}(Y^2)_n\text{-}(\text{Alk})_p\text{-}(R^5)_q \qquad (ii)$$

wherein:
m, n and p are the same or different and are each independently 0 or 1;
each Alk is the same or different and is independently selected from $C_{1-4}$alkylene and $C_{3-4}$alkenylene;
$Y^2$ is —O—, —C(O)—, —S(O)$_f$—, —N(H)— or —N(Alk)-;
q is 1 or 2;
each $R^5$ is the same or different and is independently selected from H, halo, alkyl, alkenyl, cycloalkyl, cycloalkenyl, Ay, Het, oxo, —$OR^6$, —OAy, —C(O)$R^6$, —OC(O)$R^6$, —C(O)Ay, —OC(O)Ay, —C(O)$NR^6R^7$, —$CO_2R^6$, —$CO_2$Ay, —S(O)$_fR^6$, S(O)$_f$Ay, —S(O)$_2NR^6R^7$, —C(S)$R^6$, —C(S)$NR^6R^7$, —C(S)N(H)Ay, —$NR^6R^7$, —N(H)Ay, —N(H)Het, —N($R^6$)—$R^4R^7$, —N($R^6$)—$R^4$—$OR^7$, —N($R^6$)—$R^4$—S(O)$_fR^7$, —N($R^6$)—$R^4$—CN, —NHC(O)$R^6$, —N(H)S(O)$_2R^6$, —C(NH)$NR^6R^7$, —N($R^6$)—C(O)—$NR^6R^7$, —N($R^6$)—S(O)$_2$—$NR^6R^7$, —N($R^6$)—C(O)—$R^4NR^6R^7$, —N($R^6$)—S(O)$_2$—$R^4NR^6R^7$, —CN and —$NO_2$; and
each $R^6$ and $R^7$ are the same or different and are each independently selected from H, alkyl, alkenyl, alkynyl, $C_{3-6}$cycloalkyl and $C_{3-6}$cycloalkenyl;

or a pharmaceutically acceptable salt or solvate thereof.

In one embodiment, the compounds of formula (I) are defined wherein a is 1 or 2. In one particular embodiment, a is 0. In one particular embodiment, a is 2. In one particular embodiment, a is 3.

Each $R^1$ may be bound to Ring A through any suitable carbon or heteroatom (to provide, for example, N-methyl or N-oxides). In one embodiment, the compounds of formula (I) are defined wherein each $R^1$ is the same or different and is independently selected from halo, alkyl, alkenyl, alkynyl, cycloalkyl, cycloalkenyl, Ay, Het, —$OR^6$, —$R^4OR^6$, —OC(O)$R^6$, —C(O)$R^6$, —$R^4$C(O)$R^6$, —C(O)$NR^6R^7$, —$CO_2R^6$, C(S)$R^6$, C(S)$NR^6R^7$, —S(O)$_fR^6$, —$R^4$S(O)$_fR^6$, —S(O)$_2NR^6R^7$, —$NR^6R^7$, —$R^4NR^6R^7$, —N($R^6$)C(O)$R^6$, —N($R^6$)S(O)$_2R^6$, —N($R^6$)—C(O)—$NR^6R^7$, —N($R^6$)—S(O)$_2$—$NR^6R^7$, —CN and —$NO_2$, or any subset thereof. In one particular embodiment, the compounds of formula (I) are defined wherein each $R^1$ is the same or different and is independently selected from halo, alkyl, alkenyl, alkynyl, cycloalkyl, cycloalkenyl, —$OR^6$, —$R^4OR^6$, —OC(O)$R^6$, —C(O)$R^6$, —$R^4$C(O)$R^6$, —C(O)$NR^6R^7$, —S(O)$_fR^6$, —$R^4$S(O)$_fR^6$, —$NR^6R^7$, —$R^4NR^6R^7$, —N($R^6$)C(O)$R^6$, —N($R^6$)S(O)$_2R^6$, —CN and —$NO_2$ or any subset thereof. In one particular embodiment, the compounds of formula (I) are defined wherein each $R^1$ is the same or different and is independently selected from halo, alkyl, alkenyl, alkynyl, —$OR^6$, —C(O)$NR^6R^7$, —S(O)$_fR^6$, —S(O)$_2NR^6R^7$, —$NR^6R^7$, —N(H)C(O)$R^6$, —N(H)S(O)$_2R^6$, —CN and —$NO_2$, or any subset thereof. In one preferred embodiment, each $R^1$ is the same or different and is independently selected from F, Cl, alkyl and —$OR^6$ or any subset thereof.

Specific examples of groups defining $R^1$ include but are not limited to F, Cl, Br, $CH_3$, $CF_3$, $CH_2CH_3$, $CH(CH_3)_2$, $OCH_3$, $OCF_3$, $OCH_2CH_3$, $NH_2$, N(H)alkyl (e.g., N(H)$CH_3$), N(H)C(O)alkyl (e.g., N(H)C(O)$CH_3$), CN and $NO_2$. In one particular embodiment, each $R^1$ is the same or different and is independently selected from F, Cl, $CH_3$, $CF_3$, $OCH_3$, and $OCF_3$.

in formula (I) is referred to herein as "Ring A." Ring A is selected from aryl, heterocycle and heteroaryl. Ring A may be bonded to $Y^1$ through any suitable carbon or heteroatom. In one embodiment, Ring A is aryl. In another embodiment, Ring A is heterocycle or heteroaryl. In one embodiment, the compounds of formula (I) are defined wherein Ring A is aryl or heteroaryl. In one particular embodiment, Ring A is phenyl. In another particular embodiment, Ring A is a 5-6 membered heteroaryl having 1 or 2 heteroatoms selected from N, O and S.

Specific examples of groups defining Ring A include but are not limited to furan, tetrahydrofuran, thiophene, pyrrole, pyrroline, pyrrolidine, oxazole, isoxazole, thiazole, isothiazole, imidazole, imidazolidine, pyrazole, pyrazoline, pyrazolidine, triazole, phenyl, pyran, tetrahydropyrane, pyridine, piperidine, iosxane, morpholine, thiomorpholine, pyridazine, pyrimidine, pyrazine, piperiazine, naphthyl, dihydro-naphthyline, indene, dihydro-indene, benzofuran, benzothiophene, indole, insoindole, indoline, indazole, benzimidazole, quinoline, isoquinoline, tetrahydroisoquinoline, quinazoline, quinoxaline, benzopiperidine, benzopiperazine, benzotriazole, benzopyran, chroman, isochroman, benzodioxane, and benzodioxolane, or any subset thereof. In one embodiment, Ring A is selected from phenyl, furan, pyrrole, pyrazole, thiophene, isoxazole, pyridine, benzofuran and benzodioxane, or any subset thereof. In one preferred embodiment Ring A is phenyl.

In one embodiment the compounds of formula (I) are defined wherein $Y^1$ is —C(O)—, —N(H)C(O)— or —N(H)C(S)—. In one particular embodiment, $Y^1$ is —C(O)— or —N(H)C(O)—. In one preferred embodiment, $Y^1$ is —C(O)—.

In one embodiment, the compounds of formula (I) are defined wherein b is 0 or 1. In one preferred embodiment, b is 0.

In one embodiment, the compounds of formula (I) are defined wherein c is 0 or 1. In one preferred embodiment, c is 0.

In one embodiment wherein b and/or c is 1, 2 or 3, each $R^2$ is the same or different and is independently selected from halo, alkyl, —$OR^6$, —$NR^6R^7$ and —CN. In one particular embodiment, each $R^2$ is the same or different and is independently selected from halo, alkyl, —$OR^6$ and —CN. In one preferred embodiment, when b and/or c is 1, 2 or 3, each $R^2$ is the same or different and is independently selected from halo and alkyl; more preferably halo, particularly F or Cl.

In one embodiment, the compounds of formula (I) are defined wherein d is 0 or 1. In one particular embodiment, d is 1.

In particular embodiments of the present invention wherein d is 1 or 2, each $R^3$ is the same or different and is independently selected from halo, alkyl, alkenyl, alkynyl, cycloalkyl, Ay, Het, —$OR^6$, —$R^4OR^6$, —$OC(O)R^6$, —$COR^6$, —$R^4C(O)R^6$, —$C(O)NR^6R^7$, —$S(O)_fR^6$, —$R^4S(O)_fR^6$, —$S(O)_2NR^6R^7$, —$NR^6R^7$, —$R^4NR^6R^7$, —N(H)Ay, —$R^4$N(H)Ay, —N(H)Het, —N($R^6$)—$R^4$—$OR^7$, —N($R^6$)—$R^4$—$S(O)_fR^7$, —N($R^6$)—$R^4$—CN, —N(H)C(O)$R^6$, —N(H)$SO_2R^6$, —N($R^6$)—C(O)—$NR^6R^7$, —N($R^6$)—$S(O)_2$—$NR^6R^7$, —CN and —$NO_2$. In one particular embodiment the compounds of formula (I) are defined wherein each $R^3$ is the same or different and is independently selected from halo, alkyl, cycloalkyl, Ay, Het, —$OR^6$, —$COR^6$, —$C(O)NR^6R^7$, —$S(O)_fR^6$, —$S(O)_2NR^6R^7$, —$NR^6R^7$, —$R^4NR^6R^7$, —N(H)Ay, —N(H)Het, —N(H)C(O)$R^6$, —N(H)$SO_2R^6$, —CN and —$NO_2$. In one preferred embodiment, the compounds of formula (I) are defined wherein each $R^3$ is the same or different and is independently selected from halo, alkyl, cycloalkyl, —$OR^6$, —$COR^6$, —$C(O)NR^6R^7$, —$S(O)_fR^6$, —$S(O)_2NR^6R^7$, —$NR^6R^7$ and —CN.

In one embodiment, the compounds of formula (I) are defined wherein e is 0. In one embodiment wherein e is 1, the group $(R^4)_e$ is $C_{1-4}$alkylene. In one particular embodiment, the group $(R^4)_e$ is $C_{1-3}$alkylene. In one embodiment, the group $(R^4)_e$ is methylene. In another embodiment, the group $(R^4)_e$ is —CH($CH_3$)—. In another embodiment, the group $(R^4)_e$ is propylene or isopropylene.

in Formula (I) is referred to herein as "Ring B." Ring B may be bonded to $R^4$ or —N(H)— (when e is 0) through any suitable carbon or heteroatom. In one preferred embodiment, Ring B is aryl. In another embodiment, Ring B is heteroaryl. In one preferred embodiment, Ring B is phenyl. In another preferred embodiment, Ring B is a 5-10 membered heteroaryl group having 1, 2 or 3 heteroatoms selected from N, O and S. In another preferred embodiment, Ring B is a 5-6 membered heteroaryl group having 1, 2 or 3 heteroatoms selected from N, O and S.

Specific groups defining Ring B include but are not limited to furan, thiophene, pyrrole, oxazole, isoxazole, thiazole, isothiazole, imidazole, pyrazole, triazole, phenyl, pyran, pyridine, pyridazine, pyrimidine, pyrazine, naphthyl, indene, dihydro-indene, benzofuran, benzothiophene, indole, isoindole, indoline, indazole, benzimidazole, quinoline, isoquinoline, tetrahydroisoquinoline, quinazoline, quinoxaline, benzopiperidine, benzopiperazine, benzotriazole, benzopyran, chroman, isochroman, benzodioxane, and benzodioxolane, or any subset thereof. In one embodiment, Ring B is selected from phenyl, furan, pyrrole, pyrazole, thiophene, isoxazole, pyridine, tetrahydroisoquinoline, benzofuran and benzodioxane, or any subset thereof. In one preferred embodiment Ring B is phenyl. In one preferred embodiment, Ring B is tetrahydroisoquinoline.

The definition of the variable g, indicating the number of possible substituents Z on Ring B should be understood to be consistent with and dependent upon the size of ring B. Thus, in the embodiment wherein Ring B is a 10-membered heteroaryl, up to 4 substituents Z may be bound to Ring B. The substituents Z may be bound to Ring B through any available carbon or heteroatom.

Similarly, the moiety Z should be understood to be defined in view of the definition of Ring B so as to avoid embodiments which the organic chemist of ordinary skill would consider to be obviously inoperative. For example, in those embodiments wherein Ring B is a heteroaryl, g is not 0, and Z is bound to a heteroatom of Ring B; then Z is defined as a moiety bound to Ring B through either carbon or a heteroatom suitable for binding to the heteroatom of Ring B. Thus, when Ring B is a heteroaryl and Z is bound to a N of Ring B, then Z is defined as a moiety capable of binding to the N of Ring B; accordingly in such embodiment, Z may not for example, be a moiety halo, —$OR^6$, —$SR^6$ or —$NR^6R^7$. Examples of Z moieties capable of binding to a N of Ring B include but are not limited to H, alkyl (e.g., N-methyl) and oxo (e.g., N-oxide). Other suitable definitions of Z for binding to a heteroatom of Ring B will be apparent to those skilled in the art.

In one embodiment, the compounds of formula (I) are defined wherein g is 0, 1, 2 or 3. In one particular embodiment, g is 0, 1 or 2. In one preferred embodiment g is 1. In another preferred embodiment, g is 2.

In the embodiments wherein g is 1, 2, 3 or 4, each Z is the same or different and is independently a moiety of formula ii:

(ii)

wherein:
m, n and p are the same or different and are each independently 0 or 1 (meaning that the variables Alk, $Y^2$ and Alk, respectively in formula (II) above are either present or absent);
each Alk is the same or different and is independently selected from $C_{1-4}$alkylene and $C_{3-4}$alkenylene;
$Y^2$ is —O—, —C(O)—, —S(O)$_f$—, —N(H)— or —N(Alk)-;
q is 1 or 2; and
each $R^5$ is the same or different and is independently selected from H, halo, alkyl, alkenyl, cycloalkyl, cycloalkenyl, Ay, Het, oxo, —OR$^6$, —OAy, —C(O)R$^6$, —OC(O)R$^6$, —C(O)Ay, —OC(O)Ay, —C(O)NR$^6$R$^7$, —CO$_2$R$^6$, —CO$_2$Ay, —S(O)$_f$R$^6$, —S(O)$_f$Ay, —S(O)$_2$NR$^6$R$^7$, —C(S)R$^6$, —C(S)NR$^6$R$^7$, —C(S)N(H)Ay, —NR$^6$R$^7$, —N(H)Ay, —N(H)Het, —N(R$^6$)—R$^4$R$^7$, —N(R$^6$)—R$^4$—OR$^7$, —N(R$^6$)—R$^4$—S(O)$_f$R$^7$, —N(R$^6$)—R$^4$—CN, —NHC(O)R$^6$, —N(H)S(O)$_2$R$^6$, —C(NH)NR$^6$R$^7$, —N(R$^6$)—C(O)—NR$^6$R$^7$, —N(R$^6$)—S(O)$_2$—NR$^6$R$^7$, —N(R$^6$)—C(O)—R$^4$NR$^6$R$^7$, —N(R$^6$)—S(O)$_2$—R$^4$NR$^6$R$^7$, —CN and —NO$_2$.

In one embodiment, the compounds of formula (I) are defined wherein g is 1, 2, 3 or 4 and m is 0. In another embodiment, wherein m is 1, the group (Alk)$_m$ is preferably $C_{1-3}$alkylene.

In one embodiment, the compounds of formula (I) are defined wherein g is 1, 2, 3 or 4 and n is 0. In one embodiment, wherein n is 1, $Y^2$ is —O—, —C(O)— or —N(H)—.

In one particular embodiment, g is 1, 2, 3 or 4, n is 1 and $Y^2$ is —O— or —C(O)—. In one particular embodiment, $Y^2$ is —C(O)—. In one preferred embodiment, $Y^2$ is —O—.

In one embodiment, the compounds of formula (I) are defined wherein g is 1, 2, 3 or 4 and p is 0. In another embodiment, wherein p is 1, the group (Alk)$_p$ is preferably $C_{1-3}$alkylene.

In one embodiment, the compounds of formula (I) are defined wherein g is 1, 2, 3 or 4 and q is 1.

In one particular embodiment wherein g is 1, 2, 3 or 4 and q is 1, each $R^5$ is the same or different and is independently selected from H, halo, alkyl, alkenyl, cycloalkyl, Ay, Het, oxo, —OR$^6$, —OAy, —C(O)R$^6$, —OC(O)R$^6$, —C(O)Ay, —C(O)NR$^6$R$^7$, —CO$_2$R$^6$, —S(O)$_f$R, —S(O)$_2$NR$^6$R$^7$, —C(S)NR$^6$R$^7$, —NR$^6$R$^7$—N(H)Ay, —N(H)Het, —N(R$^6$)—R$^4$R$^7$, —N(R$^6$)—R$^4$—OR$^7$, —N(R$^6$)—R$^4$—S(O)$_f$R$^7$, —N(R$^6$)—R$^4$—CN, —NHC(O)R$^6$, —N(H)S(O)$_2$R$^6$, —C(NH)NR$^6$R$^7$, —N(R$^6$)—C(O)—NR$^6$R$^7$, —N(R$^6$)—S(O)$_2$—NR$^6$R$^7$, —N(R$^6$)—C(O)—R$^4$NR$^6$R$^7$, —CN and —NO$_2$. In one particular embodiment, each $R^5$ is the same or different and is independently selected from H, halo, alkyl, cycloalkyl, Ay, Het, —OR$^6$, —C(O)R$^6$, —OC(O)R$^6$, —C(O)NR$^6$R$^7$, —S(O)$_f$ R$^6$, —S(O)$_2$NR$^6$R$^7$, —C(S)NR$^6$R$^7$, —NR$^6$R$^7$, —N(H)Ay, —N(H)Het, —N(R$^6$)—R$^4$—OR$^7$, —N(R$^6$)—R$^4$—S(O)$_f$R$^7$, —N(R$^6$)—R$^4$—CN, —NHC(O)R$^6$, —N(H)S (O)$_2$R$^6$, and —CN. In one preferred embodiment, each $R^5$ is the same or different and is independently selected from H, halo, alkyl, cycloalkyl, Ay, Het, —OR$^6$, —C(O)R$^6$, —C(O)NR$^6$R$^7$, —S(O)$_f$R$^6$, —S(O)$_2$NR$^6$R$^7$, —NR$^6$R$^7$, —N(R$^6$)—R$^4$—CN, and —CN.

Each of the individual variables n, $Y^2$, p, q and $R^5$ should be understood to be defined in view of the definition of the other variables comprising moiety Z so as to avoid embodiments which the skilled organic chemist would consider to be obviously inoperative. For example, in those embodiments wherein n is 1 and p is 0 such that Z is the moiety (ii-a)

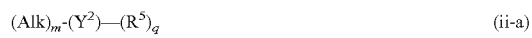

(ii-a)

(wherein all variables are as defined above) the variable $R^5$ should be defined in view of $Y^2$ such that embodiments which the organic chemist of ordinary skill would consider to be obviously inoperative, are avoided. For example, if $Y^2$ is O and p is 0, then $R^5$ is not halo or a group that would result in a peroxide, etc. Accordingly, in one embodiment wherein n is 1 and p is 0; then q is 1 and $R^5$ is a group bound through either carbon or a heteroatom suitable for binding to $Y^2$.

In one particular embodiment, when Z is defined as a moiety wherein:
1) n is 1, $Y^2$ is —O— and p is 0; then q is 1 and $R^5$ is not halo, oxo, nitrile, nitro or a group bound through O or S;
2) n is 1 $Y^2$ is —C(O)— and p is 0; then q is 1 and $R^5$ is not halo, oxo, nitrile, nitro or a group bound through —CO$_2$— or —C(S)—;
3) n is 1 $Y^2$ is —N(H)— or —N(Alk)- and p is 0; then q is 1 and $R^5$ is not halo, oxo, nitrile, or nitro; or
4) n is 1 $Y^2$ is —S(O)$_f$— and p is 0; then q is 1 and $R^5$ is not halo, oxo, nitrile, nitro or a group bound through S.

In one particular embodiment, when Z is defined as a moiety wherein:
1) n is 1, $Y^2$ is —O— and p is 0; then q is 1 and $R^5$ is not: halo, Het bound through a heteroatom, oxo, —OR$^6$, —OAy, —OC(O)R$^6$, —OC(O)Ay, —NR$^6$R$^7$, —N(H)Ay, —N(H)Het, —N(R$^6$)—R$^4$R$^7$, —N(R$^6$)—R$^4$—OR$^7$, —N(R$^6$)—R$^4$—S(O)$_f$R$^7$, —N(R$^6$)—R$^4$—CN, —NHC(O)R$^6$, —N(H)S(O)$_2$R$^6$, —C(NH)NR$^6$R$^7$, —N(R$^6$)—C(O)—NR$^6$R$^7$, —N(R$^6$)—S(O)$_2$—NR$^6$R$^7$, —N(R$^6$)—C(O)—R$^4$NR$^6$R$^7$, —N(R$^6$)—S (O)$_2$—R$^4$NR$^6$R$^7$, —CN or —NO$_2$;
2) n is 1 $Y^2$ is —C(O)— and p is 0; then q is 1 and $R^5$ is not: halo, oxo, —C(O)NR$^6$R$^7$, —CO$_2$R$^6$, —CO$_2$Ay, —S(O)$_f$R$^6$, —S(O)Ay, —S(O)$_2$NR$^6$R$^7$, —C(S)R$^6$, —C(S)NR$^6$R$^7$, —C(S)N(H)Ay, —CN or —NO$_2$;
3) n is 1 $Y^2$ is —N(H)— or —N(Alk)- and p is 0; then q is 1 and $R^5$ is not:
halo, —OC(O)R$^6$, —OC(O)Ay, —C(NH)NR$^6$R$^7$, —N(R$^6$)—C(O)—NR$^6$R$^7$, —N(R$^6$)—S(O)$_2$—NR$^6$R$^7$, —N(R$^6$)—C(O)—R$^4$NR$^6$R$^7$, —N(R$^6$)—S (O)$_2$—R$^4$NR$^6$R$^7$, —CN or —NO$_2$; or
4) n is 1 $Y^2$ is —S(O)$_f$— and p is 0; then q is 1 and $R^5$ is not: halo, oxo, —OR$^6$, —OAy, —OC(O)R$^6$, —OC(O)Ay, —S(O)$_f$R$^6$, —S(O)$_f$AY, —S(O)$_2$NR$^6$R$^7$, —C(S)R$^6$, —C(S)NR$^8$R$^7$, —C(S)N(H)Ay, —CN or —NO$_2$.

Specific examples of groups defining Z include but are not limited to
H (e.g., g is 0)
halo (e.g., F or Cl)
alkyl (e.g., CH$_3$, CF$_3$)
Het (e.g., 5-6 membered heterocycle or heteroaryl having 1 or 2 heteroatoms selected from N, O and S and substituted variants thereof)
OR$^6$ (e.g., OH, OCH$_3$)

CN
C(O)R$^6$ (e.g., C(O)CH$_3$ and C(O)CF$_3$)
C(O)Ay (e.g., C(O)phenyl and substituted variants thereof)
C(O)NR$^6$R$^7$ (e.g., C(O)NH$_2$)
C(O)Het (e.g., C(O)morpholine and substituted variants thereof)
C(O)-Alk-Ay (e.g., C(O)—CH$_2$-phenyl and substituted variants thereof)
SO$_2$R$^6$ (e.g., SO$_2$CH$_3$, SO$_2$CH$_2$CH$_3$, SO$_2$CH$_2$CH$_2$OH)
SO$_2$NR$^6$R$^7$ (e.g., SO$_2$NH$_2$, SO$_2$N(H)CH$_3$ and SO$_2$N(H)cyclopropyl)
Alk-NR$^6$R$^7$ (e.g., —(CH$_2$)$_3$—N(CH$_3$)$_2$)
N(H)C(O)R$^6$ (e.g., NHC(O)CH$_3$)
N(H)-Alk-NR$^6$R$^7$ (e.g., NH—(CH$_2$)$_3$—N(CH$_3$)$_2$)
N(H)C(O)-Alk-NR$^6$R$^7$ (e.g., N(H)C(O)—CH$_2$—NH$_2$)
N(H)-Alk-Het (NH—(CH$_2$)$_3$-piperazine-N—CH$_3$)
Alk-SO$_2$R$^6$ (CH$_2$—SO$_2$CH$_3$, CH$_2$—SO$_2$CH$_2$CH$_3$, CH$_2$CH$_3$—SO$_2$CH$_3$ and CH$_2$CH$_3$—SO$_2$CH$_2$CH$_3$)
Alk-SO$_2$NR$^6$R$^7$ (e.g., CH$_2$CH$_3$—SO$_2$NH$_2$)
Alk-Het (e.g., Alk-morpholine, Alk-piperidine, and Alk-pyrrolidine)
O-Alk-OR$^6$ (e.g., O—CH$_2$—OCH$_3$, O—CH$_2$CH$_3$—OCH$_3$)
O-Alk-NR$^6$R$^7$ (e.g., O—(CH$_2$)$_2$—NH$_2$, O—(CH$_2$)$_2$—N(H)CH$_3$, O—(CH$_2$)$_2$—N(CH$_3$)$_2$, O—(CH$_2$)$_2$—N(CH$_2$CH$_3$)$_2$, O—(CH$_2$)$_3$—NH$_2$, O—(CH$_2$)$_3$—N(H)CH$_3$, O—(CH$_2$)$_3$—N(CH$_3$)$_2$, O—(CH$_2$)$_3$—N(CH$_2$CH$_3$)$_2$, O—CH$_2$CH(CH$_3$)—NH$_2$, O—CH$_2$CH(CH$_3$)—N(H)CH$_3$, O—CH$_2$CH(CH$_2$)—N(CH$_3$)$_2$, O—CH$_2$CH(CH$_3$)—N(CH$_2$CH$_3$)$_2$)
O-Alk-Het (e.g., O—(CH$_2$)$_2$-morpholino, O—CH$_2$-pyrrolidine, O—(CH$_2$)$_2$-pyrrolidine, O—CH$_2$-piperidine, O—(CH$_2$)$_2$-piperidine and substituted variants thereof).

In one embodiment of the invention, each R$^6$ and R$^7$ is the same or different and is independently selected from H and alkyl.

It is to be understood that the present invention includes all combinations and subsets of the particular groups defined hereinabove.

Specific examples of compounds of the present invention include those recited in the Examples which follow and pharmaceutically acceptable salts or solvates thereof.

It will be appreciated by those skilled in the art that the compounds of the present invention may also be utilized in the form of a pharmaceutically acceptable salt or solvate thereof. The pharmaceutically acceptable salts of the compounds of formula (I) include conventional salts formed from pharmaceutically acceptable (i.e., non-toxic) inorganic or organic acids or bases as well as quaternary ammonium salts. Representative salts include the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium and valerate. Other salts, such as oxalic, which are not themselves pharmaceutically acceptable, may be useful in the preparation of salts useful as intermediates in obtaining compounds of this invention and these form a further aspect of the invention.

The term "solvate" as used herein refers to a complex of variable stoichiometry formed by a solute (a compound of formula (I)) and a solvent. Such solvents for the purpose of the invention may not interfere with the biological activity of the solute. Examples of suitable solvents include, but are not limited to, water, MeOH, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water.

Processes for preparing pharmaceutically acceptable salts and solvates of compounds such as the compounds of formula (I) are conventional in the art. See, e.g., Burger's Medicinal Chemistry And Drug Discovery 5th Edition, Vol 1: Principles And Practice.

As will be apparent to those skilled in the art, in the processes described below for the preparation of compounds of formula (I) certain intermediates may be in the form of pharmaceutically acceptable salts or solvates of the compound. Those terms as applied to any intermediate employed in the process of preparing compounds of formula (I) have the same meanings as noted above with respect to compounds of formula (I). Processes for preparing pharmaceutically acceptable salts and solvates of intermediates are known in the art and are analogous to the process for preparing pharmaceutically acceptable salts and solvates of compounds such as the compounds of formula (I).

Certain compounds of formula (I) may exist in stereoisomeric forms (e.g. they may contain one or more asymmetric carbon atoms or may exhibit cis-trans isomerism). The individual stereoisomers (enantiomers and diastereomers) and mixtures of these are included within the scope of the present invention. The present invention also covers the individual isomers of the compounds represented by formula (I) as mixtures with isomers thereof in which one or more chiral centres are inverted. Certain compounds of formula (I) may be prepared as a mixture of regioisomers. The present invention covers both the mixture of regioisomers as well as the individual compounds. Likewise, it is understood that compounds of formula (I) may exist in tautomeric forms other than that shown in the formula and these are also included within the scope of the present invention.

The compounds of formula (I) and salts and solvates thereof, are believed to have anticancer and antitumor activity. This effect is currently believed to result from inhibition of one or more ErbB family protein kinases and the effect of such inhibition on cell lines whose growth is dependent on ErbB family protein kinase activity. It is well documented in the literature that inhibition of one or more ErbB family protein kinases is believed to result in therapeutic anti-tumor and anticancer effects. See, e.g., Normanno, N., Bianco, C., Strizzi, L., Mancino, M., Maiello, M. R., DeLuca, A., Caponigro, F., Salomon, D. S. *Current Drug Targets*, 2005, 6, 243-257; Hynes, N. E., Lane, H. A. *Nature Reviews Cancer*, 2005, 5, 341-345; and Ben-Baruch, N., Yarden, Y. *Progress in Oncology*, 2004, 46-72.

The compounds of the present invention are typically inhibitors of one or more ErbB family kinases (EGFR, ErbB-2, and/or ErbB-4). The present invention is not limited to compounds of formula (I) which are selective for ErbB family kinases; rather, the present invention expressly contemplates compounds of formula (I) which may possess activity against kinases other than ErbB family kinases, as well. By "ErbB inhibitor" is meant a compound which exhibits a pIC$_{50}$ of greater than about 6 against at least one ErbB family kinase in the ErbB inhibition enzyme assay described below and/or an IC$_{50}$ of at least about 1 µM potency against at least one cell line that overexpresses at least one ErbB family kinase (e.g., BT474 or HN5) in the methylene blue cellular assay described below. In a more particular embodiment "ErbB inhibitor" refers to a compound which exhibits a $pIC_{50}$ of greater than about 6.5 against at least one ErbB family kinase in the ErbB inhibition enzyme assay described below and/or an $IC_{50}$ of at least 100 nM potency against at least one cell line that overexpresses at least one ErbB family kinase (e.g., BT474 or HN5) in the methylene blue assay described below.

The present invention further provides compounds of formula (I) for use in medical therapy in a mammal, e.g. a human. In particular, the present invention provides compounds of formula (I) for use in the treatment of a condition mediated by at least one ErbB family kinase in a mammal, and more particularly conditions mediated by inappropriate activity of one or more ErbB family kinase in a mammal. In one embodiment, the present invention provides compounds of formula (I) for use in the treatment of a condition mediated by at least two ErbB family kinases, and more particularly conditions mediated by inappropriate activity of one or more ErbB family kinase in a mammal.

The inappropriate ErbB family kinase activity referred to herein is any ErbB kinase activity that deviates from the normal ErbB family kinase activity expected in a particular mammalian subject. The inappropriate activity may arise from one or more of EGFR (ErbB-1), ErbB-2, or ErbB-4. Inappropriate ErbB family kinase activity may take the form of, for instance, an abnormal increase in activity, or an aberration in the timing and/or control of ErbB family kinase activity. Such inappropriate activity may result then, for example, from overexpression or mutation of the protein kinase or ligand leading to inappropriate or uncontrolled activation of the receptor. Furthermore, it is also understood that unwanted ErbB family kinase activity may reside in an abnormal source, such as a malignancy. That is, the level of ErbB family activity does not have to be abnormal to be considered inappropriate, rather the activity derives from an abnormal source.

The present invention also provides compounds of formula (I) for use in the treatment of a susceptible neoplasm.

"Susceptible neoplasm" as used herein refers to neoplasms which are susceptible to treatment with an ErbB inhibitor. Neoplasms which have been associated with inappropriate activity of one or more ErbB family kinases and are therefor susceptible to treatment with an ErbB inhibitor are known in the art, and include both primary and metastatic tumors and cancers. For example, susceptible neoplasms within the scope of the present invention include but are not limited to breast cancer, colon cancer, non-small cell lung cancer, prostate cancer, bladder cancer, ovarian cancer, gastric cancer, pancreatic cancer, carcinoma of the head and neck, esophageal carcinoma, melanoma and renal carcinoma.

The present invention provides methods for the treatment of several conditions in a mammal in need thereof, all of which comprise the step of administering a therapeutically effective amount of a compound of formula (I). The mammal in need of treatment with a compound of the present invention is typically a human.

As used herein, the term "treatment" refers to alleviating the specified condition, eliminating or reducing the symptoms of the condition, slowing or eliminating the progression of the condition and preventing or delaying the reoccurrence of the condition in a previously afflicted subject.

As used herein, the term "therapeutically effective amount" means an amount of a compound of formula (I) which is sufficient, in the subject to which it is administered, to elicit the biological or medical response of a cell culture, tissue, system, mammal (including human) that is being sought, for instance, by a researcher or clinician. The term also includes within its scope amounts effective to enhance normal physiological function. For example, a therapeutically effective amount of a compound of formula (I) for the treatment of a condition mediated by inappropriate activity of at least one ErbB family kinase is an amount sufficient to treat the condition in the subject. Similarly, a therapeutically effective amount of a compound of formula (I) for the treatment of a susceptible neoplasm is an amount sufficient to treat the susceptible neoplasm in the subject. In one embodiment of the present invention, a therapeutically effective amount of a compound of formula (I) is an amount sufficient to regulate, modulate, bind or inhibit at least one ErbB family kinase.

The present invention provides a method for treating a condition mediated by at least one ErbB family kinase (and particularly inappropriate activity of at least one ErbB family kinase) in a mammal (e.g., a human), which method comprises administering to the mammal a therapeutically effective amount of the compound of formula (I). Conditions which are mediated by inappropriate activity of at least one ErbB family kinase are known in the art and include but are not limited to neoplasms.

A further aspect of the invention provides a method of treatment of a mammal suffering from a condition mediated by inappropriate activity of one or more ErbB family kinases, which comprises administering to the mammal a therapeutically effective amount of a compound of formula (I). In one embodiment, the condition mediated by inappropriate activity of one or more ErbB family kinases is a susceptible neoplasm.

The present invention also provides a method for treating a susceptible neoplasm (cancer or tumor) in a mammal (e.g., a human) in need thereof, which method comprises administering to the mammal a therapeutically effective amount of the compound of formula (I).

In one particular embodiment, the present invention provides a method for treating breast cancer in a mammal in need thereof comprising administering to the mammal a therapeutically effective amount of the compound of formula (I). In another embodiment, the present invention provides a method for treating colon cancer in a mammal in need thereof comprising administering to the mammal a therapeutically effective amount of the compound of formula (I). In another embodiment, the invention provides a method for treating non-small cell lung cancer in a mammal in need thereof comprising administering to the mammal a therapeutically effective amount of the compound of formula (I).

The precise therapeutically effective amount of the compounds of formula (I) will depend on a number of factors including, but not limited to, the age and weight of the subject being treated, the precise condition requiring treatment and its severity, the nature of the formulation, and the route of administration, and will ultimately be at the discretion of the attendant physician or veterinarian. Typically, the compound of formula (I) will be given for treatment in the range of 0.1 to 200 mg/kg body weight of recipient (mammal) per day and more usually in the range of 1 to 100 mg/kg body weight per day. Acceptable daily dosages, may be from about 0.1 to about 2000 mg/day, and preferably from about 0.1 to about 100 mg/day. Thus, for a 70 kg adult human being treated for a condition mediated by at least one ErbB family kinase, the actual amount per day would usually be from 70 to 700 mg and this amount may be given in a single dose per day or more usually in a number (such as two, three, four, five or six) of sub-doses per day such that the total daily dose is the same. A therapeutically effective amount of a salt or solvate, may be determined as a proportion of the therapeutically effective amount of the compound of formula (I) per se. It is envisaged that similar dosages would be appropriate for treatment of the other conditions referred to above.

The compounds of formula (I) can be used alone in the treatment of each of the foregoing conditions or can be used to provide additive or synergistic effects with certain existing chemotherapies, and/or be used to restore effectiveness of certain existing chemotherapies and radiation.

As one aspect, the present invention provides methods of regulating, modulating, binding, or inhibiting at least one ErbB family kinase for the treatment of conditions mediated by at least one ErbB family kinase, by administering a therapeutically effective amount of a compound of formula (I). "Regulating, modulating, binding or inhibiting at least one ErbB family kinase" refers to regulating, modulating, binding or inhibiting activity of at least one ErbB family kinase (e.g., c-ErbB-2, EGFR, and ErbB-4), as well as regulating, modulating, binding or inhibiting overexpression of at least one ErbB family kinase. Such conditions include certain neoplasms (including cancers and tumors) which have been associated with overexpression of at least one ErbB family kinase.

The present invention also provides the use of a compound of formula (I) for the preparation of a medicament for the treatment of condition mediated by at least one ErbB family kinase in a mammal (e.g., a human) in need thereof. The present invention further provides the use of a compound of formula (I) for the preparation of a medicament for the treatment of a susceptible neoplasm in a mammal. The present invention further provides the use of a compound of formula (I) for the preparation of a medicament for the treatment of breast cancer in a mammal. The present invention further provides the use of a compound of formula (I) for the preparation of a medicament for the treatment of colon cancer in a mammal. The present invention further provides the use of a compound of formula (I) for the preparation of a medicament for the treatment of non-small cell lung cancer in a mammal.

While it is possible that, for use in therapy, a therapeutically effective amount of a compound of formula (I) may be administered as the raw chemical, it is typically presented as the active ingredient of a pharmaceutical composition or formulation. Accordingly, the invention further provides a pharmaceutical composition comprising a compound of the formula (I). The pharmaceutical composition may further comprise one or more pharmaceutically acceptable carriers, diluents, and/or excipients. The carrier(s), diluent(s) and/or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I) with one or more pharmaceutically acceptable carriers, diluents and/or excipients.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the formula (I), depending on the condition being treated, the route of administration and the age, weight and condition of the patient, or pharmaceutical formulations may be presented in unit dose forms containing a predetermined amount of active ingredient per unit dose. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula (I) can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula (I) may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example those suitable for oral administration may include flavouring agents.

In the above-described methods of treatment and uses, a compound of formula (I) may be employed alone, in combination with one or more other compounds of formula (I) or in combination with other therapeutic agents. In particular, in methods of treating a condition mediated by at least one ErbB family kinase and methods of treating susceptible neoplasms, combination with other chemotherapeutic, hormonal and/or antibody agents is envisaged as well as combination with surgical therapy and radiotherapy. The term "chemotherapeutic" as used herein refers to any chemical agent having a therapeutic effect on the subject to which it is administered. "Chemotherapeutic" agents include but are not limited to anti-neoplastic agents, analgesics and anti-emetics. Anti-emetics include but are not limited to $5HT_3$ antagonists such as ondansetron, granisetron, and the like; metaclopromide; dexamethasone and neurokinin-1 antagonists. As used herein, "anti-neoplastic agents" include both cytostatic and cytotoxic agents. Combination therapies according to the present invention thus comprise the administration of at least one compound of formula (I) and the use of at least one other treatment method. In one embodiment, combination therapies according to the present invention comprise the administration of at least one compound of formula (I) and at least one other chemotherapeutic agent. In one particular embodiment, the present invention comprises the administration of at least one compound of formula (I) and at least one anti-neoplastic agent. As an additional aspect, the present invention provides the methods of treatment and uses as described above, which comprise administering a compound of formula (I) together with at least one chemotherapeutic agent. In one particular embodiment, the chemotherapeutic agent is an anti-neoplastic agent. In another embodiment, the present invention provides a pharmaceutical composition as described above further comprising at least one other chemotherapeutic agent, more particularly, the chemotherapeutic agent is an anti-neoplastic agent.

The compounds of the formula (I) and at least one additional cancer treatment therapy may be employed in combination concomitantly or sequentially in any therapeutically appropriate combination with such other anti-cancer therapies. In one embodiment, the other anti-cancer therapy is at least one additional chemotherapeutic therapy including administration of at least one anti-neoplastic agent. In another embodiment, the other anti-cancer therapy is at least one additional chemotherapeutic therapy including administration of at least one anti-emetic. The administration in combination of a compound of formula (I) with other anti-neoplastic agents may be in combination in accordance with the invention by administration concomitantly in (1) a unitary pharmaceutical composition including both compounds or (2) separate pharmaceutical compositions each including one of the compounds. The combination may be administered separately in a sequential manner wherein one anti-neoplastic agent is administered first and the other second or vice versa. Such sequential administration may be close in time or remote in time. When a compound of formula (I) is used in combination with a chemotherapeutic agent, the dose of each compound may differ from that when the compound is used alone. Appropriate doses will be readily appreciated by those skilled in the art. The appropriate dose of the compound(s) of formula (I) and the other therapeutically active agent(s) and the relative timings of administration will be selected in order to achieve the desired combined therapeutic effect, and are within the expertise and discretion of the attendant clinician.

Among the many chemotherapeutic agents which may be used in combination with a compound of the present invention are anti-neoplastic agents. Anti-neoplastic agents may induce anti-neoplastic effects in a cell-cycle specific manner, i.e., are phase specific and act at a specific phase of the cell cycle, or bind DNA and act in a non cell-cycle specific manner, i.e., are non-cell cycle specific and operate by other mechanisms. Both types of anti-neoplastic agents may be employed in combination with the compounds of the present invention.

Typically, any chemotherapeutic agent that has activity versus a susceptible neoplasm being treated may be utilized in combination with the compounds of formula (I), provided that the particular agent is clinically compatible with therapy employing a compound of formula (I). Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphor-ines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and antifolate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signaling inhibitors.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids. Examples of diterpenoids include, but are not limited to, paclitaxel and its analog docetaxel. Examples of vinca alkaloids include, but are not limited to, vinblastine, vincristine, and vinorelbine.

Platinum coordination complexes are non-phase specific anti-neoplastic agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Alkylating agents are non-phase anti-neoplastic specific agents and strong electrophiles. Typically, alkylating agents form covalent linkages, by alkylation, to DNA through nucleophilic moieties of the DNA molecule such as phosphate, amino, and hydroxyl groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Antibiotic chemotherapeutic agents are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Topoisomerase II inhibitors include, but are not limited to, epipodophyllotoxins. Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Antimetabolite neoplastic agents are phase specific anti-neoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mercaptopurine and thioguanine.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin.

Hormones and hormonal analogues are useful compounds for treating cancers in which there is a relationship between the hormone(s) and growth and/or lack of growth of the cancer. Examples of hormones and hormonal analogues believed to be useful in the treatment of neoplasms include, but are not limited to, adrenocorti-costeroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene and iodoxyfene useful in the treatment of hormone dependent breast carcinoma; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagonists such as goserelin acetate and luprolide.

Signal transduction pathway inhibitors are those inhibitors which block or inhibit a chemical process which evokes an intracellular change. As used herein this change is cell proliferation or differentiation or survival. Signal transduction inhibitors useful in the present invention include inhibitors of receptor tyrosine kinases, non-receptor tyrosine kinases, SH2/SH3 domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Other receptor tyrosine kinases involved in the regulation of cell growth and sometimes termed growth factor receptors, may also be combined with a compound of the present invention. In addition to the epidermal growth factor receptors (EGFr, ErbB2 and ErbB4), other growth factor receptor inhibitors that may be combined with a compound of formula (I) include, for example, platelet derived growth factor receptor (PDGFr), vascular endothelial growth factor receptor (VEGFR), tyrosine kinase with immunoglobulin-like and epidermal growth factor homology domains (TIE-2), insulin growth factor receptor-1 (IGFR-1), macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene and inhibitors of Akt kinases. Several inhibitors of growth factor receptors are under development and include ligand antagonists, antibodies, tyrosine kinase inhibitors, anti-sense oligonucleotides and aptamers. Growth factor receptors and agents that inhibit growth factor receptor function are described, for instance, in Kath, John C., Exp. Opin. Ther. Patents (2000) 10(6):803-818; Shawver et al DDT Vol 2, No. 2 Feb. 1997; and Lofts, F. J. et al, "Growth Factor Receptors as Targets", New Molecular Targets for Cancer Chemotherapy, Ed. Workman, Paul and Kerr, David, CRC Press 1994, London. In one embodiment, the present invention provides methods of treatment of the various conditions enumerated above comprising administering a compound of formula (I) in combination with a different ErbB inhibitor. In one preferred embodiment, the methods comprise administering a compound of formula (I) in combination with lapatinib.

Tyrosine kinases which are not growth factor receptor kinases are termed non-receptor tyrosine kinases. Non-receptor tyrosine kinases useful in the present invention, which are targets or potential targets of anti-neoplastic drugs, include cSrc, Lck, Fyn, Yes, Jak, cAbi, FAK (Focal adhesion kinase), Brutons tyrosine kinase, and Bcr-Abl. Such non-receptor kinases and agents which inhibit non-receptor tyrosine kinase function are described in Sinh, S, and Corey, S. J., (1999) Journal of Hematotherapy and Stem Cell Research 8 (5): 465-80; and Bolen, J. B., Brugge, J. S., (1997) Annual Review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases include Polo-like kinases ("PLK" e.g., PLK1, PLK2 and PLK3) which play critical roles in regulating processes in the cell cycle including the entry into and the exit from mitosis; MAP kinase cascade blockers which include blockers of Raf kinases (Rafk), Mitogen or Extracellular Regulated Kinase (MEKs), and Extracellular Regulated Kinases (ERKs); and Protein kinase C family member blockers including blockers of subtypes of PKCs (alpha, beta, gamma, epsilon, mu, lambda, iota, zeta), IkB kinase family (IKKa, IKKb), PKB family kinases, Akt kinase family members, and TGF beta receptor kinases may also be used in combination with a compound of the present invention. Such Serine/Threonine kinases and inhibitors thereof are described in PCT Publication No. WO04/014899 to GlaxoSmithKline; Yamamoto, T., Taya, S., Kaibuchi, K., (1999), Journal of Biochemistry. 126 (5) 799-803; Brodt, P, Samani, A., and Navab, R. (2000), Biochemical Pharmacology, 60.1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; and Martinez-Iacaci, L., et al, Int. J. Cancer (2000), 88(1), 44-52. In one embodiment, the methods of the present invention comprise administering a compound of formula (I) in combination with a PLK inhibitor, more preferably a compound described in PCT Publication No. WO04/014899.

Inhibitors of Phosphotidyl Inositol-3 Kinase family members including blockers of PI3-kinase, ATM, DNA-PK, and Ku are also useful in combination with the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer Res, (2000) 60(6), 1541-1545.

Also useful in combination with the present invention are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC Press 1994, London.

Another group of signal transduction pathway inhibitors useful in combination with the present invention are inhibitors of Ras Oncogene. Such inhibitors include inhibitors of farnesyltransferase, geranyl-geranyl transferase, and CAMX proteases as well as anti-sense oligonucleotides, ribozymes and immunotherapy. Such inhibitors have been shown to block Ras activation in cells containing wild type mutant Ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9(2)99-102; and BioChim. Biophys. Acta, (1989) 1423(3):19-30.

As mentioned above, antibodies to receptor kinase ligand binding may also serve as signal transduction inhibitors. This group of signal transduction pathway inhibitors includes the use of humanized antibodies to the extracellular ligand binding domain of receptor tyrosine kinases. For example, Imclone C225 EGFR specific antibody (see Green, M. C. et al, Monoclonal Antibody Therapy for Solid Tumors, Cancer Treat. Rev., (2000), 26(4), 269-286); Herceptin® ErbB2 antibody (see Tyrosine Kinase Signaling in Breast Cancer:ErbB Family Receptor Tyrosine Kinases, Breast Cancer Res., 2000, 2(3), 176-183); and 2CB VEGFR2 specific antibody (see Brekken, R. A. et al, Selective Inhibition of VEGFR2 Activity by a Monoclonal Anti-VEGF Antibody Blocks Tumor Growth in Mice, Cancer Res. (2000) 60, 5117-5124). Receptor kinase angiogenesis inhibitors may also find use in the present invention. Inhibitors of angiogenesis related VEGFR and TIE2 are discussed above in regard to signal transduction inhibitors (both receptors are receptor tyrosine kinases). Other inhibitors may be used in combination with the compounds of the present invention. For example, anti-VEGF antibodies, which do not recognize VEGFR (the receptor tyrosine kinase), but bind to the ligand; small molecule inhibitors of integrin (alpha$_v$ beta$_3$) that will inhibit angiogenesis; endostatin and angiostatin (non-RTK) may also prove useful in combination with PLK inhibitors.

Agents used in immunotherapeutic regimens may also be useful in combination with the compounds of formula (I).

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al., *J. Clin. Oncol* 18:1812-1823 (2000); and Kitada S et al., *Antisense Res. Dev.* 4:71-79 (1994).

Cell cycle signaling inhibitors inhibit molecules involved in the control of the cell cycle. Cyclin dependent kinases (CDKs) and their interaction cyclins control progression through the eukaryotic cell cycle. The coordinated activation and inactivation of different cyclin/CDK complexes is necessary for normal progression through the cell cycle. Several inhibitors of cell cycle signaling are under development. For instance, examples of cyclin dependent kinases, including CDK2, CDK4, and CDK6 and inhibitors for the same are described in, for instance, Rosania, et al., *Exp. Opin. Ther. Patents* 10(2):215-230 (2000).

In one embodiment, the methods of the present invention comprise administering to the mammal a compound of formula (I) in combination with a signal transduction pathway inhibitor, particularly erlotinib (TARCEVA®).

Compounds of formula (I) may be prepared using the methods described below. In all of the schemes described below, it is understood that protecting groups may be employed where necessary in accordance with general principles known to those of skill in the art, for example, see T. W. Green and P. G. M. Wuts (1991) Protecting Groups in Organic Synthesis, John Wiley & Sons. These groups may be removed at a convenient stage of the compound synthesis using methods known to those of skill in the art. The selection of processes as well as the reaction conditions and order of their execution shall be consistent with the preparation of compounds of formula (I).

Compounds of formula (I) may be conveniently prepared by the methods outlined in Scheme 1 below.

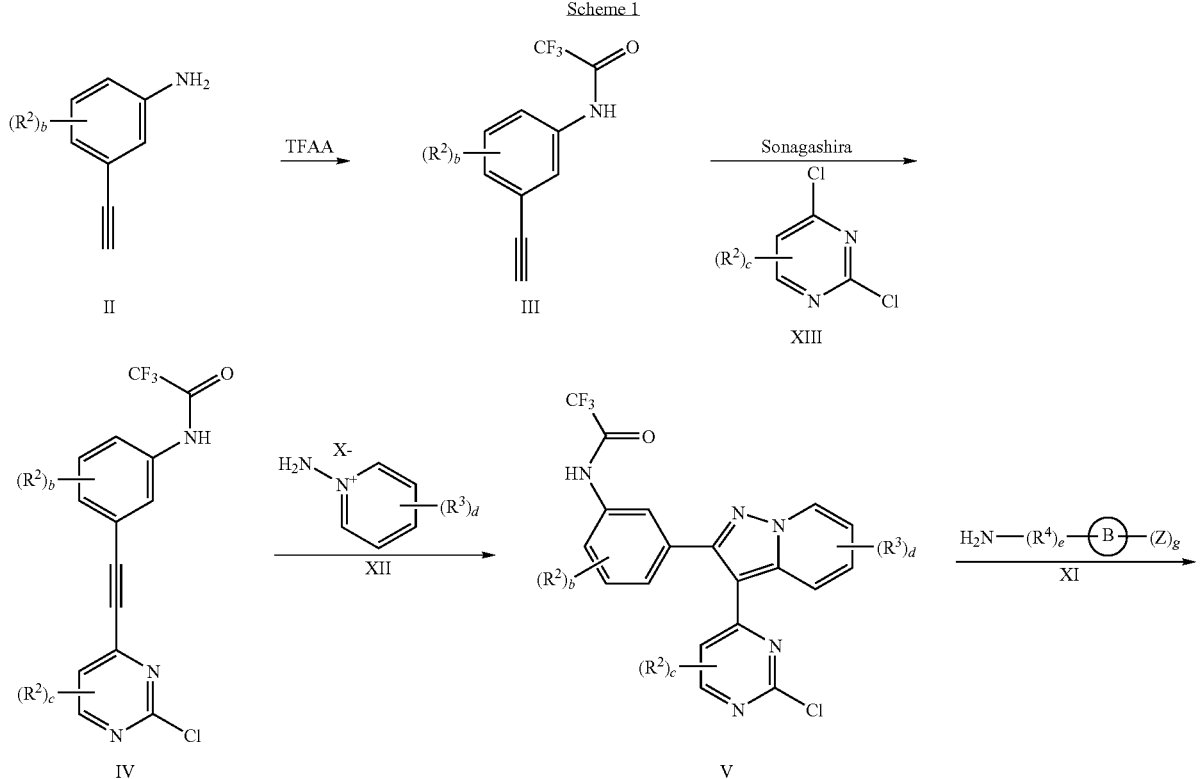

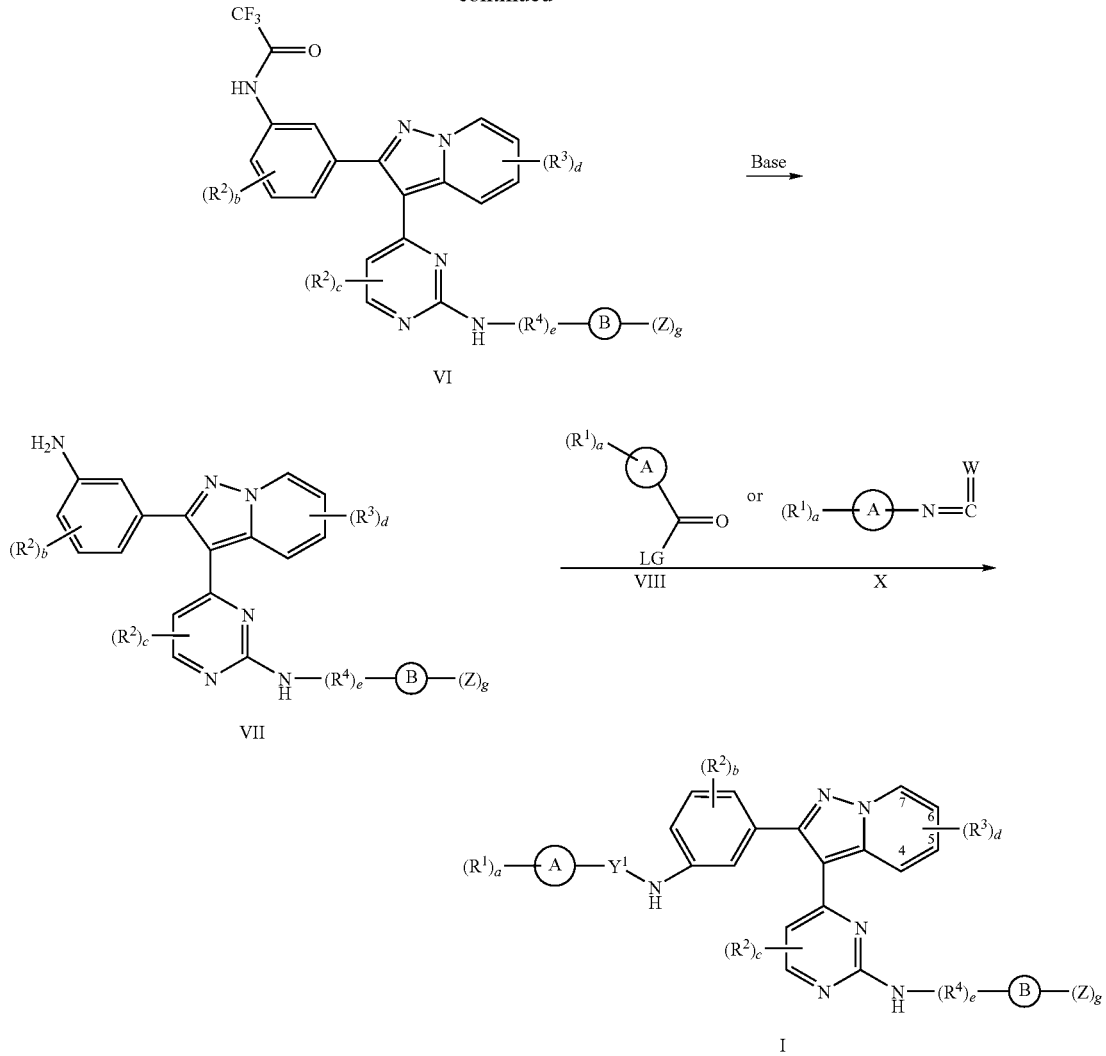

wherein:
X⁻ is an anion (preferably halide);
LG is a suitable leaving group;
W is O or S; and
and all other variables are as defined above.

Generally, the process for preparing the compounds of formula (I) (all formulas and all variables having been defined above) comprises the steps of:

a) reacting a compound of formula (VII) with a compound of formula (VIII) or a compound of formula (X) to prepare a compound of formula (I);

b) optionally converting the compound of formula (I) to a pharmaceutically acceptable salt or solvate thereof; and c) optionally converting the compound of formula (I) or a pharmaceutically acceptable salt or solvate thereof to a different compound of formula (I) or a pharmaceutically acceptable salt or solvate thereof.

More specifically, the process for preparing compounds of formula (I) comprises the steps of:

a) reacting the compound of formula (II) with a trifluoroacetic acid derivative to prepare a compound of formula (III);

b) reacting the compound of formula (III) with a compound of formula (XIII) to prepare a compound of formula (IV);

c) reacting the compound of formula (IV) with a 1-aminopyridinium compound of formula (XII) to prepare a compound of formula (V);

d) reacting the compound of formula (V) with a compound of formula (XI) to prepare a compound of formula (VI);

e) reacting the compound of formula (VI) with a base to prepare a compound of formula (VI);

f) reacting a compound of formula (VII) with a compound of formula (VIII) or a compound of formula (X) to prepare a compound of formula (I);

g) optionally converting the compound of formula (I) to a pharmaceutically acceptable salt or solvate thereof; and h) optionally converting the compound of formula (I) or a pharmaceutically acceptable salt or solvate thereof to a different compound of formula (I) or a pharmaceutically acceptable salt or solvate thereof.

As will be apparent to those skilled in the art, the order of the foregoing steps is not critical to the process of the present invention, and the process may be carried out using any suitable order of steps.

Compounds of formula (I) wherein $Y^1$ is —C(O)— (i.e., compounds of formula (I-A)) are prepared by reacting a compound of formula (VII) with a compound of formula (VIII).

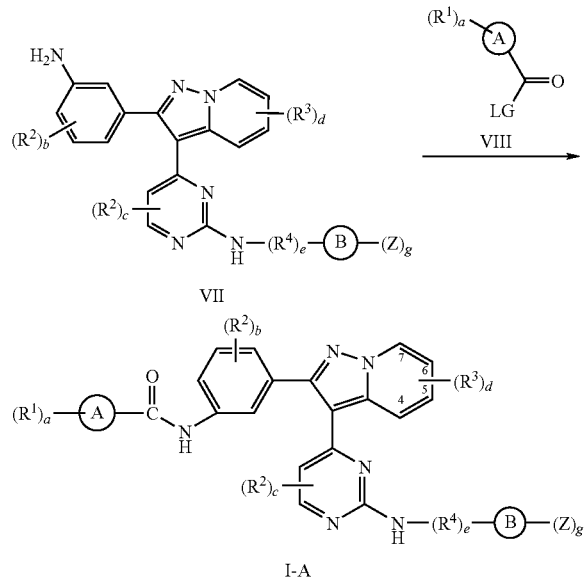

wherein all variables are as defined above.

Suitable leaving groups in the compounds of formula (VIII) will be apparent to those skilled in the art and include, for example, halide and hydroxyl groups. Typically, the reaction is carried out in a suitable solvent such as DCM or tetrahydrofuran. It will be understood by those skilled in the art that when LG is hydroxyl, the reaction can be carried out in the presence of an appropriate coupling agent such as dicyclohexylcarbodiimide (DCC) or ethylcarbodiimide hydrochloride (EDC). Compounds of formula (VIII) are commercially available or may be synthesized using techniques conventional in the art. It will be appreciated by those skilled in the art that the compounds of formula (I-A) may be converted to a different compound of formula (I), e.g., a compound of formula (I) wherein $Y^1$ is other than —C(O)—, using the conventional techniques. Representative transformations of compounds of formula (I-A) are described herein below.

Compounds of formula (I) wherein $Y^1$ is —N(H)C(O)— or $Y^1$ is —N(H)C(S)— (i.e., compounds of formula (I-B)), can be prepared by reacting a compound of formula (VII) with a suitable isocyanate or isothiocyanate of formula (X).

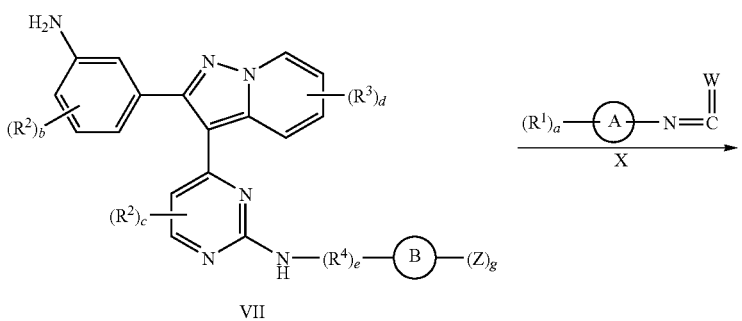

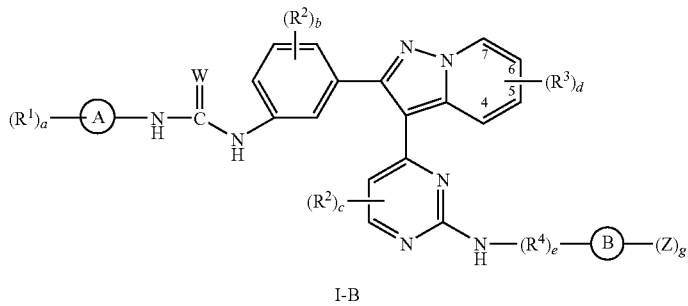

wherein all variables are as defined above.

This reaction may be carried out using conditions conventional in the art for such coupling reactions, including the use of a solvent such as tetrahydrofuran, 1,4-dioxane or DCM at ambient temperature or with heating from about 40 to about 100° C. Compounds of formula (X) are commercially available or may be synthesized using techniques conventional in the art.

A compound of formula (VII) may be prepared by reacting a compound of formula (VI) with a base.

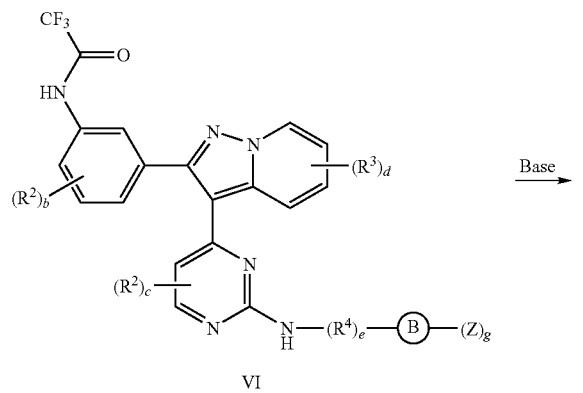

wherein all variables are as defined above.

Suitable bases include lithium hydroxide or sodium hydroxide. This reaction may be carried out in a suitable solvent. Examples of suitable solvents for this reaction include but are not limited to tetrahydrofuran and water. The reaction may be carried out at ambient temperature or with heating from about 40 to about 60° C.

Compounds of formula (VI) may be prepared by reacting a compound of formula (V) with an amine of formula (XI)

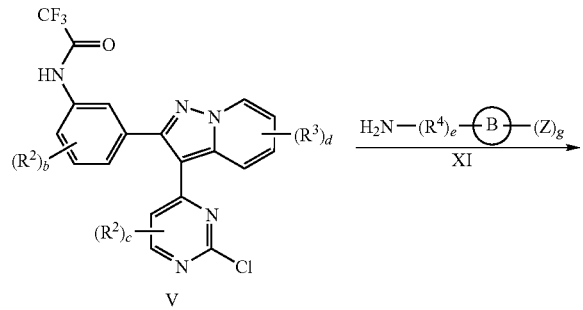

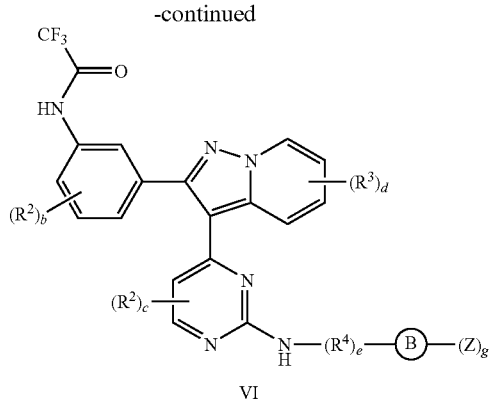

wherein all variables are as defined above.

The reaction may be carried out in a solvent. Examples of suitable solvents for this reaction include but are not limited to isopropanol, 1,4-dioxane, ethanol and N,N-dimethylformamide under reflux conditions or in a microwave apparatus at a temperature of from about 100 to about 180° C. in a suitable vessel. As will be apparent to those skilled in the art of organic chemistry, it may be desirable to catalyze this reaction for the preparation of certain compounds of formula (VI). For example, for compounds of formula (XI) and (VI), wherein e is 0 and Ring B is aryl, it may be desirable to carry out the reaction in the presence of a catalytic amount of an acid such as hydrochloric acid or hydrobromic acid. As will further be apparent to those skilled in the art, it may also be desirable to install appropriate protecting groups prior to reacting the compound of formula (V) with the compound of formula (XI). For example, in the embodiment, wherein Z is a group containing a primary or secondary amine, the addition is preferably carried out when the amine is protected as, for example, its corresponding trifluoracetamide. The choice, installation and removal of appropriate protecting groups for reactions such as this is conventional in the art. Compounds of formula (XI) are commercially available or may be synthesized using techniques conventional in the art.

Compounds of formula (V) may be prepared by reacting a compound of formula (IV) with an 1-aminopyridinium compound of formula (XII).

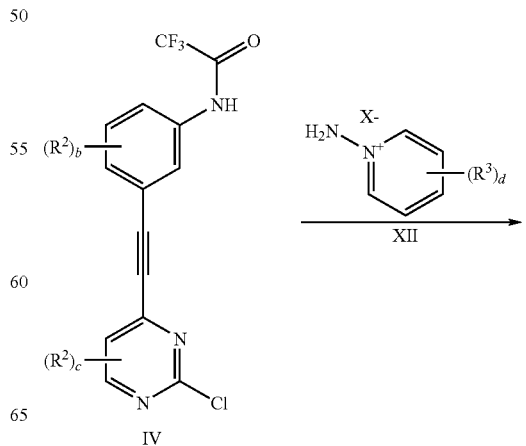

-continued

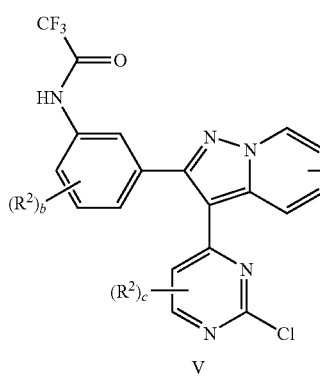

V wherein all variables are as defined above.

The reaction is typically carried out in the presence of a base in a suitable solvent. Examples of suitable bases include but are not limited to potassium carbonate and KOH. Examples of suitable solvents include but are not limited to dimethyl sulfoxide, DCM, water, MeOH and N,N-dimethylformamide at ambient temperature. Compounds of formula (XII) are commercially available or may be synthesized using techniques conventional in the art.

Compounds of formula (IV) may be prepared by reacting a compound of formula (III) with a compound of formula (XIII).

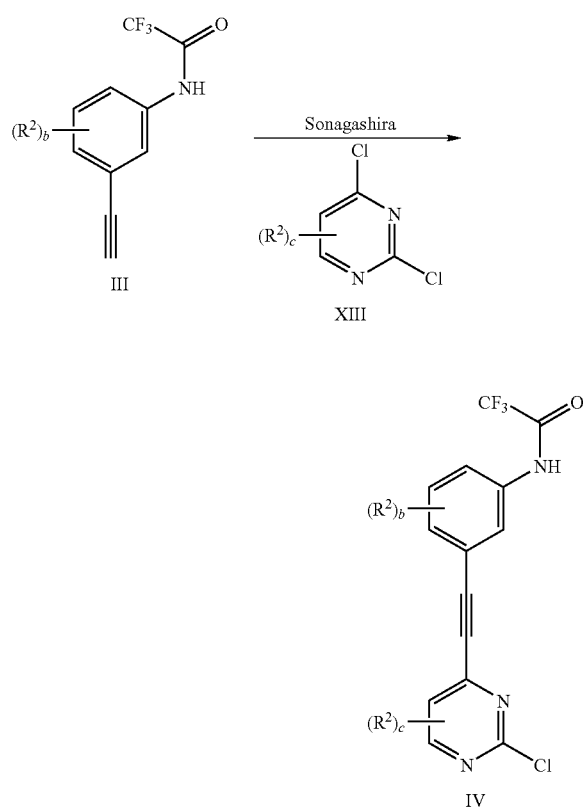

wherein all variables are as defined above.

The reaction is typically carried out using conventional Sonagashira reaction conditions. In particular, the reaction typically is carried out in the presence of a catalyst, copper (I) species and base in a solvent such as tetrahydrofuran according to the method of Sonogashira, Kenkichi. "Palladium-catalyzed alkynylation, HANDBOOK OF ORGANOPALLADIUM CHEMISTRY FOR ORGANIC SYNTHESIS 1, 493-529, 2002. Examples of suitable catalysts include palladium catalysts such as dichlorobis(triphenylphosphine)palladium (II). An example of a suitable base is triethylamine. Compounds of formula (XIII) are commercially available or may be synthesized using techniques conventional in the art.

Compounds of formula (III) may be prepared from the corresponding 3-ethynylaniline compound of formula (II) using a trifluoroacetic acid derivative such as trifluoroacetic anhydride under conditions well known to those skilled in the art.

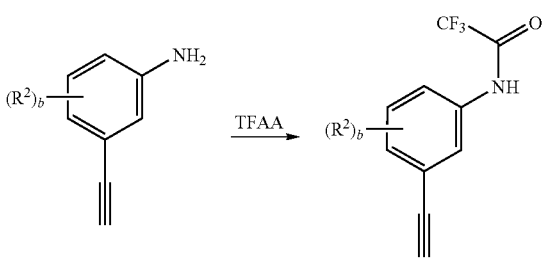

wherein all variables are as defined above.

Compounds of formula (II) are commercially available or may be synthesized using techniques conventional in the art.

As indicated above, the order of the steps of the process is not critical to the practice of the present invention. For example, it will be apparent to those skilled in the art that reaction with a compound of formula (VIII) or (X) for installation of the moiety (i.e.,

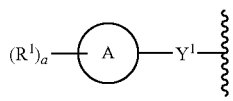

can be effected prior to reaction with the compound of formula (XI). This process may be carried out by reacting a compound of formula (XVI) with an amine of formula (XI) using standard reaction conditions.

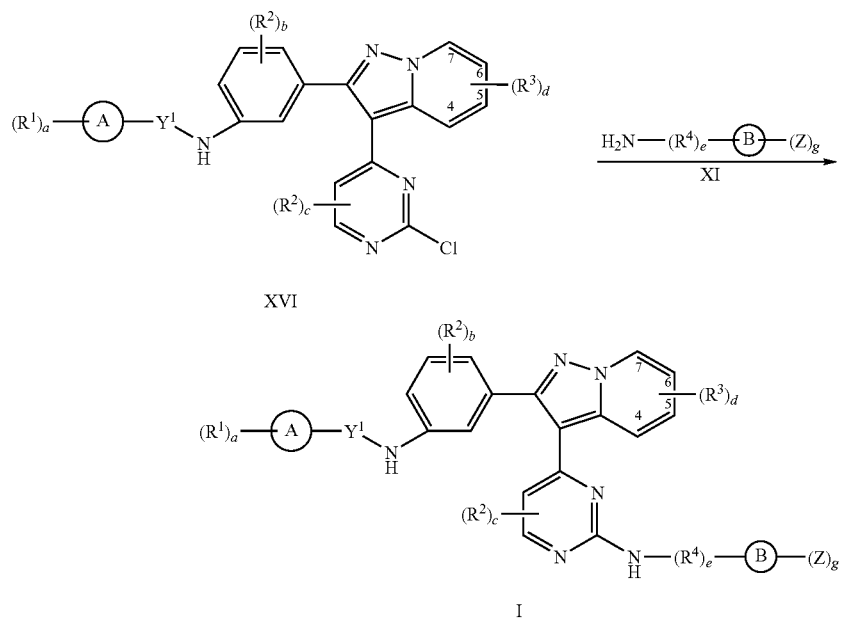

wherein all variables are as defined above.

The compound of formula (XVI) may conveniently be prepared by removal of the trifluoroacetyl group of a compound of formula (V) and reaction with a compound of formula (VIII) or (X) as described above. The removal of trifluoroacetyl group of the compound of formula (V) may be accomplished using techniques well known in the art for the removal of such groups.

According to another process of the present invention, compounds of formula (I) may be prepared as outlined in Scheme 2 below.

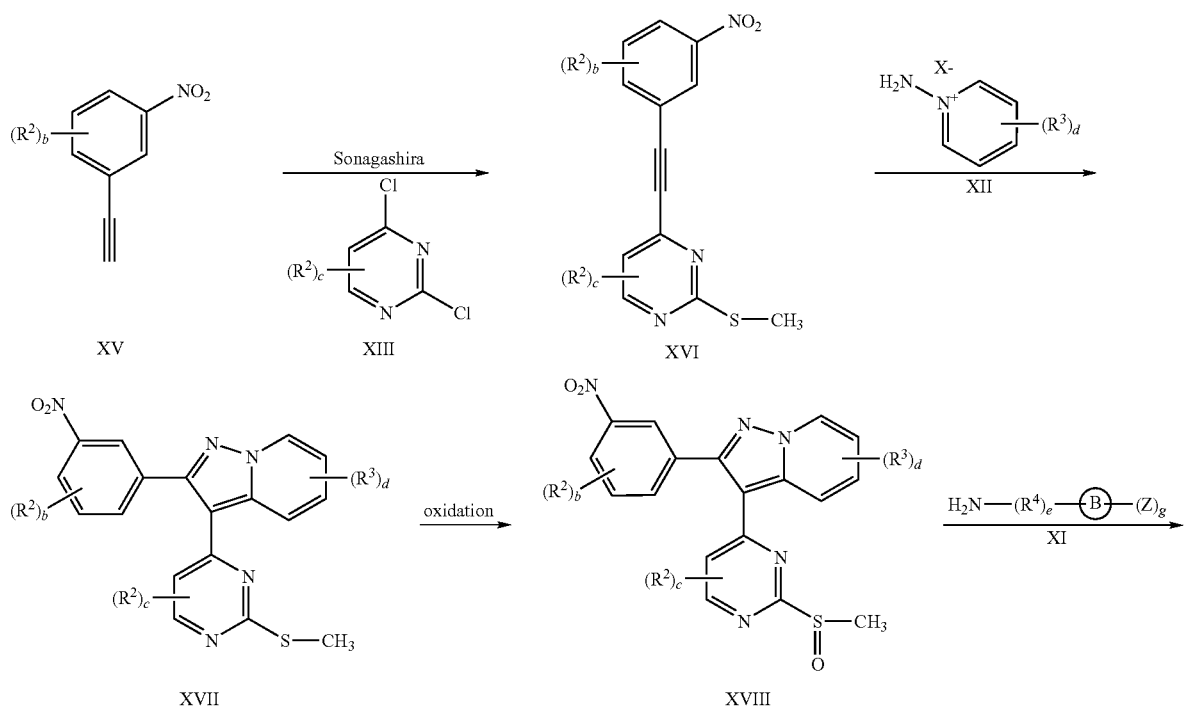

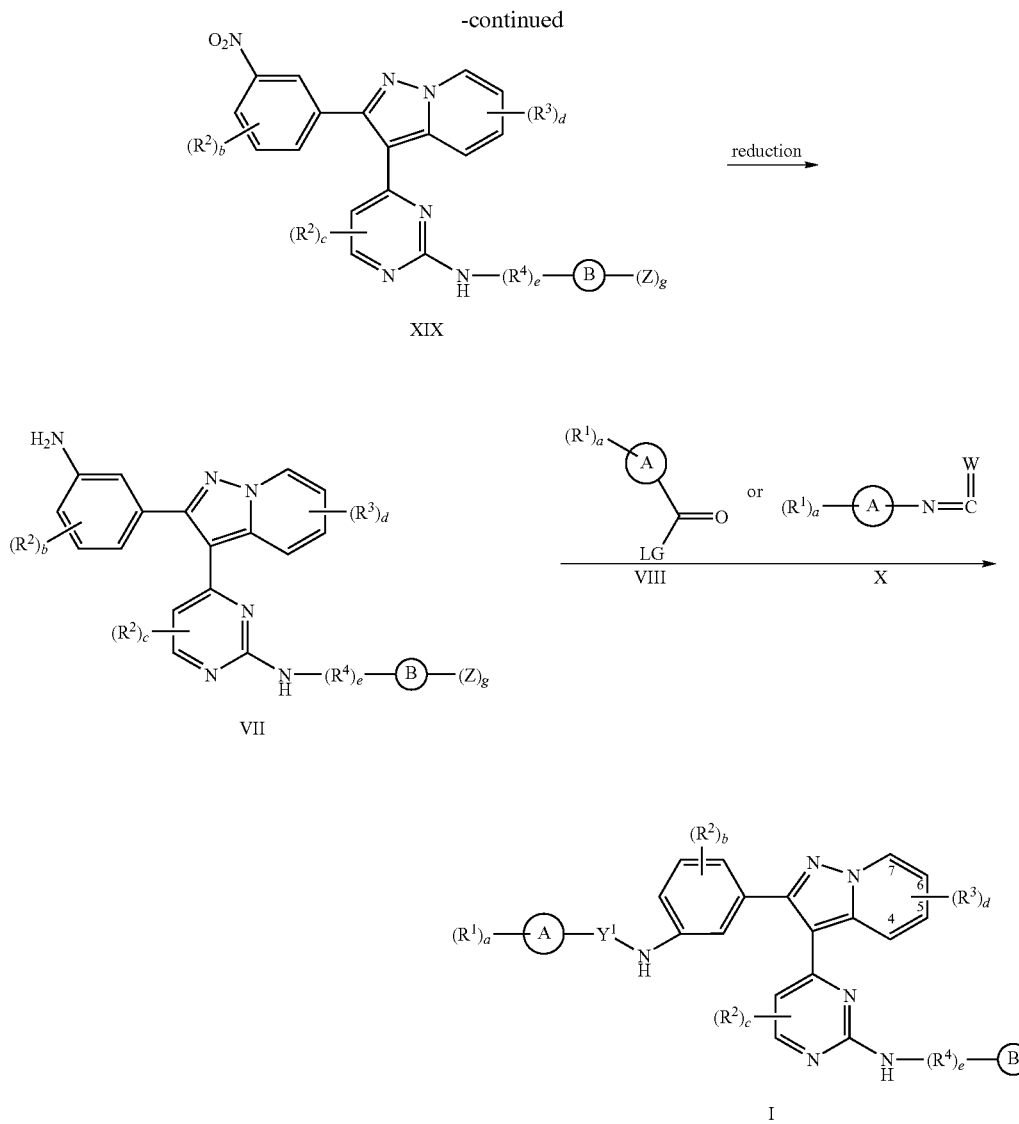

wherein:

X⁻ is an anion (preferably halide);

LG is a suitable leaving group;

W is O or S; and and all other variables are as defined above.

Generally, the process for preparing the compounds of formula (I) (all formulas and all variables having been defined above) comprises the steps of:

a) reacting the compound of formula (XV) with a compound of formula (XIII) to prepare a compound of formula (XVI);

b) reacting the compound of formula (XVI) with a 1-aminopyridinium compound of formula (XII) to prepare a compound of formula (XVII);

c) oxidizing the compound of formula (XVII) to prepare a compound of formula (XVIII);

d) reacting the compound of formula (XVIII) with a compound of formula (XI) to prepare a compound of formula (XIX);

e) reducing the compound of formula (XIX) to prepare a compound of formula (VII);

f) reacting a compound of formula (VII) with a compound of formula (VIII) or a compound of formula (X) to prepare a compound of formula (I);

g) optionally converting the compound of formula (I) to a pharmaceutically acceptable salt or solvate thereof; and h) optionally converting the compound of formula (I) or a pharmaceutically acceptable salt or solvate thereof to a different compound of formula (I) or a pharmaceutically acceptable salt or solvate thereof.

As will be apparent to those skilled in the art, the order of the foregoing steps is not critical to the process of the present invention, and the process may be carried out using any suitable order of steps.

Methods for reacting a compound of formula (VII) with a compound of formula (VIII) or (X) to prepare a compound of formula (I) are described above.

According to Scheme 2, the compounds of formula (VII) may be prepared by reducing a compound of formula (XIX).

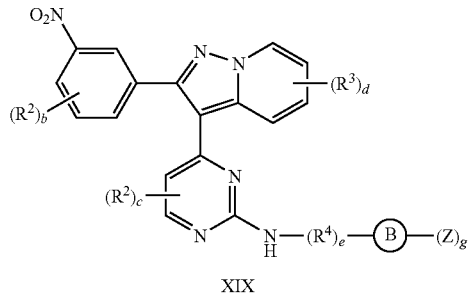

XIX reduction

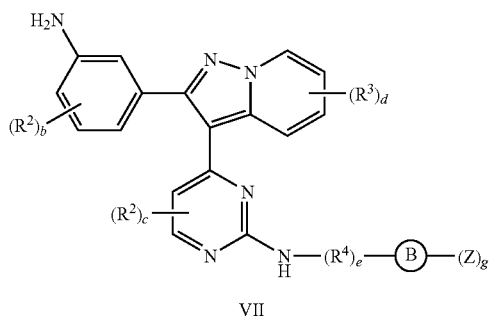

VII wherein all variables are as defined above.

Conveniently, standard conditions for the reduction of a nitro group may be employed to reduce the nitro group of the compound of formula (XIX) to prepare a compound of formula (VII). An example of suitable reaction conditions for this reduction include, but are not limited to reaction with sodium sulfide nonhydrate in ethanol.

A compound of general formula (XIX) may be prepared by reacting a compound of formula (XVIII) with a compound of formula (XI).

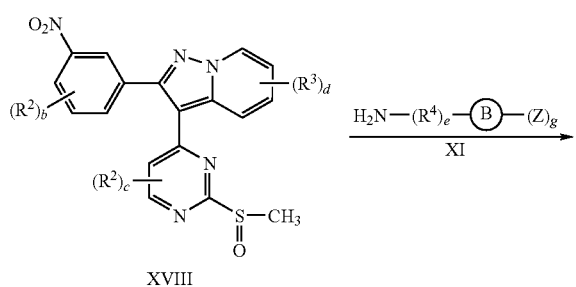

XVIII

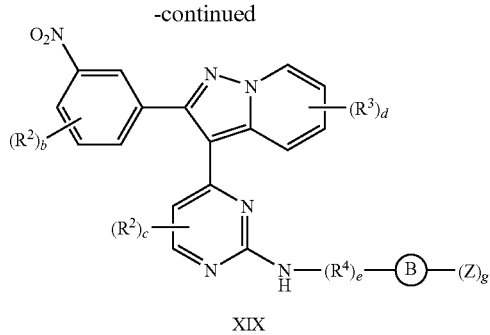

XIX wherein all variables are as defined above.

This reaction is typically carried out by microwave heating of a solution of the compound of formula (XVIII) and a compound of formula (XI) to a temperature of from about 120 to about 180° C. in a solvent, such as ethanol, with a catalytic amount of an acid, such as hydrochloric acid.

A compound of formula (XVIII) may be prepared by oxidizing a compound of formula (XVII) using standard reagents.

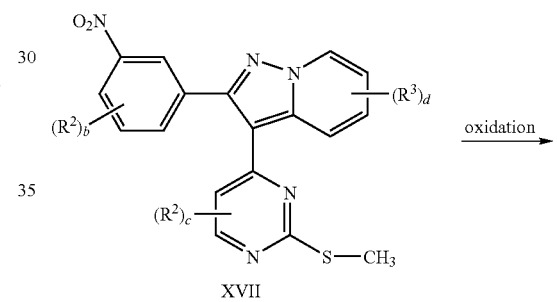

XVII oxidation

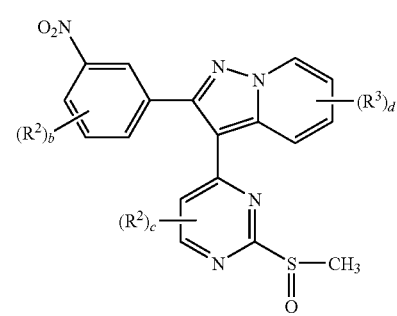

XVIII wherein all variables are as defined above.

Examples of suitable oxidation reagents useful for this reaction include but are not limited to 50% meta-chloroperbenzoic acid (mCPBA) in a solvent such as DCM.

The compounds of formula (XVII) may be prepared using procedures analogous to those described above for the preparation of a compound of formula (V).

An alternative method of producing a compound of Formula (I) wherein c is 0 (i.e., a compound of formula (I-D), is shown in Scheme 3, below.

Scheme 3
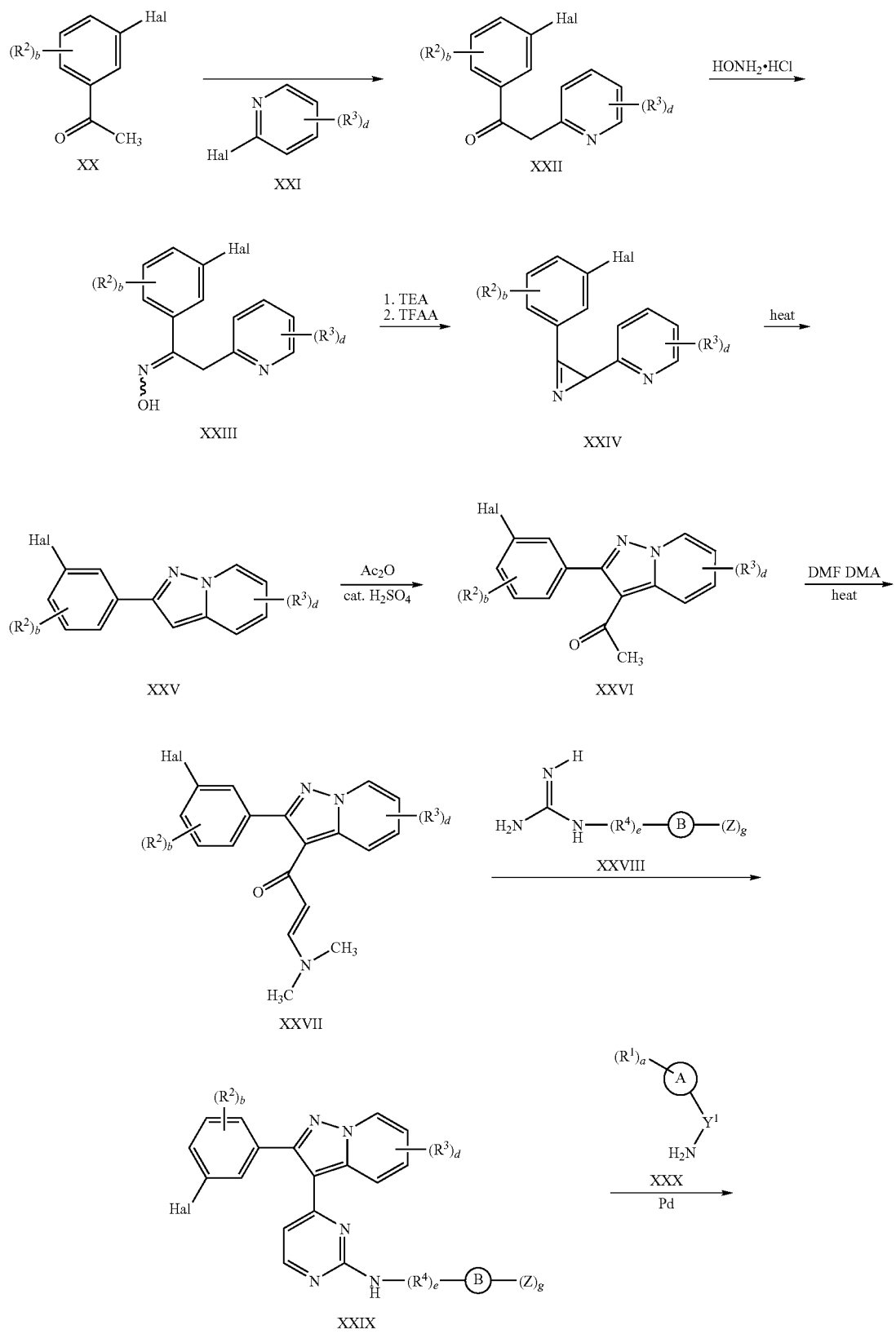

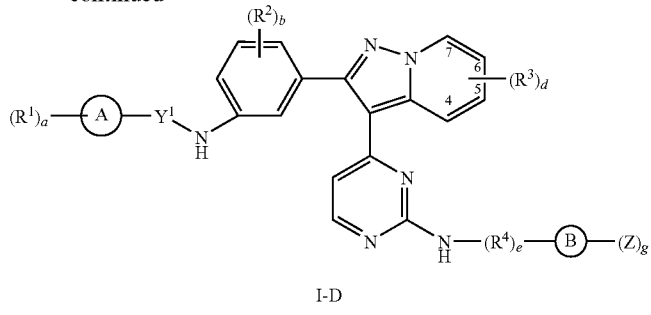

I-D wherein:
each Hal is the same or different halogen; and
all other variables are as defined above.

Generally, the process for preparing the compounds of formula (I) (all formulas and all variables having been defined above) comprises the steps of:

a) reacting the compound of formula (XX) with a compound of formula (XXI) to prepare a compound of formula (XXII);
b) reacting the compound of formula (XXII) with hydroxylamine to prepare a compound of formula (XXIII);
c) reacting the compound of formula (XXIII) with an agent suitable for converting the hydroxylamine to a leaving group in the presence of a base, to prepare a compound of formula (XXIV);
d) heating the compound of formula (XXIV) to prepare a compound of formula (XXV);
e) acetylating the compound of formula (XXV) to prepare a compound of formula (XXVI);
f) reacting the compound of formula (XXVI) with dimethyl formamide dimethyl acetyl to prepare the vinylogous compound of formula (XXVII);
g) reacting with a compound of formula (XXVII) with a compound of formula (XXVIII) with heating to prepare a compound of formula (XXIX);
h) reacting the compound of formula (XXIX) with a compound of formula (XXX) to prepare a compound of formula (I-D);
i) optionally converting the compound of formula (I-D) to a pharmaceutically acceptable salt or solvate thereof; and
j) optionally converting the compound of formula (I-D) or a pharmaceutically acceptable salt or solvate thereof to a different compound of formula (I) or a pharmaceutically acceptable salt or solvate thereof.

As will be apparent to those skilled in the art, the order of the foregoing steps is not critical to the process of the present invention, and the process may be carried out using any suitable order of steps. For example, compound of formula (XXVI) may be amidated by a reagent of formula (XXX) prior to formation of the pyrimidine ring through the sequence of reactions outlined in Scheme 3.

More specifically, a compound of formula (I) may be prepared by reacting the compound of formula (XXIX) with a compound of formula (XXX).

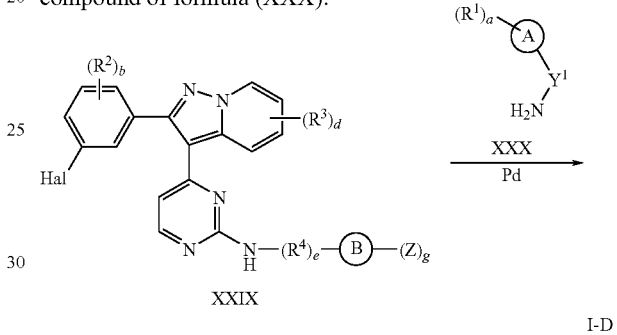

wherein all variables are as defined above.

The reaction is typically carried out heating a mixture of a compound of formula (XXX) with a compound of formula (XXIX) in the presence of a suitable palladium catalyst such as $Pd_2 dba_3$ in the presence of a base such as $Cs_2CO_3$ with an additive such as Xantphos in a solvent such as 1,4-dioxane. A preferred method of reacting a compound of formula (XXIX) into a compound of formula (XXX) using these conditions is by irradiation in a microwave apparatus at a temperature of at least 150° C.

It will be appreciated by those skilled in the art that a compound of formula (XXX) is an amide derivative such that $Y^1$ contains CO bonded to the amine of the compound in formula (XXX). The reaction therefore provides a target compound of formula (I) containing an amide such that $Y^1$ is a carbonyl group bonded to the amine.

A compound of formula (XXVI) may be converted to a compound of formula (XXIX) by a two-step procedure of first converting the compound of formula (XXVI) into a vinylogous amide of formula (XXVII) and then reacting the vinylogous amide with a guanidine of formula (XXVIII).

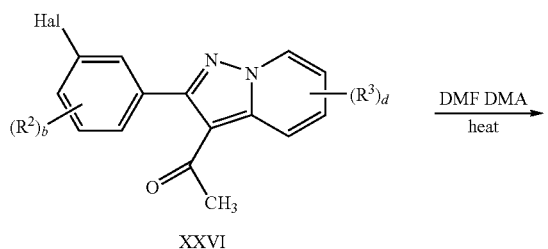

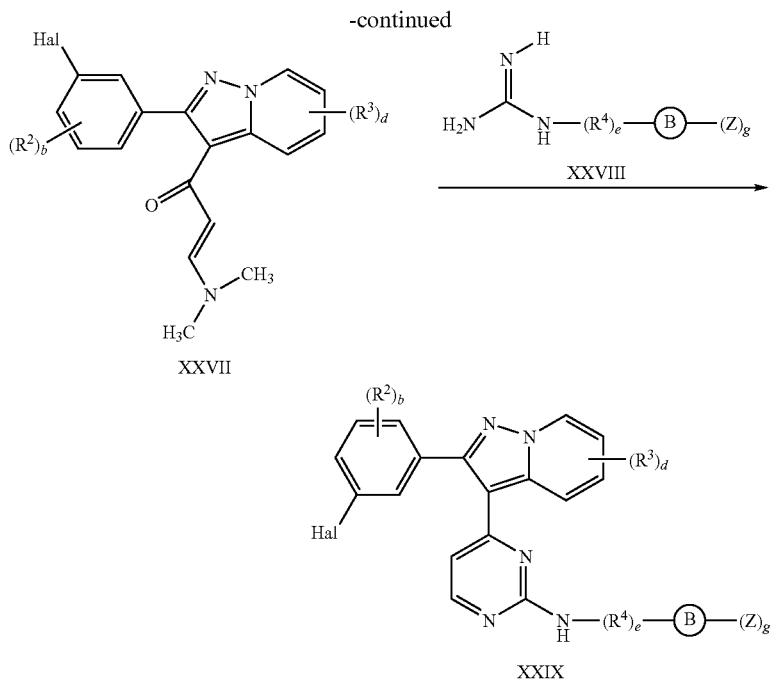

wherein all variables are as defined above.

The conversion of the compound of formula (XXVI) to the vinylogous amide of formula (XXVII) may be accomplished by heating the compound of formula (XXVI) with a reagent such as dimethylformamide dimethyl acetal at a temperature of around 100° C. Alternative reagents for effecting this transformation include, but are not limited to, dimethylformamide di-tert-butyl acetal.

The reaction of the vinylogous amide of formula (XXVII) with the guanidine of formula (XXVIII) is typically carried out under heating in a solvent such as dioxane in the presence of a base such as triethylamine and potassium carbonate. A preferred method for heating the reaction is irradiating this mixture in a microwave apparatus at a temperature of at least 150° C.

The compound of formula (XXVI) may be prepared by acetylation of a compound of formula (XXV).

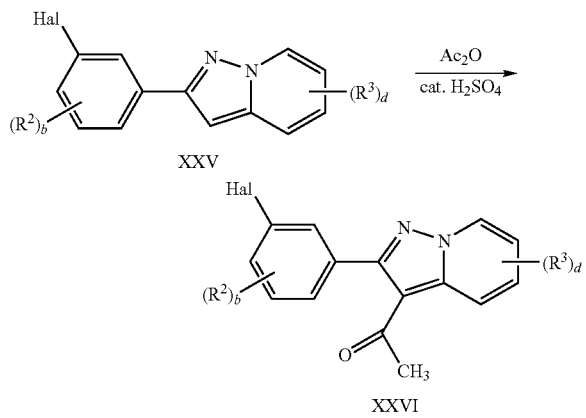

wherein all variables are as defined above.

The reaction may be carried out by reacting a compound of formula (XXV) with a suitable acetylating reagent in the presence of an acid catalyst under heating. Preferably, the reaction is heated to a temperature of about 100° C. Examples of suitable acetylating reagents include, but are not limited to, acetic anhydride. An example of a suitable acid catalyst is sulfuric acid.

A compound of formula (XXV) may be obtained by heating a compound of formula (XXIV).

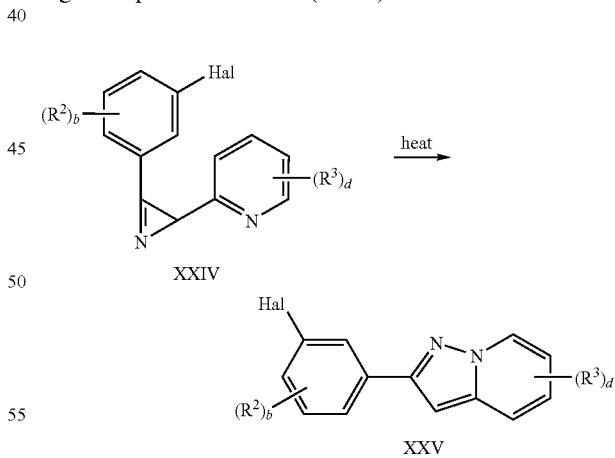

Typically, the reaction is carried out in a solvent such as 1,2-dichloroethane at a temperature of at least 150° C. A useful method of heating a compound of formula (XXIV) to effect this conversion is to use a microwave apparatus.

A compound of formula (XXIV) may be prepared by treatment of a compound of formula (XXIII) with an suitable agent for converting the hydroxylamine moiety into a leaving group in the presence of a base.

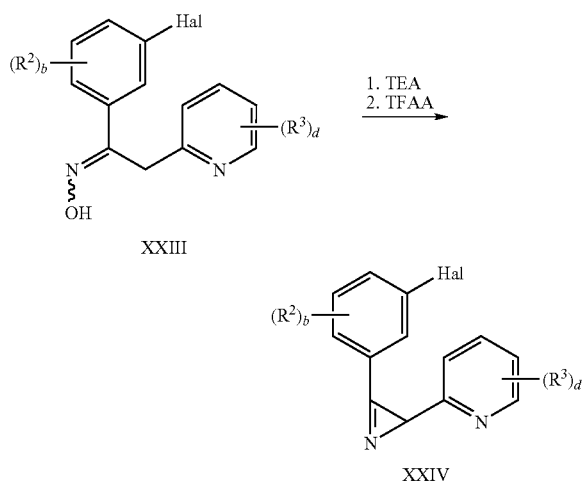

wherein all variables are as defined above.

Suitable agents to affect such a conversion include trifluoroacetic anhydride with a base such as triethylamine in a solvent such as DCM.

A compound of formula (XXIII) may be prepared by reacting a compound of formula (XXII) with hydroxylamine.

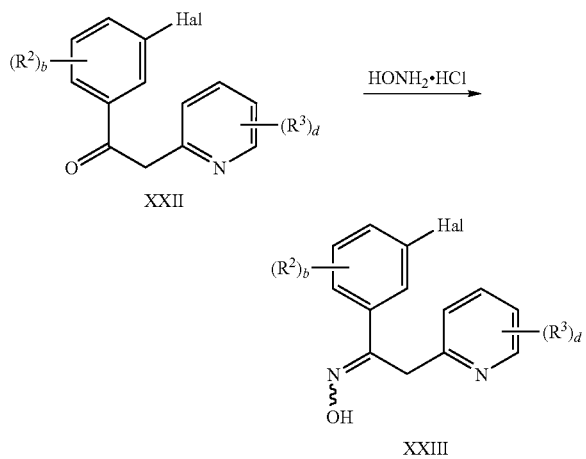

wherein all variables are as defined above.

The reaction may be carried out in a solvent, such as MeOH in the presence of a base, such as sodium hydroxide, and particularly 10% aqueous sodium hydroxide.

The compound of formula (XXII) may be prepared by condensing a compound of formula (XX) with a pyridine compound of formula (XXI).

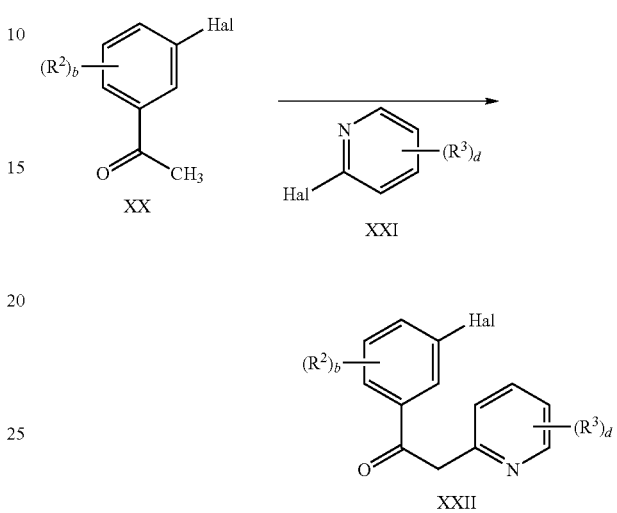

wherein all variables are as defined above.

Suitable conditions for reacting a compound of formula (XX) with a compound of formula (XXI) include, but are not limited to treatment of a compound of formula (XX) with a base such as sodium hydride in a solvent such as tetrahydrofuran and treating this mixture with a compound of formula (XXI). Hal is preferably Br or I in a compound of formula (XX). In a compound of formula (XXI), Hal is preferably Cl.

In a further embodiment of the invention, a compound of formula (I) wherein c is 1 and $R^2$ is F (i.e., a compound of formula (I-E)) may be prepared according to the method shown in Scheme 3a, below. According to this method a compound of formula (XXVI) may be converted into a fluoro derivative of formula (XXXII) via a two-step protocol. The fluoro derivative of formula (XXXII) may be converted to a compound of formula (I-E) using procedures analogous to those described above in Scheme 3.

Scheme 3a

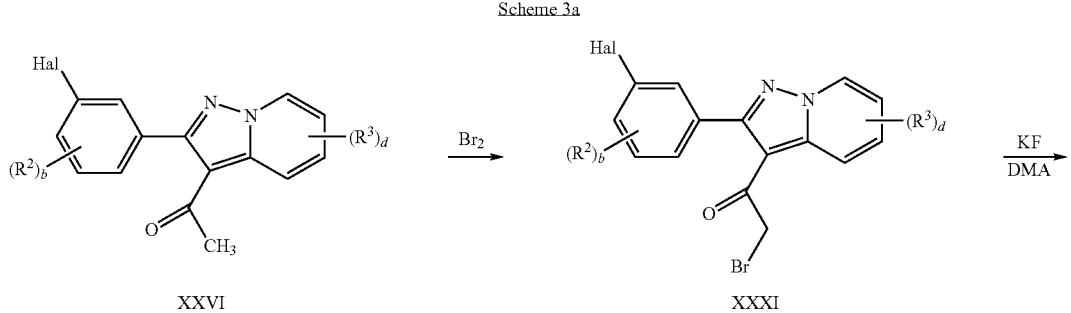

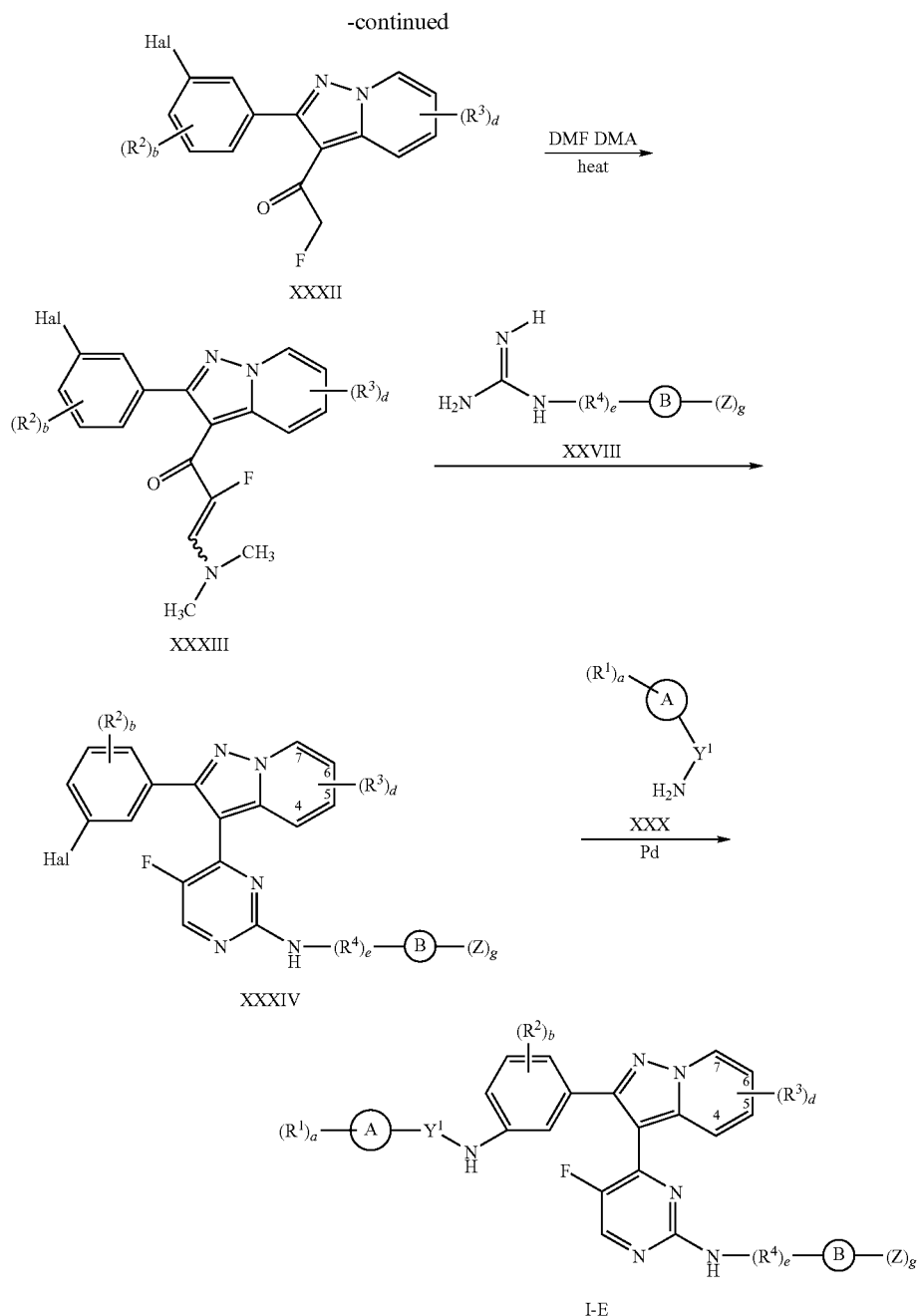

wherein each Hal is the same or different halogen; and all other variables are as defined above.

Generally, the process for preparing the compounds of formula (I) (all formulas and all variables having been defined above) comprises the steps of:

a) brominating the compound of formula (XXVI) to prepare a compound of formula (XXXI);

b) fluorinating the compound of formula (XXXI) to prepare a compound of formula (XXXII);

c) reacting the compound of formula (XXXII) with dimethyl formamide di-tert-butylacetal to prepare the compound of formula (XXXIII);

d) reacting with a compound of formula (XXXIII) with a compound of formula (XXVIII) with heating to prepare a compound of formula (XXXIV);

e) reacting the compound of formula (XXXIV) with a compound of formula (XXX) to prepare a compound of formula (I-E);

f) optionally converting the compound of formula (I-E) to a pharmaceutically acceptable salt or solvate thereof; and g) optionally converting the compound of formula (I-E) or a pharmaceutically acceptable salt or solvate thereof to a different compound of formula (I) or a pharmaceutically acceptable salt or solvate thereof.

As will be apparent to those skilled in the art, the order of the foregoing steps is not critical to the process of the present invention, and the process may be carried out using any suitable order of steps.

More specifically, a compound of formula (I-E) may be prepared by reacting the compound of formula (XXXIV) with a compound of formula (XXX) in a manner analogous to the reaction of the compound of formula (XXIX) with a compound of formula (XXX) in Scheme 3 above.

The compound of formula (XXXIV) may be prepared by reacting with a compound of formula (XXXIII) with a compound of formula (XXVIII) with heating in a manner analogous to the reaction of the vinylogous compound of formula (XXVII) with the compound of formula (XXVIII) in Scheme 3 above.

A compound of formula (XXXIII) may be prepared by reacting the compound of formula (XXXII) with dimethyl formamide di-tert-butylacetal to prepare the compound of formula (XXXIII) in a manner analogous to the reaction of the vinylogous compound of formula (XXVII) to prepare the compound of formula (XXIX) in Scheme 3 above.

The compound of formula (XXXII) may be prepared by fluorinating the compound of formula (XXXI) to prepare a compound of formula (XXXII).

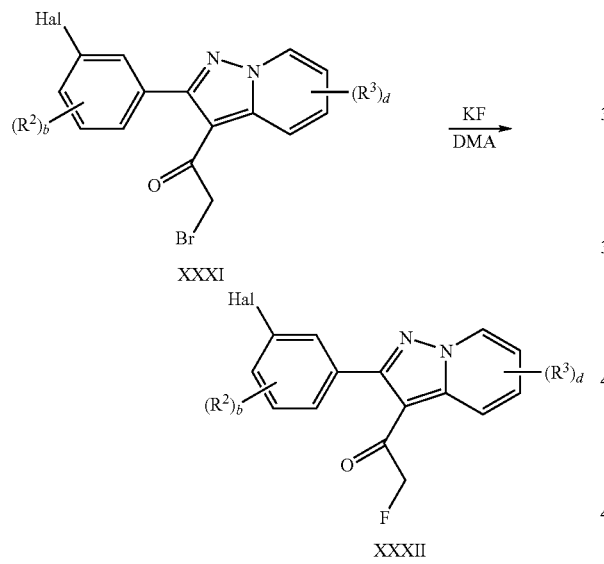

wherein all variables are as defined above.

This reaction may be carried out by treating the bromide compound of formula (XXXI) with a fluorinating reagent such as potassium fluoride in a solvent such as dimethyl acetamide. An example of an appropriate fluorinating reagent includes, but is not limited to potassium fluoride.

The compound of formula (XXXI) may be prepared by brominating the compound of formula (XXVI) with an appropriate brominating agent in a suitable solvent.

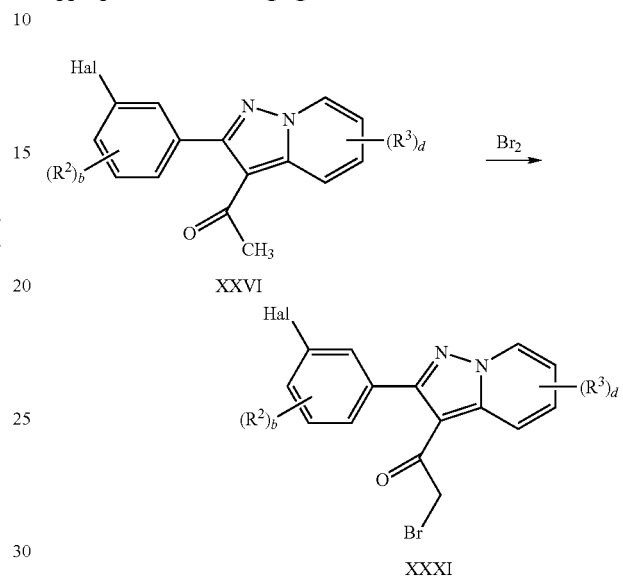

wherein all variables are as defined above.

An example of a brominating agent includes bromine. An example of a suitable solvent is glacial acetic acid.

It will be appreciated by those skilled in the art that choice of the reaction sequence employed to prepare a particular compound of formula (I) may depend upon the specific compound of formula (I) that is desired as well as the availability of starting materials.

As will be apparent to those skilled in the art, a compound of formula (I) may be converted to another compound of formula (I) using techniques well known in the art. For example, one method of converting a compound of formula (I) wherein $Y^1$ is —C(O)— (i.e., a compound of formula (I-A)) to another compound of formula (I) comprises treating a compound of formula (I-A) with Lawesson's reagent.

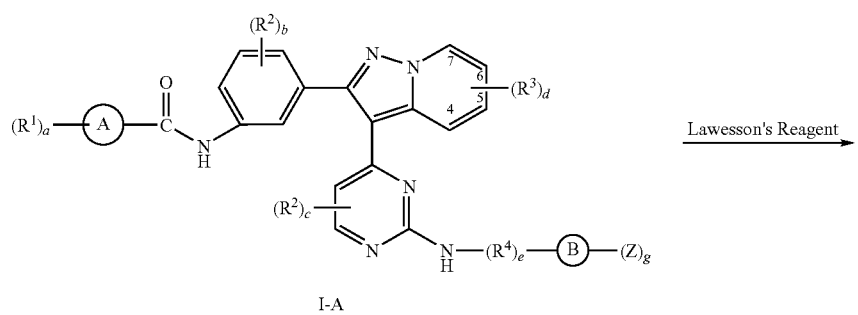

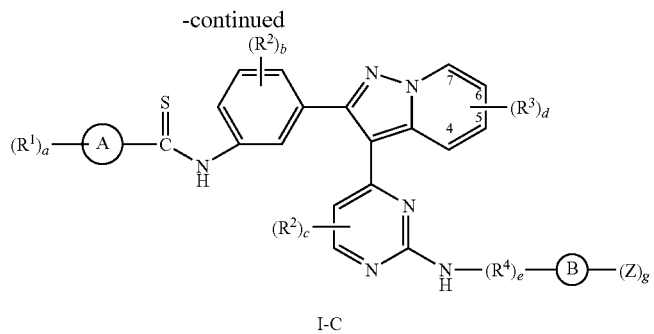

I-C

Suitable conditions for this reaction will be apparent to those skilled in the art of organic synthesis.

A compound of formula (I) wherein the moiety Ring B-(Z)$_g$ is a tetrahydroisoquinoline group wherein the tetrahydroisoquinoline amine is a secondary amine may be converted into another compound of formula (I) wherein the amine is a tertiary amine bearing an alkyl group. This transformation may be accomplished through a reductive amination procedure. Procedures for reductive amination are well known in the literature and include, for example, in the case where the alkyl group is methyl, stirring the secondary amine bearing compound in a suitable solvent in the presence of aqueous formaldehyde and sodium triacetoxyborohydride and catalytic acid. Examples of suitable solvents include DCM or N,N-dimethylformamide. An example of a suitable acid is acetic acid.

Based upon this disclosure and the examples contained herein one skilled in the art can readily convert a compound of formula (I) or a pharmaceutically acceptable salt or solvate thereof into a different compound of formula (I), or a pharmaceutically acceptable salt or solvate thereof.

The present invention also provides radiolabeled compounds of formula (I) and biotinylated compounds of formula (I) and solid-support-bound versions thereof. Radiolabeled compounds of formula (I) and biotinylated compounds of formula (I) can be prepared using conventional techniques. For example, radiolabeled compounds of formula (I) can be prepared by reacting the compound of formula (I) with tritium gas in the presence of an appropriate catalyst to produce a compound of formula (I) having a radiolabel bound thereto (i.e., a radiolabled compound of formula (I)).

In one embodiment, the compounds of formula (I) are tritiated.

The radiolabeled compounds of formula (I) and biotinylated compounds of formula (I) are useful in assays for the identification of compounds which inhibit at least one ErbB family kinase, for the identification of compounds for the treatment of a condition mediated by at least one ErbB family kinase, for the treatment of susceptible neoplasms. Accordingly, the present invention provides an assay method for identifying such compounds, which method comprises the step of specifically binding the radiolabeled compound of formula (I) or the biotinylated compound of formula (I) to the target protein or cellular homogenates. More specifically, suitable assay methods will include competition binding assays. The radiolabeled compounds of formula (I) and biotinylated compounds of formula (I) and solid-support-bound versions thereof, can be employed in assays according to the methods conventional in the art.

The following examples are intended for illustration only and are not intended to limit the scope of the invention in any way, the invention being defined by the claims which follow.

EXAMPLES

As used herein, the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

g (grams); mg (milligrams);
L (liters); mL (milliliters);
μL (microliters); psi (pounds per square inch);
M (molar); mM (millimolar);
i.v. (intravenous); Hz (Hertz);
MHz (megahertz); mol (moles);
mmol (millimoles); rt (room temperature);
min (minutes); h (h);
mp (melting point); TLC (thin layer chromatography);
T$_r$ (retention time); RP (reverse phase);
MeOH (methanol); i-PrOH (isopropanol);
TEA (triethylamine); TFA (trifluoroacetic acid);
TFAA (trifluoroacetic anhydride); THF (tetrahydrofuran);
DMSO (dimethylsulfoxide); AcOEt (EtOAc);
DME (1,2-dimethoxyethane); DCM (CH$_2$Cl$_2$; dichloromethane);
DCE (dichloroethane); DMF (N,N-dimethylformamide);
DMPU (N,N'-dimethylpropyleneurea); CDI (1,1-carbonyldiimidazole);
IBCF (isobutyl CHCl3ate); HOAc (acetic acid);
HOSu (N-hydroxysuccinimide); HOBT (1-hydroxybenzotriazole);
mCPBA (meta-chloroperbenzoic acid); KOH (potassium hydroxide);
Na$_2$CO$_3$ (sodium carbonate); NaHCO$_3$ (sodium bicarbonate);
LiOH.H$_2$O (lithium hydroxide monohydrate); K$_2$CO$_3$ (potassium carbonate);
CHCl$_3$ (chloroform); Na$_2$SO$_4$ (sodium sulfate);
BOC (tert-butyloxycarbonyl); Ac (acetyl);
DCC (dicyclohexylcarbodiimide); CBZ (benzyloxycarbonyl);
FMOC (9-fluorenylmethoxycarbonyl); atm (atmosphere);

TMSE (2-(trimethylsilyl)ethyl); TMS (trimethylsilyl);
TIPS (triisopropylsilyl); TBS (t-butyldimethylsilyl);
DMAP (4-dimethylaminopyridine); BSA (bovine serum albumin)
ATP (adenosine triphosphate); HRP (horseradish peroxidase);
Ac$_2$O (acetic anhydride); DMA (dimethyl acetyl);
Pd$_2$ dba$_3$ (Tris(dibenzylidineacetone)dipalladium (0));
NaCNBH$_3$ (Sodium cyanoborohydride); TMSCI (Chlorotrimethylsilane);
DMEM (Dulbecco's modified Eagle medium);
HPLC (high pressure liquid chromatography);
BOP (bis(2-oxo-3-oxazolidinyl)phosphinic chloride);
TBAF (tetra-n-butylammonium fluoride);
HBTU (O-Benzotriazole-1-yl-N,N,N',N'-tetramethyluronium hexafluorophosphate);
HEPES (4-(2-hydroxyethyl)-1-piperazine ethane sulfonic acid);
DPPA (diphenylphosphoryl azide); fHNO$_3$ (fumed HNO$_3$);
EDC (ethylcarbodjimide hydrochloride); and
EDTA (ethylenediaminetetraacetic acid).

All references to ether are to diethyl ether; brine refers to a saturated aqueous solution of NaCl. Unless otherwise indicated, all temperatures are expressed in ° C. (degrees Centigrade). All reactions are conducted under an inert atmosphere at rt unless otherwise noted.

$^1$H NMR spectra were recorded on a Varian VXR-300, a Varian Unity-300, a Varian Unity-400 instrument, or a General Electric QE-300. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), m (multiplet), br (broad).

Low-resolution mass spectra (MS) were recorded on a JOEL JMS-AX505HA, JOEL SX-102, or a SCIEX-APIiii spectrometer; high resolution MS were obtained using a JOEL SX-102A spectrometer. All mass spectra were taken under electrospray ionization (ESI), chemical ionization (CI), electron impact (EI) or by fast atom bombardment (FAB) methods. Infrared (IR) spectra were obtained on a Nicolet 510 FT-IR spectrometer using a 1-mm NaCl cell. All reactions were monitored by thin-layer chromatography on 0.25 mm E. Merck silica gel plates (60F-254), visualized with UV light, 5% ethanolic phosphomolybdic acid or p-anisaldehyde solution or mass spectrometry (electrospray or AP). Flash column chromatography was performed on silica gel (230-400 mesh, Merck) or using automated silica gel chromatography (Isco, Inc. Sq 16× or 100 sg Combiflash).

Reported HPLC retention times (RT) were obtained on a Waters 2795 instrument attached to a Waters 996 diode array detector reading 210-500 nm. The column used was a Synergi Max-RP (50×2 mm) model #00B-4337-B0, Solvent gradient was 15% MeOH:water to 100% MeOH (0.1% formic acid) over 6 min. Flow rate was 0.8 mL/min. Injection volume was 3 microliters.

Example 1

1-(3-{3-[2-(2,3-Dihydro-benzo[1,4]dioxin-6-ylamino)-pyrimidin-4-yl]-pyrazolo[1,5-]pyridin-2-yl}-phenyl)-3-phenyl-urea

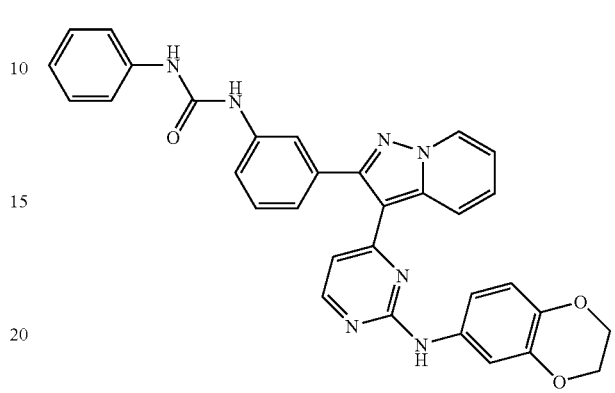

Step A: Trimethyl[(3-nitrophenyl)ethynyl]silane

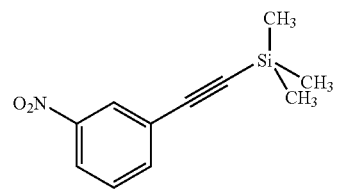

3-Nitroiodebenzene (50 g, 0.201 mol) and diisopropylamine (56.3 mL, 0.402 mol) are dissolved in dry-THF (1000 mL) and argon gas is bubbled through the solution for 20 min. Copper (I) iodide (3.83 g, 0.02 mol) and bis(triphenylphosphine)palladium dichloride (7.05 g, 0.01 mol) are added and then trimethylsilylacetylene (31.2 mL, 0.221 mol) is added dropwise over about 30 min with the temperature being maintained at about 25° C. Following complete addition, the mixture is stirred at rt overnight. The mixture is filtered and washed with THF. The filtrate is concentrated under reduced pressure. The residue is purified via silica-gel chromatography with Hexane/EtOAc-20/1 to give product (43.22 g) as a pale-brown solid.

Step B: 1-Ethynyl-3-nitrobenzene

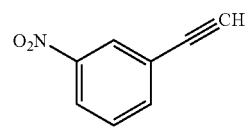

A solution of 1-(3-nitrophenyl)-2-trimethylsilylacetylene (43 g, 0.197 mol) in diethylether (800 mL) is cooled to 0° C. under argon atmosphere. To this solution is added, dropwise over 30 min, a solution of TBAF (1M in THF, 217 mL, 0.217 mol) maintaining temperature below 10° C. The reaction mixture is stirred for 30 min at 0° C. The reaction mixture is Step C: 4-Iodo-2-(methylthio)pyrimidine

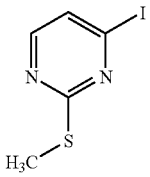

4-Chloro-2-methylthiopyrimidine (40 g, 249 mmol) is added to Hydroiodic acid (57% in water, 200 mL). The suspension is vigorously stirred in the absence of light for 72 h at rt. A bright yellow solid formed which is collected by filtration. The solid is added to saturated aqueous NaHCO$_3$ (500 mL) and stirred for 2 min. CHCl$_3$ (600 mL) is added and the solid dissolved. The aqueous layer is extracted 2 times with CHCl$_3$ (350, then 300 mL) and the organic extracts combined, washed with water (100 mL), dried over MgSO$_4$ and filtered. The organic solvent is removed in vacuo to give colorless oil. Addition of n-hexane and removal of solvent again produced the title compound as a white solid (57.9 g, 230 mmol, 92%).

Step D: 2-(Methylthio)-4-[(3-nitrophenyl)ethynyl]pyrimidine

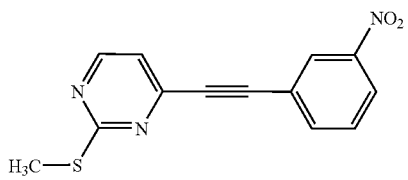

4-Iodo-2-(methylthio)pyrimidine (39.7 g, 0.157 mol) and diisopropylamine (44.2 mL, 0.315 mol) are dissolved in dry THF (720 mL) and argon gas is bubbled through the solution for 20 min. Copper(I) iodide (2.99 g, 14.3 mmol) and bis(triphenylphosphine)palladium dichloride (5.51 g, 7.85 mmol) are added and then 1-ethynyl-3-nitrobenzene (25.4 g, 0.173 mol) in dry THF (100 mL) is added dropwise over about 30 min with the temperature being maintained at about 25° C. Following complete addition, the mixture is stirred at rt for overnight. The mixture is filtered and washed with THF. The filtrate is concentrated under reduced pressure. The residue is washed with EtOAc/MeOH to give pale-yellow solid (42 g).

Step E: 3-[2-(Methylthio)-4-pyrimidinyl]-2-(3-nitrophenyl)pyrazolo[1,5-a]pyridine

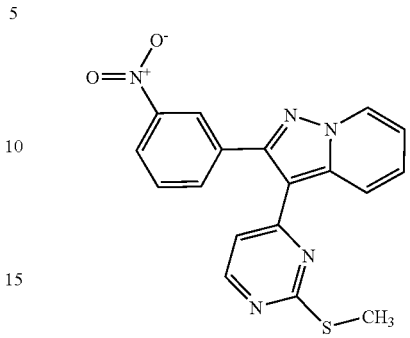

To a 0° C. solution of 2-(methylthio)-4-[(3-nitrophenyl)ethynyl]pyrimidine (4.0 g, 14.7 mmol) and N-aminopyridinium iodide (6.53 g, 29.4 mmol) in DCM (150 mL) is added KOH (2.06 g, 36.8 mmol) in H$_2$O (50 mL). The reaction is allowed to warm to rt and stirred for 16 h. The mixture is diluted with DCM and H$_2$O. The organic layer is separated and the aqueous layer is extracted with DCM. The combined organic layers are dried over MgSO$_4$, filtered and concentrated to give a dark solid. The residue is dissolved in DCM and MeOH is added until the product formed as a precipitate. The product is collected by filtration and dried to supply the title compound (2.02 g) as an off-white solid. $^1$H NMR (400 MHz, d$_6$-DMSO): δ 11.36 (s, 1H), 8.62 (d, 1H, J=9.2), 8.54 (d, 1H, J=5.6), 7.94 (s, 1H), 7.82 (d, 1H, J=8.8), 7.54 (t, 1H, J=8.0), 7.46 (d, 1H, J=9.2), 7.16 (d, 1H, J=5.2), 2.59 (s, 3H).

Step F: 3-[2-(Methylsulfinyl)-4-pyrimidinyl]-2-(3-nitrophenyl)pyrazolo[1,5-a]pyridine

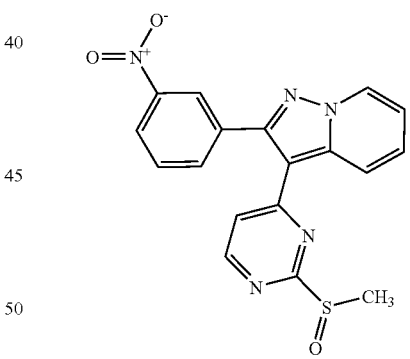

To a solution of 3-[2-(methylthio)-4-pyrimidinyl]-2-(3-nitrophenyl)pyrazolo[1,5-a]pyridine (0.82 g, 2.26 mmol) in DCM (22 mL) is added a solution of 50% mCPBA (818 mg, 2.37 mmol) in DCM (6 mL) through an addition funnel. The reaction is stirred for 10 min and saturated aqueous NaHCO$_3$ and the layers are separated. The aqueous layer is extracted with DCM, and the combined organic layers are dried over MgSO$_4$, filtered and concentrated. The residue is purified by silica gel chromatography (50% EtOAC/hexanes eluant) to provide the product (567 mg) as a yellow solid. $^1$H NMR (400 MHz, d$_6$-DMSO) δ 8.93 (d, 1H, J=6.8), 8.68 (d, 1H, J=5.6), 8.57 (d, 1H, J=8.8), 8.44 (s, 1H, 8.37-8.35 (m, 1H, 8.08 (d, 1H, J=7.6), 7.78 (t, 1H, J=8.0), 7.61-7.65 (m, 1H), 7.21-7.26 (m, 2H), 2.84 (s, 3H).

Step G: N-(2,3-Dihydro-1,4-benzodioxin-6-yl)-4-[2-(3-nitrophenyl)pyrazolo[1,5-a]pyridin-3-yl]-2-pyrimidinamine

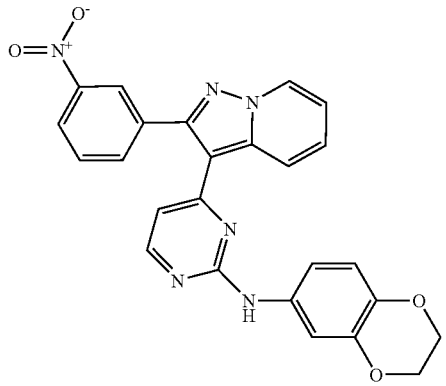

To a solution of 3-[2-(methylsulfinyl)-4-pyrimidinyl]-2-(3-nitrophenyl)pyrazolo[1,5-a]pyridine (1.32 g, 3.49 mmol) in ethanol (4.0 mL) is added 1,4-benzodioxan-6-amine (0.56 mL, 4.54 mmol) and conc. HCl (3 drops). The dark mixture is heated in a microwave apparatus at 160° C. for 20 min. The mixture is monitored, and heated for an additional 10 min. The mixture is diluted with DCM and concentrated to a brown foam. The crude material is purified by silica gel chromatography (30-50% EtOAc/hexanes) to give the desired product (1.09 g). ¹H NMR (400 MHz, d₆-DMSO) δ 9.36 (s, 1H), 8.88 (d, 1H, J=6.8), 8.45 (s, 1H), 8.28-8.31 (m, 3H), 8.01-8.03 (m, 1H), 7.72 (t, 1H, J=8.0), 7.47-7.51 (m, 1H), 7.13-7.18 (m, 2H), 6.97-6.95 (m, 1H), 6.63-6.65 (m, 2H), 4.14 (m, 1H), 7.13-7.18 (m, 2H), 6.95-6.97 (m, 1H), 6.63-6.65 (m, 2H), 4.14 (s, 4H).

Step H: 4-[2-(3-Aminophenyl)pyrazolo[1,5-a]pyridin-3-yl]-N-(2,3-dihydro-1,4-benzodioxin-6-yl)-2-pyrimidinamine

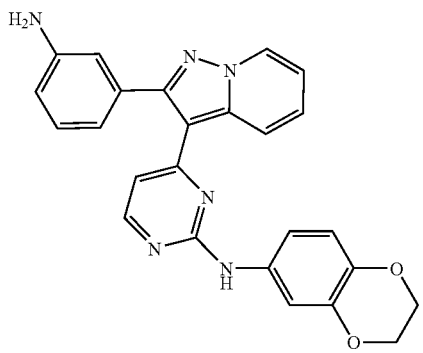

To a solution of N-(2,3-dihydro-1,4-benzodioxin-6-yl)-4-[2-(3-nitrophenyl)pyrazolo[1,5-a]pyridin-3-yl]-2-pyrimidinamine (1.09 g, 2.3 mmol) in ethanol (2 mL) was added sodium sulfide nonhydrate (2.76 g, 11.5 mmol) in H₂O (2 mL). The mixture was heated at 80° C. for 16 h, allowed to cool to rt and filtered. The filtrate was concentrated to afford the product (1 g) as a yellow solid. ¹H NMR (400 MHz, d₆-DMSO) δ9.29 (s, 1H), 8.76 (d, 1H, J=7.2), 8.51 (d, 1H, J=8.8), 8.15 (d, 1H, J=5.2), 7.39-7.43 (m, 1H), 7.35 (m, 1H), 7.04-7.12 (m, 3H), 6.76-6.72 (m, 2H), 6.65-6.62 (m, 2H), 6.43 (d, 1H, J=5.2), 5.21 (s, 2H), 4.16-4.20 (m, 4H).

Step I: 1-(3-{3-[2-(2,3-Dihydro-benzo[1,4]dioxin-6-ylamino)-pyrimidin-4-yl]-pyrazolo[1,5-]pyridin-2-yl}-phenyl)-3-phenyl-urea (title compound)

To a solution of {4-[2-(3-amino-phenyl)-pyrazolo[1,5-a]pyridin-3-yl]-pyrimidin-2-yl}-(2,3-dihydro-benzo[1,4]dioxin-6-yl)-amine (100 mg, 0.23 mmol) in 5 mL THF was added phenylisocyanate (27 μL, 0.25 mmol), and the reaction is stirred for 16 h. The reaction is concentrated, triturated with diethyl ether, filtered and dried to give the title compound as a pale yellow solid (103 mg, 80%). ¹H NMR (400 MHz, d₆-DMSO) δ 9.32 (s, 1H), 8.95 (s, 1H), 8.81-8.77 (m, 2H), 8.49 (d, J=8.4 Hz, 1H), 8.18 (d, J=5.2 Hz, 1H), 7.72 (s, 1H), 7.55 (d, J=8.0 Hz, 1H), 7.46-7.38 (m, 3H), 7.36-7.34 (m, 2H), 7.25-7.21 (m, 2H), 7.15-7.08 (m, 3H), 6.94-6.90 (m, 1H), 6.71 (d, J=8.8 Hz, 1H), 6.42 (d, J=4.8 Hz, 1H), 4.19-4.16 (m, 4H) ppm. HRMS calculated C₃₂H₂₅N₇O₃ [M+H]⁺ 556.2097 found 556.2096.

Example 2

N-(2-Chlorophenyl)-N-(3-{3-[2-(2,3-dihydro-1,4-benzodioxin-6-ylamino)-4-pyrimidinyl]pyrazolo[1,5-a]pyridin-2-yl}phenyl)urea

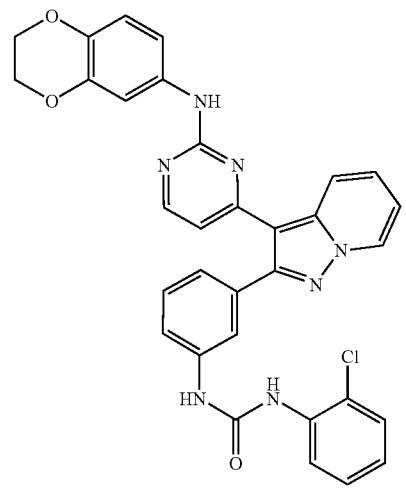

The same procedure as Example 1 was used with {4-[2-(3-amino-phenyl)-pyrazolo[1,5-a]pyridin-3-yl]-pyrimidin-2-yl}-(2,3-dihydro-benzo[1,4]dioxin-6-yl)-amine and 2-chlorophenylisocyanate to give the title compound. ¹H NMR (400 MHz, d₆-DMSO) δ 9.32 (s, 1H), 8.95 (s, 1H), 8.81-8.77 (m, 2H), 8.49 (d, J=8.4 Hz, 1H), 8.18 (d, J=5.2 Hz, 1H), 7.72 (s, 1H), 7.55 (d, J=8.0 Hz, 1H), 7.46-7.38 (m, 3H), 7.36-7.34 (m, 2H), 7.25-7.21 (m, 2H), 7.15-7.08 (m, 3H), 6.94-6.90 (m, 1H), 6.71 (d, J=8.8 Hz, 1H), 6.42 (d, J=4.8 Hz, 1H), 4.19-4.16 (m, 4H). MS (ESI) m/z=556 [M+H]+

Example 3

1-Methyl-1H-pyrrole-2-carboxylic acid (3-{3-[2-(2,3-dihydro-benzo[1,4]dioxin-6-ylamino)-pyrimidin-4-yl]-pyrazolo[1,5-a]pyridin-2-yl}-phenyl)-amide

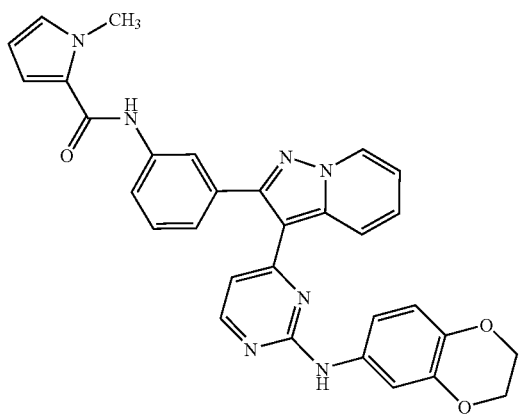

To a solution of {4-[2-(3-amino-phenyl)-pyrazolo[1,5-a]pyridin-3-yl]-pyrimidin-2-yl}-(2,3-dihydro-benzo[1,4]dioxin-6-yl)-amine (105 mg, 0.24 mmol) in 5 mL THF was added N-methylpyrrole carbonyl chloride (37 mg, 0.26 mmol). When TLC showed the reaction to be complete, the solution was diluted with DCM and washed with a solution of saturated NaHCO$_3$ and with brine. The organic phase was dried over MgSO$_4$ and concentrated. The residue was triturated with diethyl ether to give the title compound as a yellow solid (119 mg, 92%). $^1$H NMR (400 MHz, d$_6$-DMSO) δ 9.90 (s, 1H), 9.80 (s, 1H), 8.87 (d, J=6.8 Hz, 1H), 8.50 (s, 1H), 8.14 (d, J=6.0 Hz, 1H), 8.05 (s, 1H), 7.88 (d, J=8.0 Hz, 1H), 7.51 (m, 1H), 7.43 (m, 1H), 7.27-7.22 (m, 2H), 7.17 (t, J=6.8 Hz, 1H), 7.05-7.04 (m, 2H), 7.00 (s, 1H), 6.81 (d, J=8.4 Hz, 1H), 6.47 (d, J=6.0 Hz, 1H), 6.08-6.07 (m, 1H), 4.22 (m, 4H), 3.85 (s, 3H) ppm. HRMS calculated C$_{31}$H$_{25}$N$_7$O$_3$ [M+H]$^+$ 544.2097 found 544.2101.

Example 4

N-(3-{3-[2-(2,3-Dihydro-benzo[1,4]dioxin-6-ylamino)-pyrimidin-4-yl]-pyrazolo[1,5-]pyridin-2-yl}-phenyl)-benzamide

{4-[2-(3-Amino-phenyl)-pyrazolo[1,5-a]pyridin-3-yl]-pyrimidin-2-yl}-(2,3-dihydro-benzo[1,4]dioxin-6-yl)-amine (150 mg, 0.34 mmol) was acylated with benzoyl chloride (43 μL, 0.37 mmol) in a manner analogous to Example 3 above, to give the title compound as a yellow solid. HRMS calculated C$_{32}$H$_{24}$N$_6$O$_3$ [M+H]$^+$ 541.1988 found 541.1995.

Example 5

N-(3-{3-[2-(2,3-Dihydro-benzo[1,4]dioxin-6-ylamino)-pyrimidin-4-yl]-pyrazolo[1,5]-pyridin-2-yl}-phenyl)-3-methoxy-benzamide

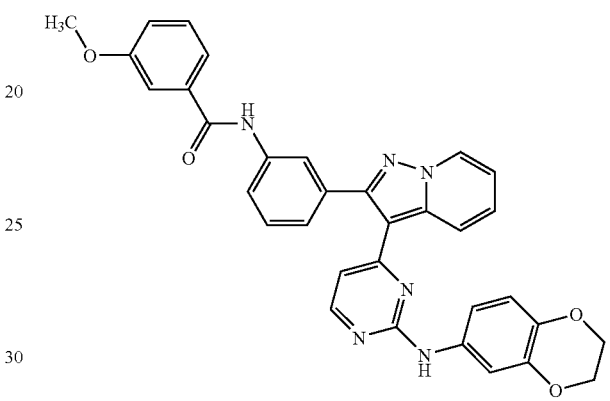

{4-[2-(3-Amino-phenyl)-pyrazolo[1,5-a]pyridin-3-yl]-pyrimidin-2-yl}-(2,3-dihydro-benzo[1,4]dioxin-6-yl)-amine (150 mg, 0.34 mmol) was acylated with m-anisoyl chloride (52 μL, 0.37 mmol) in a manner analogous to Example 3 above, to give the title compound as a yellow solid. HRMS calculated C$_{33}$H$_{26}$N$_6$O$_4$ [M+H]$^+$ 571.2094 found 571.2101.

Example 6

2-Chloro-N-(3-{3-[2-(2,3-dihydro-benzo[1,4]dioxin-6-ylamino)-pyrimidin-4-yl]-pyrazolo[1,5-a]pyridin-2-yl}-phenyl)-benzamide

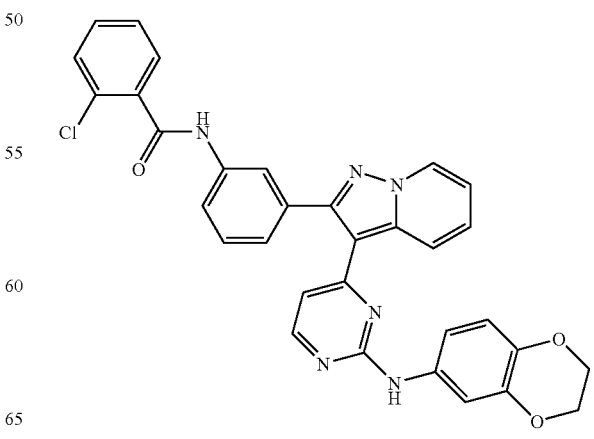

{4-[2-(3-Amino-phenyl)-pyrazolo[1,5-a]pyridin-3-yl]-pyrimidin-2-yl}-(2,3-dihydro-benzo[1,4]dioxin-6-yl)-amine (150 mg, 0.34 mmol) was acylated with 2-chlorobenzoyl chloride (47 μL, 0.37 mmol) in a manner analogous to Example 3 above, to give the title compound as a yellow solid. HRMS calculated $C_{32}H_{23}ClN_6O_3$ [M+H]$^+$ 575.1598 found 575.1600.

Example 7

N-(3-{3-[2-(2,3-Dihydro-benzo[1,4]dioxin-6-ylamino)-pyrimidin-4-yl]-pyrazolo[1,5-a]pyridin-2-yl}-phenyl)-thiobenzamide

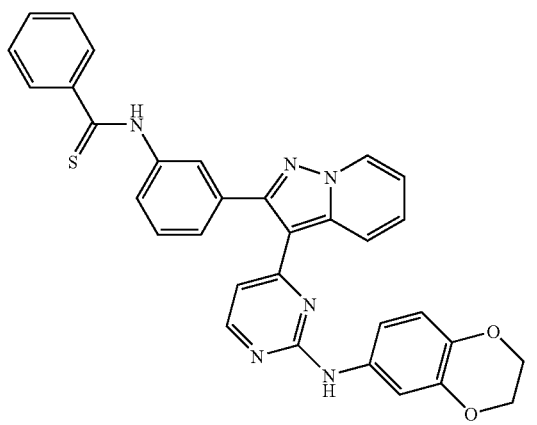

A mixture of N-(3-{3-[2-(2,3-dihydro-benzo[1,4]dioxin-6-ylamino)-pyrimidin-4-yl]-pyrazolo[1,5-a]pyridin-2-yl}-phenyl)-benzamide (43 mg, 0.08 mmol) and excess of Lawesson's Reagent in 1,4-dioxane (1 mL) was heated at 100° C. in a sealed tube. When LC/MS showed the starting material to be consumed, the mixture was cooled to ambient temperature and diluted with DCM. The organic phase was washed with water, dried over MgSO$_4$ and concentrated. The crude material was purified through silica gel to give the title compound as a yellow solid. $^1$H NMR (400 MHz, d$_6$-DMSO): δ 11.85 (s, 1H), 9.34 (s, 1H), 8.82 (d, J=6.8 Hz, 1H), 8.49 (d, J=8.4 Hz, 1H), 8.20 (d, J=5.6 Hz, 1H), 8.14 (s, 1H), 7.97 (d, J=8.0 Hz, 1H), 7.80 (d, J=7.2 Hz, 1H), 7.57-7.42 (m, 6H), 7.35 (m, 1H), 7.13-7.10 (m, 2H), 6.73 (d, J=8.8 Hz, 1H), 6.49 (d, J=5.2 Hz, 1H), 4.19 (m, 4H). MS (ESI) m/z=557 [M+H]$^+$.

Example 8

2-Chloro-N-(3-{3-[2-(2,3-dihydro-benzo[1,4]dioxin-6-ylamino)-pyrimidin-4-yl]-pyrazolo[1,5-a]pyridin-2-yl}-phenyl)-thiobenzamide

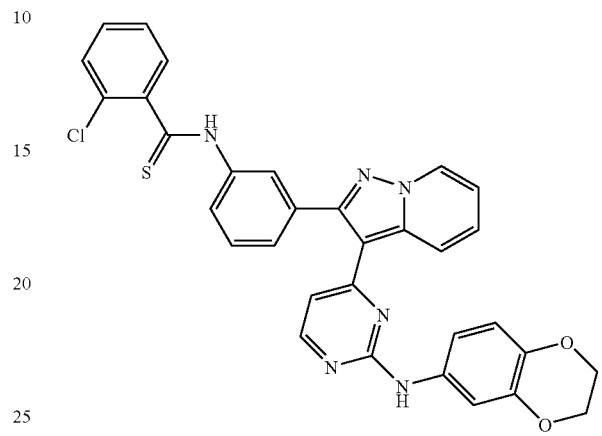

2-Chloro-N-(3-{3-[2-(2,3-dihydro-benzo[1,4]dioxin-6-ylamino)-pyrimidin-4-yl]-pyrazolo[1,5-a]pyridin-2-yl}-phenyl)-benzamide (56 mg, 0.10 mmol) was converted to the title compound according to the procedure of Example 7. MS (ESI) m/z=591 [M+H]$^+$.

Example 9

N-(3-{3-[2-(2,3-Dihydro-benzo[1,4-]dioxin-6-ylamino)-pyrimidin-4-yl]-pyrazolo[1,5-a]pyridin-2-yl}-phenyl)-3-methoxy-thiobenzamide

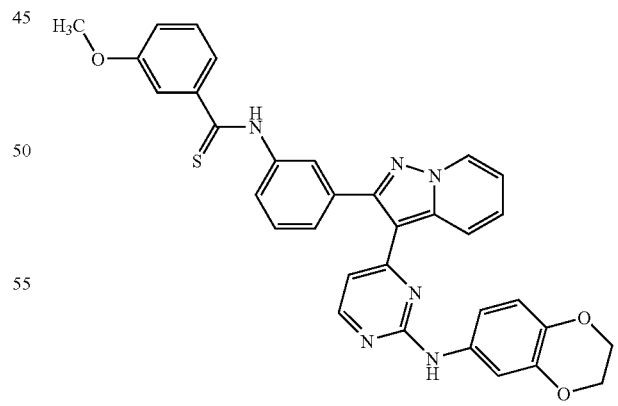

N-(3-{3-[2-(2,3-Dihydro-benzo[1,4]dioxin-6-ylamino)-pyrimidin-4-yl]-pyrazolo[1,5-]pyridin-2-yl}-phenyl)-3-methoxy-benzamide (98 mg, 0.17 mmol) was converted to the title compound according to the procedure of Example 7. HRMS calculated $C_{33}H_{26}ClN_6O_3S$ [M+H]$^+$ 587.1865 found 587.1880.

Example 10

1-Methyl-1H-pyrrole-2-carbothioic acid (3-{3-[2-(2,3-dihydro-benzo[1,4]dioxin-6-ylamino)-pyrimidin-4-yl]pyrazolo[1,5-a]pyridin-2-yl}-phenyl)-amide

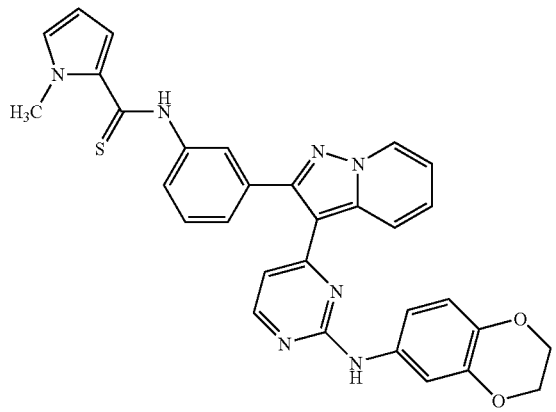

1-Methyl-1H-pyrrole-2-carboxylic acid (3-{3-[2-(2,3-dihydro-benzo[1,4]dioxin-6-ylamino)-pyrimidin-4-yl]-pyrazolo[1,5-a]pyridin-2-yl}-phenyl)-amide (86 mg, 0.16 mmol) was converted to the title compound according to the procedure of Example 7.

HRMS calculated $C_{31}H_{25}ClN_7O_2S$ $[M+H]^+$ 560.1869 found 560.1877.

Example 11

2-Chloro-5-fluoro-N-(3-{3-[2-(3-fluoro-phenylamino)-pyrimidin-4-yl]-pyrazolo[1,5-a]pyridin-2-yl}-phenyl)-benzamide

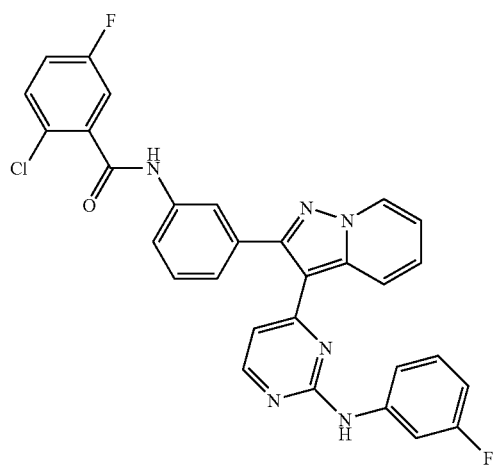

Step A:
N-(3-Ethynyl-phenyl)-2,2,2-trifluoro-acetamide

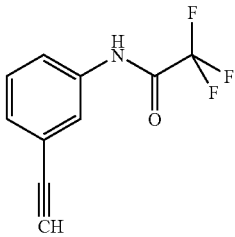

To a solution of 3-ethynyl aniline (10 g, 86 mmol) in DCM cooled to 0° C. was added triethylamine (17 mL, 128 mmol) and trifluoroacetic anhydride (14.3 mL, 102 mmol). When TLC showed the reaction to be complete, the solution was diluted with DCM and water. The layers were separated. The organic phase was washed with water and brine, dried over $MgSO_4$ and concentrated to give the title compound as an off-white solid which was used crude in the next reaction. $^1$H NMR (400 MHz, $d_6$-DMSO): δ 11.32 (s, 1H), 7.78 (d, J=1.6 Hz, 1H), 7.67 (d, J=8.0 Hz, 1H), 7.41 (t, J=8.0 Hz, 1H), 7.32 (m, 1H), 4.25 (s, 1H) ppm.

Step B: N-[3-(2-Chloro-pyrimidin-4-ylethynyl)-phenyl]-2,2,2-trifluoro-acetamide

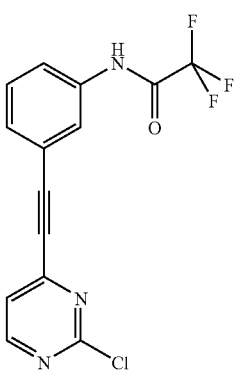

To a mixture of 2,4-dichloropyrimidine (14.5 g, 97.5 mmol), dichlorobis(triphenyl-phosphine)palladium(II) (1.3 g, 2.6 mmol), and copper(I) iodide (25 mg, 0.13 mmol) in degassed THF was added triethylamine (34 mL, 263 mmol), and the mixture was heated to 50° C. A solution of N-(3-ethynyl-phenyl)-2,2,2-trifluoro-acetamide (14 g, 65 mmol) in THF was added to the mixture over 45 min. After several h, the reaction was cooled to rt and diluted with DCM. The organic mixture was washed with water and brine, dried over $MgSO_4$ and concentrated. The crude material was purified through silica to give the title compound as an off-white solid. $^1$H NMR (400 MHz, $d_6$-DMSO): δ 11.43 (s, 1H), 8.83 (d, J=4.8 Hz, 1H), 8.00 (s, 1H), 7.80 (d, J=4.8 Hz, 1H), 7.76 (m, 1H), 7.54-7.52 (m, 2H).

Step C: N-{3-[3-(2-chloro-4-pyrimidinyl)pyrazolo[1,5-a]pyridin-2-yl]phenyl}-2,2,2-trifluoroacetamide

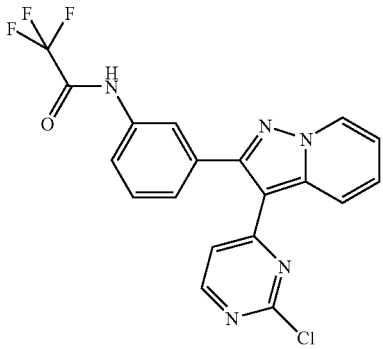

N-[3-(2-Chloro-pyrimidin-4-ylethynyl)-phenyl]-2,2,2-trifluoro-acetamide (9.14 g, 28.1 mmol), N-aminopyridinium iodide (6.24 g, 28.1 mmol), KOH (1.57 g, 28.9 mmol) and K$_2$CO$_3$ (7.76 g) were heated in DMSO (175 mL) were reacted according to earlier examples to afford, after workup, 7.45 g of the title compound, R$_f$=0.2 (2:1 Hex/EtOAc).

Step D: 2,2,2-Trifluoro-N-[3-(3-{2-[(3-fluorophenyl)amino]-4-pyrimidinyl}pyrazolo-[1,5-a]pyridin-2-yl)phenyl]acetamide

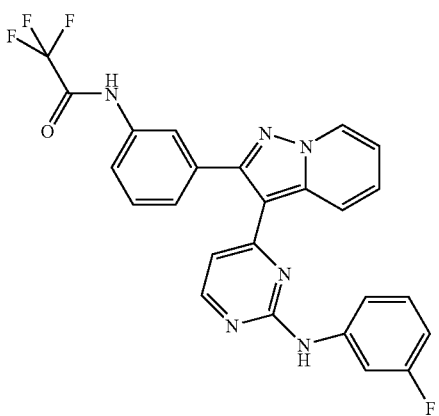

To a mixture of N-{3-[3-(2-chloro-4-pyrimidinyl)pyrazolo[1,5-a]pyridin-2-yl]phenyl}-2,2,2-trifluoroacetamide (2.27 g, 5.4 mmol) in ethanol (60 mL) was added 3-fluoroaniline (0.62 mL, 6.48 mmol) and 5 drops of conc. HCl. The reaction was heated to 80° C. for 16 h, allowed to cool to rt and concentrated. The mixture was partioned between DCM and saturated aq. NaHCO$_3$. The separated aqueous layer was extracted with DCM (2×) and the combined organic layers were dried over MgSO$_4$, filtered and concentrated to give, after trituration of the residue, the title compound as an off-white solid. $^1$H NMR (400 MHz, DMSO-d6) δ 11.34 (s, 1H), 9.78 (s, 1H), 8.83 (d, 1H, J=7.2), 8.43 (d, 1H, J=9.2), 8.30 (d, 1H, J=5.2), 7.97 (s, 1H), 7.79-7.72 ((m, 2H), 7.52-7.40 (m, 4H), 7.22 (q, 1H, J=7.6), 7.12 (t, 1H, J=6.8), 6.69 (m, 1H), 6.56 (d, 1H, J=5.2).

Step E: {4-[2-(3-Amino-phenyl)-pyrazolo[1,5-a]pyridin-3-yl]-pyrimidin-2-yl}-(3-fluoro-phenyl)-amine

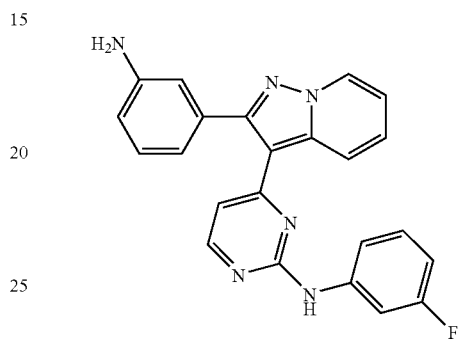

A solution of 2,2,2-trifluoro-N-(3-{3-[2-(3-fluoro-phenylamino)-pyrimidin-4-yl]-pyrazolo[1,5-a]pyridin-2-yl}-phenyl)-acetamide (2.15 g, 4.4 mmol) and lithium hydroxide (277 mg, 6.6 mmol) in THF (44 mL) and water (10 mL) was stirred for 16 h. The reaction was extracted with DCM. The combined organic phases were dried over MgSO$_4$ and purified through silica gel to give the title compound as a white solid. $^1$H NMR (400 MHz, d$_6$-DMSO): δ 9.75 (s, 1H), 8.78 (d, J=6.8 Hz, 1H), 8.52 (d, J=9.2 Hz, 1H), 8.25 (d, J=5.6 Hz, 1H), 7.80 (d, J=12.4 Hz, 1H), 7.47-7.43 (m, 2H), 7.29-7.23 (m, 1H), 7.12-7.06 (m, 2H), 6.77 (s, 1H), 6.71 (dt, J=8.4 and 2.4 Hz, 1H), 6.66-6.62 (m, 2H), 6.54 (d, J=5.6 Hz, 1H), 5.21 (s, 2H) ppm. HRMS calculated C$_{23}$H$_{17}$FN$_6$ [M+H]+ 397.1577 found 397.1558.

Step F: 2-Chloro-5-fluoro-N-(3-{3-[2-(3-fluoro-phenylamino)-pyrimidin-4-yl]-pyrazolo[1,5-a]pyridin-2-yl}-phenyl)-benzamide (title compound)

To a solution of {4-[2-(3-amino-phenyl)-pyrazolo[1,5-a]pyridin-3-yl]-pyrimidin-2-yl}-(3-fluoro-phenyl)-amine (80 mg, 0.20 mmol) in 2 mL THF was added 2-chloro-5-fluorobenzoyl chloride (26 μL, 0.22 mmol). When LC/MS indicated the reaction was complete, several equivalents of PS-trisamine were added and the mixture was stirred for 16 h. Et$_3$N was added if necessary to get the reaction into solution. The mixture was filtered and the resin washed well with THF. The filtrate was concentrated and triturated with DCM to give the title compound (51 mg, 46%). $^1$H NMR (400 MHz, d$_6$-DMSO) δ 10.66 (s, 1H), 9.78 (s, 1H), 8.84 (d, J=6.8 Hz, 1H), 8.45 (d, J=8.8 Hz, 1H), 8.30 (d, J=5.2 Hz, 1H), 8.01 (s, 1H), 7.80-7.74 (m, 2H), 7.61-7.42 (m, 5H), 7.39-7.32 (m, 2H), 7.26-7.20 (m, 1H), 7.11 (t, J=6.4 Hz, 1H), 6.72-6.67 (m, 1H), 6.57 (d, J=5.2 Hz, 1H) ppm. MS (ESI) m/z=553 [M+H]$^+$.

Example 12

2-Fluoro-N-(3-{3-[2-(3-fluoro-phenylamino)-pyrimidin-4-yl]-pyrazolo[1,5-a]pyridin-2-yl}-phenyl)-benzamide

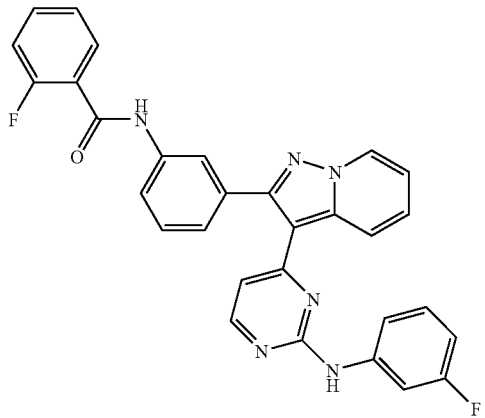

{4-[2-(3-Amino-phenyl)-pyrazolo[1,5-a]pyridin-3-yl]-pyrimidin-2-yl}-(3-fluoro-phenyl)-amine (80 mg, 0.20 mmol) was acylated with 2-fluorobenzoyl chloride (26 µL, 0.22 mmol) in a manner analogous to Example 11, to give the title compound as a white solid (52 mg, 49%). MS (ESI) m/z=519 [M+H]$^+$.

Example 13

2-Fluoro-N-(3-{3-[2-(3-fluoro-phenylamino)-pyrimidin-4-yl]-pyrazolo[1,5-a]pyridin-2-yl}-phenyl)-6-trifluoromethyl-benzamide

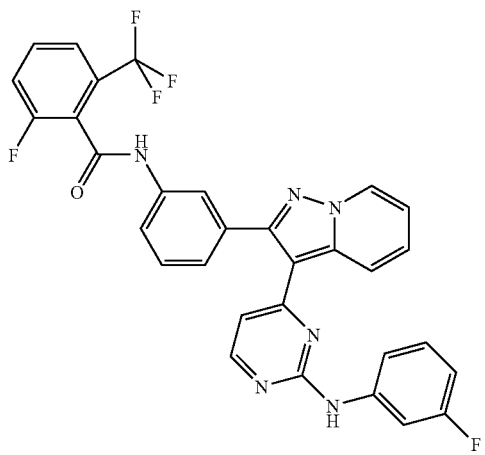

{4-[2-(3-Amino-phenyl)-pyrazolo[1,5-a]pyridin-3-yl]-pyrimidin-2-yl}-(3-fluoro-phenyl)-amine (80 mg, 0.20 mmol) was acylated with 2-fluoro-6-trifluoromethylbenzoyl chloride (34 µL, 0.22 mmol) in a manner analogous to Example 11, to give the title compound as a white solid (63 mg, 54%). HRMS calculated $C_{31}H_{19}F_5N_6O$ [M+H]$^+$ 587.1619 found 587.1630.

Example 14

2,3-Difluoro-N-(3-{3-[2-(3-fluoro-phenylamino)-pyrimidin-4-yl]-pyrazolo[1,5-a]pyridin-2-yl}-phenyl)-benzamide

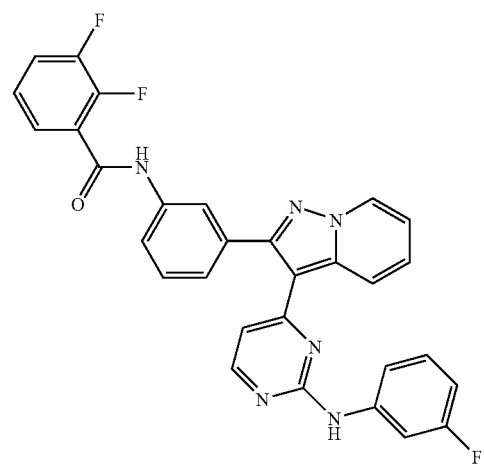

{4-[2-(3-Amino-phenyl)-pyrazolo[1,5-a]pyridin-3-yl]-pyrimidin-2-yl}-(3-fluoro-phenyl)-amine (80 mg, 0.20 mmol) was acylated with 2,3-difluorobenzoyl chloride (27 µL, 0.22 mmol) in a manner analogous to Example 11, to give the title compound as a white solid (94 mg, 88%). HRMS calculated $C_{30}H_{19}F_3N_6O$ [M+H]$^+$ 537.1651 found 537.1675.

Example 15

4-Fluoro-N-(3-{3-[2-(3-fluoro-phenylamino)-pyrimidin-4-yl]-pyrazolo[1,5-a]pyridin-2-yl}-phenyl)-benzamide

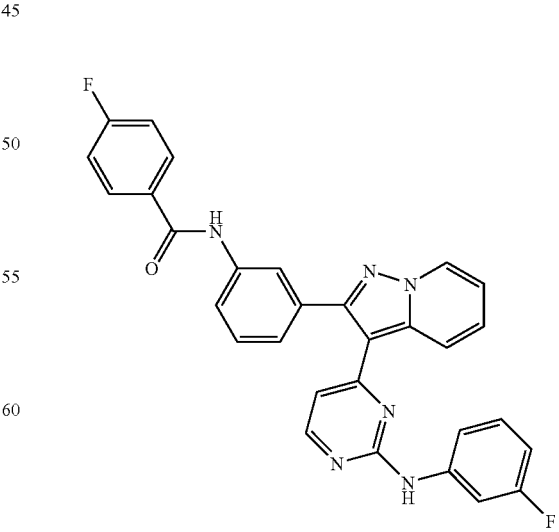

{4-[2-(3-Amino-phenyl)-pyrazolo[1,5-a]pyridin-3-yl]-pyrimidin-2-yl}-(3-fluoro-phenyl)-amine (80 mg, 0.20 mmol) was acylated with 4-fluorobenzoyl chloride (26 µL, 0.22 mmol) in a manner analogous to Example 11, to give the title compound as a white solid (78 mg, 75%). HRMS calculated $C_{30}H_{20}F_2N_6O$ [M+H]$^+$ 519.1745 found 519.1741.

Example 16

N-(3-{3-[2-(3-Fluoro-phenylamino)-pyrimidin-4-yl]-pyrazolo[1,5-a]pyridin-2-yl}-phenyl)-2-trifluoromethyl-benzamide

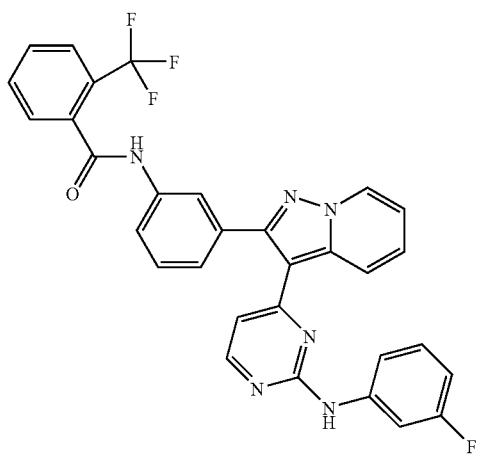

{4-[2-(3-Amino-phenyl)-pyrazolo[1,5-a]pyridin-3-yl]-pyrimidin-2-yl}-(3-fluoro-phenyl)-amine (80 mg, 0.20 mmol) was acylated with 2-trifluoromethylbenzoyl chloride (32 µL, 0.22 mmol) in a manner analogous to Example 11, to give the title compound as a white solid (35 mg, 31%). HRMS calculated $C_{31}H_{20}F_4N_6O$ [M+H]$^+$ 569.1713 found 569.1712.

Example 17

3-Fluoro-N-(3-{3-[2-(3-fluoro-phenylamino)-pyrimidin-4-yl]-pyrazolo[1,5-a]pyridin-2-yl}-phenyl)-benzamide

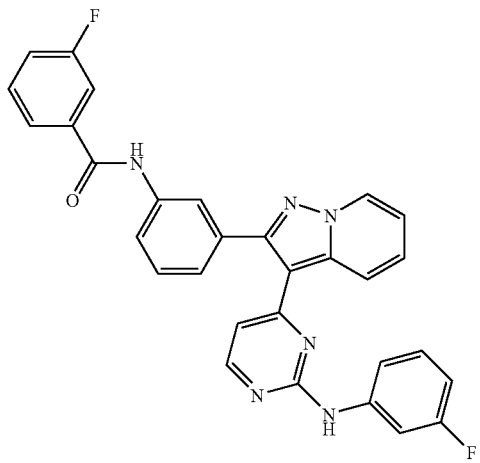

{4-[2-(3-Amino-phenyl)-pyrazolo[1,5-a]pyridin-3-yl]-pyrimidin-2-yl}-(3-fluoro-phenyl)-amine (80 mg, 0.20 mmol) was acylated with 3-fluorobenzoyl chloride (26 µL, 0.22 mmol) in a manner analogous to Example 11, to give the title compound as a white solid (75 mg, 72%). HRMS calculated $C_{30}H_{20}F_2N_6O$ [M+H]+ 519.1745 found 519.1748.

Example 18

N-(3-{3-[2-(3-Fluoro-phenylamino)-pyrimidin-4-yl]-pyrazolo[1,5-a]pyridin-2-yl}-phenyl)-3-methyl-benzamide

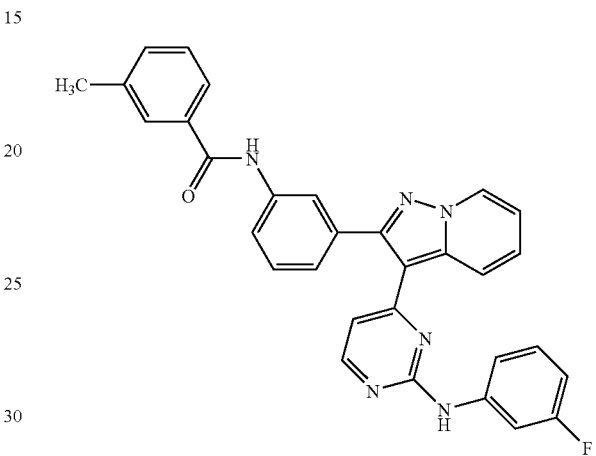

{4-[2-(3-Amino-phenyl)-pyrazolo[1,5-a]pyridin-3-yl]-pyrimidin-2-yl}-(3-fluoro-phenyl)-amine (80 mg, 0.20 mmol) was acylated with m-toluoyl chloride (29 µL, 0.22 mmol) in a manner analogous to Example 11, to give the title compound as a yellow solid (39 mg, 38%). HRMS calculated $C_{31}H_{23}FN_6O$ [M+H]$^+$ 515.1996 found 515.2006.

Example 19

2,4-Difluoro-N-(3-{3-[2-(3-fluoro-phenylamino)-pyrimidin-4-yl]-pyrazolo[1,5-a]pyridin-2-yl}-phenyl)-benzamide

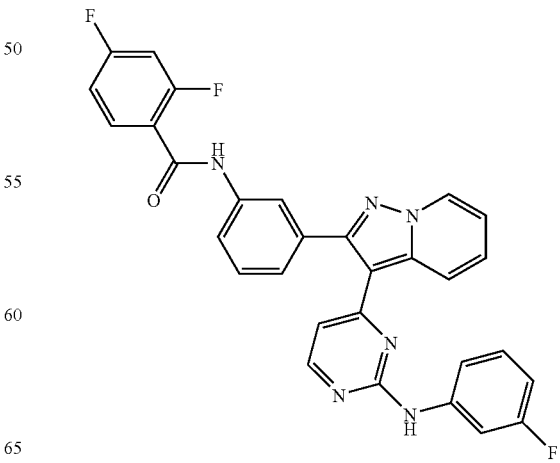

{4-[2-(3-Amino-phenyl)-pyrazolo[1,5-a]pyridin-3-yl]-pyrimidin-2-yl}-(3-fluoro-phenyl)-amine (80 mg, 0.20 mmol) was acylated with 2,4-difluorobenzoyl chloride (27 µL, 0.22 mmol) in a manner analogous to Example 11, to give the title compound as a white solid (96 mg, 90%). HRMS calculated $C_{30}H_{19}F_3N_6O$ [M+H]$^+$ 537.1651 found 537.1651.

Example 20

2-Chloro-4-fluoro-N-(3-{3-[2-(3-fluoro-phenylamino)-pyrimidin-4-yl]-pyrazolo[1,5-a]pyridin-2-yl}-phenyl)-benzamide

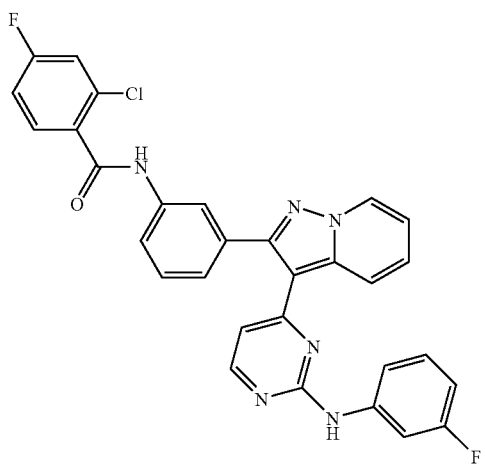

{4-[2-(3-Amino-phenyl)-pyrazolo[1,5-a]pyridin-3-yl]-pyrimidin-2-yl}-(3-fluoro-phenyl)-amine (80 mg, 0.20 mmol) was acylated with 2-chloro-4-fluorobenzoyl chloride (30 µL, 0.22 mmol) in a manner analogous to Example 11, to give the title compound as a white solid (88 mg, 80%). HRMS calculated $C_{30}H_{19}ClF_2N_6O$ [M+H]$^+$ 553.1355 found 553.1356.

Example 21

2-Chloro-3,6-difluoro-N-(3-{3-[2-(3-fluoro-phenylamino)-pyrimidin-4-yl]-pyrazolo[1,5-a]pyridin-2-yl}-phenyl)-benzamide

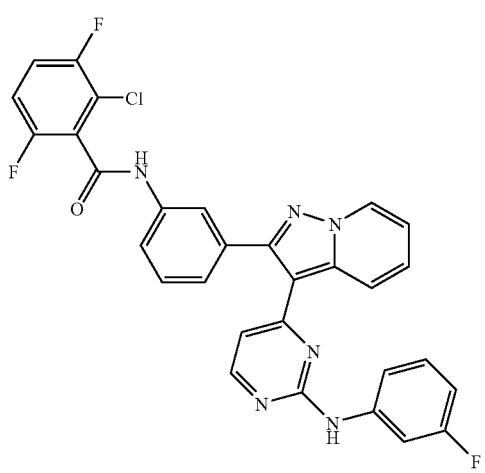

{4-[2-(3-Amino-phenyl)-pyrazolo[1,5-a]pyridin-3-yl]-pyrimidin-2-yl}-(3-fluoro-phenyl)-amine (80 mg, 0.20 mmol) was acylated with 2-chloro-3,6-difluorobenzoyl chloride (30 µL, 0.22 mmol) in a manner analogous to Example 11, to give the title compound as an orange solid (80 mg, 70%). HRMS calculated $C_{30}H_{18}ClF_3N_6O$ [M+H]$^+$ 571.1261 found 571.1267.

Example 22

Pyridine-2-carboxylic acid (3-{3-[2-(3-fluoro-phenylamino)-pyrimidin-4-yl]-pyrazolo[1,5-a]pyridin-2-yl-phenyl)-amide

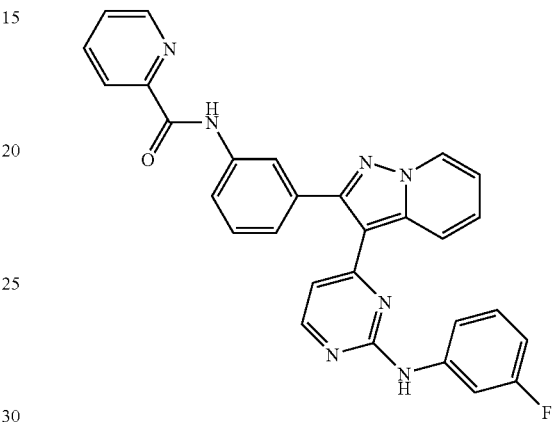

{4-[2-(3-Amino-phenyl)-pyrazolo[1,5-b]pyridazin-3-yl]-pyrimidin-2-yl}-(3-fluoro-phenyl)-amine (82 mg, 0.20 mmol) was acylated with picolinoyl chloride hydrochloride (39 mg, 0.22 mmol) in a manner analogous to Example 11, to give the title compound as a yellow solid (50 mg, 49%). HRMS calculated $C_{29}H_{21}FN_8O$ [M+H]$^+$ 517.1901 found 517.1916.

Example 23

N-[3-(3-{2-[(3-Fluorophenyl)amino]-4-pyrimidinyl}pyrazolo[1,5-a]pyridin-2-yl)phenyl]-1,3-dimethyl-1H-pyrazole-5-carboxamide

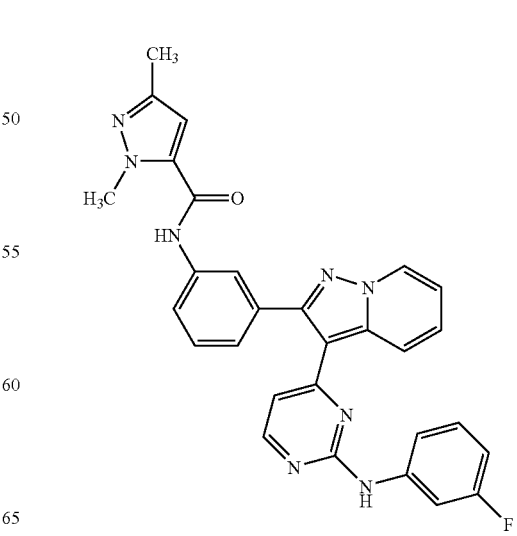

In an analogous procedure to Example 11, 40 mg of the title compound was prepared from 79 mg of 1,3-dimethyl-1H-pyrazole-5-carbonyl chloride to give the product as a white solid: $^1$H NMR (d$_6$-DMSO, 300 MHz) δ 2.23 (s, 3H), 4.02 (s, 3H), 6.62 (d, 1H, J=5.2 Hz), 6.77 (td, 1H, J=9.0 and 2.3 Hz), 6.87 (s, 1H), 7.18 (td, 1H, J=6.9 and 1.3 Hz), 7.29-7.38 (m, 2H), 7.48-7.57 (m, 3H), 7.84 (d, 1H, J=10.8 Hz), 7.93 (d, 1H, J=6.4 Hz), 8.11 (s, 1H), 8.36 (d, 1H, J=5.2 Hz), 8.55 (d, 1H, J=8.8 Hz), 8.90 (d, 1H, J=6.8 Hz), 9.85 (s, 1H), and 10.28 (s, 1H); HRMS calcd for C29H23FN8O: 518.1979, found: 519.2060 (M+H$^+$).

Example 24

N-[3-(3-{2-[(3-Fluorophenyl)amino]-4-pyrimidinyl}pyrazolo[1,5-a]pyridin-2-yl)phenyl]-2-quinoxalinecarboxamide

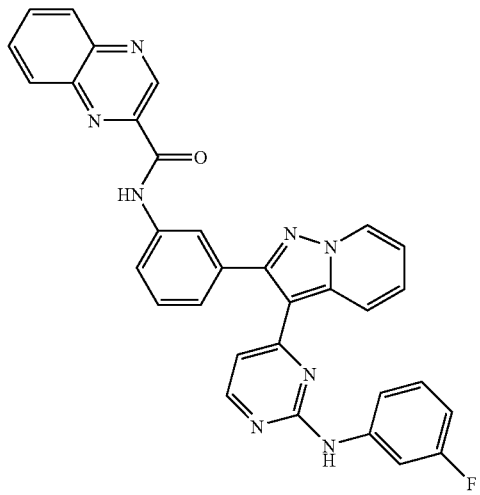

{4-[2-(3-Amino-phenyl)-pyrazolo[1,5-b]pyridazin-3-yl]-pyrimidin-2-yl}-(3-fluoro-phenyl)-amine was acylated with 2-quinoxalinecarbonyl chloride in a manner analogous to Example 11, to give the title compound, $^1$H NMR (d$_6$-DMSO, 300 MHz) 66.65 (d, 1H, J=5.3 Hz), 6.70 (td, 1H, J=7.1 and 2.2 Hz), 7.20 (td, 1H, J=7.0 and 1.2 Hz), 7.26-7.32 (m, 1H), 7.43 (d, 1H, J=7.7 Hz), 7.50-7.61 (m, 3H), 7.85 (d, 1H, J=12.4 Hz), 8.04-8.07 (m, 3H), 8.14 (d, 1H, J=8.6 Hz), 8.25-8.28 (m, 1H), 8.32-8.37 (m, 2H), 8.57 (d, 1H, J=8.9 Hz), 8.92 (d, 1H, J=6.8 Hz), 9.58 (s, 1H), 9.87 (s, 1H), and 11.05 (s, 1H). HRMS calcd for C$_{32}$H$_{21}$FN$_8$O: 552.1822, found: 553.1910 (M+H$^+$).

Example 25

N-[3-(3-{2-[(3-fluorophenyl)amino]-4-pyrimidinyl}pyrazolo[1,5-a]pyridin-2-yl)phenyl]-2-thiophenecarboxamide

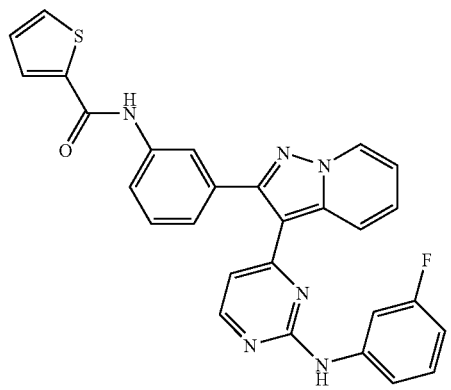

{4-[2-(3-Amino-phenyl)-pyrazolo[1,5-b]pyridazin-3-yl]-pyrimidin-2-yl}-(3-fluoro-phenyl)-amine was acylated with 2-thiophenecarbonyl chloride in a manner analogous to Example 11, to give the title compound. HRMS calcd for C28H19F1N6O1S1: 506.1325: Found: 507.1427[M+H]$^+$ Example 26

N-[3-(3-{2-[(3-fluorophenyl)amino]-4-pyrimidinyl}pyrazolo[1,5-a]pyridin-2-yl)phenyl]-1-methyl-1H-1,2,3-benzotriazole-5-carboxamide

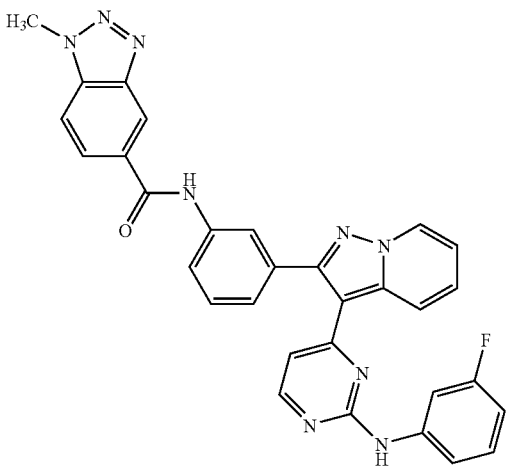

{4-[2-(3-Amino-phenyl)-pyrazolo[1,5-b]pyridazin-3-yl]-pyrimidin-2-yl}-(3-fluoro-phenyl)-amine was acylated with 1-methyl-1H1,2,3-benzotriazole-5-carbonyl chloride in a manner analogous to Example 11, to give the title compound, $^1$H NMR (300 MHz, DMSO-d6): δ 10.54 (s, 1H), 9.81 (s, 1H), 8.86 (d, 1H), 8.73 (s, 1H), 8.52 (d, 1H), 8.32 (d, 1H), 8.16 (s, 1H), 8.12 (d, 1H), 8.02-7.90 (m, 2H), 7.80 (m, 1H), 7.54-7.45 (m, 3H), 7.37-7.20 (m, 2H), 7.14 (t, 1H), 6.72 (m, 1H), 6.60 (d, 1H), 4.38 (s, 3H). HRMS: calc. C$_{31}$H$_{23}$N$_9$OF (M+H)+ 556.2013 found 556.2021.

Example 27

2,6-Difluoro-N-{3-[3-(2-{[4-(4-morpholinyl)phenyl]amino}-4-pyrimidinyl)pyrazolo[1,5-a]pyridin-2-yl]phenyl}benzamide

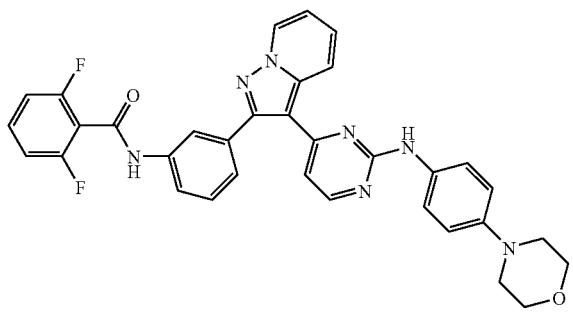

Step A: N-(3-Ethynylphenyl)-2,6-difluorobenzamide

To 3-aminophenylacetylene (14.5 g, 124 mmol) was added DCM (500 mL). The mixture was cooled to 0° C. followed by addition of TEA (34 mL, 248 mmol). 2,6-Difluorobenzoyl chloride (21.8 g, 124 mmol) was then added dropwise over 30 min. The reaction was stirred for 16 h then poured into ice water, extracted with DCM (3×200 mL), washed with Brine (100 mL), filtered, dried (MgSO₄), and concentrated to dryness by rotary evaporation. The material was then triturated by addition of Et₂O and isolated by filtration to yield the title compound (21.8 g, 70%) as a brown powder. LC MS (ES)+= 258.1.

Step B: N-{3-[(2-Chloro-4-pyrimidinyl)ethynyl]phenyl}-2,6-difluorobenzamide

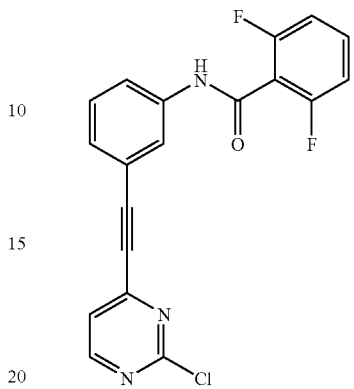

To N-(3-ethynylphenyl)-2,6-difluorobenzamide (17.3 g, 67.5 mmol) in THF (350 mL) was added 2,4-dichloropyrimidine (10 g, 67.5 mmol), PdCl₂(PPh₃)₃ (2.3 g, 3.4 mmol), CuI (1.3 g, 6.75 mmol), and TEA (20 g, 202 mmol). The mixture was heated at 45° C. for 12 h. Silica gel (50 g) and DCM (200 mL) was added and evaporated to dryness. The adsorbed material was purified via column chromatography (20-50% gradient of EtOAc in hexanes) to yield the title compound (12 g, 50%) as a brown solid.

Step C: N-{3-[3-(2-Chloro-4-pyrimidinyl)pyrazolo[1,5-a]pyridin-2-yl]phenyl}-2,6-difluorobenzamide

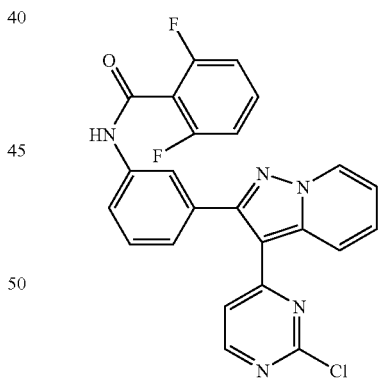

To N-{3-[(2-chloro-4-pyrimidinyl)ethynyl]phenyl}-2,6-difluorobenzamide (144 mg, 0.39 mmol) in DMSO (4 mL) was added 1-aminopyridinium iodide (173 mg, 0.78 mmol), KOH (21 mg, 0.39 mmol), and K₂CO₃ (26 mg, 0.2 mmol) at RT. The reaction was stirred for 16 h then poured into water (40 mL) followed by extraction with DCM (3×50 mL). The combined organics were washed with Brine, dried (MgSO₄), filtered, and concentrated to dryness by rotary evaporation. The material was purified via column chromatography (20-60% gradient of EtOAc in hexanes) to yield the title compound (130 mg, 72%) as a brown solid.

Step C (Alternative): N-{3-[3-(2-Chloro-4-pyrimidinyl)pyrazolo[1,5-a]pyridin-2-yl]phenyl}-2,6-difluorobenzamide

Example 28

2,6-Difluoro-N-{3-[3-(2-{[3-(methyloxy)phenyl]amino}-4-pyrimidinyl)pyrazolo[1,5-a]pyridin-2-yl]phenyl}benzamide

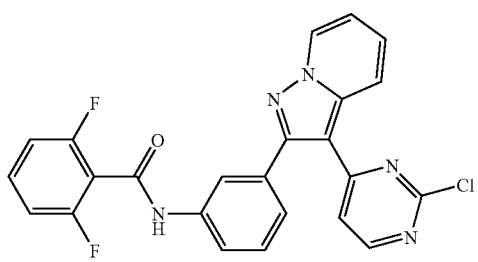

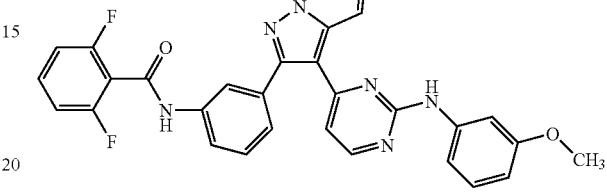

KOH (1.0 g, 17.4 mmol) was ground to a powder and added to a rt solution of N-{3-[(2-chloro-4-pyrimidinyl)ethynyl]phenyl}-2,6-difluorobenzamide (6.4 g, 17.4 mmol), 1-aminopyridinium iodide (3.85 g, 17.4 mmol), $K_2CO_3$ (4.8 g, 34.7 mmol) and DMSO (100 mL) at rt. The reaction was stirred for 3 h and the product crystallized out of the reaction mixture. The reaction was combined with an equal volume of water and the suspension was filtered. The solids were washed with water, then triturated with diethyl ether. The resulting brown solid was dried for 24 h at 60° C. under vacuum to give 7.1 g (89%) of the crude title compound as a brown powder. MS (ESI): M+H=461.99.

Step D: 2,6-Difluoro-N-{3-[3-(2-{[4-(4-morpholinyl)phenyl]amino}-4-pyrimidinyl)pyrazolo[1,5-a]pyridin-2-yl]phenyl}benzamide (title compound)

To a slurry of N-{3-[3-(2-chloro-4-pyrimidinyl)pyrazolo[1,5-a]pyridin-2-yl]phenyl}-2,6-difluorobenzamide (100 mg, 0.216 mmol.) in 1 mL of EtOH, added 4-(4-morpholinyl)aniline (38 mg, 0.216 mmol.) and 5 µL of conc. HCl. The reaction contents were heated to 80° C. After heating for 18 h, the reaction was cooled to rt and partitioned between EtOAc and sat. aq. $NaHCO_3$. The layers were separated, extracted the aqueous layer with EtOAc (2×10 mL), the organic layers were pooled, dried over $MgSO_4$, filtered, reduced in vacuo onto silica. Purified via ISCO chromatography (hexanes:EtOAc) to afford the desired compound as a yellow solid, 56 mg, 43% yield. $^1$H NMR (400 MHz, $CD_3OD$): δ 8.61 (d, J=7 Hz, 1H); 8.40 (d, J=9 Hz, 1H); 8.14 (d, J=5 Hz, 1H); 7.98 (bs, 1H); 7.86 (d, J=7H, 1H); 7.56-7.48 (m, 3H); 7.48-7.37 (m, 3H); 7.12-7.05 (m, 3H); 6.92 (d, J=9 Hz, 2H) 6.58 (d, J=5 Hz, 1H); 3.85-3.83 (m, 4H); 3.11-3.09 (m 4H). HRMS calculated $C_{34}H_{28}F_2N_7O_2$ [M+H]$^+$ 604.2273, found 604.2271.

The title compound was prepared via reaction of N-{3-[3-(2-chloro-4-pyrimidinyl)pyrazolo[1,5-a]pyridin-2-yl]phenyl}-2,6-difluorobenzamide with [3-(methyloxy)phenyl]amine to afford the desired product in a manner analogous to Example 27, Step D. HRMS calculated $C_{31}H_{23}F_2N_6O_2$ [M+H]$^+$ 549.1851, found 549.1850.

Example 29

2,6-Difluoro-N-{3-[3-(2-{[3-fluoro-4-(methyloxy)phenyl]amino}-4-pyrimidinyl)pyrazolo[1,5-a]pyridin-2-yl]phenyl}benzamide

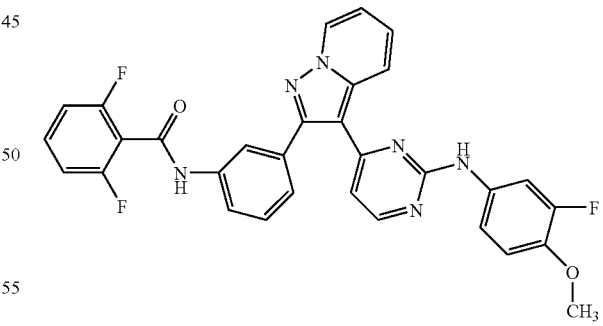

The title compound was prepared via addition of N-{3-[3-(2-chloro-4-pyrimidinyl)pyrazolo[1,5-a]pyridin-2-yl]phenyl}-2,6-difluorobenzamide and [3-fluoro-4-(methyloxy)phenyl]amine to afford the desired product in a manner analogous to Example 27, Step D. HRMS calculated $C_{31}H_{22}F_3N_6O_2$ [M+H]$^+$ 567.1756, found 567.1749.

Example 30

N-[3-(3-{2-[(3-cyanophenyl)amino]-4-pyrimidinyl}pyrazolo[1,5-a]pyridin-2-yl)phenyl]-2,6-difluorobenzamide

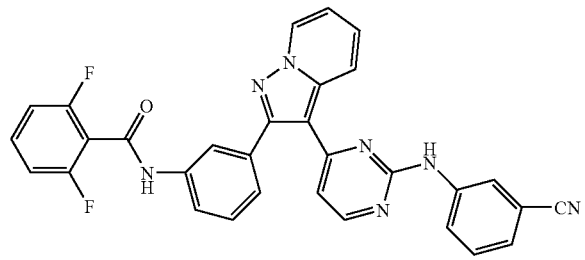

The title compound was prepared via addition of N-{3-[3-(2-chloro-4-pyrimidinyl)pyrazolo[1,5-a]pyridin-2-yl]phenyl}-2,6-difluorobenzamide and 3-aminobenzonitrile to afford the desired product in a manner analogous to Example 27, Step D. HRMS calculated $C_{31}H_{20}F_2N_7O$ $[M+H]^+$ 544.1697, found 544.1710.

Example 31

N-(3-{3-[2-(1H-1,2,3-benzotriazol-5-ylamino)-4-pyrimidinyl]pyrazolo[1,5-a]pyridin-2-yl}phenyl)-2,6-difluorobenzamide

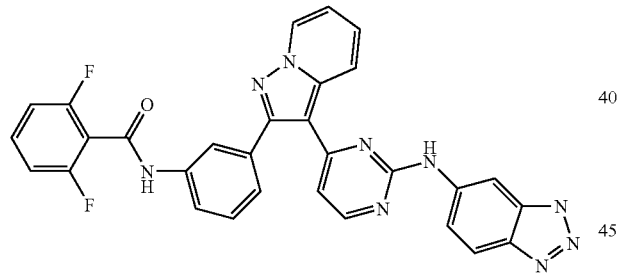

To a slurry of N-{3-[3-(2-chloro-4-pyrimidinyl)pyrazolo[1,5-a]pyridin-2-yl]phenyl}-2,6-difluorobenzamide (103 mg, 0.223 mmol.) in 1 mL of EtOH/0.5 mL of DMF, 1H-1,2,3-benzotriazol-5-amine (32 mg, 0.245 mmol) and 5 µL of conc. HCl, the reaction contents were heated to 80° C. After heating for 18 h, the reaction mixture was cooled to rt and partitioned between DCM and sat. aq. NaHCO$_3$. The layers were separated, extracted the aqueous layer with DCM (2×10 mL), the organic layers were pooled, dried over MgSO$_4$, filtered, reduced in vacuo. Addition of TFA, followed by titration with Et$_2$O afforded the desired product as a yellow solid 93 mg, 63% yield. $^1$H NMR (400 MHz, d$_6$-DMSO): δ 10.91 (s, 1H); 9.91 (s, 1H); 8.54 (d, J=7 Hz, 1H); 8.52-8.49 (m, 2H); 8.31 (d, J=5 Hz, 1H); 7.99 (s, 1H); 7.82 (t, J$_1$=10 Hz, 2H); 7.60-7.53 (m, 2H); 7.50-7.45 (m, 2H); 7.37 (d, J=8 Hz, 1H); 7.23 (t, J=9 Hz, 2H); 7.13 (t, J=7 Hz, 1H); 6.55 (d, J=5 Hz, 1H). HRMS calculated $C_{30}H_{20}F_2N_9O$ $[M+H]^+$ 560.1759, found 560.1763.

Example 32

N-{3-[3-(2-{[4-(aminosulfonyl)phenyl]amino}-4-pyrimidinyl)pyrazolo[1,5-a]pyridin-2-yl]phenyl}-2,6-difluorobenzamide

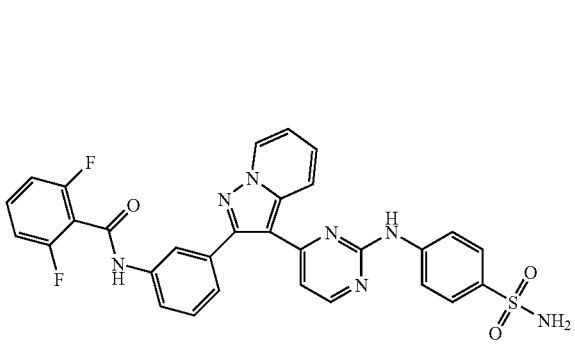

The title compound was prepared via addition of N-{3-[3-(2-chloro-4-pyrimidinyl)pyrazolo[1,5-a]pyridin-2-yl]phenyl}-2,6-difluorobenzamide and 4-aminobenzenesulfonamide to afford the desired product in a manner analogous to Example 27, Step D. HRMS calculated $C_{30}H_{22}F_2N_7O_3S$ $[M+H]^+$ 598.1473, found 598.1475.

Example 33

2,6-Difluoro-N-{3-[3-(2-{[3-(trifluoromethyl)phenyl]-amino}-4-pyrimidinyl)pyrazolo[1,5-a]pyridin-2-yl]phenyl}benzamide

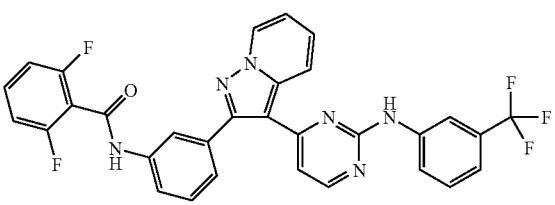

The title compound was prepared via addition of N-{3-[3-(2-chloro-4-pyrimidinyl)pyrazolo[1,5-a]pyridin-2-yl]phenyl}-2,6-difluorobenzamide and 3-(trifluoromethyl)aniline in a manner analogous to Example 27, Step D. HRMS calculated $C_{31}H_{20}F_5N_6O$ $[M+H]^+$ 587.1619, found 544.1610.

Example 34

2,6-Difluoro-N-(3-{3-[2-(phenylamino)-4-pyrimidinyl]pyrazolo[1,5-a]pyridin-2-yl}phenyl)benzamide

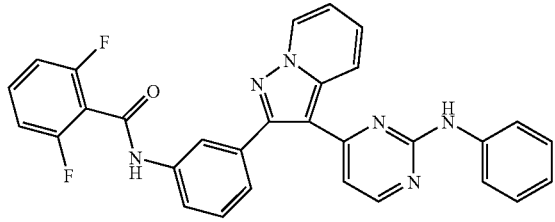

The title compound was prepared via addition of N-{3-[3-(2-chloro-4-pyrimidinyl)pyrazolo[1,5-a]pyridin-2-yl]phenyl}-2,6-difluorobenzamide and aniline in a manner analogous to Example 27, Step D. HRMS calculated $C_{30}H_{21}F_2N_6O$ [M+H]$^+$ 519.1745, found 519.1750.

Example 35

2,6-Difluoro-N-{3-[3-(2-{[3-(1,3-oxazol-5-yl)phenyl]amino}-4-pyrimidinyl)pyrazolo[1,5-a]pyridin-2-yl]phenyl}benzamide

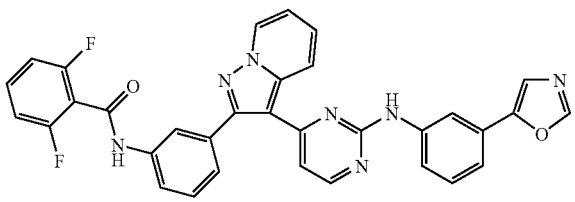

To a slurry of N-{3-[3-(2-chloro-4-pyrimidinyl)pyrazolo[1,5-a]pyridin-2-yl]phenyl}-2,6-difluorobenzamide (100 mg, 0.216 mmol.) in 1 mL of EtOH/0.25 mL of DMF, added [3-(1,3-oxazol-5-yl)phenyl]amine (41 mg, 0.26 mmol.) and 5 uL of conc. HCl, the reaction contents were heated to 70° C. After heating for 18 h, the reaction was cooled to RT, partitioned the reaction with EtOAc and sat. aq. NaHCO$_3$. The layers were separated, extracted the aqueous layer with EtOAc (2×10 mL), the organic layers were pooled, dried over MgSO$_4$, filtered, reduced in vacuo onto silica. Purification via ISCO (hexanes:EtOAc) afforded 73 mg (59% yield) of the title compound as a yellow solid. $^1$H NMR (400 MHz, d$_6$-DMSO): δ 10.91 (s, 1H); 9.71 (s, 1H); 8.83 (d, J=6 Hz, 1H); 8.51 (d, J=9 Hz, 1H); 8.37 (s, 1H); 8.28 (d, J=5 Hz, 1H); 8.17 (s, 1H); 7.99 (s, 1H); 7.79 (d, J=9 Hz, 1H); 7.68 (d, J=7 Hz, 1H); 7.60-7.53 (m, 2H); 7.46 (t, J=15 Hz, 1H); 7.39-7.28 (m, 5H); 7.23 (t, J=15 Hz, 2H); 7.20 (t, J=6 Hz, 1H). HRMS calculated $C_{33}H_{22}F_2N_7O_2$ [M+H]$^+$ 586.1803, found 586.1802.

Example 36

N-{3-[3-(2-{[3-(Acetylamino)phenyl]amino}-4-pyrimidinyl)pyrazolo[1,5-a]pyridin-2-yl]phenyl}-2,6-difluorobenzamide

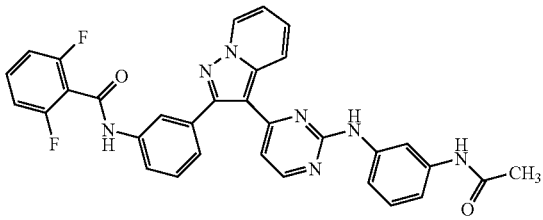

To a slurry of N-{3-[3-(2-chloro-4-pyrimidinyl)pyrazolo[1,5-a]pyridin-2-yl]phenyl}-2,6-difluorobenzamide (133 mg, 0.288 mmol.) in 1 mL of EtOH/0.25 mL of DMF, N/(3-aminophenyl)acetamide (71 mg, 0.32 mmol.) and 5 uL of conc. HCl, the reaction contents were heated to 70° C. After heating for 18 h, the reaction was cooled to rt, partitioned the reaction with EtOAc and sat. aq. NaHCO$_3$. The layers were separated, extracted the aqueous layer with EtOAc (2×10 mL), the organic layers were pooled, dried over MgSO$_4$, filtered, reduced in vacuo onto silica. Purification via ISCO (hexanes:EtOAc) to afforded a white solid, 43 mg (26% yield). $^1$H NMR (400 MHz, d$_6$-DMSO): δ 10.92 (s, 1H); 9.81 (s, 1H); 9.52 (s, 1H); 8.81 (d, J=7 Hz, 1H); 8.54 (d, J=9 Hz, 1H); 8.21 (d, J=6, 1H); 7.94 (d, J=16 Hz, 2H); 7.81 (d, J=9 Hz, 1H); 7.58-7.54 (m, 1H); 7.47-7.41 (m, 2H); 7.34 (t, J=10 Hz, 2H); 7.25-7.09 (m, 5H); 6.47 (d, J=5 Hz, 1H); 5.72 (s, 1H); 1.99 (s, 3H). HRMS calculated $C_{32}H_{24}F_2N_7O_2$ [M+H]$^+$ 576.1960, found 576.1945.

Example 37

2-Chloro-6-fluoro-N-[3-(3-{2-[(3-fluorophenyl)amino]-4-pyrimidinyl}pyrazolo[1,5-a]pyridin-2-yl)phenyl]benzamide

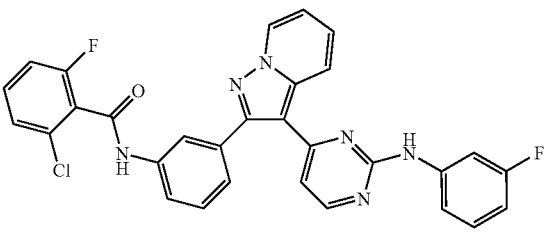

To a solution of 4-[2-(3-aminophenyl)pyrazolo[1,5-a]pyridin-3-yl]-N-(3-fluorophenyl)-2-pyrimidinamine (92 mg, 0.23 mmol) in 2 mL of THF, added 2-chloro-6-fluorobenzoyl chloride (48 mg, 0.27 mmol). The reaction was stirred for 30 min at rt and quenched by addition of polystyrene-trisamine resin (20 mg). The reaction was allowed to stir overnight. The reaction was treated with excess Et$_3$N, filtered, and washed with THF. The filtrate was collected, reduced in vacuo, and upon treatment with DCM, a white solid formed. Filtration and washing with the solid with Et$_2$O yielded the desired product as a white solid, 96 mg, 65% yield. $^1$H NMR (400 MHz, d$_6$-DMSO): δ 10.89 (s, 1H); 9.78 (s, 1H); 8.84 (d, J=6

Hz, 1H); 8.30 (d, J=5 Hz, 1H); 8.00 (s, 1H); 7.77-7.23 (m, 2H); 7.55-7.33 (m, 7H); 7.22 (q, J=8 Hz, 1H); 7.11 (t, J=7 Hz, 1H); 6.69 (td, J=2, 8 Hz, 1H); 6.60 (d, J=5 Hz, 1H). HRMS calculated $C_{30}H_{20}ClF_2N_6O$ [M+H]$^+$ 553.1355, found 553.1360.

Example 38

N-[3-(3-{2-[(3-fluorophenyl)amino]-4-pyrimidinyl}-pyrazolo[1,5-a]pyridin-2-yl)phenyl]-3,5-dimethyl-4-isoxazolecarboxamide

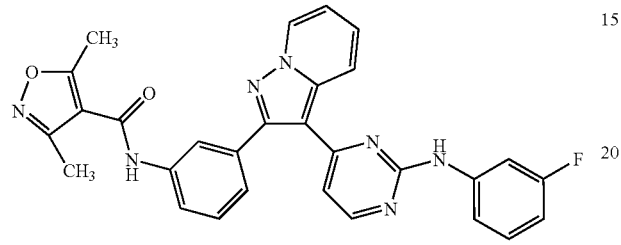

The title compound was prepared via addition of 4-[2-(3-aminophenyl)pyrazolo[1,5-a]pyridin-3-yl]-N-(3-fluorophenyl)-2-pyrimidinamine (97 mg, 0.24 mmol) and 3,5-dimethyl-4-isoxazolecarbonyl chloride (43 mg, 0.26 mmol) in a manner analogous to Example 37. HRMS calculated $C_{29}H_{23}FN_7O$ [M+H]$^+$ 520.1897, found 553.1888.

Example 39

2,5-Difluoro-N-[3-(3-{2-[(3-fluorophenyl)amino]-4-pyrimidinyl}pyrazolo[1,5-a]pyridin-2-yl)phenyl]benzamide

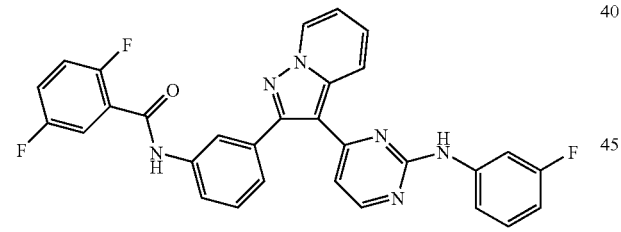

The title compound was prepared via addition of 4-[2-(3-aminophenyl)pyrazolo[1,5-a]pyridin-3-yl]-N-(3-fluorophenyl)-2-pyrimidinamine (93 mg, 0.23 mmol) and 2,5-difluorobenzoyl chloride (48 mg, 0.27 mmol) in a manner analogous to Example 37. HRMS calculated $C_{30}H_{20}F_3N_6O$ [M+H]$^+$ 537.1651, found 537.1650.

Example 40

2,5-Difluoro-N-[3-(3-{2-[(3-fluorophenyl)amino]-4-pyrimidinyl}-6-methylpyrazolo[1,5-a]pyridin-2-yl)phenyl]benzamide

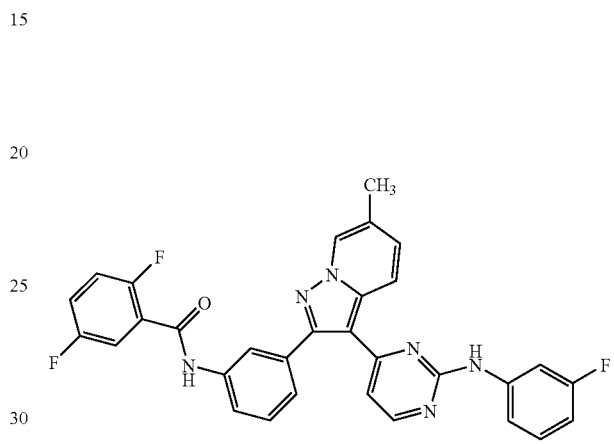

The title compound was prepared via addition of 4-[2-(3-aminophenyl)-6-methylpyrazolo[1,5-a]pyridin-3-yl]N-(3-fluorophenyl)-2-pyrimidinamine (82 mg, 0.2 mmol) and 2,5-difluorobenzoyl chloride (38 mg, 0.22 mmol) in a manner analogous to Example 37. HRMS calculated $C_{30}H_{21}F_3N_7O$ [M+H]$^+$ 552.1760, found 552.1769.

Example 41

N-[3-(3-{2-[(4-{[3-(dimethylamino)propyl]amino}-3-fluorophenyl)amino]-4-pyrimidinyl}pyrazolo[1,5-a]pyridin-2-yl)phenyl]-2,6-difluorobenzamide

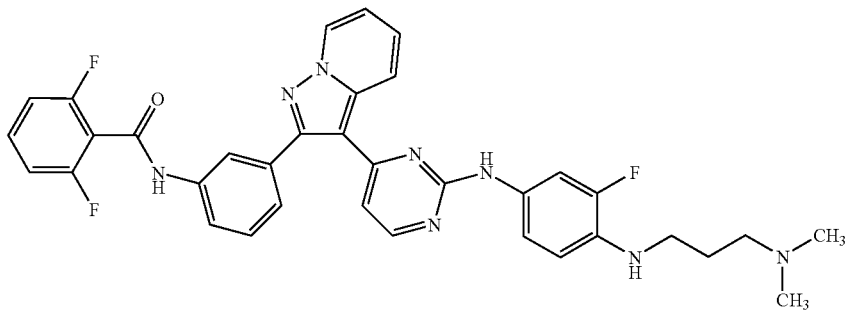

Step A: N-(2-Fluoro-4-nitrophenyl)-N,N-dimethyl-1,
3-propanediamine[3-(dimethylamino)propyl](2-
fluoro-4-nitrophenyl)amine

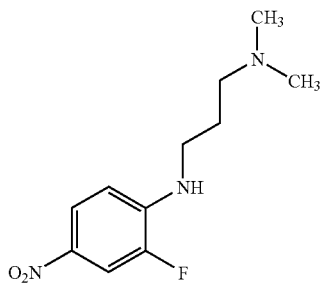

To a solution of 1,2-difluoro-4-nitrobenzene (1 g, 6.28 mmol) in 62 mL of THF, added Et$_3$N (1.58 g, 15.7 mmol) followed by N,N-dimethyl-1,3-propanediamine (0.77 g, 7.54 mmol) the resulting reaction was stirred at rt for 18 h. The reaction was diluted with EtOAc, and quenched with sat aq. NaHCO$_3$. The layers were separated, and the aqueous was extracted with EtOAc. The organics were combined, filtered over MgSO$_4$, filtered, reduced in vacuo onto silica. Purification via ISCO chromatography (hexanes: EtOAc) afforded a yellow solid as the desired product. LRMS calculated for C$_{11}$H$_{17}$FN$_3$O$_2$ [M+H]$^+$ 242, found 242.

Step B: N-[3-(3-{2-[(4-{[3-(Dimethylamino)propyl]
amino}-3-fluorophenyl)amino]-4-
pyrimidinyl}pyrazolo[1,5-a]pyridin-2-yl)phenyl]-2,
6-difluorobenzamide (title compound)

(Dimethylamino)propyl](2-fluoro-4-nitrophenyl)amine (0.72 g, 2.9 mmol) was dissolved into EtOAc (50 mL) and treated with Pd/C (10%, 0.16 g, 0.15 mmol), placed at rt under 1 atm of H2. The reaction was allowed to stir for 24 h. The reaction was treated with Celite, and the resulting slurry was filtered over Celite. The filtrate was reduced in vacuo to afford the intermediate aniline as a dark-red oil that was used without further purification. To a slurry of N-{3-[3-(2-chloro-4-pyrimidinyl)pyrazolo[1,5-a]pyridin-2-yl]phenyl}-2,6-difluorobenzamide (100 mg, 0.22 mmol.) in 1 mL of IPA, crude amine (55 mg, 0.26 mmol) and 5 uL of conc. HCl, the reaction contents were placed in microwave reactor (20 min @ 160° C.). After heating, the reaction was cooled to rt, partitioned the reaction with DCM and sat. aq. NaHCO$_3$. The layers were separated, extracted the aqueous layer with DCM (2×10 mL), the organic layers were pooled, dried over MgSO$_4$, filtered, reduced in vacuo. Addition of TFA, followed by titration with Et$_2$O afforded the desired product (51 mg, 37% yield) as a yellow solid. $^1$H NMR (400 MHz, d$_6$-DMSO): δ 10.90 (s, 1H); 9.26 (s, 1H); 8.81 (d, J=7 Hz, 1H); 8.41 (bm, 1H); 8.18 (d, J=5 Hz, 1H); 7.96 (s, 1H); 7.80 (d, J=9 Hz, 1H); 7.60-7.40 (m, 4H); 7.33 (d, J=8 Hz, 1H); 7.21 (q, J=8 Hz, 3H); 7.09 (t, J=7H, 1H); 6.60 (m, 1H); 6.40 (d, J=5 Hz, 1H); 5.11 (bm, 1H); 3.04 (q, J=6 Hz, 2H); 2.47 (t, J=2 Hz, 2H); 2.10 (s, 6H); 1.66 (m, 2H). LRMS calculated C$_{35}$H$_{32}$F$_3$N$_8$O [M+H]$^+$ 637, found 637.

Example 42

2,6-Difluoro-N-[3-(3-{2-[(3-fluoro-4-{[3-(4-methyl-
1-piperazinyl)propyl]amino}phenyl)amino]-4-
pyrimidinyl}pyrazolo[1,5-a]pyridin-2-yl)phenyl]
benzamide

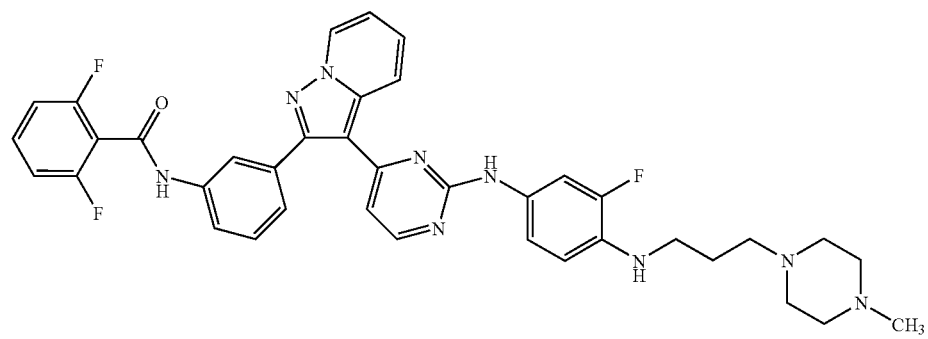

2-Fluoro-1-[3-(4-methyl-1-piperazinyl)propyl]-1,4-benzenediamine was prepared from 1,2-difluoro-4-nitrobenzene and 3-(4-methyl-1-piperazinyl)-1-propanamine in a manner analogous to Example 41. The title compound was prepared from 2-fluoro-N1-[3-(4-methyl-1-piperazinyl)propyl]-1,4-benzenediamine in a manner analogous to Example 41. HRMS calculated for $C_{38}H_{37}F_3N_9O$ [M+H]$^+$ 692.3073, found 692.3052.

Example 43

2,5-Difluoro-N-(3-{3-[2-(phenylamino)-4-pyrimidinyl]pyrazolo[1,5-a]pyridin-2-yl}phenyl)benzamide

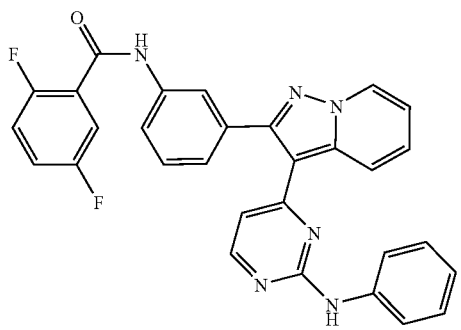

Step A: N-{3-[3-(2-Chloro-4-pyrimidinyl)pyrazolo[1,5-a]pyridin-2-yl]phenyl}-2,5-difluorobenzamide

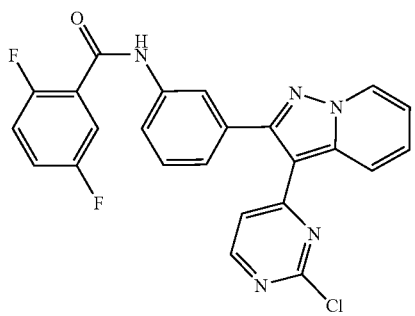

A mixture of N-{3-[(2-chloro-4-pyrimidinyl)ethynyl]phenyl}-2,5-difluorobenzamide (6.4 g, 17.4 mmol) and 1-aminopyridinium iodide (3.85 g, 17.4 mmol) were reacted in DMSO (100 mL) in the presence of KOH (1 g, 17.4 mmol) and potassium carbonate (4.8 g, 34.7 mmol) in a manner analogous to that used in Example 27, Step C, for N-{3-[3-(2-Chloro-4-pyrimidinyl)pyrazolo[1,5-a]pyridin-2-yl]phenyl}-2,6-difluorobenzamide to give 7.1 g of the title compound. MS (ESI): M+H=487.05.

Step B: (title compound) 2,5-Difluoro-N-(3-{3-[2-(phenylamino)-4-pyrimidinyl]pyrazolo[1,5-a]pyridin-2-yl}phenyl)benzamide

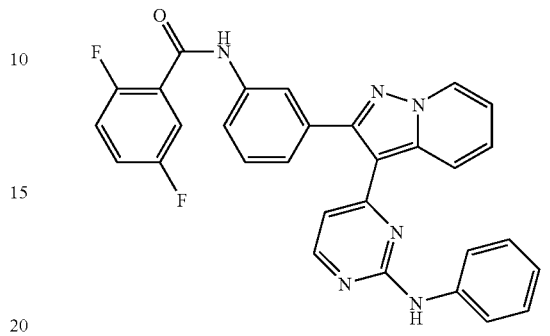

N-{3-[3-(2-Chloro-4-pyrimidinyl)pyrazolo[1,5-a]pyridin-2-yl]phenyl}-2,5-difluorobenzamide and aniline were reacted according to a procedure similar to that used in Example 27, Step D, to give the title compound, MS (ESI): M+H=519.15.

Example 44

2,5-Difluoro-N-{3-[3-(2-{[3-(1,3-oxazol-5-yl)phenyl]amino}-4-pyrimidinyl)pyrazolo[1,5-a]pyridin-2-yl]phenyl}benzamide

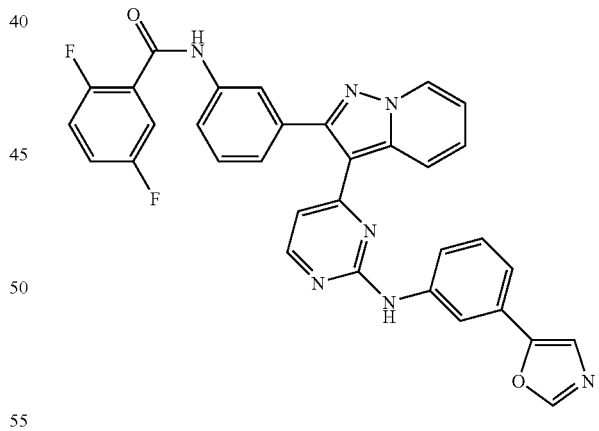

N-{3-[3-(2-Chloro-4-pyrimidinyl)pyrazolo[1,5-a]pyridin-2-yl]phenyl}-2,5-difluorobenzamide and 3-(1,3-oxazol-5-yl)aniline were reacted in a manner analogous to Example 27, Step D, to give the title compound. $^1$H NMR (400 MHz, DMSO-d$_6$) δ 10.63 (s, 1H), 9.73 (s, 1H), 8.85 (d, 1H), 8.53 (d, 1H), 8.39 (s, 1H), 8.30 (m, 1H), 8.20 (s, 1H), 8.03 (s, 1H), 7.86 (d, 1H), 7.72 (d, 1H), 7.63-7.26 (m, 9H), 7.12 (m, 1H), 6.54 (m, 1H). HRMS calculated $C_{33}H_{22}F_2N_7O_2$ [M+H]$^+$ 586.1803, found 586.1799.

Example 45

2,5-Difluoro-N-{3-[3-(2-{[4-(4-morpholinyl)phenyl]amino}-4-pyrimidinyl)pyrazolo[1,5-a]pyridin-2-yl]phenyl}benzamide

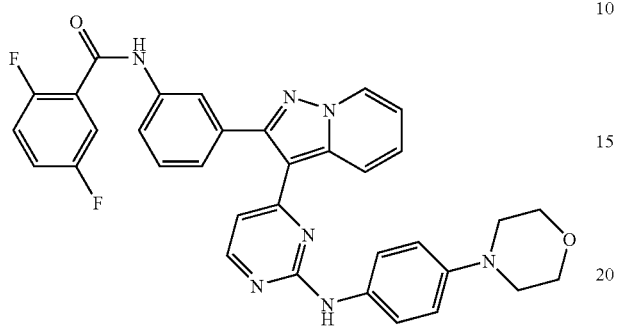

N-{3-[3-(2-Chloro-4-pyrimidinyl)pyrazolo[1,5-a]pyridin-2-yl]phenyl}-2,5-difluorobenzamide and 4-(4-morpholinyl)aniline were reacted in a manner analogous to Example 27, Step D, to give the title compound. $^1$H NMR (400 MHz, DMSO-d$_6$) δ 10.64 (s, 1H), 9.28 (s, 1H), 8.84 (d, 1H), 8.41 (s, 1H), 8.21 (d, 1H), 8.03 (s, 1H), 7.84 (d, 1H), 7.67-7.36 (m, 7H), 7.32 (d, 1H), 7.11 (t, 1H), 6.84 (d, 2H), 6.49 (m, 1H), 3.70 (s, 4H), 3.02 (s, 4H). HRMS calculated C$_{34}$H$_{28}$F$_2$N$_7$O$_2$ [M+H]$^+$ 604.2273, found 604.2269.

Example 46

2,5-Difluoro-N-{3-[3-(2-{[3-fluoro-4-(methyloxy)phenyl]amino}-4-pyrimidinyl)pyrazolo[1,5-a]pyridin-2-yl]phenyl}benzamide

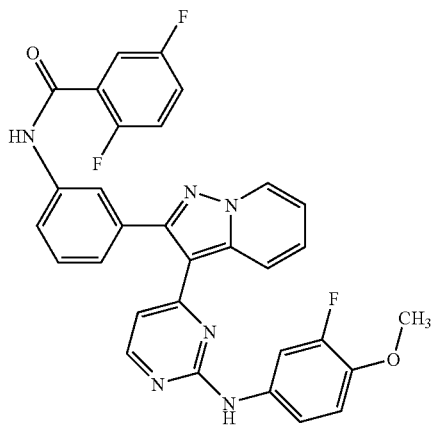

N-{3-[3-(2-Chloro-4-pyrimidinyl)pyrazolo[1,5-a]pyridin-2-yl]phenyl}-2,5-difluorobenzamide and 3-fluoro-4-(methyloxy)aniline were reacted in a manner analogous to Example 27, Step D, to give the title compound. MS (ESI): M+H=567.18.

Example 47

N-{3-[3-(2-{[3-(acetylamino)phenyl]amino}-4-pyrimidinyl)pyrazolo[1,5-a]pyridin-2-yl]phenyl}-2,5-difluorobenzamide

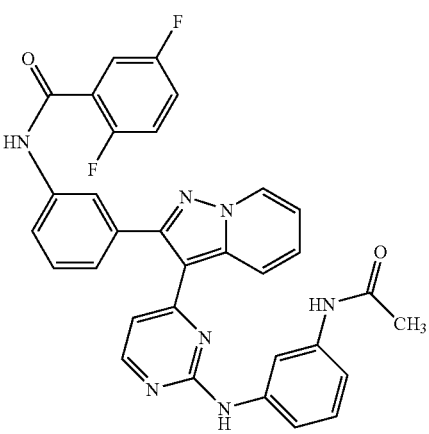

N-{3-[3-(2-Chloro-4-pyrimidinyl)pyrazolo[1,5-a]pyridin-2-yl]phenyl}-2,5-difluorobenzamide and N-(3-aminophenyl)acetamide were reacted in a manner analogous to Example 27, Step D, to give the title compound. MS (ESI): M+H=576.19.

Example 48

N-[3-(3-{2-[(3-Cyanophenyl)amino]-4-pyrimidinyl}pyrazolo[1,5-a]pyridin-2-yl)phenyl]-2,5-difluorobenzamide

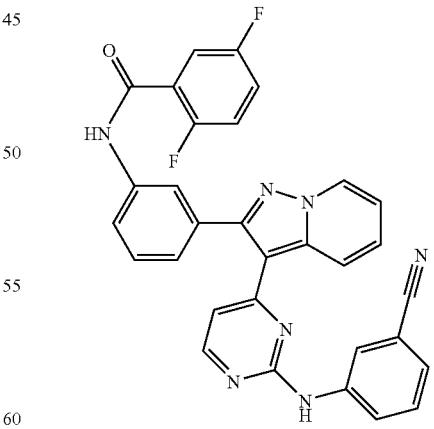

N-{3-[3-(2-Chloro-4-pyrimidinyl)pyrazolo[1,5-a]pyridin-2-yl]phenyl}-2,5-difluorobenzamide and 3-(cyanophenyl)amine were reacted in a manner analogous to Example 27, Step D, to give the title compound. MS (ESI): M+H=544.36.

Example 49

2,5-Difluoro-N-{3-[3-(2-{[3-(2-oxo-1-pyrrolidinyl)phenyl]amino}-4-pyrimidinyl)pyrazolo[1,5-a]pyridin-2-yl]phenyl}benzamide

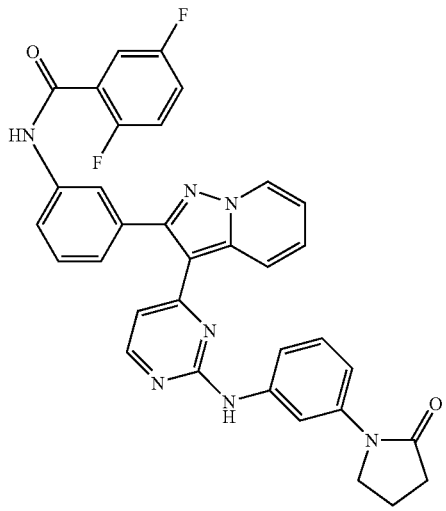

N-{3-[3-(2-Chloro-4-pyrimidinyl)pyrazolo[1,5-a]pyridin-2-yl]phenyl}-2,5-difluorobenzamide and 1-(3-aminophenyl)-2-pyrrolidinone were reacted in a manner analogous to Example 27, Step D, to give the title compound. MS (ESI): M+H=602.14.

Example 50

2,5-Difluoro-N-{3-[3-(2-{[4-(2-oxo-1-pyrrolidinyl)phenyl]amino}-4-pyrimidinyl)pyrazolo[1,5-a]pyridin-2-yl]phenyl}benzamide

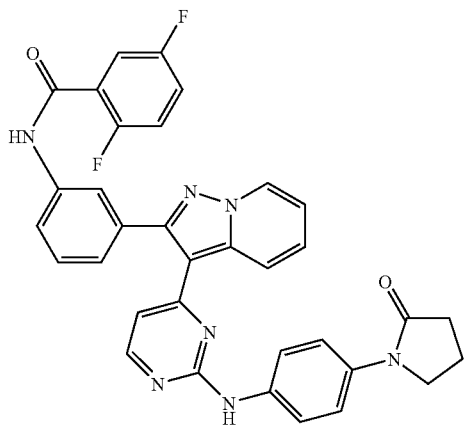

N-{3-[3-(2-Chloro-4-pyrimidinyl)pyrazolo[1,5-a]pyridin-2-yl]phenyl}-2,5-difluorobenzamide and 1-(4-aminophenyl)-2-pyrrolidinone were reacted in a manner analogous to Example 27, Step D, to give the title compound. MS (ESI): M+H=602.16.

Example 51

N-(3-{3-[2-({4-[(ethylsulfonyl)methyl]phenyl}amino)-4-pyrimidinyl]pyrazolo[1,5-a]pyridin-2-yl}phenyl)-2,5-difluorobenzamide

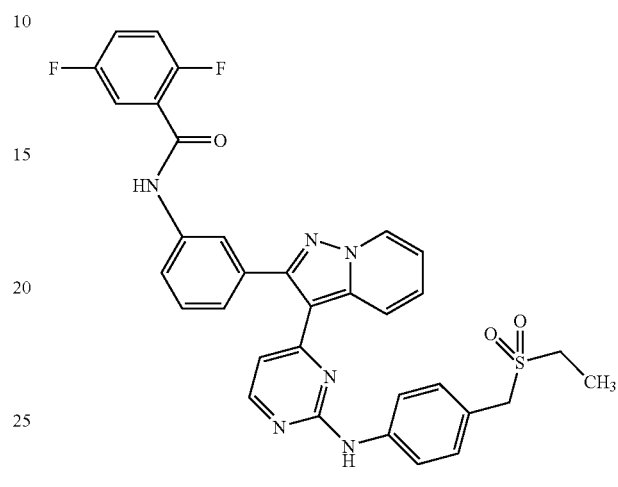

N-{3-[3-(2-Chloro-4-pyrimidinyl)pyrazolo[1,5-a]pyridin-2-yl]phenyl}-2,5-difluorobenzamide and 4-[(ethylsulfonyl)methyl]aniline were reacted in a manner analogous to Example 27, Step D, to give the title compound. MS (ESI): M+H=625.24.

Example 52

N-{3-[3-(2-{[3-(Aminosulfonyl)-4-methylphenyl]amino}-4-pyrimidinyl)pyrazolo[1,5-a]pyridin-2-yl]phenyl}-2,5-difluorobenzamide

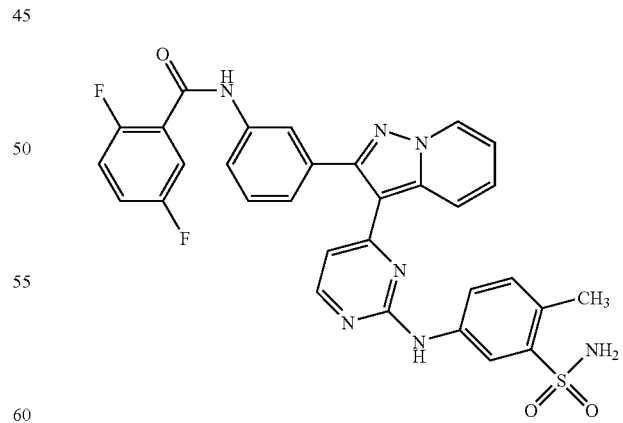

N-{3-[3-(2-Chloro-4-pyrimidinyl)pyrazolo[1,5-a]pyridin-2-yl]phenyl}-2,5-difluorobenzamide and 5-amino-2-methylbenzenesulfonamide were reacted in a manner analogous to Example 27, Step D, to give the title compound. MS (ESI): M+H=612.20.

Example 53

2,5-Difluoro-N-(3-{3-[2-({4-[(methylsulfonyl)methyl]-phenyl}amino)-4-pyrimidinyl]pyrazolo[1,5-a]pyridin-2-yl}phenyl)benzamide

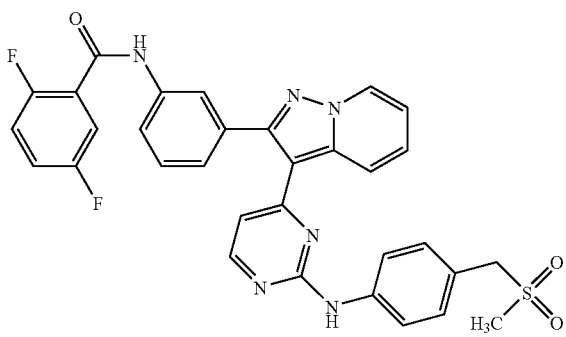

N-{3-[3-(2-Chloro-4-pyrimidinyl)pyrazolo[1,5-a]pyridin-2-yl]phenyl}-2,5-difluorobenzamide and 4-[(methylsulfonyl)methyl]aniline were reacted in a manner analogous to Example 27, Step D, to give the title compound. MS (ESI): M+H=611.14.

Example 54

2,6-Difluoro-N-(3-{3-[2-({3-[2-(4-morpholinyl)ethyl]-phenyl}amino)-4-pyrimidinyl]pyrazolo[1,5-a]pyridin-2-yl}phenyl)benzamide

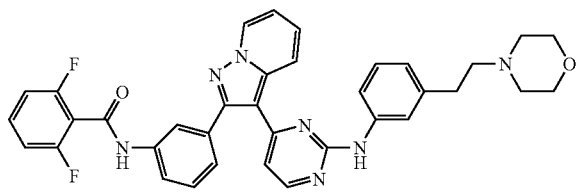

The title compound was prepared by reacting N-{3-[3-(2-Chloro-4-pyrimidinyl)pyrazolo[1,5-a]pyridin-2-yl]phenyl}-2,6-difluorobenzamide and {3-[3-(4-morpholinyl)propyl]phenyl}amine in a manner analogous to Example 27, Step D, to give the title compound. $^1$H NMR (400 MHz, DMSO-d$_6$): δ 10.93 (s, 1H), 9.49 (s, 1H), 8.85 (d, 1H), 8.48 (d, 1H), 8.26 (d, 1H), 8.01 (s, 1H), 7.82 (d, 1H), 7.66 (s, 1H), 7.58 (m, 1H), 7.48 (m, 3H), 7.36 (d, 1H), 7.24 (m, 2H), 7.17-7.05 (m, 2H), 6.81 (d, 1H), 6.52 (d, 1H), 3.53 (s, 4H), 2.67 (m, 2H), 2.40 (2H), 2.35 (m, 4H). HRMS calculated C$_{36}$H$_{32}$F$_2$N$_7$O$_2$ [M+H]$^+$ 632.2586, found 632.2581.

Example 55

2,6-Difluoro-N-(3-{3-[2-({3-[3-(4-morpholinyl)propyl]-phenyl}amino)-4-pyrimidinyl]pyrazolo[1,5-a]pyridin-2-yl}phenyl)benzamide

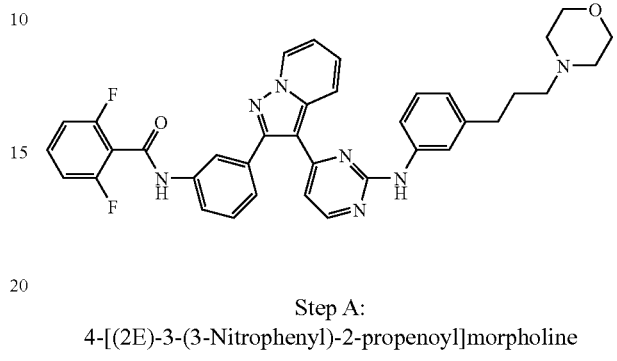

Step A: 4-[(2E)-3-(3-Nitrophenyl)-2-propenoyl]morpholine

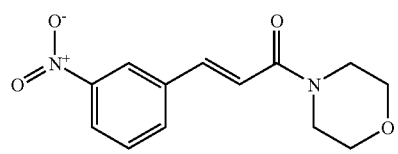

(2E)-3-(3-Nitrophenyl)-2-propenoic acid (1.0 g, 5.2 mmol), morpholine (1.8 mL, 20.7 mmol), 1-(3-Dimethylaminopropyl)-3-ethylcarbodiimide hydrochloride (1.5 g, 7.8 mmol), 1-Hydroxy-7-azabenzotriazole (1.1 g, 7.8 mmol) and anhydrous DMF (50 mL) were stirred under a nitrogen at rt for 15 h. The solvent was removed under vacuum and the residue was dissolved in DCM. The solution was washed with 5% aqueous sodium hydrogen sulfate, saturated aqueous NaHCO$_3$, brine and dried over MgSO$_4$. The reaction was concentrated under vacuum, yielding 1.1 g (81%) of the title compound, a light yellow solid. $^1$H NMR (400 MHz, DMSO-d$_6$) δ 8.62 (m, 1H), 8.19 (dd, 1H), 8.16 (d, 1H), 7.69 (t, 1H), 7.55 (dd, 2H), 3.75 (m, 2H), 3.60 (m, 4H), 3.57 (m, 2H).

Step B: {3-[3-(4-Morpholinyl)-3-oxopropyl]phenyl}amine

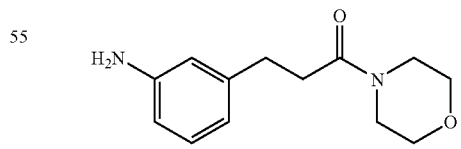

4-[(2E)-3-(3-nitrophenyl)-2-propenoyl]morpholine (200 mg, 0.76 mmol) and 10% Pd on carbon (50 mg) were stirred vigorously in MeOH (10 mL) under an atmosphere of hydrogen. The reaction stirred at rt for 15 h. The suspension was filtered through Celite and concentrated to yield 120 mg (67%) of the title compound, a pink oil. $^1$H NMR (400 MHz, DMSO-d$_6$): δ 6.88 (t, 1H), 6.34 (d, 2H), 5.75 (s, 1H), 4.91 (s, 2H), 3.44 (m, 8H), 2.63 (m, 2H), 2.51 (m, 2H).

Step C: {3-[3-(4-Morpholinyl)propyl]phenyl}amine

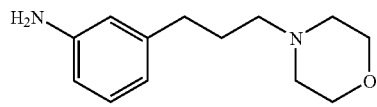

A solution of 1M lithium aluminum hydride in THF (2.6 mL) was injected into a stirred suspension of {3-[3-(4-morpholinyl)-3-oxopropyl]phenyl}amine (120 mg, 0.51 mmol) in anhydrous THF (5 mL). The reaction was refluxed for 1 h under nitrogen. The suspension was cooled to 0° C. and quenched by careful addition of 1N NaOH. The base was added until gas evolution stopped. The reaction was concentrated to a white solid under vacuum, triturated with diethyl ether and filtered. The filtrate was concentrated under vacuum to 113 mg (89%) of the title compound, a clear oil. MS (ESI): M+H=221.17.

Step D: 2,6-Difluoro-N-(3-{3-[2-({3-[3-(4-morpholinyl)propyl]phenyl}amino)-4-pyrimidinyl]pyrazolo[1,5-a]pyridin-2-yl}phenyl)benzamide (title compound)

N-{3-[3-(2-Chloro-4-pyrimidinyl)pyrazolo[1,5-a]pyridin-2-yl]phenyl}-2,6-difluorobenzamide and {3-[3-(4-morpholinyl)propyl]phenyl}amine were reacted in a manner analogous to Example 27, Step D, to give the title compound. MS (ESI): M+H=646.27.

Example 56

2,6-Difluoro-N-(3-{3-[2-({4-[2-(4-morpholinyl)ethyl]-phenyl}amino)-4-pyrimidinyl]pyrazolo[1,5-a]pyridin-2-yl}phenyl)benzamide

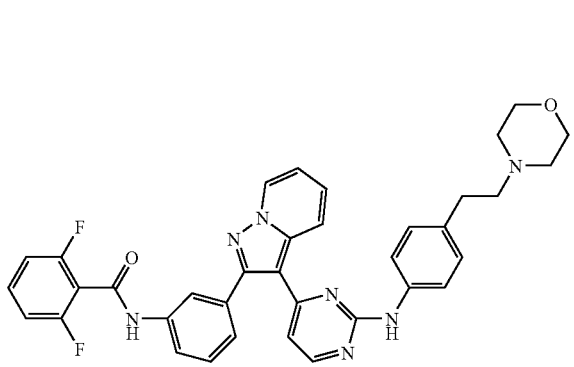

N-{3-[3-(2-Chloro-4-pyrimidinyl)pyrazolo[1,5-a]pyridin-2-yl]phenyl}-2,6-difluorobenzamide and 4-[2-(4-morpholinyl)ethyl]aniline were reacted in a manner analogous to Example 27, Step D, to give the title compound. MS (ESI): M+H=632.25.

Example 57

2,6-Difluoro-N-(3-{3-[2-({3-[(4-methyl-1-piperazinyl)-methyl]phenyl}amino)-4-pyrimidinyl]pyrazolo[1,5-a]pyridin-2-yl}phenyl)benzamide

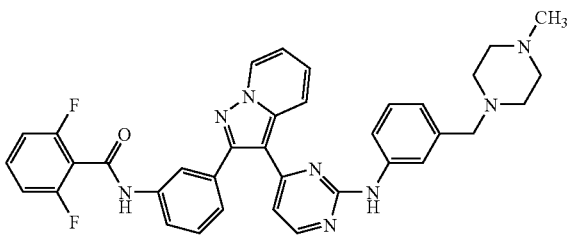

N-{3-[3-(2-Chloro-4-pyrimidinyl)pyrazolo[1,5-a]pyridin-2-yl]phenyl}-2,6-difluorobenzamide and 3-[(4-methyl-1-piperazinyl)methyl]aniline were reacted in a manner analogous to Example 27, Step D, to give the title compound. MS (ESI): M+H=631.27.

Example 58

2,6-Difluoro-N-(3-{3-[2-({3-[(2-hydroxyethyl)sulfonyl]-phenyl}amino)-4-pyrimidinyl]pyrazolo[1,5-a]pyridin-2-yl}phenyl)benzamide

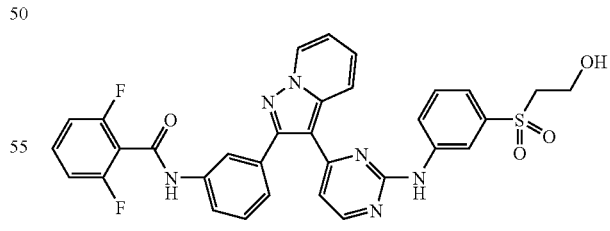

N-{3-[3-(2-Chloro-4-pyrimidinyl)pyrazolo[1,5-a]pyridin-2-yl]phenyl}-2,6-difluorobenzamide and 2-[(3-aminophenyl)sulfonyl]ethanol were reacted in a manner analogous to Example 27, Step D, to give the title compound. MS (ESI): M+H=627.15.

Example 59

2,6-Difluoro-N-[3-(3-{2-[(3-hydroxyphenyl)amino]-4-pyrimidinyl}pyrazolo[1,5-a]pyridin-2-yl)phenyl]benzamide

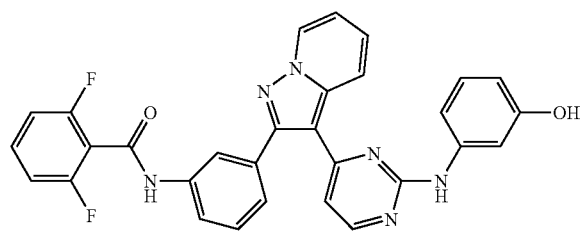

N-{3-[3-(2-Chloro-4-pyrimidinyl)pyrazolo[1,5-a]pyridin-2-yl]phenyl}-2,6-difluorobenzamide and 3-aminophenol were reacted in a manner analogous to Example 27, Step D, to give the title compound. MS (ESI): M+H=535.17.

Example 60

2,6-Difluoro-N-[3-(3-{2-[(3-{[2-(4-morpholinyl)ethyl]-oxy}phenyl)amino]-4-pyrimidinyl}pyrazolo[1,5-a]pyridin-2-yl)phenyl]benzamide

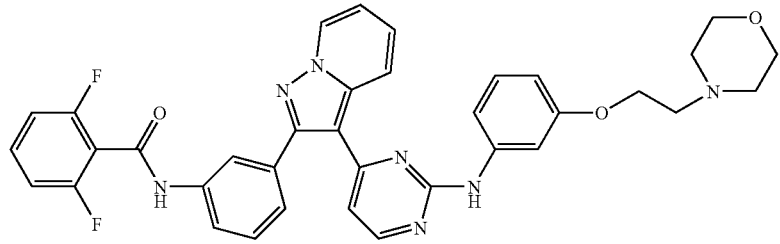

Step A: (3-{[2-(4-morpholinyl)ethyl]oxy}phenyl)amine

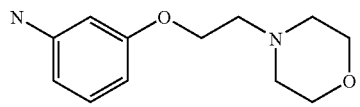

Di-tert-butylazodicarboxylate (1.58 g, 6.9 mmol) was added to a solution of 3-aminophenol (500 mg, 4.6 mmol), 2-(4-morpholinyl)ethanol (556 µL, 4.6 mmol), polymer-bound triphenylphosphine (2.29 g, 6.9 mmol) and anhydrous THF (100 mL). The reaction stirred for 15 h at rt. The reaction mixture was filtered through Celite and the filtrate was concentrated under vacuum. The residue was dissolved in neat TFA and stirred for 1 h at rt. The TFA was removed under vacuum and the residue was partitioned between EtOAc and saturated aqueous NaHCO$_3$, washed with brine and dried over magnesium sulfate. The crude material was purified by silica gel chromatography (0-20% MeOH/EtOAc). Purification yielded 500 mg (49%) of the title compound, a red oil. $^1$H NMR (400 MHz, DMSO-d$_6$) δ 6.86 (t, 1H), 6.12 (d, 1H), 6.11 (s, 1H), 6.06 (d, 1H), 5.00 (s, 2H), 3.95 (t, 2H), 3.56 (m, 4H), 2.63 (t, 2H), 2.44 (m, 4H).

Step B: 2,6-Difluoro-N-[3-(3-{2-[(3-{[2-(4-morpholinyl)ethyl]oxy}phenyl)amino]-4-pyrimidinyl}pyrazolo[1,5-a]pyridin-2-yl)phenyl]benzamide (title compound)

The title compound was prepared from (3-{[2-(4-morpholinyl)ethyl]oxy}phenyl)-amine and N-{3-[3-(2-chloro-4-pyrimidinyl)pyrazolo[1,5-a]pyridin-2-yl]phenyl}-2,6-difluorobenzamide in a manner analogous to Example 27, Step D. $^1$H NMR (400 MHz, DMSO-d$_6$) δ 10.94 (s, 1H), 9.55 (s, 1H), 8.84 (d, 1H), 8.48 (d, 1H), 8.27 (d, 1H), 8.01 (s, 1H), 7.81 (d, 1H), 7.59 (m, 1H), 7.49 (m, 3H), 7.35 (d, 1H), 7.25 (m, 3H), 7.13 (t, 2H), 6.51 (d, 2H), 4.0 (m, 2H), 3.54 (m, 4H), 2.64 (m, 2H), 2.41 (m, 4H). HRMS calculated C$_{36}$H$_{32}$F$_2$N$_7$O$_3$ [M+H]$^+$ 648.2535, found 648.2528.

Example 61

N-[3-(3-{2-[(3-{[2-(Dimethylamino)ethyl]oxy}-phenyl)amino]-4-pyrimidinyl}pyrazolo[1,5-a]pyridin-2-yl)phenyl]-2,6-difluorobenzamide

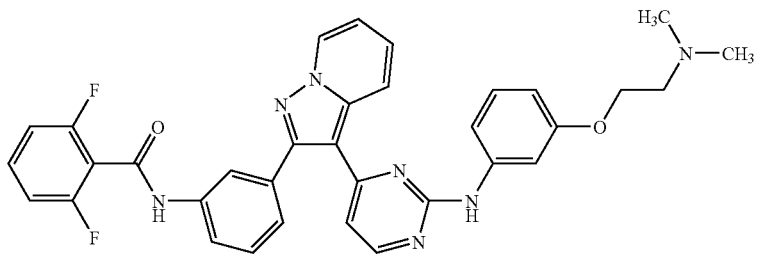

The title compound was prepared by heating N-{3-[3-(2-chloro-4-pyrimidinyl)pyrazolo[1,5-a]pyridin-2-yl]phenyl}-2,6-difluorobenzamide (100 mg, 0.22 mmol) and 3-{[2-(dimethylamino)ethyl]oxy}aniline (39 mg, 0.22 mmol) in i-PrOH for 38 min and partitioning the reaction mixture between EtOAc and saturated aqueous NaHCO$_3$. The aqueous layer was washed with brine, dried over MgSO$_4$, filtered and concentrated to leave a residue that was purified by silica gel chromatography (0 to 30% MeOH in EtOAc) to afford the title compound. LC MS (ES)+=606.27. $^1$H NMR (400 MHz, DMSO-d$_6$) δ 2.15 (s, 6H), 2.55 (t, 2H, J=5.8), 3.94 (t, 1H, J=5.8), 6.50 (d, 2H, J=5.5), 7.11 (t, 1H, J=6.3), 7.13-7.25 (m, 3H), 7.34 (d, 1H, J=7.7), 7.44-7.49 (m, 3H), 7.53-7.60 (m, 1H), 7.80 (d, 1H, J=8.0), 7.98 (s, 1H, 8.25 (d, 1H, J=5.3), 8.48 (d, 1H, J=9.0), 8.83 (d, 1H, J=6.7), 9.52 (s, 1H).

Example 62

N-(3-{3-[2-(1,2,3,4-Tetrahydro-7-isoquinolinylamino)-4-pyrimidinyl]pyrazolo[1,5-a]pyridin-2-yl}phenyl)benzamide

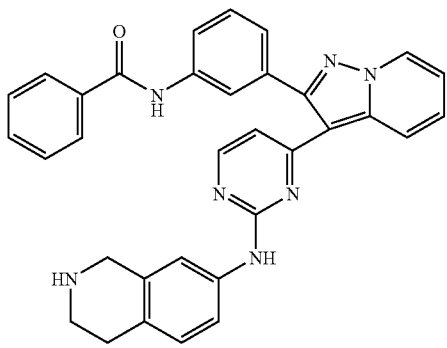

Step A: 2,2,2-Trifluoro-N-[2-(4-nitrophenyl)ethyl]acetamide

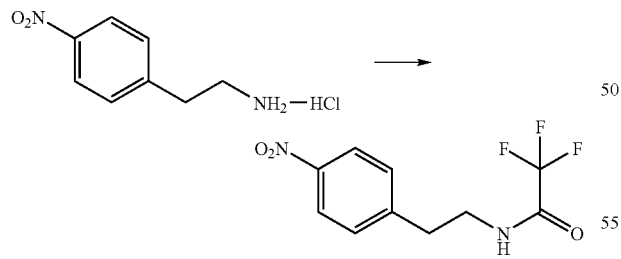

A solution of 4-nitrophenethylamine hydrochloride (4.05 g, 20 mmol) in pyridine (80 mL) was cooled to 0° C. To this solution, trifluoroacetic anhydride (3.11 mL, 22 mmol) was added dropwise. The reaction mixture was stirred for 30 min at 0° C. The mixture was poured into 5% NaHCO$_3$ aq and extracted with EtOAc. The organic layer was combined, washed with brine and dried (Na$_2$SO$_4$). The solvent was reduced under pressure. The residue was recrystallized with Hex/EtOAc to give the amide (5.56 g) as white solid.

Step B: 7-Nitro-2-(trifluoroacetyl)-1,2,3,4-tetrahydroisoquinoline

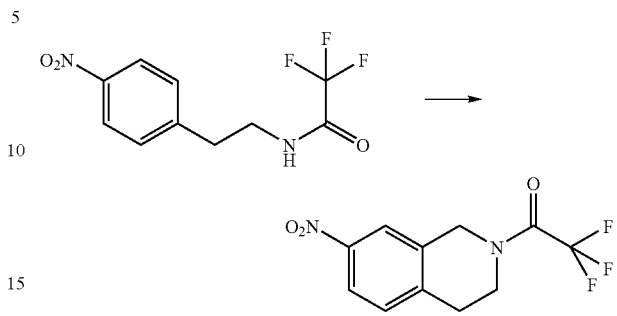

A mixture of 2,2,2-trifluoro-N-[2-(4-nitrophenyl)ethyl]acetamide (2.5 g, 9.54 mmol) and paraformaldehyde (447 mg, 14.3 mmol) was added to a solution of acetic acid (10 mL) in sulfuric acid (15 mL) at rt. After stirring for 16 h the reaction mixture was poured into ice-H$_2$O. The gummy residue was extracted with EtOAc and the organic layer was washed with sat. NaHCO$_3$, brine, dried (Mg$_2$SO$_4$) and evaporated. The residue was chromatographed on silica gel (Hex/EtOAc=4/1 to 2/1) to afford cyclic amide (2.47 g).

Step C: 2-(Trifluoroacetyl)-1,2,3,4-tetrahydro-7-isoquinolinamine

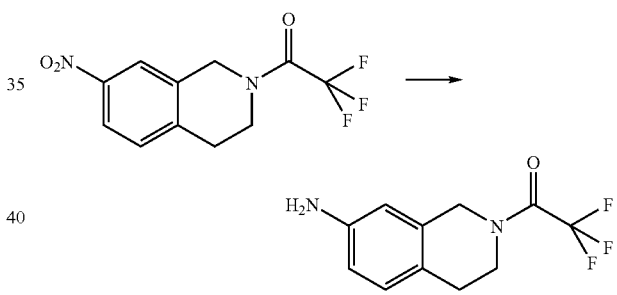

A mixture of 2-(trifluoroacetyl)-1,2,3,4-tetrahydro-7-isoquinolinamine (2.45 g) and 10% Pd/C (200 mg) in EtOH (90 mL) was stirred for 16 h under hydrogen atmosphere. The reaction mixture was filtered and the filtrate was evaporated in vacuo. Chromatography on silica gel eluting with Hex/EtOAc gradient (50%-100%) gave desired aniline (1.95 g).

Step D: N-{3-[3-(2-Chloro-4-pyrimidinyl)pyrazolo[1,5-a]pyridin-2-yl]phenyl}-benzamide

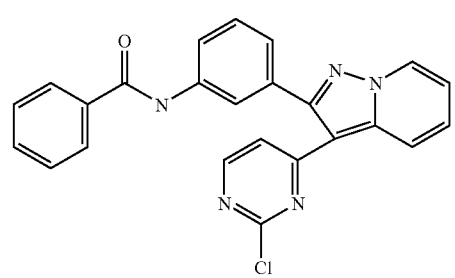

To a solution of {3-[3-(2-chloro-4-pyrimidinyl)pyrazolo[1,5-a]pyridin-2-yl]phenyl}amine (211.9 mg, 0.658 mmol) in THF (3.0 mL) was added under N₂ benzoyl chloride (107 mL, 0.921 mmol) dropwise. The mixture became a slurry and was allowed to stir for 16 h. PS-Trisamine (283 mg) was added and the mixture was stirred for 3 h. The mixture was filtered and the filtrate was concentrated to give 281 mg of crude product. Purification by silica gel chromatography (0 to 50% EtOAC gradient in hexanes) gave 152.2 mg of the title compound as a white solid. LCMS (ES)+=426.1 ¹H NMR (400, DMSO-$d_6$) δ 7.06 (d, 1H, J=5.6), 7.20 (t, 1H, J=6.8), 7.31 (d, 1H, J=7.2), 7.46-7.52 (m, 3H), 7.56 (d, 1H, J=6.8), 7.63 (t, 1H, J=6.8), 7.91-7.97 (m, 2H), 8.06 (s, 1H), 8.41 (d, 1H, J=8.8), 8.45 (d, 1H, J=5.2), 8.89 (d, 1H, J=6.8), 10.38 (s, 1H).

Step E: N-{3-[3-(2-{[2-(2,2,2-Trifluoroacetyl)-1,2,3,4-tetrahydro-7-isoquinolinyl]amino}-4-pyrimidinyl)pyrazolo[1,5-a]pyridin-2-yl]phenyl}benzamide

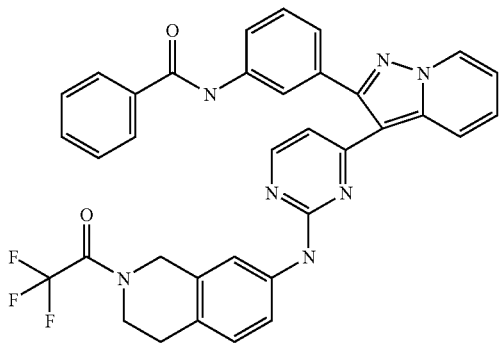

A mixture of 2-(trifluoroacetyl)-1,2,3,4-tetrahydro-7-isoquinolinamine (188 mg, 0.669 mmol), N-{3-[3-(2-chloro-4-pyrimidinyl)pyrazolo[1,5-a]pyridin-2-yl]phenyl}benzamide (229 mg, 0.538 mmol), conc HCl (1 drop) in isopropanol (4.0 mL) was heated at 85° C. for 16 h. The mixture was allowed to cool to rt and worked up according to earlier examples to obtain the crude material that was purified by silica gel chromatography (eluting with 0 to 50% EtOAc in hexanes) to afford 191 mg of the title compound as a brown solid. LCMS (ES)+ 634.2.

Step F: N-(3-{3-[2-(1,2,3,4-tetrahydro-7-isoquinolinylamino)-4-pyrimidinyl]-pyrazolo[1,5-a]pyridin-2-yl}phenyl)benzamide (title compound)

To a solution of N-{3-[3-(2-{[2-(2,2,2-Trifluoroacetyl)-1,2,3,4-tetrahydro-7-isoquinolinyl]amino}-4-pyrimidinyl)pyrazolo[1,5-a]pyridin-2-yl]phenyl}benzamide (191 mg, 0.30 mmol) in THF (4.0 mL) was added a solution of LiOH·H₂O (19.8 mg, 0.47 mmol) in H₂O (1.5 mL). The mixture was stirred at rt for 30 min. The mixture was partitioned between saturated aq. NaHCO₃ and 5:1 CHCl₃/isopropanol. The organic layer was separated, dried over Na₂SO₄, filtered and concentrated to give 191 mg of crude product. Purification by silica gel chromatography (0 to 40% sat. ammonia/MeOH in EtOAc) afforded 163.2 mg of the title compound as a white powder. LCMS ((ES)+ 538.3. ¹H NMR (400, DMSO-$d_6$) δ 2.63 (t, 2H, J=5.6), 2.96 (t, 2H, J=5.6), 3.80 (s, 2H), 6.46 (d, 1H, J=5.2), 6.95 (d, 1H, J-=8.4), 7.11 (t, 1H, J=6.4), 7.29 (d, 1H, J=8.0), 7.36 (d, 1H, J=9.2), 7.43-7.57 (m, 5H), 7.93 (d, 2H, J=7.2), 8.09 (s, 1H), 8.21 (d, 1H, J=5.6), 8.49 (d, 1H, J=8.8), 8.82 (d, 1H, J=6.8), 9.41 (s, 1H), 10.37 (s, 1H).

Example 63

N-[3-(3-{2-[(2-methyl-1,2,3,4-tetrahydro-7-isoquinolinyl)amino]-4-pyrimidinyl}pyrazolo[1,5-a]pyridin-2-yl)phenyl]benzamide

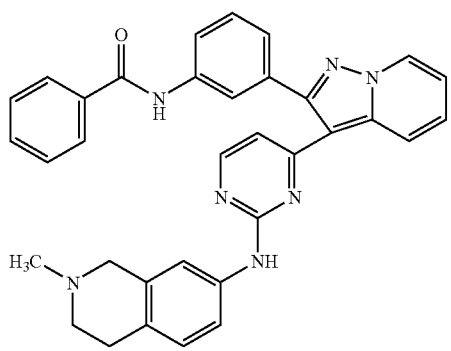

To a solution of N-(3-{3-[2-(1,2,3,4-tetrahydro-7-isoquinolinylamino)-4-pyrimidinyl]pyrazolo[1,5-a]pyridin-2-yl}phenyl)benzamide (107 mg, 0.199 mmol) in 2:1 DCM/MeOH (1.5 mL) was added 37% aq. formaldehyde (50 μL, 0.67 mmol), glacial acetic acid (13 μL) and sodium triacetoxyborohydride (64 mg, 0.30 mmol). The mixture was stirred at rt for 1 h. The mixture was worked up by removal of solvent with a totary evaporator and partitioning the residue between saturated aq. NaHCO₃ and 5:1 CHCl₃/isopropanol. The organic layer was separated, dried and concentrated to give 67 mg of crude material. Purification by silica gel chromatography (0 to 30% methanol in DCM) afforded 60.4 mg of the title compound as a cream-colored solid. LCMS (ES)+ 552.3. ¹H NMR (400 MHz, DMSO-$d_6$) δ 2.47 (s, 3H), 2.57 (bs, 2H), 2.72 (m, 2H), 3.39 (s, 2H), 6.49 (d, 1H, J=5.6), 6.95 (d, 1H, J=8.0, 7.10 (t, 1H, J=6.8), 7.28 (d, 1H, J=8.0), 7.37 (d, 1H, J=8.0), 7.42-7.56 (m, 5H), 7.93 (d, 2H, J=7.2), 8.11 (s, 1H), 8.22 (d, 1H, J=5.6), 8.45 (d, 1H, J=8.8), 8.81 (d, 1H, J=7.2, 9.41 (s, 1H), 10.37 (s, 1H).

Example 64

2,6-Difluoro-N-(3-{3-[2-(1,2,3,4-tetrahydro-7-isoquinolinylamino)-4-pyrimidinyl]pyrazolo[1,5-a]pyridin-2-yl}phenyl)benzamide

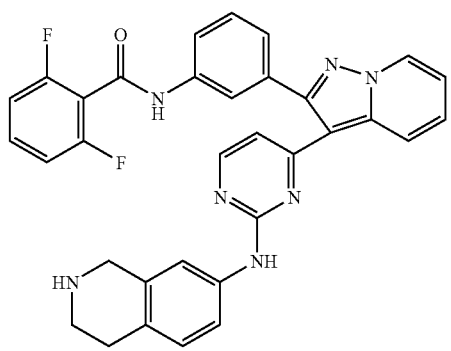

A mixture of N-{3-[3-(2-chloro-4-pyrimidinyl)pyrazolo[1,5-a]pyridin-2-yl]phenyl}-2,6-difluorobenzamide (200 mg, 0.43 mmol) and 2-(trifluoroacetyl)-1,2,3,4-tetrahydro-7-isoquinolinamine (211 mg, 0.86 mmol) in a few mL i-PrOH was heated in a microwave apparatus at 160° C. until the reaction was complete. The by partitioning the reaction mixture between saturated aqueous NaHCO$_3$ and CHCl$_3$. The organic layer was washed with brine, dried over Na$_2$SO$_4$, filtered and concentrated to give a residue that was purified by silica gel chromatography to afford the intermediate trifluoroacetamide pyrazolopyridazine (350 mg). A portion of this material (250 mg) was subjected to similar conditions as described in Example 62, step F to afford the title compound (198 mg) as a tan powder. LC-MS (AP)+=574.07. $^1$H NMR (400 MHz, DMSO-d$_6$) δ 2.59 (t, 2H, J=5.5), 2.89 (t, 2H, J=5.5), 3.74 (s, 2H), 6.46 (d, 1H, J=5.1), 6.90 (d, 1H, J=8.2), 7.10 (t, 1H, J=6.7), 7.22 (d, 1H, J=8.0), 7.24 (d, 1H, J=7.9), 7.32 (s, 1H, 7.34 (s, 1H), 7.44-7.48 (m, 3H), 7.53-7.60 (m, 1H), 7.80 (d, 1H, J=8.0), 7.97 (s, 1H), 8.21 (d, 1H, J=5.3), 8.46 (d, 1H, J=9.1), 8.82 (d, 1H, J=6.7), 9.37 (s, 1H).

Example 65

2,6-Difluoro-N-(3-{3-[2-(6-isoquinolinylamino)-4-pyrimidinyl]pyrazolo[1,5-a]pyridin-2-yl}phenyl)benzamide

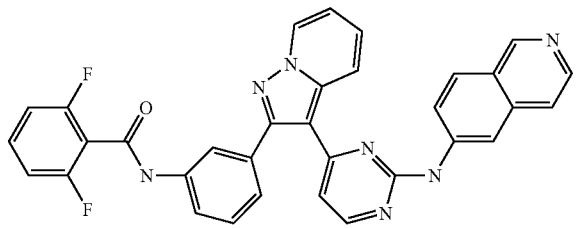

A mixture of N-{3-[3-(2-chloro-4-pyrimidinyl)pyrazolo[1,5-a]pyridin-2-yl]phenyl}-2,6-difluorobenzamide and 6-isoquinolinamine and 6-isoquinolinamine in i-PrOH was heated in a microwave in a procedure analogous to that described in Example 64 to give, after purification, the title compound. LC MS (ES)+ 570.25. $^1$H NMR (400 MHz, DMSO-d$_6$) δ 6.95 (s, 1H), 7.17-7.30 (m, 4H), 7.41 (d, 1H, J=7.5), 7.51-7.56 (m, 3H), 7.64 7.68 (m, 1H), 7.78-7.81 (m, 2H), 8.05 (s, 1H), 8.09 (bs, 2H), 8.19 (d, 1H, J=9.1), 8.41 (d, 1H, J=9.0), 8.85-8.89 (m, 2H), 8.96 (d, 1H, J=6.8), 9.8 (s, 1H), 10.94 (s, 1H).

Example 66

N-[3-(3-{2-[(3-fluorophenyl)amino]-4-pyrimidinyl}pyrazolo[1,5-a]pyridin-2-yl)phenyl]-3-pyridinecarboxamide

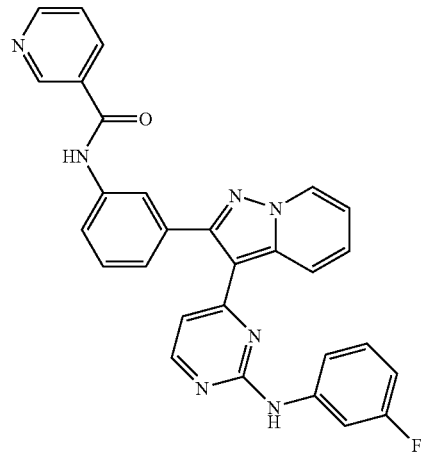

To a solution of 100 mg (0.25 mmol) of 4-[2-(3-aminophenyl)pyrazolo[1,5-a]pyridin-3-yl]-N-(3-fluorophenyl)-2-pyrimidinamine in THF at rt was added 63 mg (0.353 mmol) of 3-pyridinecarbonyl chloride. The reaction mixture was allowed to stir for 30 min. At this time, 3.0 eq of PS-Trisamine resin was added and the resulting slurry was allowed to stir overnight. Excess triethylamine was added and the resin was removed by filtration. The reaction mixture was concentrated to dryness and the product was triturated from DCM to give 20 mg of the title compound as a yellow solid: $^1$H-NMR (d$_6$-DMSO, 400 MHz) δ 6.59 (d, 1H, J=5.5 Hz), 6.73 (td, 1H, J=7.9 and 2.5 Hz), 7.14 (td, 1H, J=7.0 and 1.5 Hz), 7.26 (dd, 1H, J=15.2 and 6.9 Hz), 7.35 (d, 1H, J=7.6 Hz), 7.45-7.58 (m, 4H), 7.80 (d, 1H, J=12.0 Hz), 7.95 (d, 1H, J=8.2 Hz), 8.10 (s, 1H), 8.29 (d, 1H, J=8.6 Hz), 8.32 (d, 1H, J=5.4 Hz), 8.50 (d, 1H, J=8.6 Hz), 8.76 (dd, 1H, J=4.7 and 1.5 Hz), 8.86 (d, 1H, J=7.1 Hz), 9.10 (s, 1H), 9.81 (s, 1H), and 10.57 (s, 1H); HRMS calcd for C$_{29}$H$_{20}$FN$_7$O: 501.1713, found: 502.1801 (M+H$^+$).

Example 67

N-[3-(3-{2-[(3-fluorophenyl)amino]-4-pyrimidinyl}pyrazolo[1,5-a]pyridin-2-yl)phenyl]-5-isoxazolecarboxamide

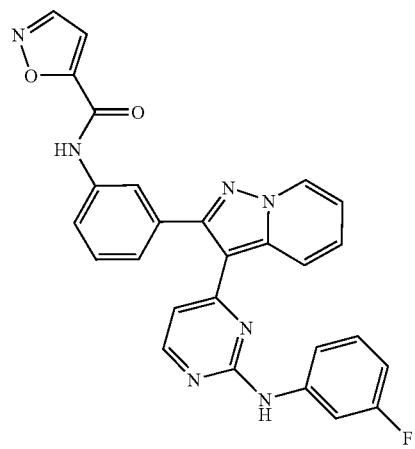

In a manner analogous to Example 66, 91 mg of the title compound was synthesized from 100 mg (0.25 mmol) of 4-[2-(3-aminophenyl)pyrazolo[1,5-a]pyridin-3-yl]-N-(3-fluorophenyl)-2-pyrimidinamine and 46 mg (0.353 mmol) of 5-isoxazolecarbonyl chloride a yellow solid: $^1$H NMR (d$_6$-DMSO, 400 MHz) δ 6.59 (d, 1H, J=5.5 Hz), 6.72 (td, 1H, J=8.0 and 2.5 Hz), 7.14 (td, 1H, J=6.8 and 1.5 Hz), 7.21-7.29 (m, 2H), 7.37-7.53 (m, 4H), 7.78 (d, 1H, J=12.3 Hz), 7.93 (d, 1H, J=8.6 Hz), 8.09 (s, 1H), 8.32 (d, 1H, J=5.4 Hz), 8.49 (d, 1H, J=8.8 Hz), 8.81 (d, 1H, J=1.7 Hz), 8.86 (d, 1H, J=6.8 Hz), 9.81 (s, 1H), and 10.87 (s, 1H); HRMS calcd for C$_{27}$H$_{18}$FN$_7$O$_2$: 491.1506, found: 492.1583 (M+H$^+$).

Example 68

N-[3-(3-{2-[(3-fluorophenyl)amino]-4-pyrimidinyl}-pyrazolo[1,5-a]pyridin-2-yl)phenyl]-2-[(trifluoromethyl)oxy]benzamide

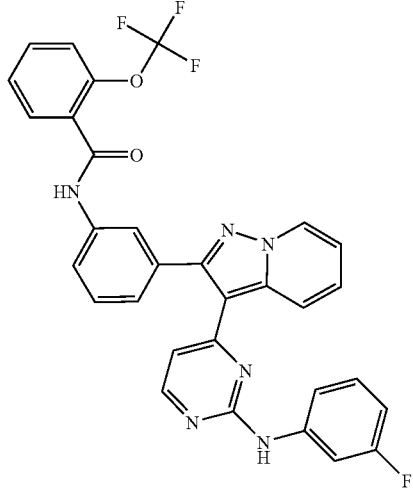

In a manner analogous to Example 66, the title compound may be obtained by reacting 4-[2-(3-aminophenyl)pyrazolo[1,5-a]pyridin-3-yl]-N-(3-fluorophenyl)-2-pyrimidinamine and 2-thiophenecarbonyl[(1,1-dimethylethyl)oxy]benzoyl chloride.

HRMS calcd for C$_{31}$H$_{20}$F$_4$N$_6$O$_2$: 584.1584, found: 585.1666 (M+H$^+$)

Example 69

N-[3-(3-{2-[(3-fluorophenyl)amino]-4-pyrimidinyl}pyrazolo[1,5-a]pyridin-2-yl)phenyl]-2-(methyloxy)benzamide

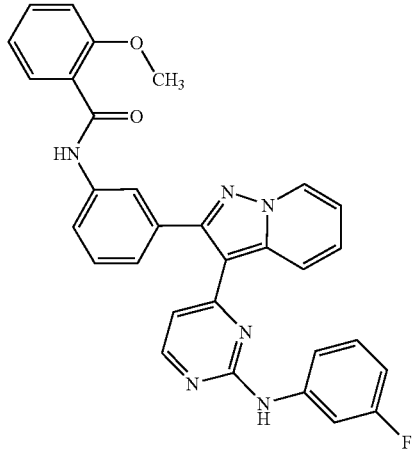

In a manner analogous to Example 66, the title compound may be obtained by reacting 4-[2-(3-aminophenyl)pyrazolo[1,5-a]pyridin-3-yl]-N-(3-fluorophenyl)-2-pyrimidinamine and 2-methoxybenzoyl chloride. HRMS: calc. C$_{28}$H$_{20}$N$_6$OFS calcd for C$_{31}$H$_{23}$FN$_6$O$_2$: 530.1867, found: 531.1941 (M+H)$^+$ 507.1403 found 507.1427$^+$).

Example 70

2-Chloro-N-[3-(3-{2-[(3-fluorophenyl)amino]-4-pyrimidinyl}pyrazolo[1,5-a]pyridin-2-yl)phenyl]-3-methylbenzamide

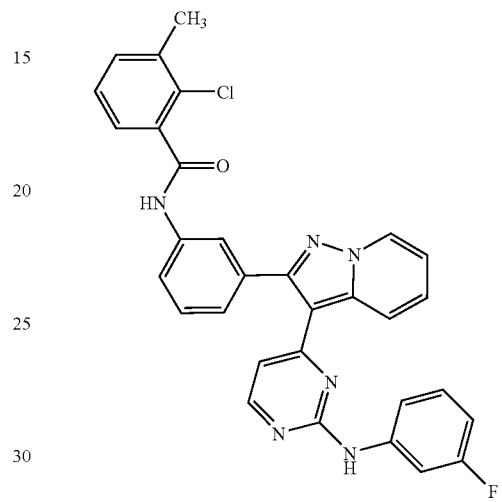

The title compound was prepared in a manner analogous to Example 66, using 4-[2-(3-aminophenyl)pyrazolo[1,5-a]pyridin-3-yl]-N-(3-fluorophenyl)-2-pyrimidinamine and 3-bromofluoro-2-thiophenecarbonylmethylbenzoyl chloride. HRMS: calc. C$_{28}$H$_{19}$N$_6$OSFBr calcd for C$_{31}$H$_{22}$F$_2$N$_6$O: 532.1823, found: 533.1921 (M+H)$^+$ 585.0508 found 585.0515$^+$).

Example 71

3-Fluoro-N-[3-(3-{2-[(3-fluorophenyl)amino]-4-pyrimidinyl}pyrazolo[1,5-a]pyridin-2-yl)phenyl]-2-methylbenzamide

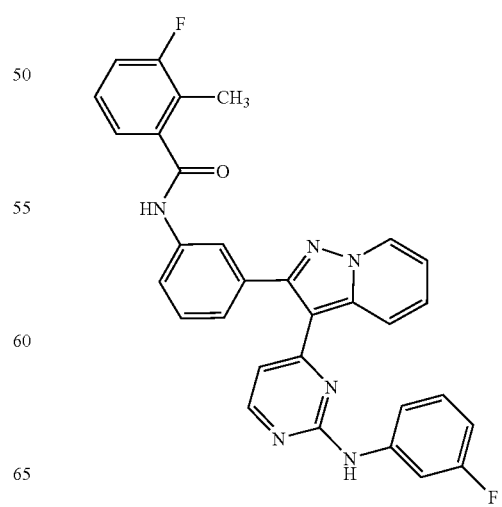

In a manner analogous to Example 66, 4-[2-(3-aminophenyl)pyrazolo[1,5-a]pyridin-3-yl]-N-(3-fluorophenyl)-2-pyrimidinamine and 3-fluoro-2-methylbenzoyl chloride are used to prepare the title compound. HRMS calcd for C₃₁H₂₂F₂N₆O: 532.1823, found: 533.1921 (M+H⁺).

Example 72

2,6-Difluoro-N-[3-(3-{2-[(3-fluorophenyl)amino]-4-pyrimidinyl}pyrazolo[1,5-a]pyridin-2-yl)phenyl]-3-methylbenzamide

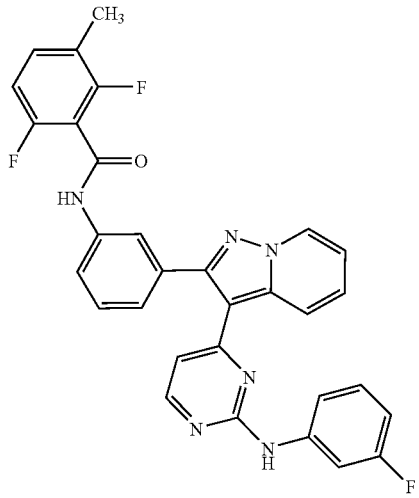

In a manner analogous to Example 66, 4-[2-(3-aminophenyl)pyrazolo[1,5-a]pyridin-3-yl]-N-(3-fluorophenyl)-2-pyrimidinamine and 2,6-difluoro-3-methylbenzoyl chloride are used to prepare the title compound. HRMS calcd for C₃₁H₂₁F₃N₆O: 550.1729, found: 551.1803 (M+H+).

Example 73

2-Chloro-N-[3-(3-{2-[(3-fluorophenyl)amino]-4-pyrimidinyl}pyrazolo[1,5-a]pyridin-2-yl)phenyl]-4-pyridinecarboxamide

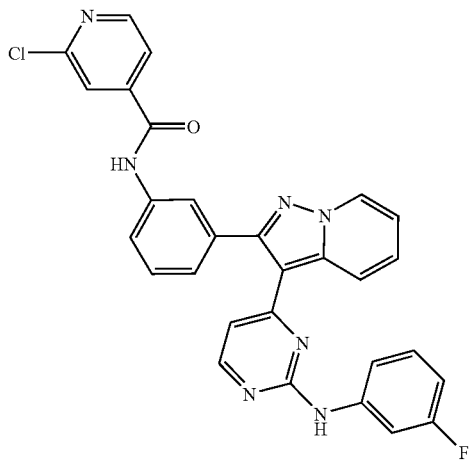

In a manner analogous to Example 66, 4-[2-(3-aminophenyl)pyrazolo[1,5-a]pyridin-3-yl]-N-(3-fluorophenyl)-2-pyrimidinamine and 2-chloro-4-pyridinecarbonyl chloride are used to prepare the title compound. HRMS calcd for C₂₉H₁₉ClFN₇O: 535.1324, found: 536.1392 (M+H⁺).

Example 74

6-Chloro-N-[3-(3-{2-[(3-fluorophenyl)amino]-4-pyrimidinyl}pyrazolo[1,5-a]pyridin-2-yl)phenyl]-3-pyridinecarboxamide

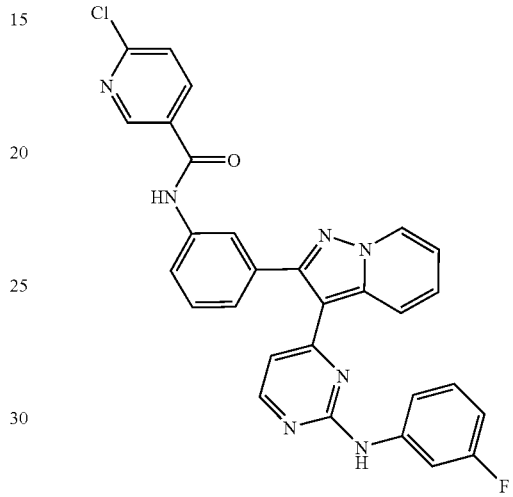

In a manner analogous to Example 66, 4-[2-(3-aminophenyl)pyrazolo[1,5-a]pyridin-3-yl]-N-(3-fluorophenyl)-2-pyrimidinamine and 4-chloro-3-pyridinecarbonyl chloride are used to prepare the title compound. HRMS calcd for C₂₉H₁₉ClFN₇O: 535.1324, found: 536.1415 (M+H⁺).

Example 75

N-[3-(3-{2-[(3-Fluorophenyl)amino]-4-pyrimidinyl}pyrazolo[1,5-a]pyrindin-2-yl)phenyl]-4-pyridinecarboxamide

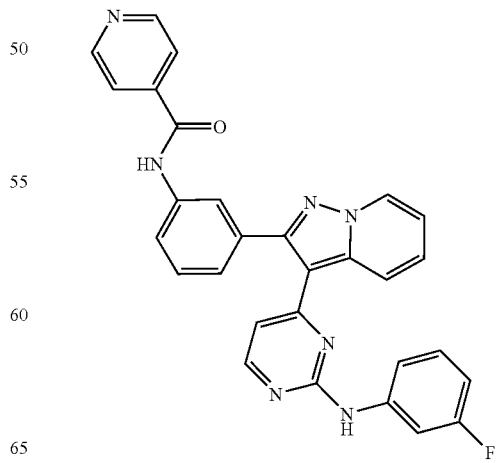

In a manner analogous to Example 66, 4-[2-(3-aminophenyl)pyrazolo[1,5-a]pyridin-3-yl]-N-(3-fluorophenyl)-2-pyrimidinamine and 4-pyridinecarbonyl chloride are used to prepare the title compound. HRMS calcd for $C_{29}H_{20}FN_7O$: 501.1713, found: 502.1805 (M+H$^+$).

Example 76

N-[3-(3-{2-[(3-fluorophenyl)amino]-4-pyrimidinyl}pyrazolo[1,5-a]pyridin-2-yl)phenyl]-2-pyridinecarboxamide

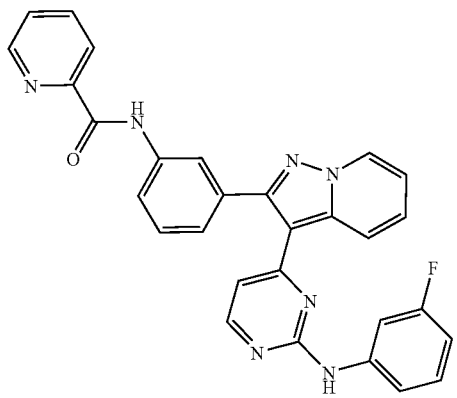

The title compound was prepared from 4-[2-(3-aminophenyl)pyrazolo[1,5-a]pyridin-3-yl]-N-(3-fluorophenyl)-2-pyrimidinamine and 2-pyridinecarbonyl chloride in a manner analogous to Example 66. HRMS: calc. $C_{29}H_{21}N_7OF$ (M+H)$^+$ 502.1792 found 502.1789.

Example 77

N-[3-(3-{2-[(3-fluorophenyl)amino]-4-pyrimidinyl}pyrazolo[1,5-a]pyridin-2-yl)phenyl]-3-methyl-2-thiophenecarboxamide

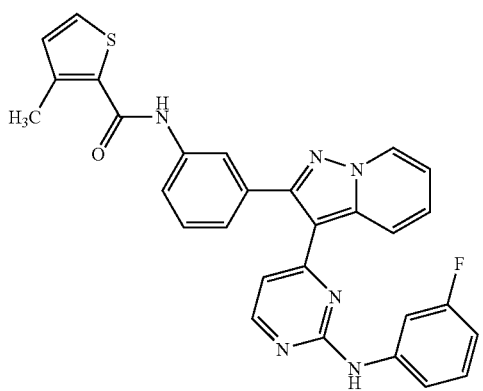

The title compound was prepared from 4-[2-(3-aminophenyl)pyrazolo[1,5-a]pyridin-3-yl]-N-(3-fluorophenyl)-2-pyrimidinamine and 3-methyl-2-thiophenecarbonyl chloride in a manner analogous to Example 66 above. $^1$H NMR (300 MHz, DMSO-d$_6$): δ 10.10 (s, 1H), 9.80 (s, 1H), 8.85 (d, 1H), 8.50 (d, 1H), 8.31 (d, 1H), 8.00 (s, 1H), 7.86-7.75 (m, 2H), 7.66 (d, 1H), 7.53-7.41 (m, 3H), 7.33-7.21 (m, 2H), 7.13 (m, 1H), 7.01 (d, 1H), 6.71 (m, 1H), 6.59 (d, 1H), 2.43 (s, 3H); HRMS: calc. $C_{29}H_{22}N_6OFS$ (M+H)$^+$ 521.156 found 521.1552.

Example 78

N-[3-(3-{2-[(3-fluorophenyl)amino]-4-pyrimidinyl}pyrazolo[1,5-a]pyridin-2-yl)phenyl]-2-thiophenecarboxamide

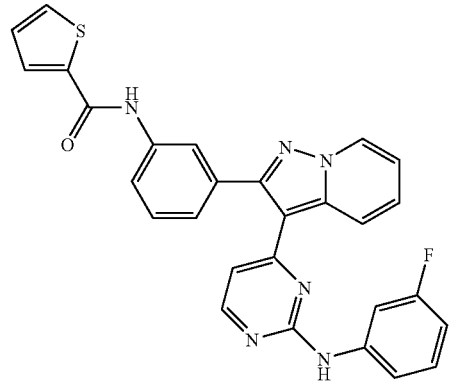

The title compound was prepared from 4-[2-(3-aminophenyl)pyrazolo[1,5-a]pyridin-3-yl]-N-(3-fluorophenyl)-2-pyrimidinamine and 2-thiophenecarbonyl chloride in a manner analogous to Example 66. $^1$H NMR (300 MHz, DMSO-d$_6$): δ 10.35 (s, 1H), 9.81 (s, 1H), 8.85 (d, 1H), 8.50 (d, 1H), 8.31 (d, 1H), 8.07-8.01 (m, 2H), 7.91 (d, 1H), 7.86 (d, 1H), 7.79 (m, 1H), 7.54-7.44 (m, 3H), 7.34-7.20 (m, 3H), 7.14 (t, 1H), 6.72 (m, 1H), 6.59 (d, 1H); HRMS: calc. $C_{28}H_{20}N_6OFS$ (M+H)+ 507.1403 found 507.1427.

Example 79

3-Chloro-N-[3-(3-{2-[(3-fluorophenyl)amino]-4-pyrimidinyl}pyrazolo[1,5-a]pyridin-2-yl)phenyl]-2-thiophenecarboxamide

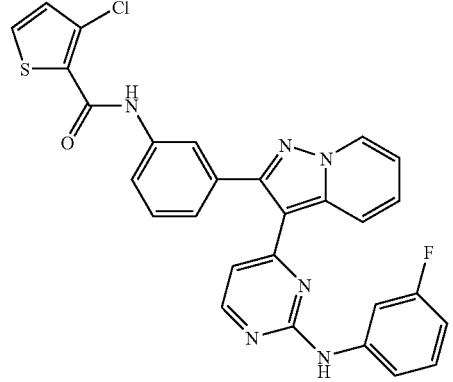

The title compound was prepared from 4-[2-(3-aminophenyl)pyrazolo[1,5-a]pyridin-3-yl]-N-(3-fluorophenyl)-2-pyrimidinamine and 3-chloro-2-thiophenecarbonyl chloride in a manner analogous to Example 66. HRMS: calc. $C_{28}H_{19}N_6OSFCl$ (M+H)$^+$ 541.1014 found 541.1011.

Example 80

3-Bromo-N-[3-(3-{2-[(3-fluorophenyl)amino]-4-pyrimidinyl}pyrazolo[1,5-a]pyridin-2-yl)phenyl]-2-thiophenecarboxamide

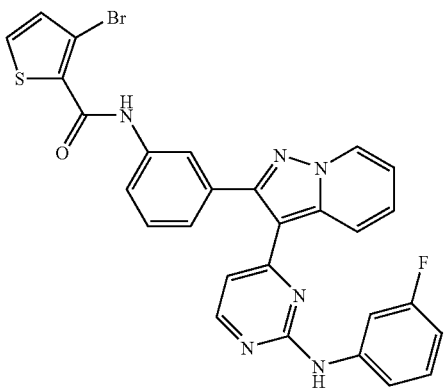

The title compound was prepared from 4-[2-(3-aminophenyl)pyrazolo[1,5-a]pyridin-3-yl]-N-(3-fluorophenyl)-2-pyrimidinamine and 3-bromo-2-thiophenecarbonyl chloride in a manner analogous to Example 66. HRMS: calc. $C_{28}H_{19}N_6OSFBr$ $(M+H)^+$ 585.0508 found 585.0515.

Example 81

N-[3-(3-{2-[(3-fluorophenyl)amino]-4-pyrimidinyl}pyrazolo[1,5-a]pyridin-2-yl)phenyl]-3-thiophenecarboxamide

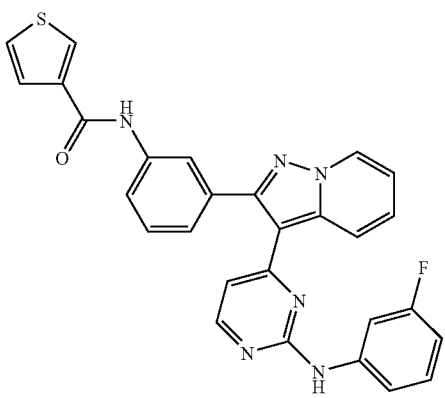

The title compound was prepared from 4-[2-(3-aminophenyl)pyrazolo[1,5-a]pyridin-3-yl]-N-(3-fluorophenyl)-2-pyrimidinamine and 3-thiophenecarbonyl chloride in a manner analogous to Example 66. HRMS: calc. $C_{28}H_{20}N_6OFS$ $(M+H)^+$ 507.1403 found 507.1403.

Example 82

N-[3-(3-{2-[(3-fluorophenyl)amino]-4-pyrimidinyl}-pyrazolo[1,5-a]pyridin-2-yl)phenyl]-1-methyl-1H-pyrrole-2-carboxamide

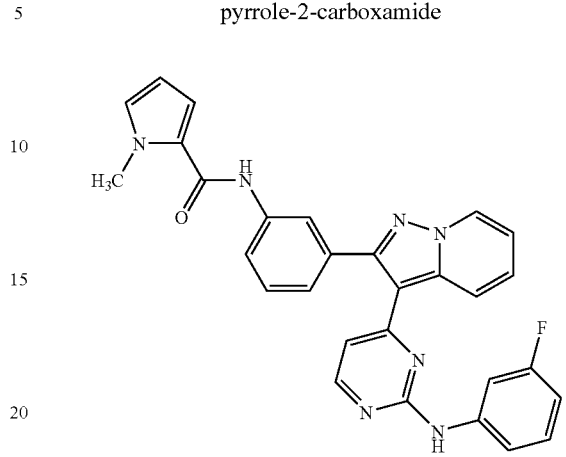

The title compound was prepared from 4-[2-(3-aminophenyl)pyrazolo[1,5-a]pyridin-3-yl]-N-(3-fluorophenyl)-2-pyrimidinamine and 1-methyl-1H-pyrrole-2-carbonyl chloride in a manner analogous to Example 66. $^1$H NMR (300 MHz, DMSO-$d_6$): δ 9.87 (s, 1H), 9.81 (s, 1H), 8.85 (d, 1H), 8.52 (d, 1H), 8.30 (d, 1H), 8.05 (s, 1H), 7.87 (d, 1H), 7.80 (m, 1H), 7.53-7.39 (m, 3H), 7.31-7.22 (m, 2H), 7.13 (m, 1H), 7.05-6.98 (m, 2H), 6.72 (m, 1H), 6.57 (d, 1H), 6.08 (m, 1H), 3.87 (s, 3H); HRMS: calc. $C_{29}H_{23}N_7OF$ $(M+H)^+$ 504.1948 found 504.1962

Example 83

5-Fluoro-N-[3-(3-{2-[(3-fluorophenyl)amino]-4-pyrimidinyl}pyrazolo[1,5-a]pyridin-2-yl)phenyl]-2-methylbenzamide

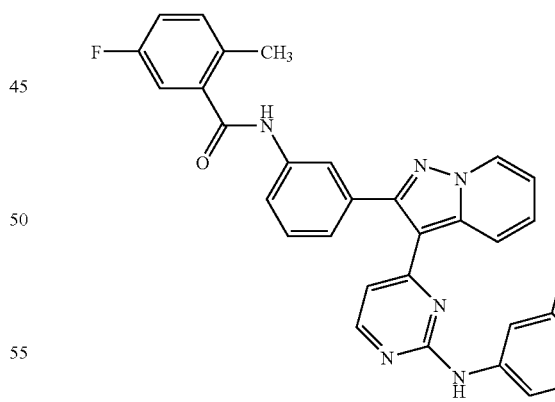

The title compound was prepared from 4-[2-(3-aminophenyl)pyrazolo[1,5-a]pyridin-3-yl]-N-(3-fluorophenyl)-2-pyrimidinamine and 5-fluoro-2-methylbenzoyl chloride in a manner analogous to Example 66. $^1$H NMR (300 MHz, DMSO-$d_6$): δ 10.48 (s, 1H), 9.80 (s, 1H), 8.85 (d, 1H), 8.47 (d, 1H), 8.32 (d, 1H), 8.07 (s, 1H), 7.84 (d, 1H), 7.77 (m, 1H), 7.53-7.42 (m, 3H), 7.36-7.28 (m, 3H), 7.26-7.18 (m, 2H), 7.13 (m, 1H), 6.71 (m, 1H), 6.60 (d, 1H), 2.32 (s, 3H); HRMS: calc. $C_{31}H_{23}N_6OF_2$ $(M+H)^+$ 533.1901 found 533.1904.

Example 84

N-[3-(3-{2-[(3-fluorophenyl)amino]-4-pyrimidinyl}-pyrazolo[1,5-a]pyridin-2-yl)phenyl]-1-methyl-1H-imidazole-5-carboxamide

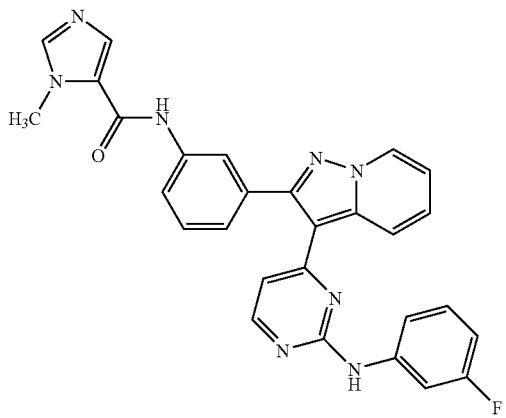

The title compound was prepared from 4-[2-(3-aminophenyl)pyrazolo[1,5-a]pyridin-3-yl]-N-(3-fluorophenyl)-2-pyrimidinamine and 1-methyl-1H-imidazole-5-carbonyl chloride in a manner analogous to Example 66. $^1$H NMR (400 MHz, DMSO-$d_6$): δ 10.14 (s, 1H), 9.80 (s, 1H), 8.84 (d, 1H), 8.50 (d, 1H), 8.30 (d, 1H), 8.04 (s, 1H), 7.87-7.76 (m, 4H), 7.52-7.41 (m, 3H), 7.29-7.22 (m, 2H), 7.13 (m, 1H), 6.72 (m, 1H), 6.57 (d, 1H), 3.83 (s, 3H); HRMS: calc. $C_{28}H_{22}N_8OF$ (M+H)$^+$ 505.1901 found 505.1903.

Example 85

2,6-Difluoro-N-(3-{3-[2-(3-isoxazolylamino)-4-pyrimidinyl]pyrazolo[1,5-a]pyridin-2-yl}phenyl)benzamide

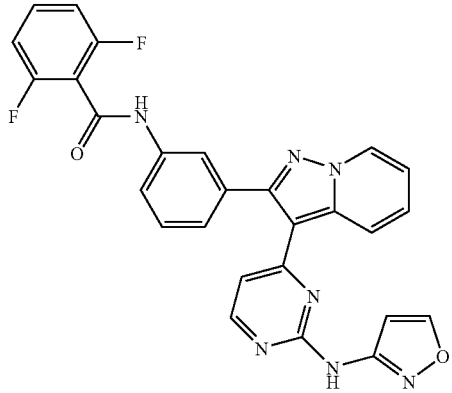

The title compound was prepared from 4-[2-(3-aminophenyl)-6-methylpyrazolo-[1,5-b]pyridazin-3-yl]-N-(3-fluorophenyl)-2-pyrimidinamine and 3-isoxazolamine in a manner analogous to Example 27, Step D. $^1$H NMR (300 MHz, DMSO-$d_6$): δ 10.94 (s, 1H), 10.47 (s, 1H), 8.83 (d, 1H), 8.74 (d, 1H), 8.66 (s, 1H), 8.28 (d, 1H), 7.97 (s, 1H), 7.81 (d, 1H), 7.58 (m, 1H), 7.49 (m, 2H), 7.35 (d, 1H), 7.24 (m, 2H), 7.15 (m, 1H), 6.89 (s, 1H), 6.01 (d, 1H); HRMS: calc. $C_{27}H_{18}N_7O_2F_2$ (M+H)$^+$ 510.1490 found 510.1490.

Example 86

N-[3-(3-{2-[(3-Chloro-4-hydroxyphenyl)amino]-4-pyrimidinyl}pyrazolo[1,5-a]pyridin-2-yl)phenyl]-2,6-difluorobenzamide

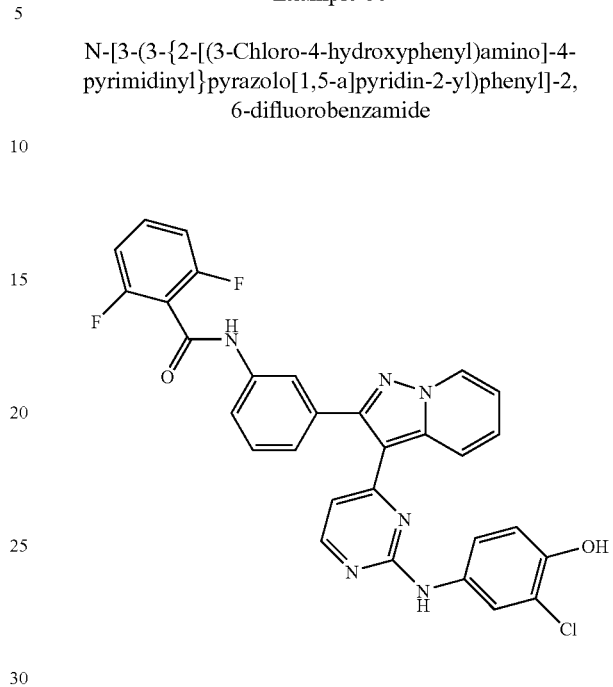

The title compound was prepared from N-{3-[3-(2-chloro-4-pyrimidinyl)pyrazolo[1,5-a]pyridin-2-yl]phenyl}-2,6-difluorobenzamide and 4-amino-2-chlorophenol in a manner analogous to Example 27, Step D. MS (ESI): 569 (M+Na)$^+$.

Example 87

N-{3-[3-(2-{[3-Chloro-4-(methyloxy)phenyl]amino}-4-pyrimidinyl)pyrazolo[1,5-a]pyridin-2-yl]phenyl}-2,6-difluorobenzamide

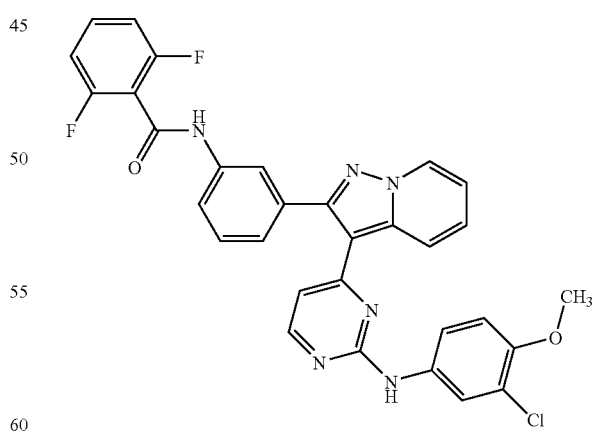

The title compound was prepared from N-{3-[3-(2-chloro-4-pyrimidinyl)pyrazolo[1,5-a]pyridin-2-yl]phenyl}-2,6-difluorobenzamide and 3-chloro-4-(methyloxy)aniline in a manner analogous to Example 27, Step D. HRMS: calc. $C_{31}H_{22}N_6O_2F_2Cl$ (M+H)$^+$ 583.1461 found 583.1453.

Example 88

N-[3-(3-{2-[3-cyano-4-fluorophenylamino]-4-pyrimidinyl}-7-trifluoropyrazolo[1,5-b]pyridin-2-yl)phenyl]-2,6-difluorobenzamide

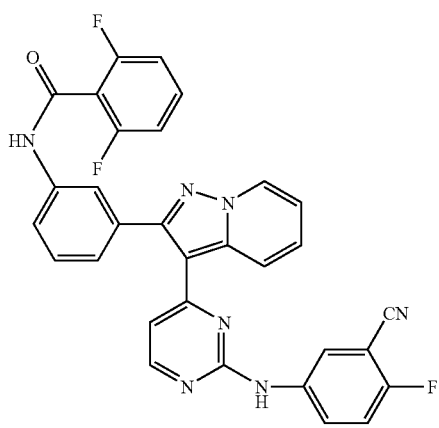

The title compound was prepared from N-{3-[3-(2-chloro-4-pyrimidinyl)pyrazolo[1,5-a]pyridin-2-yl]phenyl}-2,6-difluorobenzamide and 3-cyano-4-fluoroaniline using a procedure analogous to Example 27, Step D. $^1$H NMR (400 MHz, DMSO-d$_6$) δ 6.70 (d, 1H, J=5.4 Hz), 7.19 (t, 1H, J=6.9 Hz), 7.29 (t, 2H, J=8.0 Hz), 7.38-7.63 (m, 5H), 7.83 (d, 1H, J=8.7 Hz), 7.90-7.98 (m, 1H), 8.04 (s, 1H), 8.34 (dd, 1H, J=2.7, 5.8 Hz), 8.39 (d, 1H, J=5.3 Hz), 8.45 (d, 1H, J=8.9 Hz), 8.91 (d, 1H, J=6.9 Hz), 9.98 (s, 1H), 10.96 (s, 1H); ESIMS (M+H)$^+$=562.

Example 89

N-[3-(3-{2-[3-Trifluoromethyl-4-chlorophenylamino]-4-pyrimidinyl}-7-trifluoropyrazolo[1,5-b]pyridin-2-yl)phenyl]-2,6-difluorobenzamide

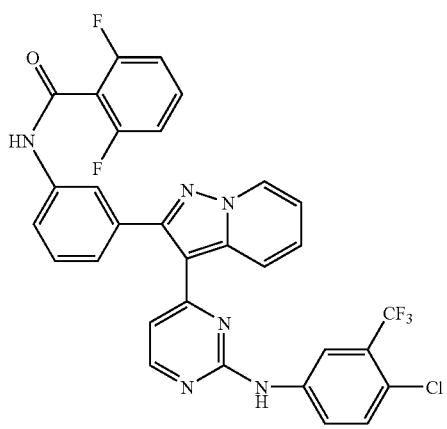

The title compound was prepared from N-{3-[3-(2-chloro-4-pyrimidinyl)pyrazolo[1,5-a]pyridin-2-yl]phenyl}-2,6-difluorobenzamide and 4-chloro-4-3-trifluoromethyl-aniline in a manner analogous to Example 27, Step D. $^1$H NMR (400 MHz, DMSO-d$_6$) δ 6.70 (d, 1H, J=5.4 Hz), 7.19 (t, 1H, J=6.9 Hz), 7.29 (t, 2H, J=8.0 Hz), 7.49-7.63 (m, 5H), 7.85 (d, 1H, J=9.0 Hz), 8.01 (d, J=2.1 Hz, 1H), 8.06 (s, 1H), 8.38-8.40 (m, 2H), 8.46 (d, 1H, J=8.9 Hz), 8.91 (d, 1H, J=6.9 Hz), 10.08 (s, 1H), 10.97 (s, 1H); ESIMS (M+H)$^+$=621.

Example 90

N-[3-(3-{2-[3-Cyano-4-N-pyrrolo-phenylamino]-4-pyrimidinyl}-7-trifluoropyrazolo[1,5-b]pyridin-2-yl)phenyl]-2,6-difluorobenzamide

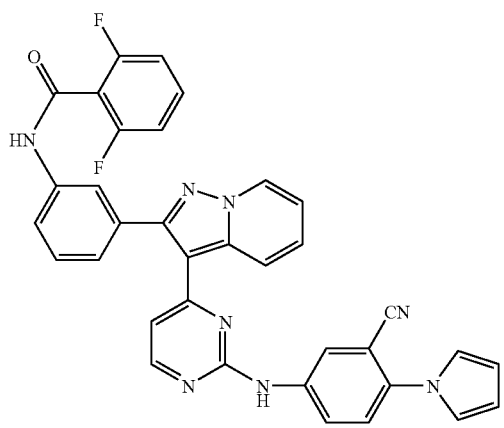

The title compound was prepared from N-{3-[3-(2-chloro-4-pyrimidinyl)pyrazolo[1,5-a]pyridin-2-yl]phenyl}-2,6-difluorobenzamide and 5-amino-2-(1H-pyrrol-1-yl)benzonitrile in a manner analogous to Example 27, Step D. $^1$H NMR (400 MHz, DMSO-d$_6$) δ 6.33 (t, 2H, J=2.0 Hz), 6.71 (d, 1H, J=5.2 Hz), 7.17-7.22 (m, 3H), 7.28 (t, 2H, J=8.0 Hz), 7.41 (d, 1H, J=7.7 Hz), 7.50-7.63 (m, 4H), 7.85 (d, 1H, J=7.7 Hz), 8.02-8.05 (m, 2H), 8.41 (m, 3H), 8.91 (d, 1H, J=6.9 Hz), 10.10 (s, 1H), 10.96 (s, 1H); ESIMS (M+H)$^+$=609.

Example 91

N-[3-(3-{2-[4-(4-methyl-1-piperazinyl)phenylamino]-4-pyrimidinyl}-7-trifluoropyrazolo[1,5-b]pyridin-2-yl)phenyl]-2,6-difluorobenzamide

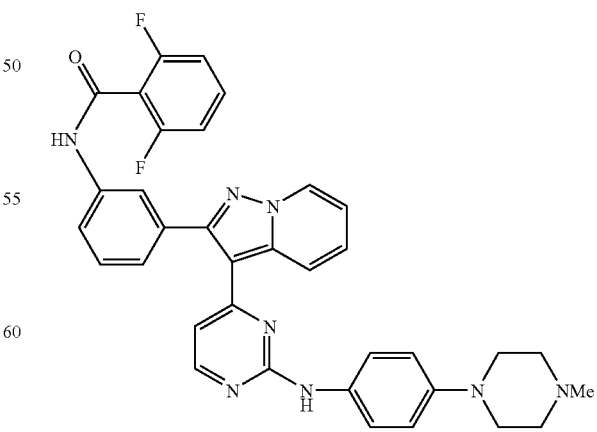

The title compound was prepared from N-{3-[3-(2-chloro-4-pyrimidinyl)pyrazolo[1,5-a]pyridin-2-yl]phenyl}-2,6-difluorobenzamide and 4-(4-methyl-1-piperazinyl)aniline by a procedure similar to Example 27, Step D. $^{1}$H NMR (400 MHz, DMSO-$d_6$) δ 2.26 (s, 3H), 2.48-2.54 (m, 4H overlapping with $d_6$-DMSO), 3.02-3.10 (m, 4H), 6.52 (d, 1H, J=5.2 Hz), 6.88 (d, 2H, J=8.8 Hz), 7.15 (t, 1H, J=6.0 Hz), 7.29 (t, 2H, J=8.0 Hz), 7.37 (d, 1H, J=7.8 Hz), 7.46-7.66 (m, 5H), 7.85 (d, 1H, J=8.7 Hz), 8.04 (s, 1H), 8.25 (d, 1H, J=5.2 Hz), 8.45 (bd, 1H, J=8.9 Hz), 8.97 (d, 1H, J=6.9 Hz), 9.31 (s, 1H), 10.98 (s, 1H); ESIMS (M+H)$^+$=617.

Example 92

N-[3-(3-{2-[4-chlorophenylamino]-4-pyrimidinyl}-7-trifluoropyrazolo[1,5-b]pyridin-2-yl)phenyl]-2,6-difluorobenzamide

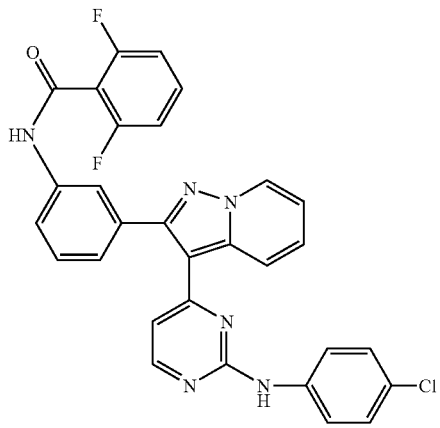

The title compound was prepared from N-{3-[3-(2-chloro-4-pyrimidinyl)pyrazolo[1,5-a]pyridin-2-yl]phenyl}-2,6-difluorobenzamide and 4-chloroaniline by a procedure similar to Example 27, Step D. $^{1}$H NMR (400 MHz, DMSO-$d_6$) δ 6.67 (d, 1H, J=5.2 Hz), 7.18 (t, 1H, J=7.0 Hz), 7.26-7.32 (m, 4H), 7.38 (d, 1H, J=7.7 Hz), 7.49-7.66 (m, 4H), 7.73 (d, 1H, J=8.9 Hz), 7.84 (d, 1H, J=8.7 Hz), 8.06 (s, 1H), 8.35 (d, 1H, J=5.4 Hz), 8.45 (d, 1H, J=8.9 Hz), 8.90 (d, 1H, J=6.8 Hz), 9.79 (s, 1H), 10.98 (s, 1H); ESIMS (M+H)$^+$=553.

Example 93

N-[3-(3-{2-[4-(4-Cyanophenyl)phenylamino]-4-pyrimidinyl}-7-trifluoropyrazolo[1,5-b]pyridin-2-yl)phenyl]-2,6-difluorobenzamide

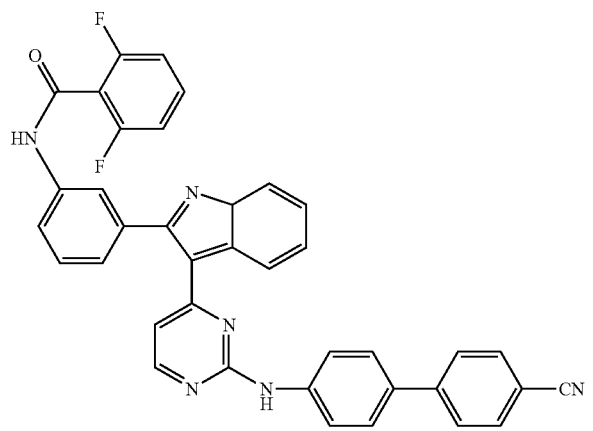

The title compound was prepared from N-{3-[3-(2-chloro-4-pyrimidinyl)pyrazolo[1,5-a]pyridin-2-yl]phenyl}-2,6-difluorobenzamide and 4-cyanoaniline by a procedure similar to Example 27, Step D. $^{1}$H NMR (400 MHz, DMSO-$d_6$) δ 6.69 (d, 1H, J=5.4 Hz), 7.18 (t, 1H, J=6.4 Hz), 7.29 (t, 2H, J=8.0 Hz), 7.39 (d, 1H, J=7.7 Hz), 7.50-7.66 (m, 3H), 7.70 (d, 2H, J=8.7 Hz), 7.84-7.89 (m, 7H), 8.08 (s, 1H), 8.38 (d, 1H, J=5.5 Hz), 8.50 (d, 1H, J=8.9 Hz), 8.91 (d, 1H, J=6.9 Hz), 9.92 (s, 1H), 11.00 (s, 1H); ESIMS (M+H)$^+$=620.

Example 94

N-[3-(3-{2-[4-(4-pyridinylmethyl)phenylamino]-4-pyrimidinyl}-7-trifluoropyrazolo[1,5-b]pyridin-2-yl)phenyl]-2,6-difluorobenzamide

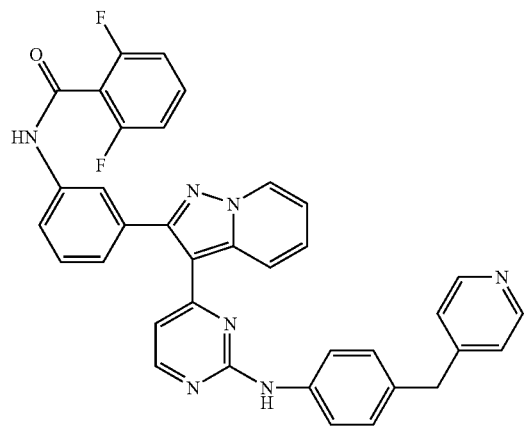

The title compound was prepared from N-{3-[3-(2-chloro-4-pyrimidinyl)pyrazolo[1,5-a]pyridin-2-yl]phenyl}-2,6-difluorobenzamide and [4-(4-pyridinylmethyl)phenyl]amine by a procedure similar to Example 27, Step D. $^{1}$H NMR (400 MHz, DMSO-$d_6$) δ 3.93 (s, 2H), 6.59 (d, 1H, J=5.2 Hz), 7.16 (d, 2H, J=8.4 Hz), 7.26-7.65 (m, 11H), 7.85 (d, 1H, J=8.0 Hz), 8.04 (s, 1H), 8.30 (d, 1H, J=5.4 Hz), 8.39-8.49 (m, 3H), 8.88 (d, 1H, J=6.9 Hz), 9.54 (s, 1H), 10.99 (s, 1H); ESIMS (M+H)$^+$= 610.

Example 95

N-[3-(3-{2-[3-Methyl-4-cyano-phenylamino]-4-pyrimidinyl}-7-trifluoropyrazolo[1,5-b]pyridin-2-yl)phenyl]-2,6-difluorobenzamide

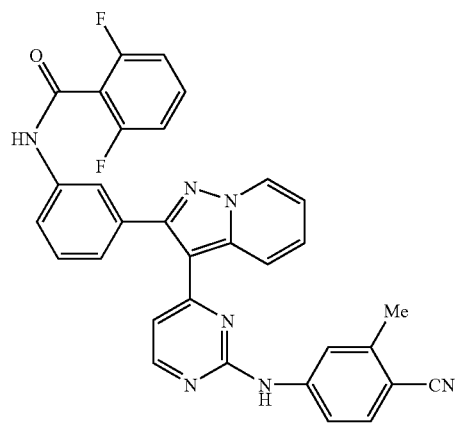

The title compound was prepared from N-{3-[3-(2-chloro-4-pyrimidinyl)pyrazolo[1,5-a]pyridin-2-yl]phenyl}-2,6-difluorobenzamide and 4-cyano-3-methylaniline by a procedure similar to Example 27, Step D. ¹H NMR (400 MHz, DMSO-d₆) δ 2.45 (s, 3H), 6.66 (d, 1H, J=5.2 Hz), 7.19 (t, 1H, J=6.8 Hz), 7.29 (t, 2H, J=8.0 Hz), 7.37 (t, 2H, J=8.8 Hz), 7.49-7.66 (m, 3H), 7.84 (m, 1H), 8.04 (s, 1H), 8.26 (d, 1H, J=1.8 Hz), 8.37 (d, 1H, J=5.4 Hz), 8.47 (d, 1H, J=8.9 Hz), 8.91 (d, 1H, J=6.9 Hz), 9.90 (s, 1H), 10.98 (s, 1H); ESIMS (M+H)⁺=558.

Example 96

N-[3-(3-{2-[4-anilino-phenylamino]-4-pyrimidinyl}-7-trifluoropyrazolo[1,5-b]pyridin-2-yl)phenyl]-2,6-difluorobenzamide

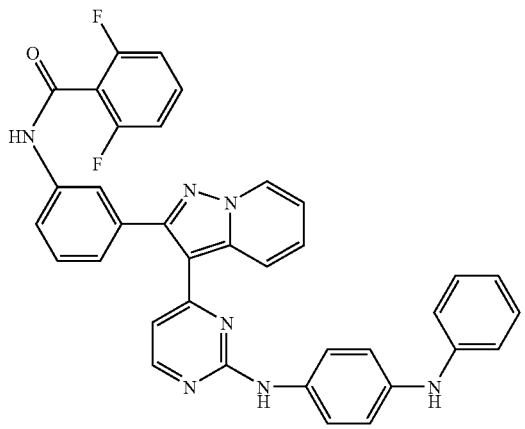

The title compound was prepared from N-{3-[3-(2-chloro-4-pyrimidinyl)pyrazolo[1,5-a]pyridin-2-yl]phenyl}-2,6-difluorobenzamide and aniline by a procedure similar to Example 27, Step D. ¹H NMR (400 MHz, DMSO-d₆) δ 6.50 (d, 1H, J=5.2 Hz), 6.76 (d, 1H, J=7.3 Hz), 7.00-7.08 (m, 4H), 7.13-7.31 (m, 5H), 7.40-7.63 (m, 6H), 7.88 (d, 1H, J=8.2 Hz), 7.98 (s, 1H), 8.02 (s, 1H), 8.25 (d, 1H, J=5.2 Hz), 8.52 (d, 1H, J=8.3 Hz), 8.87 (d, 1H, J=6.9 Hz), 9.41 (s, 1H), 10.97 (s, 1H); ESIMS (M+H)⁺=610.

Example 97

N-[3-(3-{2-[(2,3-Dimethyl-6-quinoxalinyl)amino]-4-pyrimidinyl}pyrazolo[1,5-a]pyridin-2-yl)phenyl]-2,6-difluorobenzamide

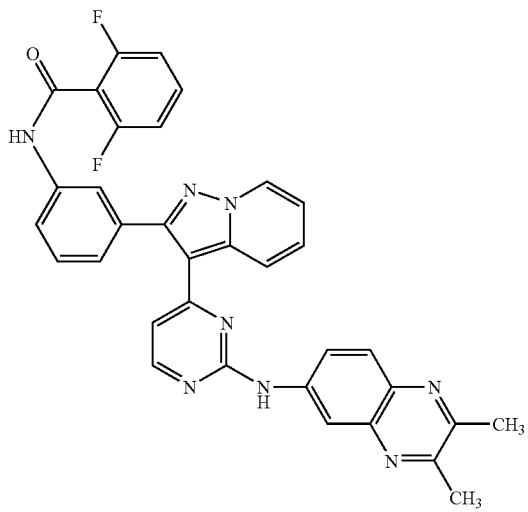

The title compound was prepared from N-{3-[3-(2-chloro-4-pyrimidinyl)pyrazolo-[1,5-a]pyridin-2-yl]phenyl}-2,6-difluorobenzamide and 2,3-dimethyl-6-quinoxalinamine by a procedure similar to Example 64. ¹H NMR (400 MHz, DMSO-d₆) δ 2.66 (s, 6H), 6.66 (d, 1H, J=5.4 Hz), 7.19 (t, 1H, J=6.9 Hz), 7.29 (t, 2H, J=8.0 Hz), 7.43 (d, 1H, J=7.7 Hz), 7.51-7.65 (m, 3H), 7.85-7.88 (m, 2H), 7.99-8.03 (dd, 1H, J=2.3, 9.0 Hz), 8.06 (s, 1H), 8.42 (d, 1H, J=5.3 Hz), 8.60-8.64 (m, 2H), 8.91 (d, 1H, J=6.9 Hz), 10.08 (s, 1H), 10.98 (s, 1H); ESIMS (M+H)+=558.

Example 98

2,6-Difluoro-N-{3-[3-(2-{[4-(phenylcarbonyl)phenyl]-amino}-4-pyrimidinyl)pyrazolo[1,5-a]pyridin-2-yl]phenyl}benzamide

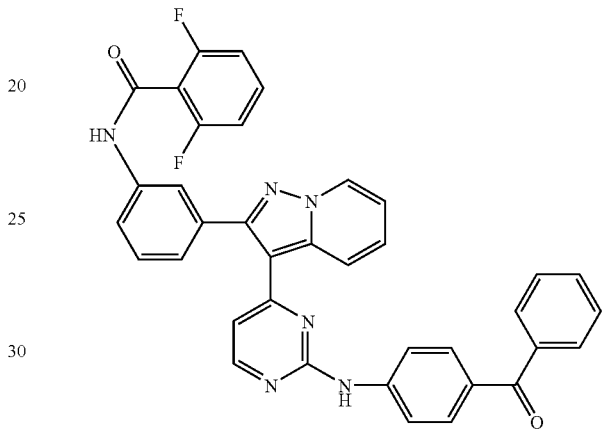

The title compound was prepared from N-{3-[3-(2-chloro-4-pyrimidinyl)pyrazolo-[1,5-a]pyridin-2-yl]phenyl}-2,6-difluorobenzamide and (4-aminophenyl)(phenyl)-methanone by a procedure similar to Example 64. ¹H NMR (400 MHz, DMSO-d₆) δ 6.71 (d, 1H, J=5.2 Hz), 7.19 (t, 1H, J=6.5 Hz), 7.28 (t, 2H, J=7.9 Hz), 7.42 (d, 1H, J=7.7 Hz), 7.13-7.31 (m, 10H), 7.87 (d, 1H, J=8.2 Hz), 7.97 (d, 2H, J=8.8 Hz), 8.05 (s, 1H), 8.41 (d, 1H, J=5.3 Hz), 8.56 (d, 1H, J=9.0 Hz), 8.91 (d, 1H, J=6.8 Hz), 10.14 (s, 1H), 10.95 (s, 1H); ESIMS (M+H)⁺= 623.

Example 99

2,6-Difluoro-N-{3-[3-(2-{[3-fluoro-4-(4-morpholinyl)-phenyl]amino}-4-pyrimidinyl)pyrazolo[1,5-a]pyridin-2-yl]phenyl}benzamide

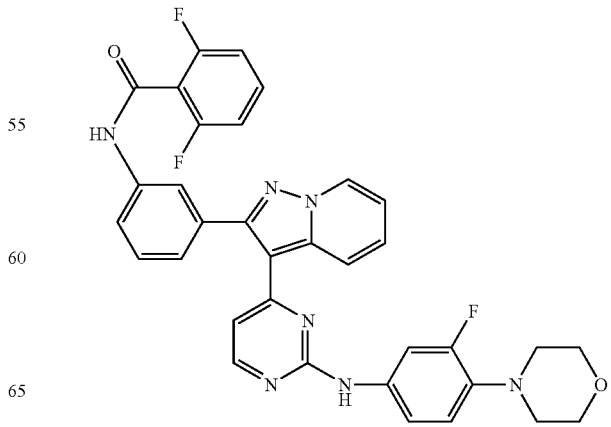

The title compound was prepared from N-{3-[3-(2-chloro-4-pyrimidinyl)pyrazolo[1,5-a]pyridin-2-yl]phenyl}-2,6-difluorobenzamide and 3-fluoro-4-(4-morpholinyl)aniline by a procedure similar to Example 64. $^1$H NMR (400 MHz, DMSO-d$_6$) δ 2.97 (t, 4H, J=4.5 Hz), 3.76 (t, 4H, J=4.5 Hz), 6.61 (d, 1H, J=5.2 Hz), 6.96 (t, 1H, J=9.4 Hz), 7.17 (t, 1H, J=6.8 Hz), 7.29 (t, 2H, J=8.0 Hz), 7.37 (d, 2H, J=7.9 Hz), 7.48-7.55 (m, 2H), 7.63 (t, 1H, J=8.3 Hz), 7.73 (d, 1H, J=15.5 Hz), 7.85 (d, 1H, J=8.8 Hz), 8.06 (s, 1H), 8.32 (d, 1H, J=5.2 Hz), 8.47 (d, 1H, J=8.0 Hz), 8.90 (d, 1H, J=6.9 Hz), 9.63 (s, 1H), 10.97 (s, 1H); ESIMS (M+H)$^+$=622.

Example 100

2,6-Difluoro-N-{3-[3-(2-{[4-(4-morpholinylcarbonyl)-phenyl]amino}-4-pyrimidinyl)pyrazolo[1,5-a]pyridin-2-yl]phenyl}benzamide

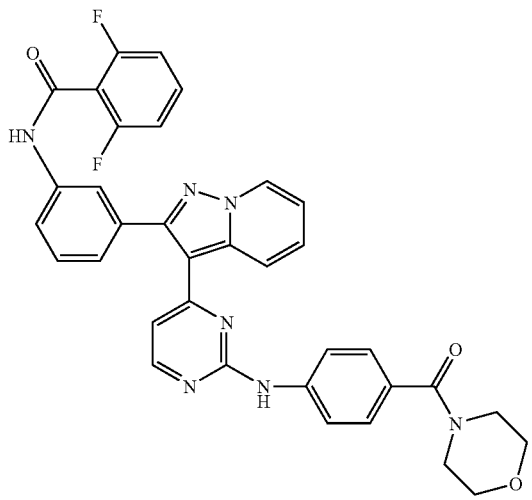

The title compound was prepared from N-{3-[3-(2-chloro-4-pyrimidinyl)pyrazolo[1,5-a]pyridin-2-yl]phenyl}-2,6-difluorobenzamide and 4-(4-morpholinylcarbonyl)aniline by a procedure similar to Example 64. $^1$H NMR (400 MHz, DMSO-d$_6$) δ 3.54 (bs, 4H), 3.63 (bs, 4H), 6.68 (d, 1H, J=5.2 Hz), 7.18 (t, 1H, J=7.0 Hz), 7.26-7.41 (m, 5H), 7.50-7.66 (m, 3H), 7.78-7.86 (m, 3H), 8.06 (s, 1H), 8.37 (d, 1H, J=5.2 Hz), 8.48 (d, 1H, J=8.9 Hz), 8.90 (d, 1H, J=6.9 Hz), 9.84 (s, 1H), 10.97 (s, 1H); ESIMS (M+H)$^+$=632.

Example 101

2,6-Difluoro-N-{3-[3-(2-{[4-(1H-pyrazol-3-yl)phenyl]amino}-4-pyrimidinyl)pyrazolo[1,5-a]pyridin-2-yl]phenyl}benzamide

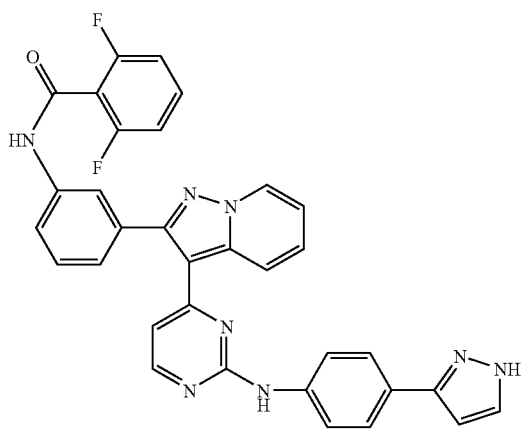

The title compound was prepared from N-{3-[3-(2-chloro-4-pyrimidinyl)pyrazolo-[1,5-a]pyridin-2-yl]phenyl}-2,6-difluorobenzamide and [4-(1H-pyrazol-3-yl)phenyl]amine 4-(1H-pyrazol-3-yl)aniline by a procedure similar to Example 64. $^1$H NMR (400 MHz, DMSO-d$_6$) δ 6.60 (d, 1H, J=5.2 Hz), 6.64 (s, 1H), 7.17 (t, 1H, J=6.8 Hz), 7.29 (t, 2H, J=8.0 Hz), 7.41 (d, 1H, J=7.7 Hz), 7.54 (t, 2H, J=7.2 Hz), 7.58-7.89 (m, 8H), 8.05 (s, 1H), 8.32 (d, 1H, J=5.2 Hz), 8.55 (d, 1H, J=9.0 Hz), 8.90 (d, 1H, J=6.9 Hz), 9.70 (s, 1H), 10.98 (s, 1H); ESIMS (M+H)$^+$=584.

Example 102

2,6-Difluoro-N-{3-[3-(2-{[4-(phenylacetyl)phenyl]amino}-4-pyrimidinyl)pyrazolo[1,5-a]pyridin-2-yl]phenyl}benzamide

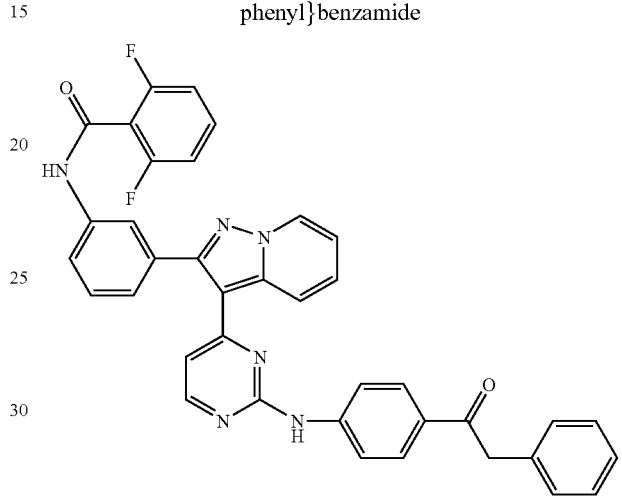

The title compound was prepared from N-{3-[3-(2-chloro-4-pyrimidinyl)pyrazolo[1,5-a]pyridin-2-yl]phenyl}-2,6-difluorobenzamide and 1-(4-aminophenyl)-2-phenylethanone 4-(1H-pyrazol-3-yl)aniline by a procedure similar to Example 64. $^1$H NMR (400 MHz, DMSO-d$_6$) δ 4.32 (s, 2H), 6.70 (d, 1H, J=5.2 Hz), 7.17-7.37 (m, 8H), 7.42 (d, 1H, J=7.7 Hz), 7.51-7.65 (m, 3H), 7.86 (d, 1H, J=8.8 Hz), 7.92 (d, 2H, J=9.0 Hz), 8.00 (d, 2H, J=8.8 Hz), 8.06 (s, 1H), 8.40 (d, 1H, J=5.4 Hz), 8.53 (d, 1H, J=9.0 Hz), 8.91 (d, 1H, J=6.8 Hz), 10.09 (s, 1H), 10.98 (s, 1H); ESIMS (M+H)$^+$=636.

Example 103

N-(3-{3-[2-({4-[(cyclopropylamino)carbonyl]phenyl}-amino)-4-pyrimidinyl]pyrazolo[1,5-a]pyridin-2-yl}phenyl)-2,6-difluorobenzamide

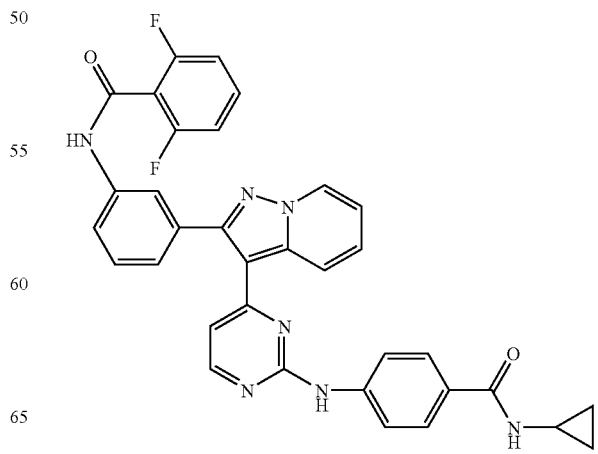

The title compound was prepared from N-{3-[3-(2-chloro-4-pyrimidinyl)pyrazolo-[1,5-a]pyridin-2-yl]phenyl}-2,6-difluorobenzamide and 4-amino-N-cyclopropylbenzamide by a procedure similar to Example 64. $^1$H NMR (400 MHz, DMSO-d$_6$) δ 0.68 (d, 2H, J=4.1 Hz), 0.71 (d, 2H, J=4.6 Hz), 2.80-2.93 (m, 1H), 6.62 (d, 1H, J=5.3 Hz), 7.18 (t, 1H, J=6.8 Hz), 7.29 (t, 2H, J=8.0 Hz), 7.41 (d, 1H, J=7.9 Hz), 7.51-7.63 (m, 3H), 7.77 (d, 2H, J=8.8 Hz), 7.87 (d, 3H, J=8.7 Hz), 8.04 (s, 1H), 8.26 (s, 1H), 8.35 (d, 1H, J=6.2 Hz), 8.53 (d, 1H, J=8.8 Hz), 8.90 (d, 1H, J=6.9 Hz), 9.88 (s, 1H), 10.97 (s, 1H); ESIMS (M+H)$^+$=602.

Example 104

N-{3-[3-(2-{[4-(Aminocarbonyl)phenyl]amino}-4-pyrimidinyl)pyrazolo[1,5-a]pyridin-2-yl]phenyl}-2,6-difluorobenzamide-ethane (1:1)

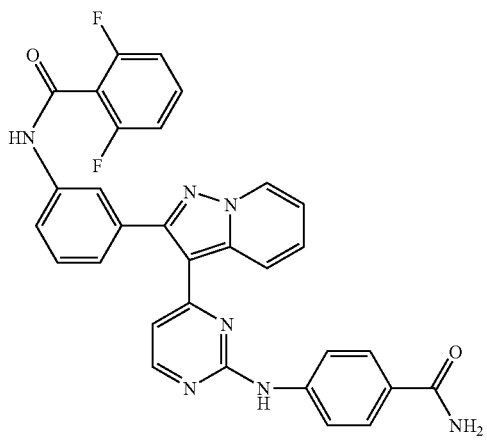

The title compound was prepared from N-{3-[3-(2-chloro-4-pyrimidinyl)pyrazolo[1,5-a]pyridin-2-yl]phenyl}-2,6-difluorobenzamide and 4-aminobenzamide by a procedure similar to Example 64. $^1$H NMR (400 MHz, DMSO-d$_6$) δ 6.62 (d, 1H, J=5.3 Hz), 7.18 (t, 2H, J=6.8 Hz), 7.29 (t, 2H, J=7.9 Hz), 7.42 (d, 1H, J=7.7 Hz), 7.52-7.65 (m, 3H), 7.81-7.88 (m, 6H), 8.04 (s, 1H), 8.36 (d, 1H, J=5.4 Hz), 8.54 (d, 1H, J=9.0 Hz), 8.91 (d, 1H, J=6.9 Hz), 9.90 (s, 1H), 10.97 (s, 1H); ESIMS (M+H)$^+$=563.

Example 105

N-[3-(3-{2-[(4-{[2-(dimethylamino)ethyl]oxy}phenyl)-amino]-4-pyrimidinyl}pyrazolo[1,5-a]pyridin-2-yl)phenyl]-2,6-difluorobenzamide

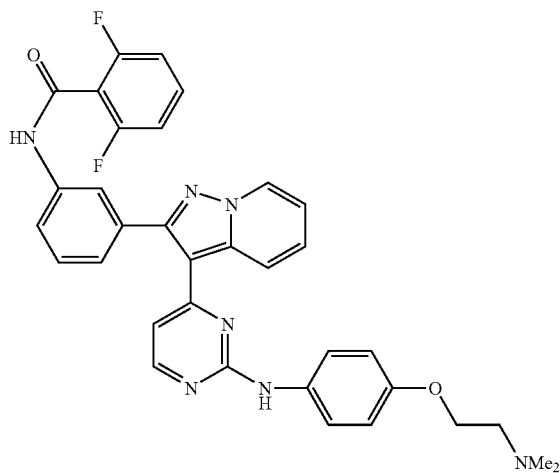

The title compound was prepared from N-{3-[3-(2-chloro-4-pyrimidinyl)pyrazolo[1,5-a]pyridin-2-yl]phenyl}-2,6-difluorobenzamide and 4-{[2-(dimethylamino)ethyl]oxy}aniline in a manner analogous to Example 64. $^1$H NMR (400 MHz, DMSO-d$_6$) δ 2.30 (s, 6H), 2.71 (t, 2H, J=5.7 Hz), 4.05 (t, 2H, J=5.7 Hz), 6.54 (d, 1H, J=5.2 Hz), 6.87 (d, 2H, J=9.0 Hz), 7.15 (t, 1H, J=6.9 Hz), 7.29 (t, 2H, J=7.9 Hz), 7.37 (d, 1H, J=7.7 Hz), 7.47-7.66 (m, 5H), 7.86 (d, 1H, J=8.0 Hz), 8.04 (s, 1H), 8.26 (d, 1H, J=5.2 Hz), 8.46 (bd, 1H, J=8.9 Hz), 8.87 (d, 1H, J=6.9 Hz), 9.39 (s, 1H), 10.98 (s, 1H); ESIMS (M+H)$^+$=606.

Example 106

2,6-Difluoro-N-[3-(3-{2-[(4-{[2-(4-methyl-1-piperazinyl)ethyl]oxy}phenyl)amino]-4-pyrimidinyl}pyrazolo[1,5-a]pyridin-2-yl)phenyl]benzamide

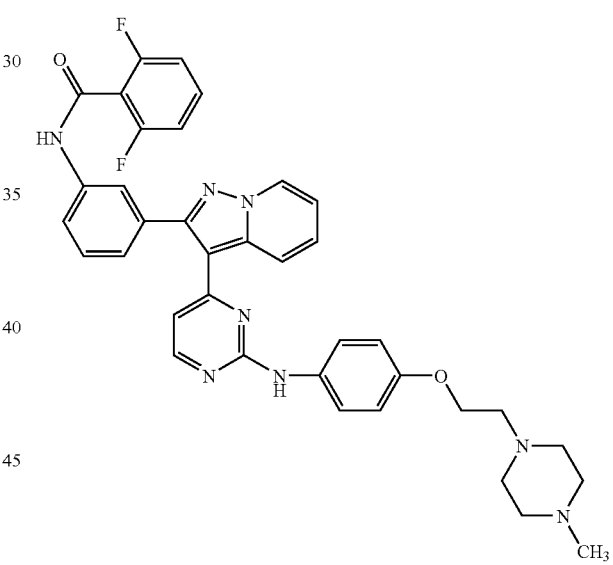

The title compound was prepared from N-{3-[3-(2-chloro-4-pyrimidinyl)pyrazolo[1,5-a]pyridin-2-yl]phenyl}-2,6-difluorobenzamide and 4-{[2-(4-methyl-1-piperazinyl)ethyl]oxy}aniline in a manner analogous to Example 64. $^1$H NMR (400 MHz, DMSO-d$_6$) δ 2.11 (s, 3H), 2.20-2.35 (m, 4H), 2.62 (t, 2H, J=5.8 Hz), 3.00-3.60 (m, 4H overlapping with H$_2$O), 3.98 (t, 2H, J=5.8 Hz), 6.47 (d, 1H, J=5.1 Hz), 6.80 (d, 2H, J=9.0 Hz), 7.08 (t, 1H, J=6.9 Hz), 7.22 (t, 2H, J=8.0 Hz), 7.31 (d, 1H, J=7.5 Hz), 7.41-7.60 (m, 5H), 7.80 (d, 1H, J=8.1 Hz), 7.97 (s, 1H), 8.16-8.21 (m, 1H), 8.39 (bd, 1H, J=7.4 Hz), 8.81 (d, 1H, J=6.8 Hz), 9.31 (s, 1H), 10.91 (s, 1H); ESIMS (M+H)$^+$= 661.

Example 107

N-{3-[3-(2-{[4-(4-ethyl-1-piperazinyl)phenyl]amino}-4-pyrimidinyl)pyrazolo[1,5-a]pyridin-2-yl]phenyl}-2,6-difluorobenzamide

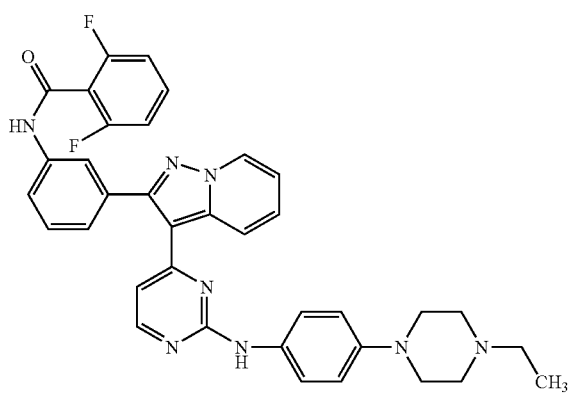

The title compound was prepared from N-{3-[3-(2-chloro-4-pyrimidinyl)pyrazolo[1,5-a]pyridin-2-yl]phenyl}-2,6-difluorobenzamide and 4-(4-ethyl-1-piperazinyl)aniline in a manner analogous to Example 64. $^1$H NMR (400 MHz, DMSO-$d_6$) δ 1.07 (t, 3H, J=7.1 Hz), 2.40 (q, 2H, J=7.1 Hz), 2.53-2.57 (m, 4H overlapping with $d_6$-DMSO), 3.08-3.11 (m, 4H), 6.52 (d, 1H, J=5.2 Hz), 6.86 (d, 2H, J=9.0 Hz), 7.15 (t, 1H, J=5.7 Hz), 7.29 (t, 2H, J=8.0 Hz), 7.36 (d, 1H, J=7.8 Hz), 7.46-7.54 (m, 4H), 7.62 (quintet, 1H, J=8.4 Hz), 7.85 (d, 1H, J=8.7 Hz), 8.04 (s, 1H), 8.25 (d, 1H, J=5.4 Hz), 8.47 (bd, 1H, J=8.9 Hz), 8.87 (d, 1H, J=6.9 Hz), 9.30 (s, 1H), 10.98 (s, 1H); ESIMS (M+H)$^+$=631.

Example 108

N-(3-{3-[2-({4-[(Dimethylamino)methyl]phenyl}amino)-4-pyrimidinyl]pyrazolo[1,5-a]pyridin-2-yl}phenyl)-2,6-difluorobenzamide

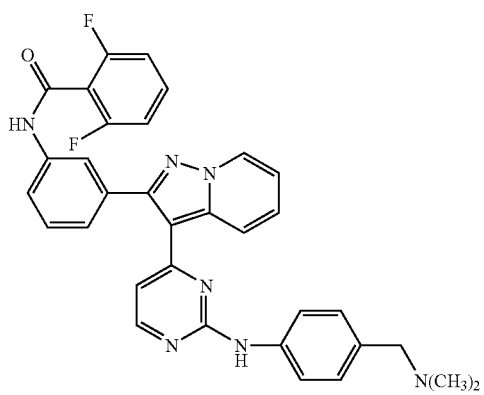

The title compound was prepared from N-{3-[3-(2-chloro-4-pyrimidinyl)pyrazolo[1,5-a]pyridin-2-yl]phenyl}-2,6-difluorobenzamide and 4-[(dimethylamino)methyl]aniline by a procedure similar to Example 64. $^1$H NMR (400 MHz, DMSO-$d_6$) δ 2.11 (s, 6H), 3.96 (s, 2H), 6.53 (d, 1H, J=5.4 Hz), 7.01 (t, 1H, J=8.1 Hz), 7.08-7.14 (m, 3H), 7.22 (t, 2H, J=8.0 Hz), 7.31 (d, 1H, J=7.7 Hz), 7.41-7.47 (m, 2H), 7.54-7.60 (m, 2H), 7.78 (d, 1H, J=8.4 Hz), 7.98 (s, 1H), 8.24 (d, 1H, J=5.3 Hz), 8.42 (bd, 1H, J=8.8 Hz), 8.82 (d, 1H, J=6.8 Hz), 9.49 (s, 1H), 10.92 (s, 1H); ESIMS (M−H)$^+$=574.

Example 109

2,6-Difluoro-N-{3-[3-(2-{[3-(4-methyl-1-piperazinyl)-phenyl]amino}-4-pyrimidinyl)pyrazolo[1,5-a]pyridin-2-yl]phenyl}benzamide

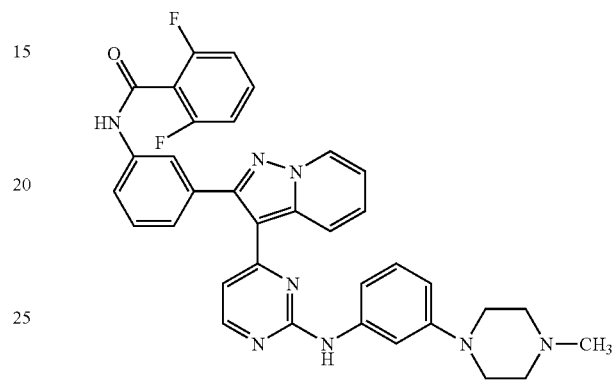

The title compound was prepared from N-{3-[3-(2-chloro-4-pyrimidinyl)pyrazolo[1,5-a]pyridin-2-yl]phenyl}-2,6-difluorobenzamide and 3-(4-methyl-1-piperazinyl)aniline in a manner analogous to Example 64. $^1$H NMR (400 MHz, DMSO-$d_6$) δ 2.25 (s, 3H), 2.46 (s, 4H), 3.11 (s, 4H), 6.53 (d, 1H, J=5.2 Hz), 6.58 (d, 1H, J=8.2 Hz), 7.09-7.19 (m, 2H), 7.24-7.31 (m, 3H), 7.239-7.65 (m, 5H), 7.86 (d, 1H, J=8.2 Hz), 8.05 (s, 1H), 8.29 (d, 1H, J=5.4 Hz), 8.53 (d, 1H, J=9.0 Hz), 8.88 (d, 1H, J=6.9 Hz), 9.42 (s, 1H), 10.98 (s, 1H); ESIMS (M+H)$^+$=617.

Example 110

N-(3-{3-[2-({3-[(N,N-dimethylglycyl)amino]phenyl}-amino)-4-pyrimidinyl]pyrazolo[1,5-a]pyridin-2-yl}phenyl)-2,6-difluorobenzamide

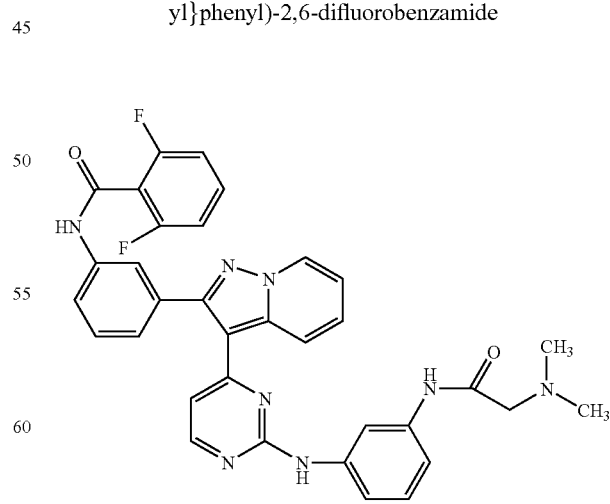

The title compound was prepared from N-{3-[3-(2-chloro-4-pyrimidinyl)pyrazolo[1,5-a]pyridin-2-yl]phenyl}-2,6-difluorobenzamide and N$^2$,N$^2$-(3-aminophenyl)-N$^2$N$^2$-dimethylglycinamide in a manner analogous to Example 64. ¹H NMR (400 MHz, DMSO-d₆) δ 2.22 (s, 6H), 3.01 (s, 2H), 6.48 (d, 1H, J=5.3 Hz), 7.08-7.58 (m, 9H), 7.81 (d, 1H, J=7.9 Hz), 7.97 (d, 2H, J=6.1 Hz), 8.22 (d, 1H, J=5.1 Hz), 8.28 (s, 1H), 8.52 (d, 1H, J=9.0 Hz), 8.82 (d, 1H, J=6.8 Hz), 9.54 (s, 2H), 10.92 (s, 1H); ESIMS (M−H)⁺=619.

Example 111

2,6-Difluoro-N-{3-[3-(2-{[4-(methyloxy)-3-(1-piperazinyl)phenyl]amino}-4-pyrimidinyl)pyrazolo[1,5-a]pyridin-2-yl]phenyl}benzamide

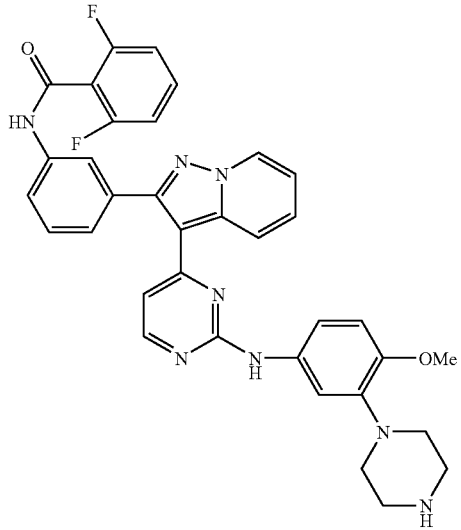

The title compound was prepared from N-{3-[3-(2-chloro-4-pyrimidinyl)pyrazolo[1,5-a]pyridin-2-yl]phenyl}-2,6-difluorobenzamide and 4-(methyloxy)-3-(1-piperazinyl)aniline in a manner analogous to Example 64. ¹H NMR (400 MHz, DMSO-d₆) δ 2.90 (s, 8H), 3.72 (s, 3H), 6.43 (d, 1H, J=5.3 Hz), 6.80 (d, 1H, J=8.8 Hz), 7.09 (t, 1H, J=6.5 Hz), 7.22 (d, 2H, J=8.1 Hz), 7.25 (d, 1H, J=3.9 Hz), 7.32 (t, 2H, J=8.3 Hz), 7.45 (q, 2H, J=7.9 Hz), 7.58 (quintet, 1H, J=8.3 Hz), 7.79 (d, 1H, J=8.2 Hz), 7.99 (s, 1H), 8.18 (d, 2H, J=5.7 Hz), 8.43 (bd, 1H, J=8.3 Hz), 8.81 (d, 1H, J=6.8 Hz), 9.26 (s, 1H), 10.92 (s, 1H); ESIMS (M+H)⁺=633.

Example 112

N-(3-{3-[2-({4-[3-(dimethylamino)propyl]phenyl}-amino)-4-pyrimidinyl]pyrazolo[1,5-a]pyridin-2-yl}phenyl)-2,6-difluorobenzamide

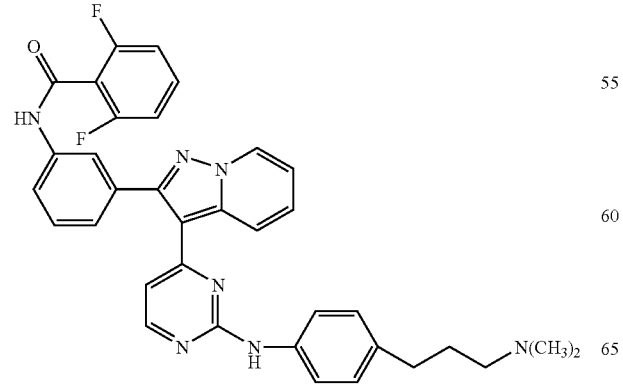

The title compound was prepared from N-{3-[3-(2-chloro-4-pyrimidinyl)pyrazolo-[1,5-a]pyridin-2-yl]phenyl}-2,6-difluorobenzamide and 4-[3-(dimethylamino)-propyl]aniline in a manner analogous to Example 64. ¹H NMR (400 MHz, DMSO-d₆) δ 1.64-1.72 (m, 2H), 2.21 (s, 6H), 2.32 (t, 2H, J=7.3 Hz), 2.47-2.51 (m, 2H, overlapping with d₆-DMSO), 6.51 (d, 1H, J=5.1 Hz), 7.03 (d, 2H, J=8.4 Hz), 7.09 (t, 1H, J=6.8 Hz), 7.23 (d, 2H, J=8.0 Hz), 7.31 (d, 1H, J=7.7 Hz), 7.42-7.47 (m, 2H), 7.53-7.59 (m, 3H), 7.79 (d, 1H, J=8.6 Hz), 7.99 (s, 1H), 8.23 (d, 1H, J=5.1 Hz), 8.42 (bd, 1H, J=8.6 Hz), 8.82 (d, 1H, J=7.0 Hz), 9.42 (s, 1H), 10.92 (s, 1H); ESIMS (M+H)⁺=604.

Example 113

N-(3-{3-[2-({4-[(N,N-dimethylglycyl)amino]phenyl}-amino)-4-pyrimidinyl]pyrazolo[1,5-a]pyridin-2-yl}phenyl)-2,6-difluorobenzamide

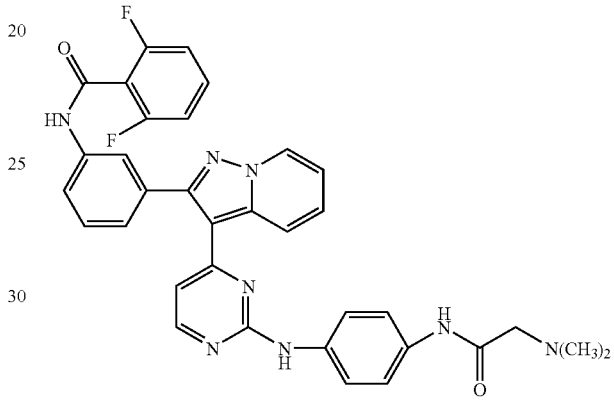

The title compound was prepared from N-{3-[3-(2-chloro-4-pyrimidinyl)pyrazolo[1,5-a]pyridin-2-yl]phenyl}-2,6-difluorobenzamide and N-(4-aminophenyl)-N²,N²-dimethylglycinamide by a procedure similar to Example 64. ¹H NMR (400 MHz, DMSO-d₆) δ 2.29 (s, 6H), 3.09 (s, 2H), 6.46 (d, 1H, J=5.3 Hz), 7.10 (t, 1H, J=6.7 Hz), 7.22 (d, 2H, J=8.0 Hz), 7.34 (d, 1H, J=7.7 Hz), 7.42-7.51 (m, 4H), 7.56 (t, 1H, J=8.2 Hz), 7.61 (d, 2H, J=8.9 Hz), 7.80 (d, 1H, J=8.0 Hz), 7.96 (s, 1H), 8.22 (d, 1H, J=5.3 Hz), 8.46 (bd, 1H, J=8.8 Hz), 8.82 (d, 1H, J=6.8 Hz), 9.47 (s, 1H), 9.60 (s, 1H), 10.91 (s, 1H); ESIMS (M+H)⁺=619.

Example 114

N-(3-{3-[2-(2,3-dihydro-1,4-benzodioxin-6-ylamino)-4-pyrimidinyl]pyrazolo[1,5-a]pyridin-2-yl}phenyl)-2,6-difluorobenzamide

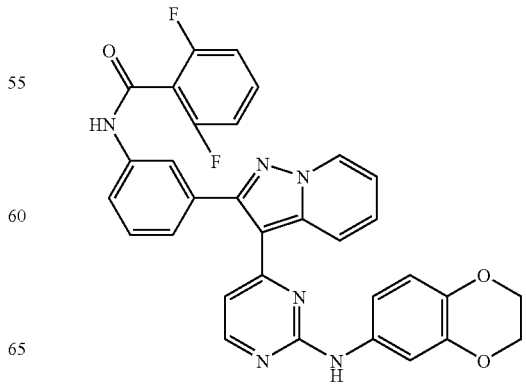

The title compound was prepared from N-{3-[3-(2-chloro-4-pyrimidinyl)pyrazolo[1,5-a]pyridin-2-yl]phenyl}-2,6-difluorobenzamide and 2,3-dihydro-1,4-benzodioxin-6-amine in a manner analogous to Example 64. ¹H NMR (400 MHz, DMSO-d₆) δ 4.20 (m, 4H), 6.45 (d, 1H, J=5.3 HZ), 6.72 (d, 1H, J=8.8 Hz), 7.10 (m, 2H), 7.22 (m, 2H), 7.28 (m, 2H), 7.35 (m, 2H), 7.46 (d, 1H, J=8.1 Hz), 7.98 (s, 1H), 8.20 (d, 1H, J=5.3 Hz), 8.83 (d, 1H, J=6.9 Hz), 9.35 (s, 1H), 10.93 (s, 1H); ESIMS (M+H)⁺=577.

Example 115

2,6-Difluoro-N-[3-(3-{2-[(3-fluorophenyl)amino]-4-pyrimidinyl}pyrazolo[1,5-a]pyridin-2-yl)phenyl]benzamide

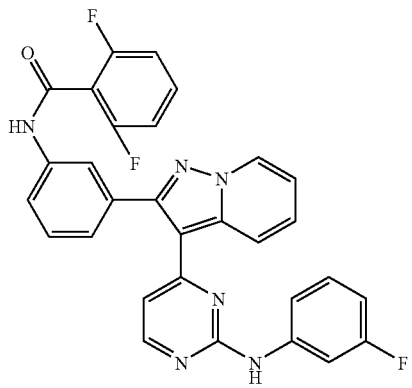

The title compound was prepared from N-{3-[3-(2-chloro-4-pyrimidinyl)pyrazolo[1,5-a]pyridin-2-yl]phenyl}-2,6-difluorobenzamide and 3-fluoroaniline in a manner analogous to Example 27, Step D. ¹H NMR (400 MHz, DMSO-d₆) δ 6.58 (d, 1H, J=5.3 Hz), 6.71 (m, 1H), 7.12 (m, 1H), 7.23 (m, 3H), 7.31 (d, 1H, J=7.7 Hz), 7.44 (m, 3H), 7.53 (m, 1H), 7.76 (m, 2H), 8.00 (s, 1H), 8.29 (d, 1H, J=5.3 Hz), 8.45 (d, 1H, J=9.0 Hz), 8.84 (d, 1H, J=7.0 Hz), 9.83 (s, 1H), 10.92 (s, 1H); ESIMS (M+H)⁺=537.

Example 116

2,6-Difluoro-N-(3-{3-[2-({4-[(methylsulfonyl)methyl]-phenyl}amino)-4-pyrimidinyl]pyrazolo[1,5-a]pyridin-2-yl}phenyl)benzamide

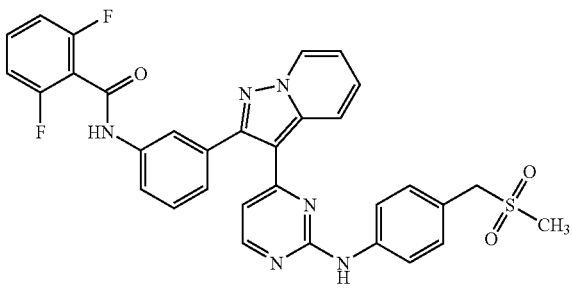

The title compound was prepared in a manner analogous to Example 27, Step D using N-{3-[3-(2-chloro-4-pyrimidinyl)pyrazolo[1,5-a]pyridin-2-yl]phenyl}-2,6-difluorobenzamide and {4-[(methylsulfonyl)methyl]phenyl}amine: ¹H NMR (400 MHz, DMSO-d₆): δ 10.93 (s, 1H); 9.66 (s, 1H); 8.85 (d, 1H); 8.49 (d, 1H); 8.27 (d, 1H); 7.99 (s, 1H); 7.82 (d, 1H); 7.73 (d, 2H); 7.58 (m, 1H); 7.48 (m, 2H); 7.36 (d, 1H); 7.26 (m, 4H); 7.12 (m, 1H); 6.56 (s, 1H); 4.37 (s, 2H); 2.86 (s, 3H). HRMS (ESI): (M+H)+calculated 611.1677, found 611.1671.

Example 117

2,6-Difluoro-N-(3-{3-[2-({3-[1-(methylsulfonyl)ethyl]-phenyl}amino)-4-pyrimidinyl]pyrazolo[1,5-a]pyridin-2-yl}phenyl)benzamide

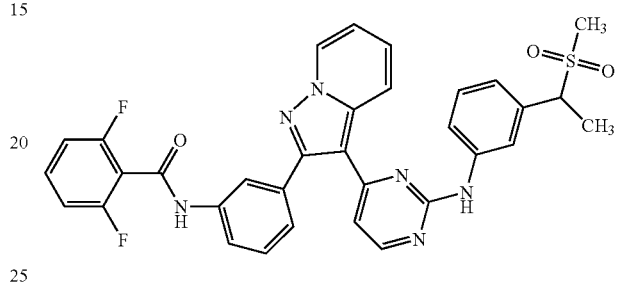

The title compound is racemic and may be prepared by a procedure similar to Example 27, Step D using N-{3-[3-(2-chloro-4-pyrimidinyl)pyrazolo[1,5-a]pyridin-2-yl]phenyl}-2,6-difluorobenzamide and racemic {3-[1-(methylsulfonyl)ethyl]-phenyl}amine. ¹H NMR (400 MHz, DMSO-d₆): δ 10.92 (s, 1H); 9.63 (s, 1H); 8.82 (d, 1H); 8.50 (d, 1H); 8.24 (d, 1H); 7.98 (s, 1H); 7.82 (d, 1H); 7.76 (br s, 2H); 7.56 (qt, 1H); 7.47 (t, 2H); 7.35 (d, 1H); 7.23 (m, 3H); 7.11 (t, 1H); 7.01 (d, 1H); 6.53 (d, 1H); 4.40 (m, 1H); 2.80 (s, 3H); 1.60 (d, 3H). HRMS (ESI): (M+H)+ calculated 625.1833, found 625.1828.

Example 118

N-{3-[3-(2-{[3-(aminosulfonyl)phenyl]amino}-4-pyrimidinyl)pyrazolo[1,5-a]pyridin-2-yl]phenyl}-2,6-difluorobenzamide

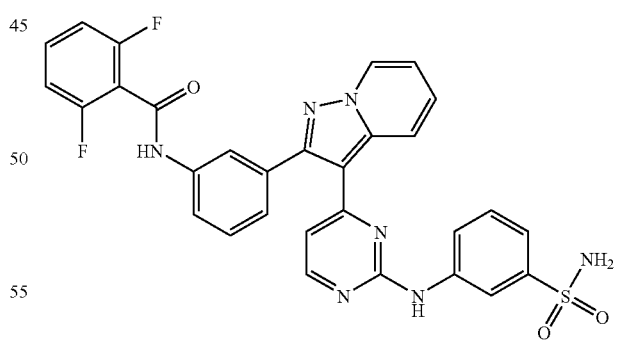

The title compound was prepared by a procedure similar to Example 27, Step D using N-{3-[3-(2-chloro-4-pyrimidinyl)pyrazolo[1,5-a]pyridin-2-yl]phenyl}-2,6-difluorobenzamide and 3-aminobenzenesulfonamide: ¹H NMR (400 MHz, DMSO-d₆): δ 10.92 (s, 1H); 9.87 (s, 1H); 8.84 (d, 1H); 8.53 (d, 1H); 7.92 (d, 1H); 7.81 (d, 1H); 7.57 (m, 1H); 7.47 (m, 1H); 7.38 (m, 2H); 7.25 (m, 3H); 7.12 (m, 3H); 6.98 (s, 1H); 6.90 (d, 1H); 6.68 (d, 1H); 6.57 (d, 1H); 5.48 (br s, 1H). HRMS (ESI): (M+H)+ calculated 598.1473, found 598.1467.

Example 119

N-(3-{3-[2-({3-[2-(aminosulfonyl)ethyl]phenyl}-amino)-4-pyrimidinyl]pyrazolo[1,5-a]pyridin-2-yl}phenyl)-2,6-difluorobenzamide

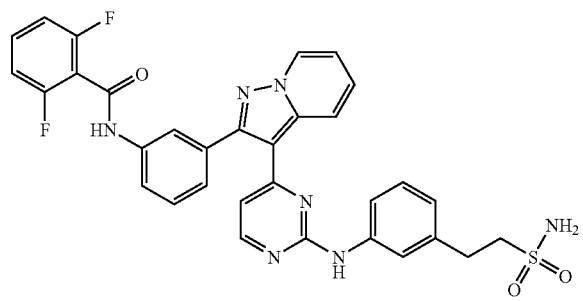

The title compound was prepared in a manner analogous to Example 27, Step D using N-{3-[3-(2-chloro-4-pyrimidinyl)pyrazolo[1,5-a]pyridin-2-yl]phenyl}-2,6-difluorobenzamide and 2-(3-aminophenyl)ethanesulfonamide. $^1$H NMR (400 MHz, DMSO-$d_6$): δ 10.91 (s, 1H); 9.51 (s, 1H); 8.83 (d, 1H); 8.49 (d, 1H); 8.25 (d, 1H); 7.98 (s, 1H); 7.82 (d, 1H); 7.63 (s, 1H); 7.56 (m, 2H); 7.47 (t, 2H); 7.35 (d, 1H); 7.23-7.08 (m, 4H); 6.84 (d, 3H); 6.51 (d, 1H); 3.20 (m, 2H); 2.94 (m, 2H). HRMS (ESI): (M+H)+ calculated 626.1786, found 626.1780.

Example 120

2,6-Difluoro-N-{3-[3-(2-{[3,4,5-tris(methyloxy)phenyl]amino}-4-pyrimidinyl)pyrazolo[1,5-a]pyridin-2-yl]phenyl}benzamide

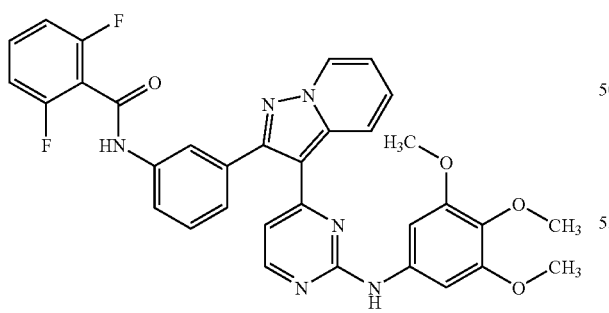

The title compound was prepared by a procedure similar to Example 27, Step D using N-{3-[3-(2-chloro-4-pyrimidinyl)pyrazolo[1,5-a]pyridin-2-yl]phenyl}-2,6-difluorobenzamide and [3,4,5-tris(methyloxy)phenyl]amine: MS (APCI): 609 (M+H)+.

Example 121

N-{3-[3-(2-{[5-(ethylsulfonyl)-2-(methyloxy)phenyl]-amino}-4-pyrimidinyl)pyrazolo[1,5-a]pyridin-2-yl]phenyl}-2,6-difluorobenzamide

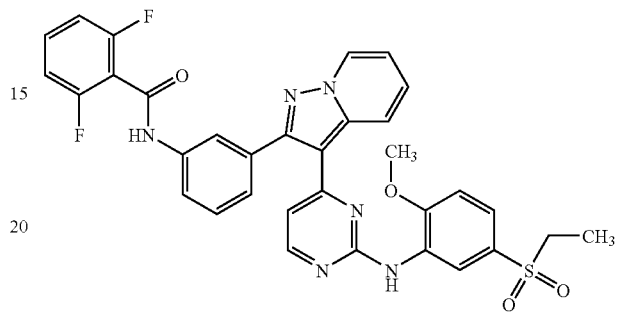

The title compound was prepared by a procedure similar to Example 27, Step D using N-{3-[3-(2-chloro-4-pyrimidinyl)pyrazolo[1,5-a]pyridin-2-yl]phenyl}-2,6-difluorobenzamide and [5-(ethylsulfonyl)-2-(methyloxy)phenyl]amine: MS (APCI): 641 (M+H)+.

Example 122

2,6-Difluoro-N-(3-{3-[2-{2-(methyloxy)-4-[(methylsulfonyl)methyl]phenyl}amino)-4-pyrimidinyl]pyrazolo[1,5-a]pyridin-2-yl}phenyl)benzamide

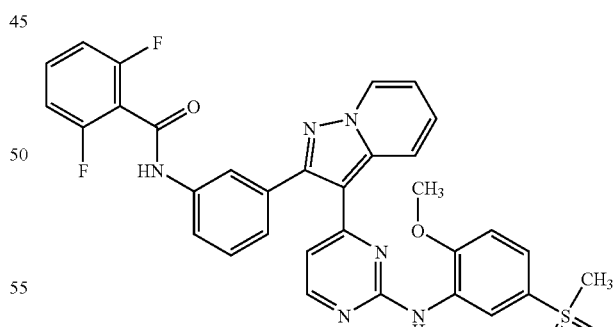

The title compound was prepared by a procedure similar to Example 27, Step D using N-{3-[3-(2-chloro-4-pyrimidinyl)pyrazolo[1,5-a]pyridin-2-yl]phenyl}-2,6-difluorobenzamide and {2-(methyloxy)-4-[(methylsulfonyl)methyl]phenyl}amine: MS (APCI): 641 (M+H)+.

Example 123

2,6-Difluoro-N-(3-{3-[2-({3-[1-(methylsulfonyl)ethyl]-phenyl}amino)-4-pyrimidinyl]pyrazolo[1,5-a]pyridin-2-yl}phenyl)benzamide

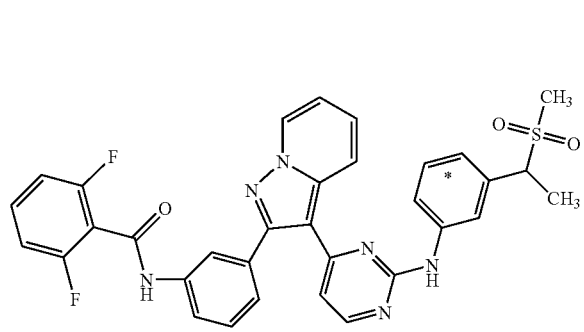

The title compound as a single enantiomer, was obtained by chiral HPLC separation of Example 117 and is the first enantiomer to elute: MS (APCI): 625 (M+H)$^+$. $^1$H NMR (400 MHz, CD$_3$OD): δ 8.59 (br d, 1H); 8.39 (br d, 1H); 8.18 (br s, 1H); 7.99 (s, 1H); 7.83 (br d, 1H); 7.77 (s, 1H); 7.67 (d, 1H); 7.47 (m, 2H); 7.41 (br s, 2H); 7.28 (t, 1H); 7.08 (br m, 4H); 6.60 (br s, 1H); 4.31 (m, 1H); 2.72 (s, 3H); 1.71 (d, 3H).

Example 124

2,6-Difluoro-N-(3-{3-[2-({3-[1-(methylsulfonyl)ethyl]-phenyl}amino)-4-pyrimidinyl]pyrazolo[1,5-a]pyridin-2-yl}phenyl)benzamide

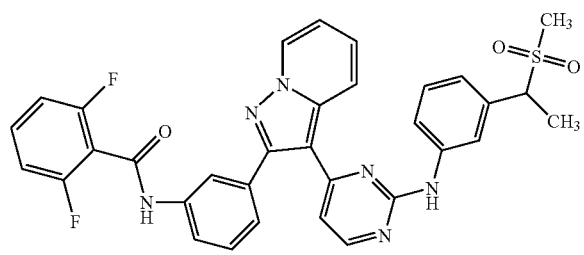

The title compound as a single enantiomer, was obtained by chiral HPLC separation of Example 117 and is the second enantiomer to elute: MS (APCI): 625 (M+H)$^+$. $^1$H NMR (400 MHz, CD$_3$OD): δ 8.61 (d, 1H); 8.42 (d, 1H); 8.22 (d, 1H); 8.00 (s, 1H); 7.85 (d, 1H); 7.79 (s, 1H); 7.69 (d, 1H); 7.49 (m, 2H); 7.43 (m, 2H); 7.30 (t, 1H); 7.09 (m, 4H); 6.63 (d, 1H); 4.33 (m, 1H); 2.74 (s, 3H); 1.73 (d, 3H).

Example 125

N-[3-(3-{2-[(3-Chloro-4-{[2-(methyloxy)ethyl]oxy}-phenyl)amino]-4-pyrimidinyl}pyrazolo[1,5-a]pyridin-2-yl)phenyl]-2,6-difluorobenzamide

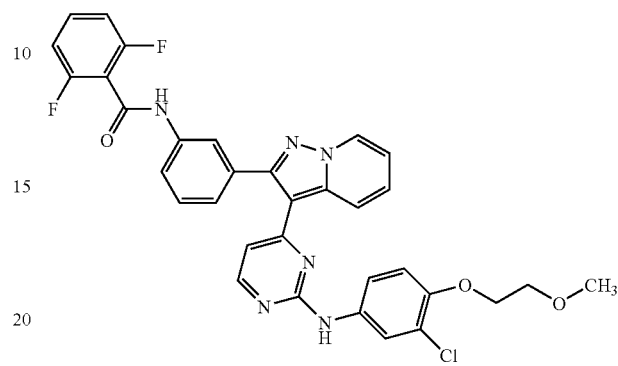

Step A: 2-Chloro-1-{[2-(methyloxy)ethyl]oxy}-4-nitrobenzene

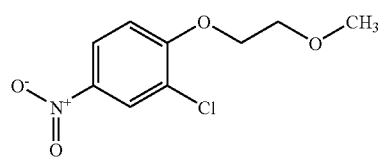

2-Chloro-1-fluoro-4-nitrobenzene (0.8 g, 4.56 mmol) and 2-(methyloxy)ethanol (0.52 g, 6.84 mmol) were combined and dissolved in Acetonitrile (15 mL). Potassium carbonate (2.4 g, 17 mmol) was then added and the resulting mixture was heated at 50° C. for 16 h. The reaction was not complete so additional potassium carbonate (1.0 g, 7.24 mmol) and 2-(methyloxy)ethanol (0.08 g, 1.05 mmol) were added as well as DMF (3 mL) to aid in solubilizing the reaction which was then heated at 85° C. for 16 h. The reaction was cooled to rt then diluted with EtOAc (250 mL) and water (150 mL). The organic layer was separated, washed with brine (100 mL), dried over Na$_2$SO$_4$, filtered and concentrated in vacuo to yield 1.0 g of the compound. $^1$H NMR (300 MHz, DMSO-d$_6$): δ 8.31 (d, 1H), 8.21 (m, 1H), 7.38 (d, 1H), 4.35 (m, 2H), 3.72 (m, 2H), 3.32 (s, 3H).

Step B: 3-Chloro-4-{[2-(methyloxy)ethyl]oxy}aniline

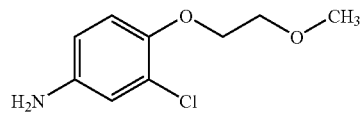

2-Chloro-1-{[2-(methyloxy)ethyl]oxy}-4-nitrobenzene (1.0 g) was dissolved in a 1:1 solution of EtOAc and ethanol (30 mL). Pt/C (0.15 g of 10% by weight) was added and the resulting mixture was placed under 50 psi of H$_2$ for 16 h. The reaction was then filtered through celite and the resulting organics were concentrated in vacuo to obtain 0.85 g of the compound. $^1$H NMR (300 MHz, DMSO-d$_6$): δ 6.88 (d, 1H), 6.66 (m, 1H), 6.50 (m, 1H), 4.00 (m, 2H), 3.63 (m, 2H), 3.33 (s, 3H).

Step C: N-[3-(3-{2-[(3-Chloro-4-{[2-(methyloxy)ethyl]oxy}phenyl)amino]-4-pyrimidinyl}pyrazolo[1,5-a]pyridin-2-yl)phenyl]-2,6-difluorobenzamide (title compound)

N-{3-[3-(2-Chloro-4-pyrimidinyl)pyrazolo[1,5-a]pyridin-2-yl]phenyl}-2,6-difluorobenzamide (0.1 g, 0.218 mmol) and 3-chloro-4-{[2-(methyloxy)ethyl]oxy}aniline (0.057 g, 0.283 mmol) were combined in a microwave safe reaction vessel. Ethylene glycol dimethyl ether (1.5 mL) and HCl (~½ drop) were then added and the resulting mixture was heated in a microwave to 160° C. for 8 min. The reaction was then cooled to rt diluted with EtOAc (100 mL) and water (50 mL). The organic layer was separated, washed with brine (50 mL), dried over Na$_2$SO$_4$, filtered and concentrated in vacuo onto silica gel. This was then purified via silica gel chromatography (EtOAc/Hexanes) to provide 55 mg of the title compound. $^1$H NMR (400 MHz, DMSO-d$_6$): δ 10.92 (s, 1H), 9.53 (s, 1H), 8.83 (d, 1H), 8.42 (br m, 1H), 8.25 (d, 1H), 8.00 (s, 1H), 7.93 (s, 1H), 7.80 (d, 1H), 7.62-7.42 (m, 4H), 7.33 (d, 1H), 7.24 (m, 2H), 7.12 (m, 1H), 7.03 (d, 1H), 6.52 (d, 1H), 4.11 (m, 2H), 3.65 (m, 2H), 3.30 (s, 3H); HRMS: calc. C$_{33}$H$_{26}$N$_6$O$_3$F$_2$ (M+H)$^+$ 627.1723 found 627.1732.

Example 126

N-[3-(3-{2-[(3-Chloro-4-{[3-(dimethylamino)propyl]-oxy}phenyl)amino]-4-pyrimidinyl}pyrazolo[1,5-a]pyridin-2-yl)phenyl]-2,6-difluorobenzamide

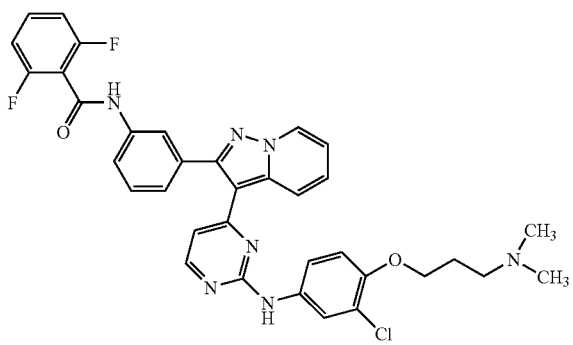

To prepare the title compound N-[3-(3-{2-[(3-chloro-4-hydroxyphenyl)amino]-4-pyrimidinyl}pyrazolo[1,5-a]pyridin-2-yl)phenyl]-2,6-difluorobenzamide (30 mg, 0.052 mmol)) and (3-chloropropyl)dimethylamine hydrochloride (8.3 mg, 0.052 mmol) were combined in a mixture of acetonitrile (1 mL) and DMF (0.2 mL). Cesium carbonate (43 mg, 0.132 mmol) was added and the resulting mixture was heated to 70° C. for 2 h then allowed to stir at rt overnight. The reaction was then diluted with EtOAc (10 mL) and water (5 mL). The organic layer was separated, washed with brine (5 mL), dried over Na$_2$SO$_4$, filtered and concentrated in vacuo. The residue was then purified via reverse phase chromatography to provide 20 mg of the title compound. $^1$H NMR (300 MHz, DMSO-d$_6$): δ 10.93 (s, 1H), 9.53 (s, 1H), 8.84 (d, 1H), 8.44 (d, 1H), 8.26 (d, 1H), 8.01 (s, 1H), 7.93 (d, 1H), 7.81 (d, 1H), 7.59 (m, 1H), 7.52-7.44 (m, 3H), 7.34 (d, 1H), 7.25 (m, 2H), 7.12 (m, 1H), 7.03 (d, 1H), 6.53 (d, 1H), 4.02 (m, 2H), 2.45 (m, 2H), 2.20 (s, 6H), 1.86 (m, 2H); HRMS: calc. C$_{35}$H$_{31}$N$_7$O$_2$F$_2$Cl (M+H)$^+$ 654.2196 found 654.2205.

Example 127

N-[3-(3-{2-[(3-Chloro-4-{[2-(4-morpholinyl)ethyl]-oxy}phenyl)amino]-4-pyrimidinyl}pyrazolo[1,5-a]pyridin-2-yl)phenyl]-2,6-difluorobenzamide

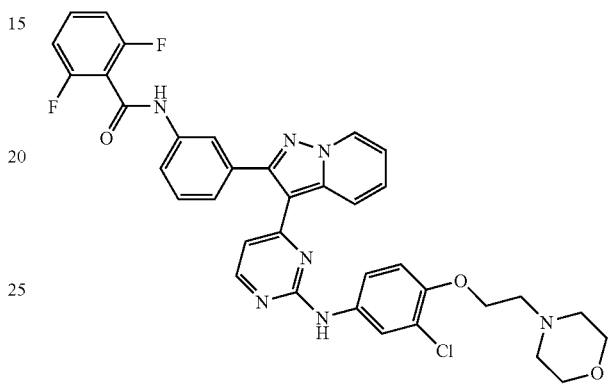

The title compound was prepared from N-[3-(3-{2-[(3-chloro-4-hydroxyphenyl)amino]-4-pyrimidinyl}pyrazolo[1,5-a]pyridin-2-yl)phenyl]-2,6-difluorobenzamide and 4-(2-chloroethyl)morpholine hydrochloride in a manner analogous to Example 126. $^1$H NMR (300 MHz, DMSO-d$_6$): δ 10.92 (s, 1H), 9.53 (s, 1H), 8.83 (d, 1H), 8.43 (d, 1H), 8.25 (d, 1H), 8.00 (s, 1H), 7.93 (m, 1H), 7.80 (d, 1H), 7.58 (m, 1H), 7.54-7.44 (m, 3H), 7.33 (d, 1H), 7.24 (m, 2H), 7.11 (m, 1H), 7.05 (d, 1H), 6.52 (d, 1H), 4.10 (m, 2H), 3.55 (m, 4H), 2.69 (m, 2H), 2.48 (m, 4H); HRMS: calc. C$_{36}$H$_{31}$N$_7$O$_3$F$_2$ (M+H)$^+$ 682.2145 found 682.2153.

Example 128

N-[3-(3-{2-[(3-Chloro-4-{[2-(dimethylamino)ethyl]-oxy}phenyl)amino]-4-pyrimidinyl}pyrazolo[1,5-a]pyridin-2-yl)phenyl]-2,6-difluorobenzamide

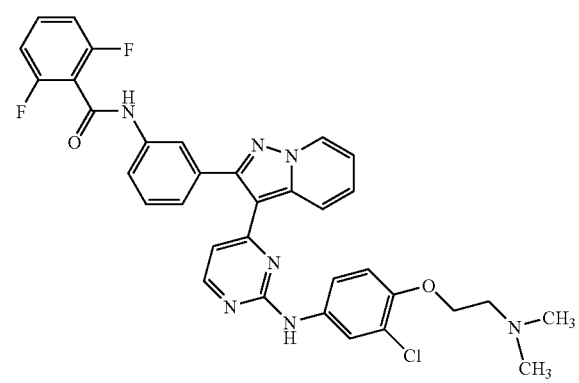

Step A: {2-[(2-Chloro-4-nitrophenyl)oxy]ethyl}dimethylamine

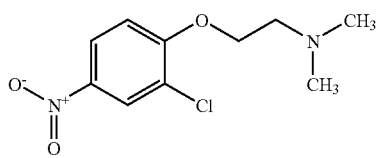

Sodium Hydride (0.274 g, 6.84 mmol, 60% disp) and THF (10 mL) were combined in a reaction vessel and cooled to 0° C. for 5 min. 2-(Dimethylamino)-ethanol (0.609 g, 6.84 mmol) was then added dropwise over 5 min and the resulting mixture was allowed to stir ~10 min. 2-Chloro-1-fluoro-4-nitrobenzene (0.8 g, 4.56 mmol) was then added in one portion and the reaction was allowed to warm to rt. Next the reaction was diluted with EtOAc (150 mL) and water (50 mL). The organic layer was separated, washed with brine (100 mL), dried over $Na_2SO_4$, filtered and concentrated in vacuo. The crude material was then chromatographed (EtOAc/Hexanes) to yield 0.56 g of the title compound. $^1$H NMR (300 MHz, DMSO-$d_6$): δ 8.30 (d, 1H), 8.21 (m, 1H), 7.38 (d, 1H), 4.29 (m, 2H), 2.69 (m, 2H), 2.23 (s, 6H).

Step B: 3-Chloro-4-{[2-(dimethylamino)ethyl]oxy}aniline

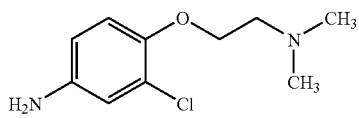

The title compound was prepared from {2-[(2-chloro-4-nitrophenyl)oxy]ethyl}dimethylamine in a manner analogous to Example 125. $^1$H NMR (300 MHz, DMSO-$d_6$): δ 6.88 (d, 1H), 6.65 (d, 1H), 6.49 (m, 1H), 4.93 (bs, 2H), 3.97 (m, 2H), 2.60 (m, 2H), 2.25 (s, 6H).

Step C: N-[3-(3-{2-[(3-Chloro-4-{[2-(dimethylamino)ethyl]oxy}phenyl)amino]-4-pyrimidinyl}pyrazolo[1,5-a]pyridin-2-yl)phenyl]-2,6-difluorobenzamide (title compound)

The title compound was prepared from N-{3-[3-(2-chloro-4-pyrimidinyl)pyrazolo-[1,5-a]pyridin-2-yl]phenyl}-2,6-difluorobenzamide and 3-chloro-4-{[2-(dimethylamino)ethyl]oxy}aniline in a manner analogous to Example 125. $^1$H NMR (400 MHz, DMSO-$d_6$): δ 10.93 (s, 1H), 9.53 (s, 1H), 8.84 (d, 1H), 8.44 (d, 1H), 8.26 (d, 1H), 8.01 (s, 1H), 7.93 (s, 1H), 7.81 (d, 1H), 7.58 (m, 1H), 7.53-7.44 (m, 3H), 7.34 (d, 1H), 7.24 (m, 2H), 7.12 (m, 1H), 7.05 (d, 1H), 4.08 (m, 2H), 2.66 (m, 2H), 2.25 (s, 6H); HRMS: calc. $C_{34}H_{29}N_7O_2F_2Cl$ (M+H)+ 640.2039 found 640.2047.

Example 129

2,6-Difluoro-N-{3-[3-(2-{[3-fluoro-4-({[(2S)-1-methyl-2-pyrrolidinyl]methyl}oxy)phenyl]amino}-4-pyrimidinyl)pyrazolo[1,5-a]pyridin-2-yl]phenyl}benzamide

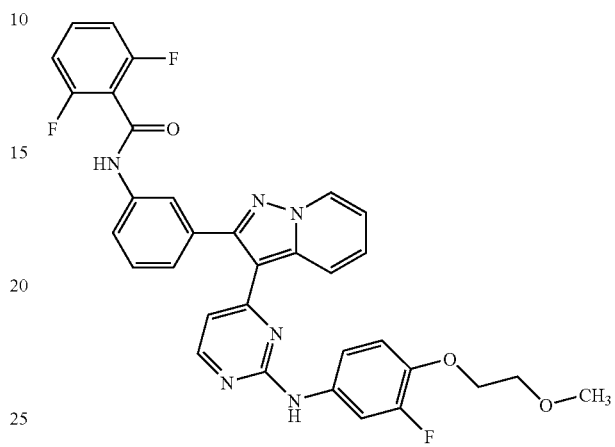

Step A: 2-Fluoro-1-{[2-(methyloxy)ethyl]oxy}-4-nitrobenzene

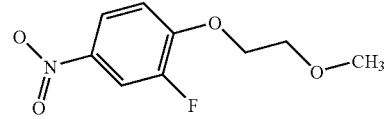

In a procedure analogous to Example 125, 0.64 g of the title compound was prepared from 0.39 mL (4.94 mmol) of 2-methoxyethanol, 0.24 g (6.11 mmol) of a 60% mineral oil dispersion of sodium hydride, and 0.75 g (4.7 mmol) of 3,4-difluoronitrobenzene as a light yellow solid. $^1$H NMR (CDCl$_3$, 400 MHz) δ 3.44 (s, 3H), 3.80 (d, 2H, J=4.6 Hz), 4.28 (t, 2H, J=4.6 Hz), 7.05 (dd, 1H, J=8.4 and 8.4 Hz), 7.98 (dd, 1H, J=10.6 and 2.7 Hz), and 8.03 (d, 1H, J=9.0 Hz).

Step B: (3-Fluoro-4-{[2-(methyloxy)ethyl]oxy}phenyl)amine

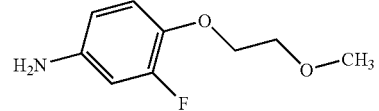

In a procedure analogous to Example 125, 250 mg of the title compound was prepared from 2-fluoro-1-{[2-(methyloxy)ethyl]oxy}-4-nitrobenzene as brown oil. $^1$H NMR (CDCl$_3$, 400 MHz) δ 3.40 (s, 3H), 3.51 (brs, 2H), 3.67 (d, 2H, J=4.7 Hz), 4.06 (t, 2H, J=4.7 Hz), 6.32 (d, 1H, J=8.6 Hz), 6.41 (dd, 1H, J=12.6 and 2.8 Hz), and 6.8 (t, 1H, J=9.0 Hz).

Step C: 2,6-Difluoro-N-{3-[3-(2-{[3-fluoro-4-({[(2S)-1-methyl-2-pyrrolidinyl]methyl}oxy)phenyl]amino}-4-pyrimidinyl)pyrazolo[1,5-a]pyridin-2-yl]phenyl}benzamide (title compound)

A solution containing 100 mg (0.261 mmol) of N-{3-[3-(2-chloro-4-pyrimidinyl)pyrazolo[1,5-a]pyridin-2-yl]phenyl}-2,6-difluorobenzamide, 56 mg (0.303 mmol) of 3-fluoro-4-{[2-(methyloxy)ethyl]oxy}phenyl)amine, one drop of HCl and 0.4 mL of DME was heated to 160° C. for 8 min in a microwave reactor. The reaction mixture was diluted in DCM and washed with aqueous NaHCO$_3$. The organic layers were dried over MgSO$_4$ and the solvent was removed under reduced pressure. The residue was subjected to silica gel chromatography to give 70 mg (44%) of the title compound as an off-white solid. $^1$H NMR (d$_6$-DMSO, 400 MHz) δ 3.30 (s, 3H), 3.63 (t, 2H, J=4.6 Hz), 4.09 (t, 2H, J=4.6 Hz), 6.54 (d, 1H, J=5.1 Hz), 7.03 (t, 1H, J=9.3 Hz), 7.12 (t, 1H, J=7.7 Hz), 7.22-7.26 (m, 2H), 7.33-7.35 (m, 2H), 7.45-7.47 (m, 2H), 7.56-7.62 (m, 1H), 7.72 (d, 1H, J=14.4 Hz), 7.80 (d, 1H, J=7.1 Hz), 8.00 (s, 1H), 8.26 (d, 1H, J=5.3 Hz), 8.42 (brd, 1H, J=7.4 Hz), 8.84 (d, 1H, J=6.9 Hz), 9.56 (s, 1H), and 10.92 (s, 1H); HRMS calcd for C$_{33}$H$_{25}$F$_3$N$_6$O$_3$: 610.1940; found: 611.2018 (M+H$^+$).

Example 130

N-[3-(3-{2-[{3-[(4-Amino-2-fluorophenyl)oxy]propyl}(methyl)amino]-4-pyrimidinyl}pyrazolo[1,5-a]pyridin-2-yl)phenyl]-2,6-difluorobenzamide

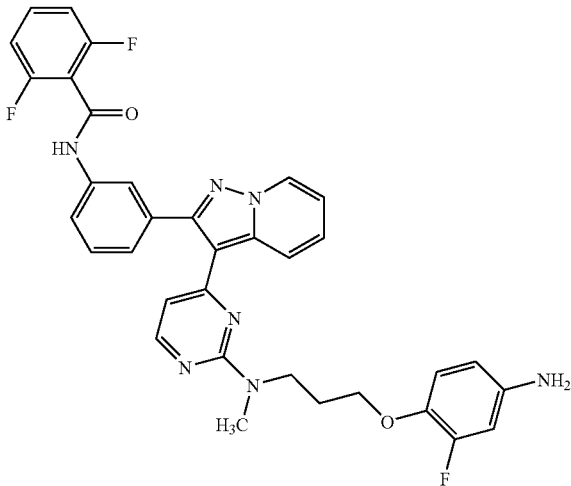

Step A {3-[(2-Fluoro-4-nitrophenyl)oxy]propyl}dimethylamine

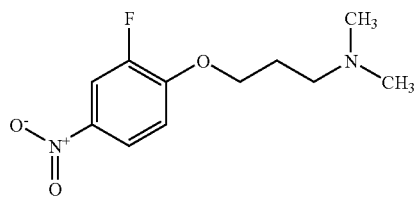

A mixture of 0.39 mL (3.3 mmol) of 3-(dimethylamino)-1-propanol, 0.16 g (4.1 mmol) of a 60% mineral oil dispersion of sodium hydride, and 0.5 g (3.1 mmol) of 3,4-difluoronitrobenzene was reacted in a procedure similar to Example 125 to give the title compound (0.4 g) as a light yellow solid: $^1$H NMR (CDCl$_3$, 400 MHz) δ 2.00-2.06 (m, 2H), 2.25 (s, 6H), 2.46 (t, 2H, J=7.0 Hz), 4.20 (t, 2H, J=6.4 Hz), 7.05 (dd, 1H, J=8.6 and 8.6 Hz), 7.98 (dd, 1H, J=10.7 and 2.7 Hz), and 8.04 (ddd, 1H, J=8.6, 2.4, and 2.4 Hz).

Step B 4-{[3-(Dimethylamino)propyl]oxy}-3-fluoroaniline

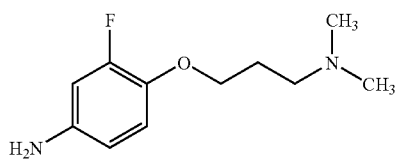

In an analogous procedure to Example 125, 343 mg of the title compound was prepared from {3-[(2-fluoro-4-nitrophenyl)oxy]propyl}dimethylamine to give the desired intermediate as brown oil: $^1$H NMR (CDCl$_3$, 400 MHz) δ 1.89-1.96 (m, 2H), 2.24 (s, 6H), 2.44 (t, 2H, J=7.1 Hz), 3.49 (brs, 2H), 3.99 (t, 2H, J=6.5 Hz), 6.36 (d, 1H, J=8.6 Hz), 6.45 (dd, 1H, J=12.6 and 2.7 Hz), and 6.81 (dd, 1H, J=9.0 and 9.0 Hz).

Step C N-[3-(3-{2-[{3-[(4-Amino-2-fluorophenyl)oxy]propyl}(methyl)amino]-4-pyrimidinyl}pyrazolo[1,5-a]pyridin-2-yl)phenyl]-2,6-difluorobenzamide (title compound)

In an analogous procedure to Example 27, Step D, 42 mg of the title compound was prepared from 100 mg (0.26 mmol) of 3-fluoro-4-{[2-(methyloxy)ethyl]oxy}phenyl)amine and 64 mg (0.303 mmol) of 4-{[3-(dimethylamino)propyl]oxy}-3-fluoroaniline as a yellow solid: $^1$H NMR (d$_6$-DMSO, 400 MHz) δ 1.90-1.97 (m, 2H), 3.12 (s, 3H), 3.73 (t, 2H, J=7.7 Hz), 3.87 (t, 2H, J=6.0 Hz), 4.90 (brs, 2H), 6.22 (d, 1H, J=8.4 Hz), 6.30 (d, 1H, J=5.5 Hz), 6.35 (dd, 1H, J=13.4 and 2.4 Hz), 6.79 (dd, 1H, J=9.1 and 9.1 Hz), 7.06 (dd, 1H, J=6.7 and 6.7 Hz), 7.22 (dd, 2H, J=7.9 and 7.9 Hz), 7.30 (d, 1H, J=7.7 Hz), 7.42-7.46 (m, 2H), 7.53-7.60 (m, 1H), 7.79 (d, 1H, J=7.9 Hz), 7.91 (s, 1H), 8.12 (d, 1H, J=5.4 Hz), 8.36 (d, 1H, J=8.9 Hz), 8.79 (d, 1H, J=7.0 Hz), and 10.88 (s, 1H); HRMS calcd for C34H28F3N7O2: 623.2257, found: 624.2354 (M+H+).

Example 131

N-[3-(3-{2-[(4-{[3-(Diethylamino)propyl]oxy}-3-fluorophenyl)amino]-4-pyrimidinyl}pyrazolo[1,5-a]pyridin-2-yl)phenyl]-2,6-difluorobenzamide

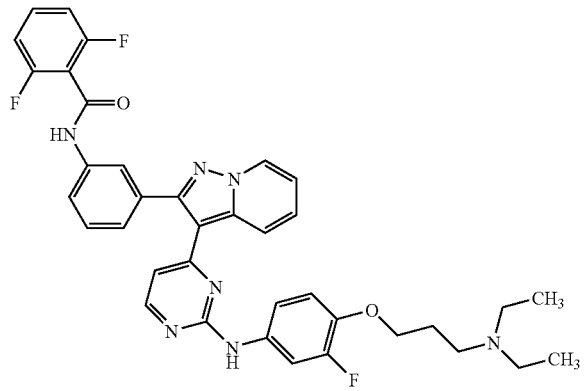

The title compound was prepared from N-{3-[3-(2-chloro-4-pyrimidinyl)pyrazolo-[1,5-a]pyridin-2-yl]phenyl}-2,6-difluorobenzamide and 4-{[3-(diethylamino)-propyl]oxy}-3-fluoroaniline in a manner analogous to Example 27, Step D. HRMS calcd for $C_{37}H_{34}F_3N_7O_2$: 665.2726; found: 666.2804 (M+H$^+$).

Example 132

2,6-Difluoro-N-{3-[3-(2-{[3-fluoro-4-({[(2S)-1-methyl-2-pyrrolidinyl]methyl}oxy)phenyl]amino}-4-pyrimidinyl)pyrazolo[1,5-a]pyridin-2-yl]phenyl}benzamide

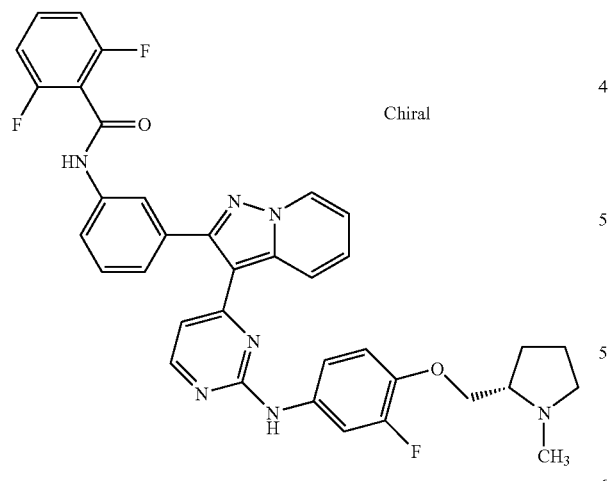

Chiral

The title compound was prepared from N-{3-[3-(2-chloro-4-pyrimidinyl)pyrazolo[1,5-a]pyridin-2-yl]phenyl}-2,6-difluorobenzamide and 3-fluoro-4-({[(2S)-1-methyl-2-pyrrolidinyl]methyl}oxy)aniline in a manner analogous to Example 27, Step D. HRMS calcd for $C_{36}H_{30}F_3N_7O_2$: 649.2413; found: 650.2491 (M+H$^+$).

Example 133

2,6-Difluoro-N-[3-(3-{2-[(3-fluoro-4-{[2-(2-oxo-1-pyrrolidinyl)ethyl]oxy}phenyl)amino]-4-pyrimidinyl}pyrazolo[1,5-a]pyridin-2-yl)phenyl]benzamide

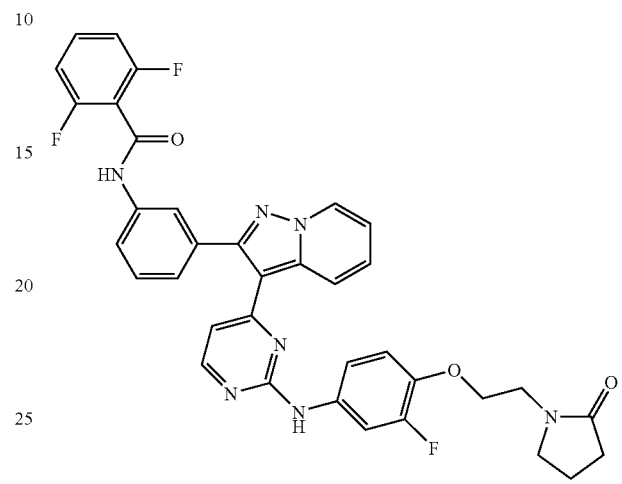

The title compound was prepared from N-{3-[3-(2-chloro-4-pyrimidinyl)pyrazolo-[1,5-a]pyridin-2-yl]phenyl}-2,6-difluorobenzamide and 1-{2-[(4-amino-2-fluorophenyl)oxy]ethyl}-2-pyrrolidinone in a manner analogous to Example 27, Step D. HRMS calcd for $C_{36}H_{28}F_3N_7O_3$: 663.2206; found: 664.2284 (M+H$^+$).

Example 134

2,6-Difluoro-N-[3-(3-{2-[(3-fluoro-4-{[2-(1-piperidinyl)ethyl]oxy}phenyl)amino]-4-pyrimidinyl}pyrazolo[1,5-a]pyridin-2-yl)phenyl]benzamide

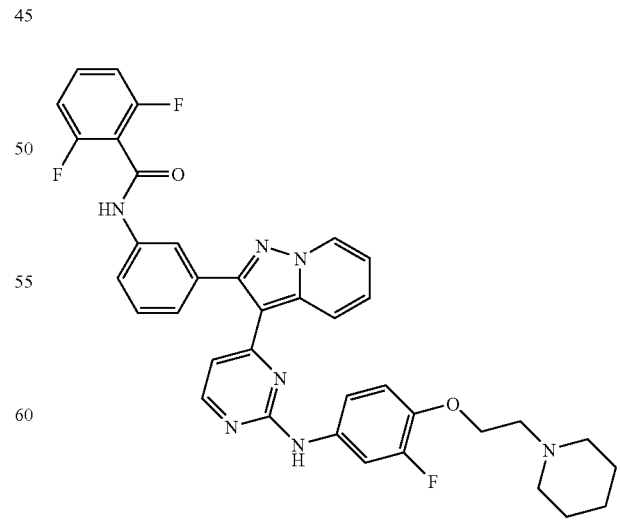

Step A: 1-{2-[(2-Fluoro-4-nitrophenyl)oxy]ethyl}piperidine

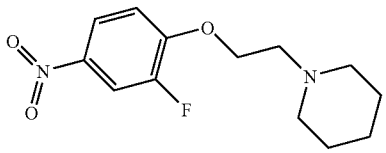

In a manner analogous to Example 125, 0.68 g of the title compound was prepared from 0.66 mL of N-(2-hydroxyethyl)piperidine as a yellow solid: $^1$H NMR (CDCl$_3$, 400 MHz) δ 1.48-1.53 (m, 2H), 1.61-1.69 (m, 4H), 2.55-2.59 (m, 4H), 2.89 (t, 2H, J=6.0 Hz), 4.31 (t, 2H, J=6.0 Hz), 7.09 (t, 1H, J=8.4 Hz), 8.04 (dd, 1H, J=8.0 and 2.6 Hz), and 8.11 (ddd, 1H, J=9.0, 2.7, and 1.3 Hz).

Step B: 3-Fluoro-4-{[2-(1-piperidinyl)ethyl]oxy}aniline

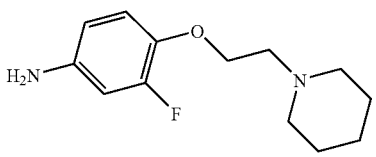

In a manner analogous to Example 125, 0.57 g of the title compound was prepared from 1-{2-[(2-fluoro-4-nitrophenyl)oxy]ethyl}piperidine as a brown oil: $^1$H NMR (CDCl$_3$, 400 MHz) δ 1.44-1.46 (m, 2H), 1.57-1.63 (m, 4H), 2.50-2.57 (m, 4H), 2.74 (t, 2H, J=6.2 Hz), 3.50 (brs, 2H), 4.08 (t, 2H, J=6.2 Hz), 6.35 (ddd, 1H, J=8.6, 2.5, and 1.5 Hz), 6.45 (dd, 1H, J=12.7 and 2.8 Hz), and 6.81 (t, 1H, J=8.8 Hz).

Step C: 2,6-Difluoro-N-[3-(3-{2-[(3-fluoro-4-{[2-(1-piperidinyl)ethyl]oxy}phenyl)-amino]-4-pyrimidinyl}pyrazolo[1,5-a]pyridin-2-yl)phenyl]benzamide (title compound)

In a manner analogous to Example 27, Step D, 27 mg of the title compound was prepared from 72 mg of 3-fluoro-4-{[2-(1-piperidinyl)ethyl]oxy}aniline and 100 mg (0.261 mmol) of N-{3-[3-(2-chloro-4-pyrimidinyl)pyrazolo[1,5-a]pyridin-2-yl]phenyl}-2,6-difluorobenzamide as a yellow solid: $^1$H NMR (DMSO-d$_6$, 400 MHz) δ 1.35-1.39 (m, 2H), 1.47-1.51 (m, 4H), 2.42-2.51 (m, 4H), 2.65-2.67 (m, 2H), 4.08 (t, 2H, J=5.8 Hz), 6.53 (d, 1H, J=5.1 Hz), 7.05 (t, 1H, J=9.2 Hz), 7.13 (t, 1H, J=5.8 Hz), 7.22-7.27 (m, 2H), 7.32-7.36 (m, 2H), 7.46-7.51 (m, 2H), 7.56-7.61 (m, 1H), 7.73 (d, 1H, J=15.8 Hz), 7.81 (d, 1H, J=7.6 Hz), 8.00 (s, 1H), 8.26 (d, 1H, J=4.8 Hz), 8.44 (brd, 1H, J=10.2 Hz), 8.85 (d, 1H, J=7.6 Hz), 9.56 (s, 1H), and 10.92 (s, 1H); HRMS calcd for C$_{37}$H$_{32}$F$_3$N$_7$O$_2$: 663.2570; found: 664.2648 (M+H$^+$).

Example 135

2,6-Difluoro-N-(3-{3-[2-({3-[(methylsulfonyl)methyl]phenyl}amino)-4-pyrimidinyl]pyrazolo[1,5-a]pyridin-2-yl}phenyl)benzamide

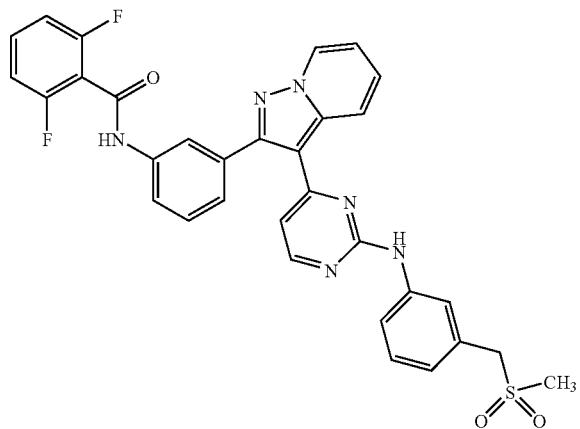

In a manner analogous to Example 27, Step D, the title compound was prepared from {3-[(methylsulfonyl)methyl]phenyl}amine and N-{3-[3-(2-chloro-4-pyrimidinyl)pyrazolo[1,5-a]pyridin-2-yl]phenyl}-2,6-difluorobenzamide. Low res MS (ES)+ 611.2.

Example 136

2,6-Difluoro-N-[3-(3-{2-[(3-{2-[(3-{[2-(1-pyrrolidinyl)ethyl]oxy}phenyl)amino]-4-pyrimidinyl}pyrazolo[1,5-a]pyridin-2-yl)phenyl]benzamide

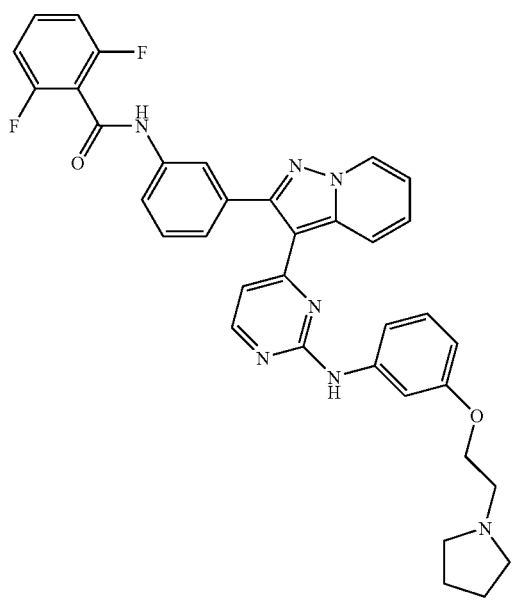

Step A: 2-Chloroethyl 3-nitrophenyl ether

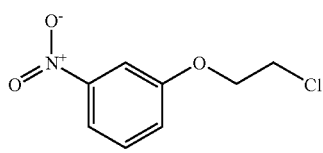

To a mixture of 3-nitrophenol (5.0 g, 35.94 mmol), $K_2CO_3$ (7.45 g, 53.9 mmol), in 2-butanone at 85° C. 1-bromo-2-chloroethane (1.723 mL, 71.88 mmol) was added and stirred for 24 h. The mixture was cooled to rt and reduced in vacuo, then diluted with EtOAc (200 mL) and water (200 mL) and separated. The aqueous layer was extracted twice with EtOAc (200 mL) and the combined organic layers were dried over $MgSO_4$ and reduced in vacuo onto silica. Purified via column chromatography using gradient of EtOAc/Hexanes to afford a yellow oil that solidified upon standing to afford 4.22 g (58% yield) of desired product as an off-white solid. $^1$H NMR (400 MHz, DMSO-$d_6$) δ 7.8 (m, 1H), 7.7 (t, J=2.4 Hz, 1H), 7.6 (t, J=8.2 Hz, 1H) 7.4 (dd, J=8.2, 2.6 Hz, 1H), 4.4 (m, 2H), 4.0 (m, 2H).

Step B: 3-[(2-Chloroethyl)oxy]aniline

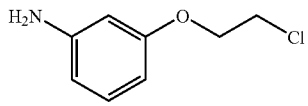

2-Chloroethyl 3-nitrophenyl ether was dissolved in 90 mL EtOAc. A portion of Pt w/sulfide (2.04 g, 0.524 mmol) was added and the reaction mixture was then purged with $H_2$ and stirred at rt under 1 atm of $H_2$ overnight. The reaction was filtered through a celite plug and reduced under vacuo to attend 3.4 g (95% yield) of a colorless oil as the desired product. $^1$H NMR (400 MHz, DMSO-$d_6$) δ 6.9 (t, J=8.0 Hz, 1H), 6.1 (m, 2H), 6.1 (ddd, J=8.1, 2.4, 0.8 Hz, 1H), 5.0 (s, 2H), 4.1 (m, 2H), 3.9 (m, 2H).

Step C: N-(3-{3-[2-({3-[(2-Chloroethyl)oxy]phenyl}amino)-4-pyrimidinyl]pyrazolo[1,5-a]pyridin-2-yl}phenyl)-2,2,2-trifluoroacetamide

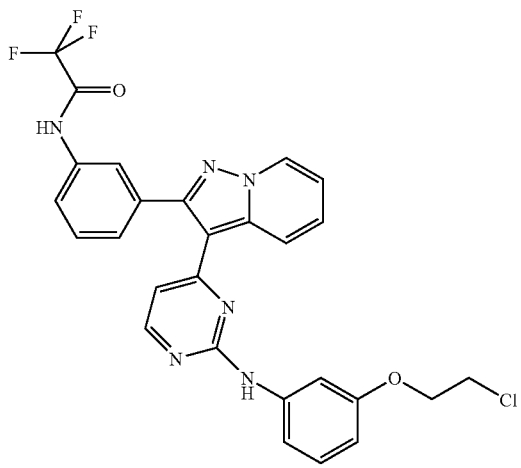

N-{3-[3-(2-Chloro-4-pyrimidinyl)pyrazolo[1,5-a]pyridin-2-yl]phenyl}-2,2,2-trifluoroacetamide (1.0 g, 2.75 mmol) was stirred in 20 ml of isopropanol, 3-[(2-chloroethyl)oxy]aniline (0.494 g, 2.89 mmol) was added along with 3 drops of conc. HCl and heated to 85° C. for 18 h. The mixture was filtered hot and washed with isopropanol. The product obtained was the HCl salt as a yellow solid (1.2 g, 74% yield). ES-LCMS m/z 553 (M+H).

Step D: 4-[2-(3-Aminophenyl)pyrazolo[1,5-a]pyridin-3-yl]-N-(3-{[2-(1-pyrrolidinyl)ethyl]oxy}phenyl)-2-pyrimidinamine

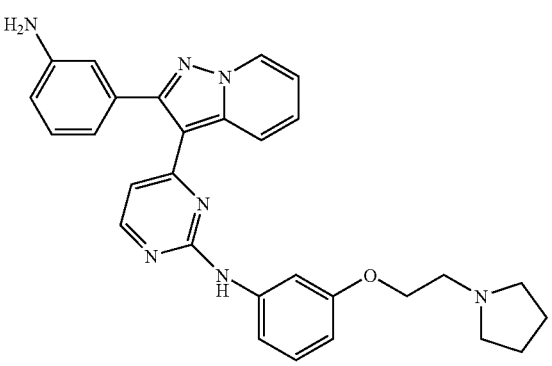

N-(3-{3-[2-({3-[(2-Chloroethyl)oxy]phenyl}amino)-4-pyrimidinyl]pyrazolo[1,5-a]pyridin-2-yl}phenyl)-2,2,2-trifluoroacetamide (0.500 g, 0.850 mmol) was dissolved in pyrrolidine and heated to 50° C. for 18 h. The reaction was cooled upon completion and absorbed directly onto silica gel. The crude product was purified via column chromatography using a 0-20% gradient of EtOAC/MeOH w/$NH_4OH$ to afford the desired product (310 mg, 74% yield) as a yellow solid. ES-LCMS m/z 492 (M+H).

Step E: 2,6-Difluoro-N-[3-(3-{2-[(3-{[2-(1-pyrrolidinyl)ethyl]oxy}phenyl)amino]-4-pyrimidinyl}pyrazolo[1,5-a]pyridin-2-yl)phenyl]benzamide

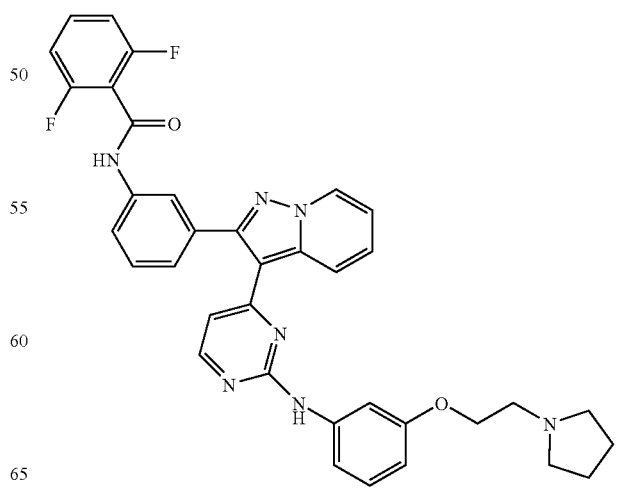

The aniline obtained from the foregoing procedure was acylated with 2-6-difluorobenzoyl chloride using conditions similar to Example 66 on 0.16 mmol scale and purified via column chromatography using a 0-20% gradient of EtOAC/MeOH w/NH₄OH to afford the desired product as a yellow solid, 45 mg, 44% yield. ¹H NMR (400 MHz, DMSO-d₆) δ 10.9 (s, 1H), 9.5 (s, 1H), 8.8 (m, 1H), 8.5 (s, 1H), 8.2 (d, J=5.3 Hz, 1H), 8.0 (t, J=1.7 Hz, 1H), 7.8 (m, 1H), 7.6 (ddd, J=8.6, 6.7, 1.7 Hz, 1H), 7.5 (m, 3H), 7.3 (dt, J=7.8, 1.2 Hz, 1H), 7.2 (t, J=8.0 Hz, 3H), 7.1 (m, 2H), 6.5 (m, 2H), 4.0 (t, J=6.0 Hz, 2H), 2.7 (t, J=6.0 Hz, H), 2.4 (s, 4H), 1.6 (dq, J=6.7, 3.2 Hz, 4H). ES-LCMS m/z 632 (M+H).

Example 137

Furan-2-carboxylic acid {3-[3-(2-phenylamino-pyrimidin-4-yl)-pyrazolo[1,5-a]pyridin-2-yl]-phenyl}-amide

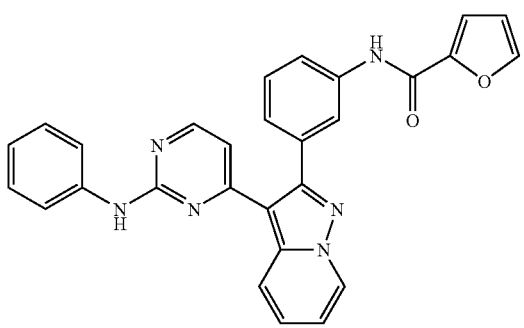

To a solution of {4-[2-(3-amino-phenyl)-pyrazolo[1,5-a]pyridin-3-yl]-pyrimidin-2-yl}-phenyl-amine (40 mg, 0.105 mmol) in mixture of DCM (1.2 mL) and pyridine (0.3 mL) was added 2-furoyl chloride (0.013 mL, 0.11 mmol). The resultant mixture was stirred at rt for 12 h. The mixture was concentrated in vacuo. The residue was purified by chromatography on a silica gel column to yield the title compound (15 mg). ¹H NMR (400 MHz, DMSO-d₆) ppm 6.55 (m, 1H), 6.70 (m, 1H), 6.94 (m, 1H), 7.14 (m, 1H), 7.31 (m, 4H), 7.48 (m, 2H), 7.71 (m, 2H), 7.93 (m, 2H), 8.09 (m, 1H), 8.26 (m, 1H), 8.50 (m, 1H), 8.85 (m, 1H), 9.60 (s, 1H), 10.3 (s, 1H). LC/MS: m/z 473 (M+1)⁺.

Example 138

N-{3-[3-(2-Phenylamino-pyrimidin-4-yl)-pyrazolo[1,5-a]pyridin-2-yl]-phenyl}-nicotinamide

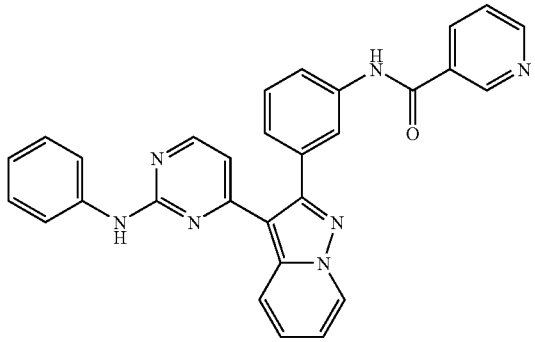

To a solution of {4-[2-(3-amino-phenyl)-pyrazolo[1,5-a]pyridin-3-yl]-pyrimidin-2-yl}-phenyl-amine (40 mg, 0.105 mmol) in mixture of DCM (1.2 mL) and pyridine (0.3 mL) was added nicotinoyl chloride hydrochloride (23 mg, 0.11 mmol). The resultant mixture was stirred at rt for 12 h. The resultant precipitate was collected by filtration, and washed with water and diethyl ether to give N-{3-[3-(2-phenylamino-pyrimidin-4-yl)-pyrazolo[1,5-a]pyridin-2-yl]-phenyl}-nicotinamide (19 mg). ¹H NMR (400 MHz, DMSO-d₆) δ 6.56 (m, 1H), 6.95 (m, 1H), 7.15 (m, 1H), 7.27 (m, 2H), 7.36 (m, 1H), 7.51 (m, 2H), 7.62 (m, 1H), 7.71 (m, 2H), 7.96 (m, 1H), 8.11 (m, 1H), 8.17 (m, 1H), 8.35 (m, 1H), 8.50 (m, 1H), 8.79 (m, 1H), 8.86 (m, 1H), 9.13 (m, 1H), 9.64 (s, 1H), 10.6 (s, 1H). LC/MS: m/z 484 (M+1)⁺.

Example 139

N-(3-[-{3-[2-(phenylamino-pyrimidin)-4-yl)-pyrimidinyl]pyrazolo[1,5-a]pyridin-2-yl]-}phenyl}-)-2-thioiphenecarboxamide

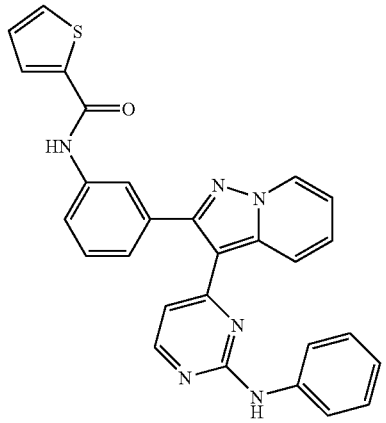

The title compound was synthesized from {4-[2-(3-amino-phenyl)-pyrazolo[1,5-a]pyridin-3-yl]-pyrimidin-2-yl}-phenyl-amine and 2-thiophenecarbonyl chloride in a manner analogous to Example 137. LC/MS: m/z 489 (M+1)⁺.

Example 140

N-(3-[-{3-(-[2-(phenylamino-pyrimidin)-4-yl)-pyrimidinyl]pyrazolo[1,5-a]pyridin-2-yl]-}phenyl}-)-2-pyridinecarboxamide

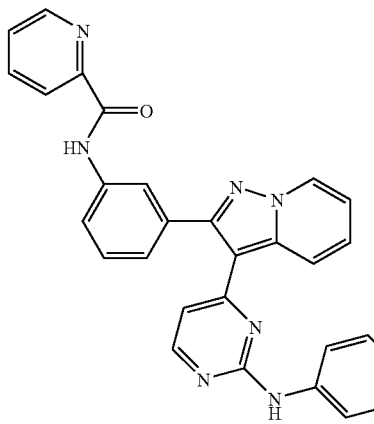

The title compound was synthesized from {4-[2-(3-amino-phenyl)-pyrazolo[1,5-a]pyridin-3-yl]-pyrimidin-2-yl}-phenyl-amine and 2-pyridinecarbonyl chloride in a manner analogous to Example 137. LC/MS: m/z 484 (M+1)⁺.

Example 141

3-Methyl-N-(3-{3-[2-(phenylamino)-4-pyrimidinyl]pyrazolo[1,5-a]pyridin-2-yl}phenyl)benzamide

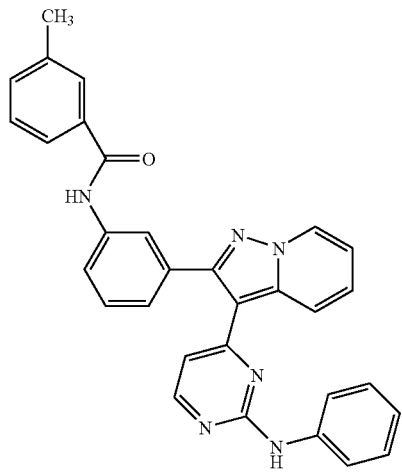

The title compound is synthesized from {4-[2-(3-amino-phenyl)-pyrazolo[1,5-a]pyridin-3-yl]-pyrimidin-2-yl}-phenyl-amine and 3-methylbenzoyl chloride in a manner analogous to Example 137 LC/MS: m/z 497 (M+1)⁺.

Example 142

4-Chloro-N-(3-{3-[2-(phenylamino)-4-pyrimidinyl]pyrazolo[1,5-a]pyridin-2-yl}phenyl)benzamide

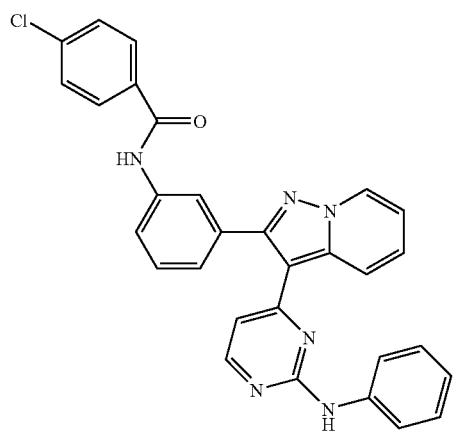

The title compound is synthesized from {4-[2-(3-amino-phenyl)-pyrazolo[1,5-a]pyridin-3-yl]-pyrimidin-2-yl}-phenyl-amine and 4-chlorobenzoyl chloride in a manner analogous to Example 137. LC/MS: m/z 517 (M+1)⁺.

Example 143

3-Amino-N-(3-{3-[2-(phenylamino)-4-pyrimidinyl]pyrazolo[1,5-a]pyridn-2-yl}phenyl)benzamide

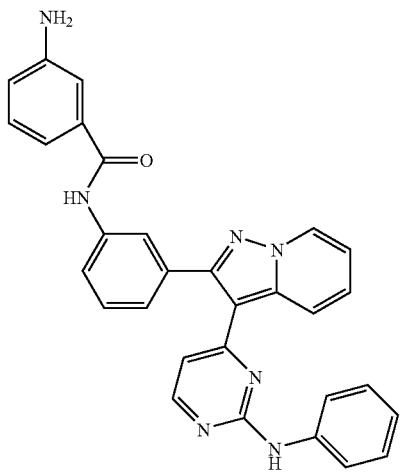

3-Nitro-N-{3-[3-(2-phenylamino-pyrimidin-4-yl)-pyrazolo[1,5-a]pyridin-2-yl]-phenyl}-benzamide is prepared from {4-[2-(3-amino-phenyl)-pyrazolo[1,5-a]pyridin-3-yl]-pyrimidin-2-yl}-phenyl-amine and 3-nitrobenzoyl chloride in a manner analogous to Example 137. The reduction of the nitro group gives the title compound. LC/MS: m/z 498 (M+1)⁺.

Example 144

4-Amino-N-(3-{3-[2-(phenylamino)-4-pyrimidinyl]pyrazolo[1,5-a]pyridin-2-yl}phenyl)benzamide

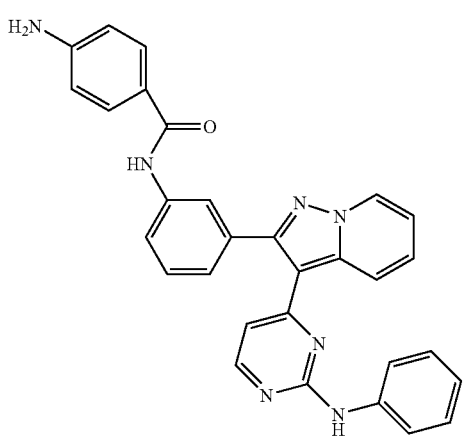

4-Nitro-N-{3-[3-(2-phenylamino-pyrimidin-4-yl)-pyrazolo[1,5-a]pyridin-2-yl]-phenyl}-benzamide was prepared from {4-[2-(3-amino-phenyl)-pyrazolo[1,5-a]pyridin-3-yl]-pyrimidin-2-yl}-phenyl-amine and 4-nitrobenzoyl chloride in a manner analogous to Example 137. The reduction of the nitro group gave the title compound. LC/MS: m/z 498 (M+1)+.

Example 145

3-Methyl-N-(3-{3-[2-(phenylamino)-4-pyrimidinyl]pyrazolo[1,5-a]pyridin-2-yl}phenyl)-2-thiophenecarboxamide

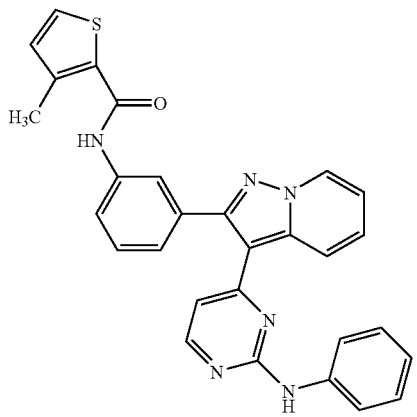

The title compound was synthesized from {4-[2-(3-aminophenyl)-pyrazolo[1,5-a]pyridin-3-yl]-pyrimidin-2-yl}-phenyl-amine and 3-methyl-2-thiophenecarbonyl chloride in a manner analogous to Example 137. LC/MS: m/z 503 (M+1)+.

Example 146

3-Methyl-N-(3-{3-[2-(phenylamino)-4-pyrimidinyl]pyrazolo[1,5-a]pyridin-2-yl}phenyl)-2-thiophenecarboxamide

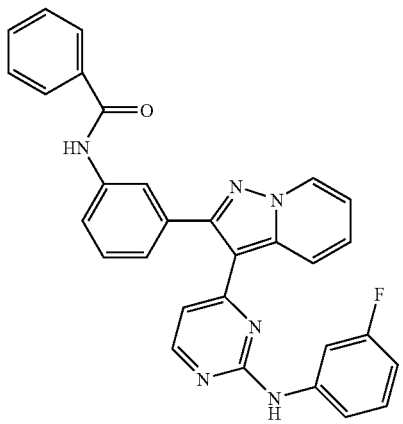

The title compound was synthesized from {4-[2-(3-aminophenyl)-pyrazolo[1,5-a]pyridin-3-yl]-pyrimidin-2-yl}-3-fluorophenyl-amine and benzoyl chloride in a manner analogous to Example 137. LC/MS: m/z 501 (M+1)+.

Example 147

2,6-Difluoro-N-{3-[3-(2-{[3-fluoro-4-(1-piperidinyl)-phenyl]amino}-4-pyrimidinyl)pyrazolo[1,5-a]pyridin-2-yl]phenyl}benzamide

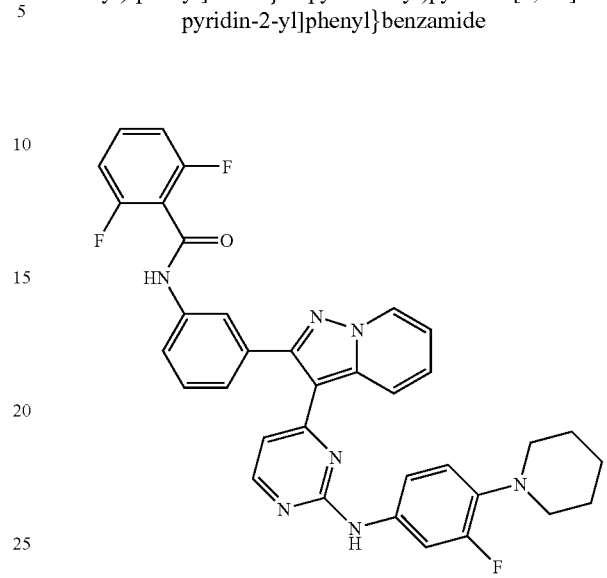

The title compound was prepared in a manner analogous to Example 27, Step D, using 3-[3-(2-chloro-4-pyrimidinyl)pyrazolo[1,5-a]pyridin-2-yl]-N-(2,6-difluorophenyl)-benzamide and 3-fluoro-4-(1-piperidinyl)aniline. ESIMS (M+H)+= 620.

Example 148

2,6-Difluoro-N-{3-[3-(2-{[3-fluoro-4-(1-pyrrolidinyl)-phenyl]amino}-4-pyrimidinyl)pyrazolo[1,5-a]pyridin-2-yl]phenyl}benzamide

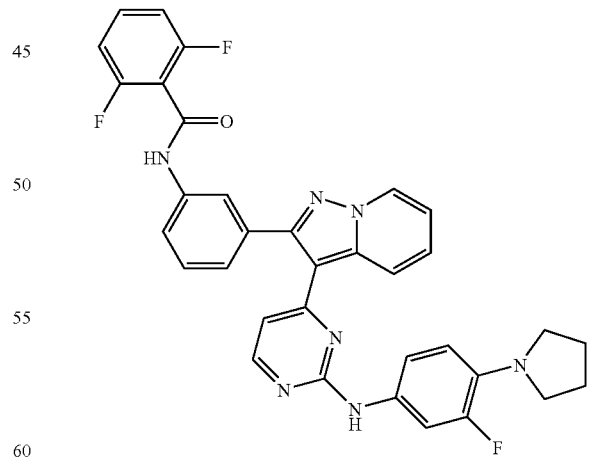

The title compound was prepared in a manner analogous to Example 27, Step D above using 3-[3-(2-chloro-4-pyrimidinyl)pyrazolo[1,5-a]pyridin-2-yl]-N-(2,6-difluorophenyl)benzamide and 3-fluoro-4-(1-pyrrolidinyl)aniline. ESIMS (M+H)+=

Example 149

N-{3-[3-(2-phenylamino-4-pyrimidinyl)-pyrazolo[1,5-b]pyridin-2-yl]phenyl}-1-methyl-1H-pyrrole-2-carboxamide

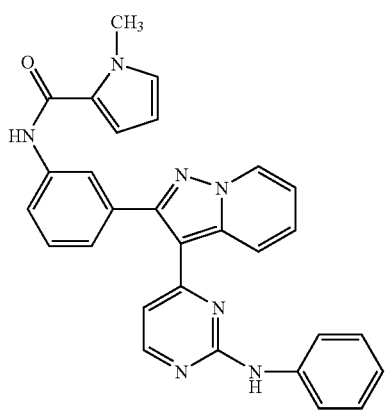

Step A: N-(3-Ethynylphenyl)-1-methyl-1H-pyrrole-2-carboxamide

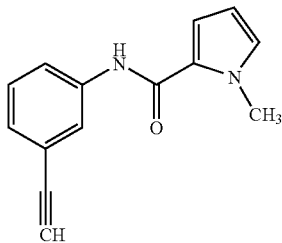

To a 0° C. solution of 3-ethynylaniline (10.35 g, 0.088 mol) in anhydrous THF (700 mL) under $N_2$ was added dropwise 1-methylpyrrole-2-carboyl chloride (12.69 g, 0.088 mol). Triethylamine (15.0 mL, 0.108 mol) was added and the mixture was allowed to warm to rt and stirred for 16 h. The mixture was partitioned between EtOAc and $H_2O$. The organic layer was dried over $Na_2SO_4$, filtered and concentrated to give a brownish solid that was triturated with diethyl ether to give 13.4 g (68%) of product. LCMS (AP)$^+$ 225.2.

Step B: N-{3-[(2-Chloro1-4-pyrimidinyl)ethynyl]phenyl}-1-methyl-1H-pyrrole-2-carboxamide

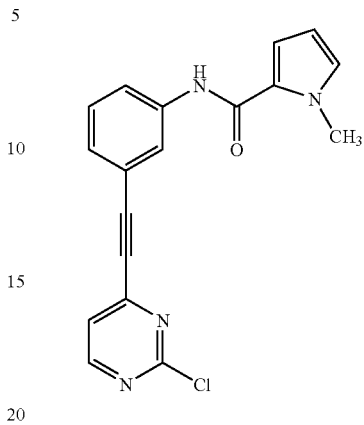

An $N_2$-flushed 3-necked 250-mL round bottom flask was charged with N-(3-ethynylphenyl)-1-methyl-1H-pyrrole-2-carboxamide (7.5 g, 33.4 mmol), 2,4-dichloropyrimidine (5.48 g, 36.8 mmol), (PPh$_3$)$_2$Cl$_2$Pd (758 mg, 1.99 mmol), Cu(I)I (164 mg, 0.90 mmol) and anhydrous THF (150 mL). Triethylamine (9.8 mL, 70.1 mmol) was added and the mixture was heated while stirring under $N_2$ for 16 h. The mixture was allowed to cool to rt and partitioned between EtOAc and $H_2O$. The separated organic layer was dried over MgSO$_4$, filtered and concentrated to give 13.7 g of crude material that was purified by silica gel chromatography to give 3.41 g (30%) of the product as a white solid. $^1$H NMR (400 MHz, DMSO-d$_6$): δ 3.28 (s, 1H), 3.82 (s, 3H), 6.06 (m, 1H), 6.99 (s, 1H), 7.00 (d, 1H), 7.11 (d, 1H), 7.30 (t, 1H), 7.70 (d, 1H), 7.88 (s, 1H), 9.80 (s, 1H).

Step C: N-{3-[3-(2-chloro-4-pyrimidinyl)-pyrazolo[1,5-b]pyridin-2-yl]phenyl}-1-methyl-1H-pyrrole-2-carboxamide

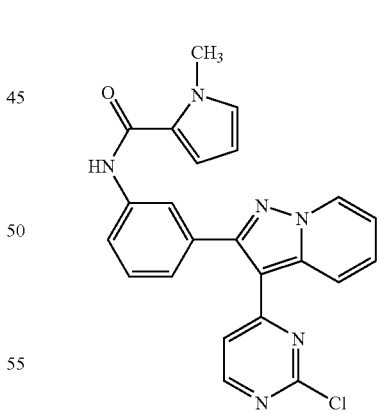

To N-{3-[(2-chloro1-4-pyrimidinyl)ethynyl]phenyl}-1-methyl-1H-pyrrole-2-carboxamide (3.31 g, 9.8 mmol) in DMSO (75 mL) at rt was added 1-amino-pyridinium iodide (2.45 g, 11 mmol), followed by KOH (1.03 g, 18.4 mmol) and K$_2$CO$_3$ (1.24 g, 9.2 mmol). The reaction was stirred for 2 h and then additional 1-amino-pyridinium iodide (0.33 g, 1.5 mmol) was added. Stirring was continued for 16 h and the DMSO was evaporated off by rotary evaporation and the dark crude partitioned between EtOAc and water. The aqueous phase was extracted with EtOAc twice and combined organics were dried over MgSO$_4$, filtered, and concentrated to dryness by rotary evaporation to yield a tan solid. Purified by crystallization from MeOH to give the desired intermediate (1.6 g, 38%) as an off-white solid. $^1$H NMR (400 MHz, DMSO-d$_6$) δ3.90 (s, 3H), 6.13 (dd, 1H, J=3.9, 2.6 Hz), 7.05-7.09 (m, 2H), 7.12 (d, 2H, J=5.3 Hz), 7.25 (dd, 1H, J=1.2, 6.8 Hz), 7.29 (d, 1H, J=8.7 Hz), 7.50 (t, 1H, J=7.9 Hz), 7.69 (t, 1H, J=7.9 Hz), 7.95 (d, 1H, J=8.0 Hz), 8.07 (s, 1H), 8.47 (d, 1H, J=8.8 Hz), 8.51 (d, 1H, J=5.5 Hz), 8.95 (d, 1H, J=6.8 Hz), 9.92 (s, 1H).

Step D: N-{3-[3-(2-phenylamino-4-pyrimidinyl)-pyrazolo[1,5-b]pyridin-2-yl]phenyl}-1-methyl-1H-pyrrole-2-carboxamide (title compound)

The title compound was prepared from aniline and N-{3-[3-(2-chloro-4-pyrimidinyl)-pyrazolo[1,5-b]pyridin-2-yl]phenyl}-1-methyl-1H-pyrrole-2-carboxamide in a manner analogous to Example 27, Step D. $^1$H NMR (400 MHz, DMSO-d$_6$) δ 3.90 (s, 3H), 6.13 (dd, 1H, J=2.7, 4.8 Hz), 6.58 (d, 1H, J=5.3 Hz), 6.98-7.09 (m, 3H), 7.17 (t, 1H, J=5.3 Hz), 7.27-7.32 (m, 3H), 7.47 (t, 1H, J=8.0 Hz), 7.53 (d, 1H, J=7.2 Hz), 7.75 (d, 2H, J=7.8 Hz), 7.92 (d, 1H, J=8.0 Hz), 8.10 (s, 1H), 8.29 (d, 1H, J=5.3 Hz), 8.55 (d, 1H, J=9.0 Hz), 8.88 (d, 1H, J=6.9 Hz), 9.63 (s, 1H), 9.92 (s, 1H); ESIMS (M+H)$^+$=486.

Example 150

N-{3-[3-(2-(3-Cyanophenyl)amino-4-pyrimidinyl)-pyrazolo[1,5-b]pyridin-2-yl]-phenyl}-1-methyl-1H-pyrrole-2-carboxamide

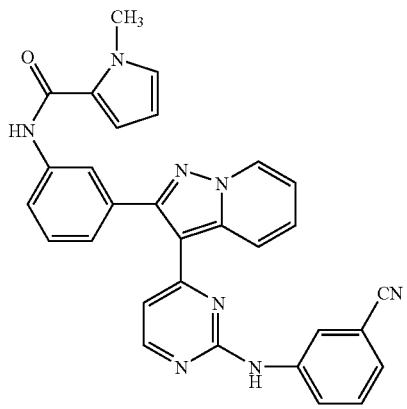

The product was prepared from 3-cyanoaniline and N-{3-[3-(2-chloro-4-pyrimidinyl)-pyrazolo[1,5-b]pyridin-2-yl]phenyl}-1-methyl-1H-pyrrole-2-carboxamide according to the methods described for earlier examples. $^1$H NMR (400 MHz, DMSO-d$_6$) δ 3.83 (s, 3H), 6.06 (dd, 1H, J=2.7, 3.7 Hz), 6.58 (d, 1H, J=5.3 Hz), 6.97 (s, 1H), 7.00 (dd, 1H, J=1.4, 5.0 Hz), 7.12 (t, 1H, J=6.8 Hz), 7.22 (d, 1H, J=7.7 Hz), 7.34 (d, 1H, J=7.5 Hz), 7.38-7.51 (m, 3H), 7.84 (d, 2H, J=8.3 Hz), 7.92 (d, 1H, J=8.8 Hz), 8.03 (s, 1H), 8.31 (d, 1H, J=5.2 Hz), 8.47 (d, 1H, J=9.0 Hz), 8.84 (d, 1H, J=6.7 Hz), 9.84 (s, 1H), 9.93 (s, 1H); ESIMS (M+H)$^+$=511.

Intermediate 1: N-{3-[5-(Hydroxymethyl)-3-(4-pyrimidinyl)pyrazolo[1,5-a]pyridin-2-yl]phenyl}benzamide

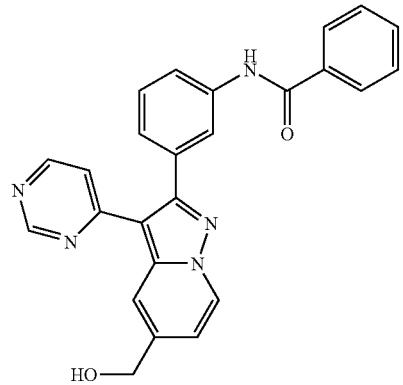

Step A: 4-({[(1,1-dimethylethyl)(dimethyl)silyl]oxy}methyl)pyridine

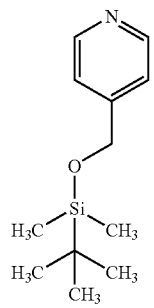

A solution of 4-pyridinemethanol (5.00 g, 45.8 mmol) in dry DMF (10 mL) was added Imidazole (8.42 g, 0.124 mol) and TBSCI (8.29 g, 55.0 mmol). The mixture was stirred at rt for 30 min. The reaction mixture was poured into water and extracted with diethyl ether (×2). The organic layers were combined, washed with brine, and dried (Na$_2$SO$_4$). The solvent was evaporated under reduced pressure. Chromatography on silica gel eluting with Hexane/EtOAc gradient (10-30% EtOAc) gave the product as a colorless oil (10.5 g).

Step B: 1-Amino-4-({[(1,1-dimethylethyl)(dimethyl)silyl]oxy}methyl)pyridinium 2,4,6-trimethylbenzenesulfonate

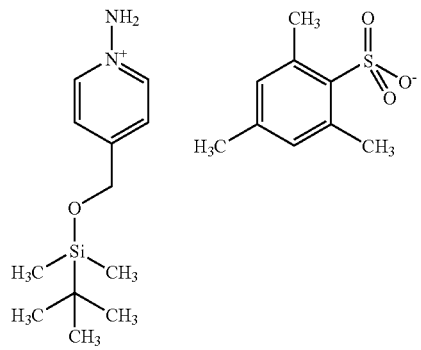

A solution of 2-[(aminooxy)sulfonyl]-1,3,5-trimethylbenzene (4.05 g, 18.8 mmol) in DCM (60 mL) was cooled to 0° C. 4-({[(1,1-dimethylethyl)(dimethyl)silyl]oxy}-methyl)pyridine (3.50 g, 15.7 mmol) in DCM (2 mL) was added dropwise. Following complete addition, the mixture was stirred at rt for 45 min. The reaction mixture was evaporated under reduced pressure to give the product as a colorless foam.

Step C: 5-({[(1,1-Dimethylethyl)(dimethyl)silyl]oxy}methyl)-3-[2-(methylthio)-4-pyrimidinyl]-2-(3-nitrophenyl)pyazolo[1,5-a]pyridine

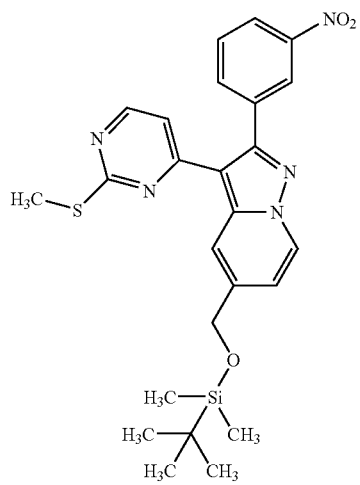

Procedure A

A solution of 1-amino-4-({[(1,1-dimethylethyl)(dimethyl)silyl]oxy}methyl)pyridinium 2,4,6-trimethylbenzenesulfonate (15.7 mmol; crude) and 2-(methylthio)-4-[(3-nitrophenyl)ethynyl]pyrimidine (2.84 g, 10.5 mmol) in dry DMF (70 mL) was cooled to 0° C. DBU (3.14 mL, 21.0 mmol) was added dropwise. Following complete addition, the mixture was stirred at rt for overnight. The reaction mixture was poured into water and extracted with EtOAc. The organic phase was combined, washed with brine, and dried (MgSO₄). The solvent was evaporated under reduced pressure. Chromatography on silica gel eluting with Hexane/EtOAc gradient (10-50% EtOAc) gave yellow solid (750 mg).

Procedure B

A solution of 1-amino-4-({[(1,1-dimethylethyl)(dimethyl)silyl]oxy}methyl)pyridinium 2,4,6-trimethylbenzenesulfonate (4.54 mmol; crude) and 2-(methylthio)-4-[(3-nitrophenyl)ethynyl]pyrimidine (820 mg, 3.03 mmol) in dry DMF (30 mL) was cooled to 0° C. Cs₂CO₃ (1.97 g, 6.05 mmol) was added. The mixture was stirred at rt overnight. The reaction mixture was poured into water and extracted with EtOAc. The organic phase was combined, washed with brine, and dried (MgSO₄). The solvent was evaporated under reduced pressure. Chromatography on silicagel eluting with Hexane/EtOAc gradient (10-50% EtOAc) gave the product (690 mg) as a yellow solid.

Step D: 1-Amino-4-[(phenylmethyl)oxy]pyridinium 2,4,6-trimethylbenzene-sulfonate

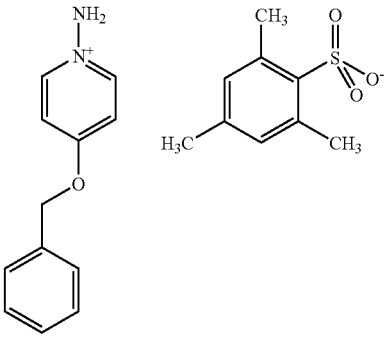

A solution of 2-[(aminooxy)sulfonyl]-1,3,5-trimethylbenzene (4.05 g, 18.8 mmol) in DCM (60 mL) was cooled to 0° C. 4-[(Phenylmethyl)oxy]pyridine (2.91 g, 15.7 mmol) in DCM (2 mL) was added dropwise. Following complete addition, the mixture was stirred at rt for 45 min. The reaction mixture was evaporated under reduced pressure to give crude white foam.

Step E: 3-[2-(Methylthio)-4-pyrimidinyl]-2-(3-nitrophenyl)-5-[(phenylmethyl)oxy]-pyrazolo[1,5-a]pyridine

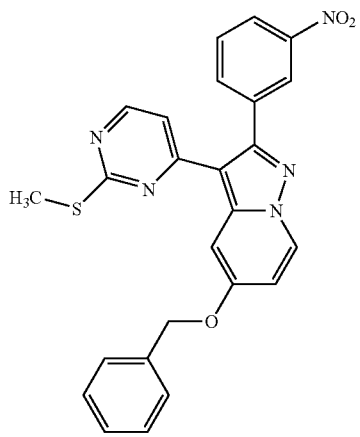

A solution of 1-amino-4-[(phenylmethyl)oxy]pyridinium 2,4,6-trimethylbenzenesulfonate (13.8 mmol; crude) and 2-(methylthio)-4-[(3-nitrophenyl)ethynyl]pyrimidine (6.30 g, 9.22 mmol) in dry-DMF (70 mL) was cooled to 0° C. Aq. K₂CO₃ (2.75 mL, 18.4 mmol) was added. The mixture was stirred at rt overnight. The reaction mixture was poured into water and extracted with EtOAc. The organic phase was combined, washed with brine, and dried (MgSO₄). The solvent was evaporated under reduced pressure. Chromatography on silica gel eluting with hexane/EtOAc gradient (15-50% EtOAc) gave yellow solid (460 mg).

Step F: 5-({[(1,1-Dimethylethyl)(dimethyl)silyl]oxy}methyl)-3-[2-(methylsulfonyl)-4-pyrimidinyl]-2-(3-nitrophenyl)pyrazolo[1,5-a]pyridine

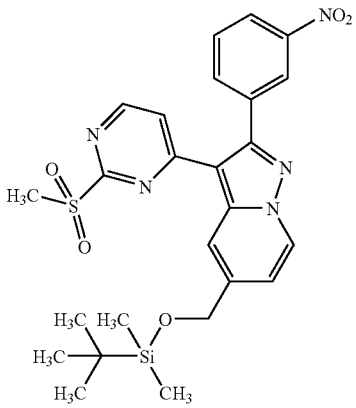

To a solution of 5-({[(1,1-dimethylethyl)(dimethyl)silyl]oxy}methyl)-3-[2-(methylthio)-4-pyrimidinyl]-2-(3-nitrophenyl)pyrazolo[1,5-a]pyridine (4.00 g, 7.88 mmol) in dichrolomethane (200 mL), m-CPBA (3.40 g, 19.7 mmol) was added one portion at rt. The mixture was stirred at rt for 1.5 h. The reaction mixture was poured into aq. $K_2CO_3$ and extracted with DCM. The organic layer was combined, washed with brine and dried ($Na_2SO_4$). The solvent was evaporated under reduced pressure. Chromatography on silica gel eluting with DCM/EtOAc gradient (0-10% EtOAc) gave the product (3.07 g) as a pale yellow solid.

Step G: 5-({[(1,1-Dimethylethyl)(dimethyl)silyl]oxy}methyl)-2-(3-nitrophenyl)-3-(4-pyrimidinyl)pyrazolo[1,5-a]pyridine

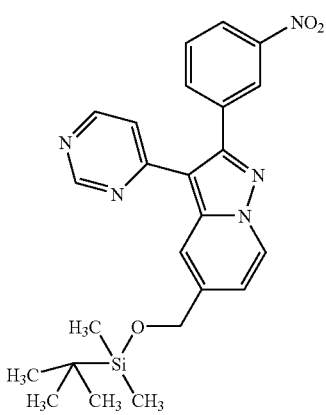

To a solution of 5-({[(1,1-dimethylethyl)(dimethyl)silyl]oxy}methyl)-3-[2-(methylsulfonyl)-4-pyrimidinyl]-2-(3-nitrophenyl)pyrazolo[1,5-a]pyridine (3.00 g, 5.56 mmol) in DCM (90 mL) and ethanol (90 mL), $NaBH_4$ (526 mg, 13.9 mmol) was added one portion at rt. The mixture was stirred at rt for 1 h. The reaction mixture was poured into aq. 1N NaOH and extracted with DCM. The organic layer was combined, washed with brine and dried ($Na_2SO_4$). The solvent was evaporated under reduced pressure. Chromatography on silica gel eluting with DCM/EtOAc gradient (0-20% EtOAc) gave a pale yellow solid (1.87 g).

Step H: [2-(3-Aminophenyl)-3-(4-pyrimidinyl)pyrazolo[1,5-a]pyridin-5-yl]methanol

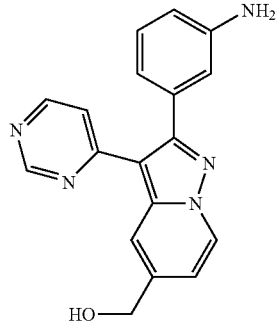

To a suspension of 5-({[(1,1-dimethylethyl)(dimethyl)silyl]oxy}methyl)-2-(3-nitrophenyl)-3-(4-pyrimidinyl)pyrazolo[1,5-a]pyridine (1.75 g, 3.79 mmol) in ethanol (88 mL), sodium sulfide nonahydrate (4.56 g, 19.0 mmol) in $H_2O$ (90 mL) was added. The mixture was heated at 100° C. under reflux for 2 h. The mixture was evaporated under reduced pressure to remove ethanol, and following the addition of $H_2O$ was cooled to 0° C. The resulting precipitate was filtered to give the product (1.16 g) as a pale orange solid.

Step I: N-{3-[5-(Hydroxymethyl)-3-(4-pyrimidinyl)pyrazolo[1,5-a]pyridin-2-yl]phenyl}benzamide (title compound)

To a suspension of [2-(3-aminophenyl)-3-(4-pyrimidinyl)pyrazolo[1,5-a]pyridin-5-yl]methanol (600 mg, 1.90 mmol) in DCM (60 mL), benzoyl chloride (0.440 mL, 3.79 mmol) was added dropwise at rt. The mixture was stirred for overnight. The reaction mixture was quenched to add MeOH, then the solvent was evaporated under reduced pressure. The residue was recrystallized from DCM (excess) and small amount of acetone. The title compound was obtained as yellow solid (820 mg).

Example 151

N-[3-(3-{2-[(3,4,5-Trimethoxyphenyl)amino]-4-pyrimidinyl}-7-trifluoropyrazolo[1,5-b]pyridin-2-yl)phenyl]-2,6-difluorobenzamide

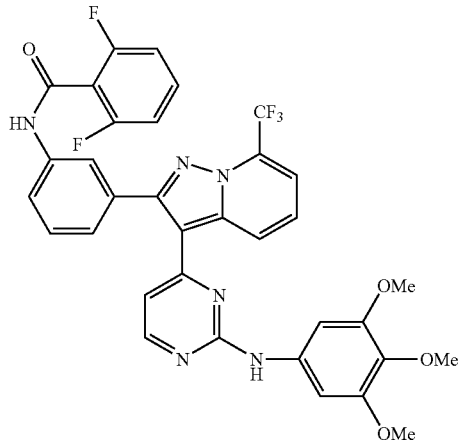

Step A: N-{3-[(2-thiomethyl-4-pyrimidinyl)ethynyl]phenyl}-2,6-difluorobenzamide

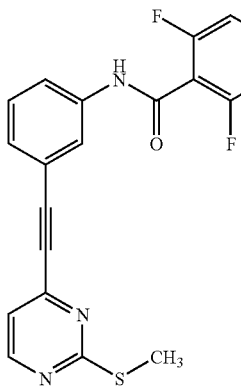

A mixture of 4-iodo-2-(methylthio)pyrimidine (0.84 g, 3.33 mmol), PdCl$_2$(PPh$_3$)$_2$ (93 mg, 0.133 mmol), Cu(I)I (13 mg, 0.067 mmol), Et$_3$N (1.95 mL, 13.9 mmol) in THF was treated by the dropwise addition of N-(3-ethynylphenyl)-2,6-difluorobenzamide (0.94 g, 3.60 mmol) over 2 h. The mixture was heated at 35° C. for 1 h, concentrated and the crude product was purified by silica gel chromatography to give the desired product (1.14 g, 83% yield). LCMS (MH)+ 382.1.

Step B: 1-Amino-2-trifluoromethylpyridinium mesitylenesulfonate

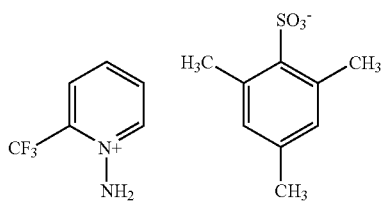

2-Trifluoromethylpyridine (7 g, 47.6 mmol) in CHCl$_3$ (100 mL) was treated with O-(mesitylenesulfonyl)-N-hydroxylamine (10.2 g, 47.6 mmol) (obtained from treatment of N-tert-butoxycarbonyl-O-(mesitylsulfonyl)hydroxylamine (15 g, 47.6 mmol) with trifluoroacetic acid (35 mL) and stirred at rt under nitrogen. After 16 h a second batch of O-(mesitylenesulfonyl)-N-hydroxylamine (4.8 g, 22.2 mmol) was added and stirring continued for 4 days. Reaction solution was evaporated to dryness, triturated with ether and filtered. Filtrate was washed with ether and dried to yield 1-amino-2-trifluoromethylpyridinium mesitylenesulfonate (9.6 g, 26.5 mmol).

Step C: N-{3-[3-(2-thiomethyl-4-pyrimidinyl)-7-trifluoromethylpyrazolo[1,5-b]pyridin-2-yl]phenyl}-2,6-difluorobenzamide

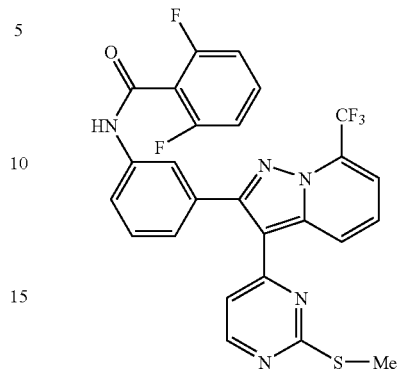

To N-{3-[(2-thiomethyl-4-pyrimidinyl)ethynyl]phenyl}-2,6-difluorobenzamide (2.5 g, 6.6 mmol) in DMSO (100 mL) at rt was added 1-amino-2-trifluoromethyl-pyridinium mesitylenesulfonate (3.5 g, 9.7 mmol), followed by KOH (1 g, 17.8 mmol) and K$_2$CO$_3$ (1 g, 17.4 mmol). The reaction was stirred for 3 h and then additional 1-amino-2-trifluoromethylpyridinium mesitylenesulfonate (2 g, 5.5 mmol) was added. Stirring was continued for 16 h and a third batch of 1-amino-2-trifluoromethyl-pyridinium mesitylenesulfonate (1 g, 2.8 mmol) added and the reaction stirred for 2 h further. The DMSO was evaporated off by rotary evaporation and the dark crude partitioned between CHCl$_3$ and water. The aqueous phase was extracted with CHCl$_3$ twice and combined organics were dried over MgSO$_4$, filtered, and concentrated to dryness by rotary evaporation. The material was purified via column chromatography (0-40% gradient of EtOAc in hexanes) to yield the title compound (2.15 g, 60%) as a yellow solid. $^1$H NMR (400 MHz, DMSO-d$_6$) δ 2.56 (s, 3H), 6.95 (d, 1H, J=5.4 Hz), 7.29 (t, 2H, J=8.1 Hz), 7.37 (d, 1H, J=7.6 Hz), 7.55 (t, 1H, J=8.3 Hz), 7.63 (t, 1H, J=8.4 Hz), 7.71 (t, 1H, J=7.5 Hz), 7.82 (d, 1H, J=6.9 Hz), 7.95-7.97 (m, 2H), 8.50 (d, 1H, J=5.2 Hz), 8.65 (d, 1H, J=7.7 Hz), 11.01 (s, 1H); ESIMS (M+H)$^+$=558.

Step D: N-{3-[3-(2-Methylsulfinyl-4-pyrimidinyl)-7-trifluoromethylpyrazolo[1,5-b]pyridin-2-yl]phenyl}-2,6-difluorobenzamide

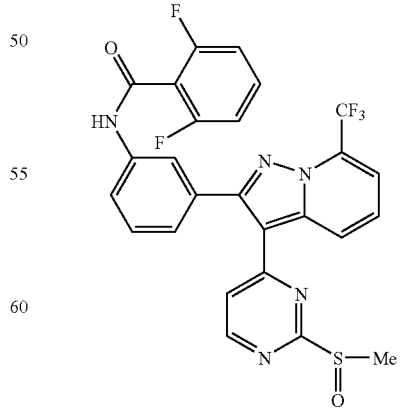

To a partial suspension of N-{3-[3-(2-thiomethyl-4-pyrimidinyl)-7-trifluoromethylpyrazolo[1,5-b]pyridin-2-yl]phenyl}-2,6-difluorobenzamide (2.12 g, 3.9 mmol) in DCM (100 mL) and 3-chloroperoxybenzoic acid (1.4 g, 50-55%, 4.0 mmol) added. After 1 h the reaction was quenched with aqueous NaHCO₃ solution and the organic phase was dried over MgSO₄, filtered, and concentrated to dryness by rotary evaporation. The material was purified via column chromatography (50-100% gradient of EtOAc in hexanes) to yield the title compound (1.85 g, 85%) as a white solid. ¹H NMR (400 MHz, DMSO-$d_6$) δ 2.95 (s, 3H), 7.30 (t, 2H, J=8.0 Hz), 7.35 (d, 1H, J=5.4 Hz), 7.43 (d, 1H, J=7.7 Hz), 7.56-7.64 (m, 2H), 7.75-7.78 (m, 1H), 7.86 (d, 1H, J=6.7 Hz), 7.96-7.99 (m, 2H), 8.82 (d, 1H, J=5.4 Hz), 8.90 (d, 1H, J=8.8 Hz), 11.04 (s, 1H); ESIMS (M+H)⁺=558.

Step E: N-[3-(3-{2-[(3,4,5-Trimethoxyphenyl) amino]-4-pyrimidinyl}-7-trifluoropyrazolo[1,5-b] pyridin-2-yl)phenyl]-2,6-difluorobenzamide (title compound)

To N-{3-[3-(2-thiomethyl-4-pyrimidinyl)-7-trifluoromethylpyrazolo[1,5-b]phenyl]-2,6-difluorobenzamide (100 mg, 0.18 mmol) in ethanol (7 mL) was added trimethoxyaniline (70 mg, 0.38 mmol). Two drops of concentrated HCl (12 M) was added from a pipette. The mixture was heated to reflux for 6 h. The reaction was cooled to rt and concentrated in vacuo. The residue was purified by column chromatography (0-50% gradient of EtOAc in hexanes) to yield the title compound (12 mg, 10%) as an off-white solid. ¹H NMR (400 MHz, DMSO-$d_6$) δ 3.66 (s, 3H), 3.73 (s, 6H), 6.58 (d, 1H, J=5.1 Hz), 7.22 (s, 2H), 7.29 (t, 2H, J=8.0 Hz), 7.40 (d, 1H, J=7.6 Hz), 7.55 (d, 2H, J=8.0 Hz), 7.63 (t, 1H, J=7.8 Hz), 7.78 (d, 1H, J=7.0 Hz), 7.95 (d, 1H, J=8.4 Hz), 8.02 (s, 1H), 8.36 (d, 1H, J=5.2 Hz), 8.81 (d, 1H, J=9.1 Hz), 9.57 (s, 1H), 11.02 (s, 1H); ESIMS (M+H)⁺=677.

Example 152

N-[3-(3-{2-[Phenylamino]-4-pyrimidinyl}-7-trifluoropyrazolo[1,5-b]pyridin-2-yl)phenyl]-2,6-difluorobenzamide

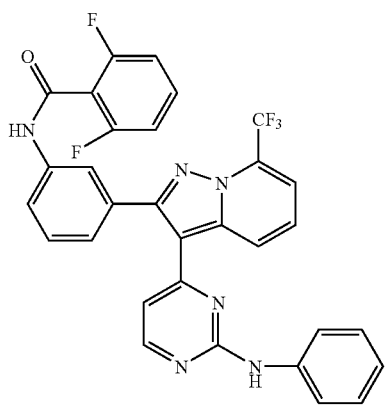

The title compound was prepared from N-{3-[3-(2-thiomethyl-4-pyrimidinyl)-7-trifluoromethylpyrazolo[1,5-b]pyridin-2-yl]phenyl}-2,6-difluorobenzamide and aniline in a manner analogous to Example 151. ¹H NMR (400 MHz, DMSO-$d_6$) δ 6.67 (d, 1H, J=5.2 Hz), 6.97 (t, 1H, J=7.0 Hz), 7.24-7.32 (m, 4H), 7.38 (d, 1H, J=7.7 Hz), 7.51-7.79 (m, 6H), 7.95 (t, 1H, J=8.2 Hz), 8.01 (s, 1H), 8.40 (d, 1H, J=5.2 Hz), 8.73 (d, 1H, J=9.0 Hz), 9.67 (s, 1H), 11.03 (s, 1H); ESIMS (M+H)⁺=587.

Example 153

N-[3-(3-{2-[3-Fluorophenylamino]-4-pyrimidinyl}-7-trifluoropyrazolo[1,5-b]pyridin-2-yl)phenyl]-2,6-difluorobenzamide

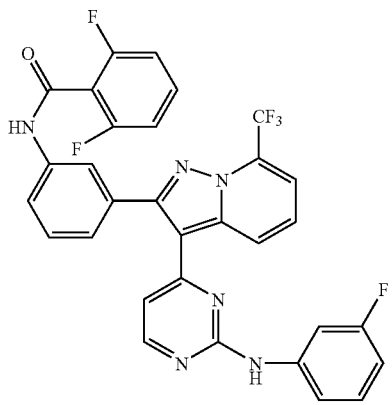

The title compound was prepared from N-{3-[3-(2-thiomethyl-4-pyrimidinyl)-7-trifluoromethylpyrazolo[1,5-b]pyridin-2-yl]phenyl}-2,6-difluorobenzamide and 3-fluoroaniline in a manner analogous to Example 151. ¹H NMR (400 MHz, DMSO-$d_6$) δ 6.70 (d, 1H, J=5.2 Hz), 6.76 (dt, 1H, J=8.4, 2.4 Hz), 7.26-7.33 (m, 3H), 7.38 (d, 1H, J=7.7 Hz), 7.46-7.68 (m, 4H), 7.76-7.80 (m, 2H), 7.95 (d, 1H, J=8.2 Hz), 8.01 (s, 1H), 8.44 (d, 1H, J=5.2 Hz), 8.74 (d, 1H, J=8.8 Hz), 9.93 (s, 1H), 11.02 (s, 1H); ESIMS (M+H)⁺=605.

Example 154

N-[3-(3-[2-{3-fluoro4-methoxyphenylamino]-4-pyrimidinyl}-7-trifluoropyrazolo[1,5-b]pyridin-2-yl) phenyl]-2,6-difluorobenzamide

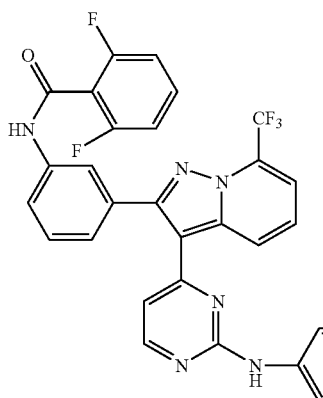

The title compound was prepared from N-{3-[3-(2-thiomethyl-4-pyrimidinyl)-7-trifluoromethylpyrazolo[1,5-b]pyridin-2-yl]phenyl}-2,6-difluorobenzamide and 3-fluoro-4-methoxyaniline in a manner analogous to Example 151. ¹H NMR (400 MHz, DMSO-$d_6$) δ 3.83 (s, 3H), 6.65 (d, 1H, J=5.2 Hz), 7.08 (t, 1H, J=9.7 Hz), 7.29 (t, 2H, J=8.0 Hz), 7.38 (d, 2H, J=7.9 Hz), 7.51-7.80 (m, 5H), 7.95 (d, 1H, J=8.3 Hz), 8.00 (s, 1H), 8.38 (d, 1H, J=5.2 Hz), 8.72 (d, 1H, J=9.0 Hz), 9.68 (s, 1H), 11.01 (s, 1H); ESIMS (M+H)$^+$=635.

Example 155

2,6-Difluoro-N-{3-[7-methyl-3-(2-{[3-(trifluoromethyl)phenyl]amino}pyrimidin-4-yl)pyrazolo[1,5-a]pyridin-2-yl]phenyl}benzamide

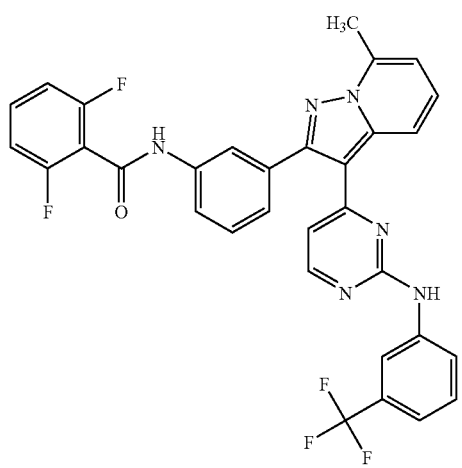

Step A: 2-Methyl-1I$^5$-pyridin-1-amine

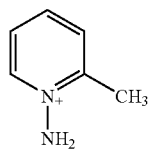

A flask was charged with 2.50 g (26.8 mmol) 2-methylpyridine and 70 mL pH-10 Buffer. In a separate flask, HOSA (4.50 g, 40.3 mmol) was dissolved in 10 mL water. KHCO$_3$ solution (2.4 M solution) was added dropwise to achieve pH of 7-8. This solution was added dropwise to the 2-methylpyridine/buffer solution and the reaction mixture heated to 70° C. After 1 h, NMR indicated 100% conversion to the aminated product. The solution was stored as a 0.28 M solution in H$_2$O. $^1$H NMR (400 MHz, D$_2$O) δ 8.52 (d, J=6.8 Hz 1H), 8.06 (t, J=8.4 Hz, 1H) 7.72 (d, J=8.0 Hz, 1H), 7.62 (t, J=7.2 Hz, 1H), 2.63 (s, 3H)

Step B: N-{3-[3-(2-chloropyrimidin-4-yl)-7-methylpyrazolo[1,5-a]pyridin-2-yl]phenyl}-2,6-difluorobenzamide

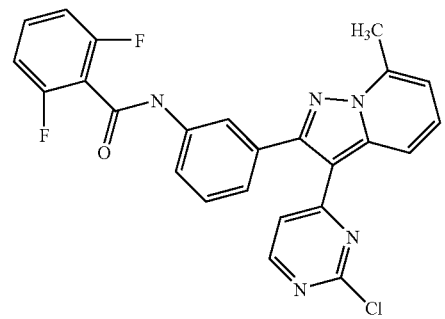

To a solution of 100 mg (0.271 mmol) of N-{3-[(2-chloropyrimidin-4-yl)ethynyl]phenyl}-2,6-difluorobenzamide in 2 mL dimethylsulfoxide was added 23.0 mg (0.406 mmole) KOH. The mixture was cooled to 0° C. and 1.5 2-methyl-1I$^5$-pyridin-1-amine (0.406 mmol, 0.28M solution in H$_2$O) was added dropwise. The ice bath was removed and the reaction stirred at rt. When all the acetylene had reacted, water was added and the title compound was filtered off as a tan solid. LCMS (APCI): [M+H]$^+$=476.

Step C: 2,6-Difluoro-N-{3-[7-methyl-3-(2-{[3-(trifluoromethyl)phenyl]amino}-pyrimidin-4-yl)pyrazolo[1,5-a]pyridin-2-yl]phenyl}benzamide (title compound)

The title compound was prepared through standard displacement conditions by microwaving N-{3-[3-(2-chloropyrimidin-4-yl)-7-methylpyrazolo[1,5-a]pyridin-2-yl]phenyl}-2,6-difluorobenzamide and 3-trifluoromethylaniline in isopropanol at 150° C. for 15 min. LCMS (ESI): [M+H]$^+$=601.

Example 156

2,6-Difluoro-N-[3-(3-{2-[(3-fluorophenyl)amino]-pyrimidin-4-yl}-7-methylpyrazolo[1,5-a]pyridin-2-yl)phenyl]benzamide

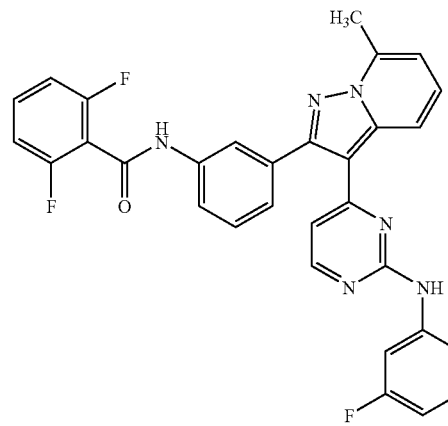

The title compound was prepared through standard displacement conditions by microwaving N-{3-[3-(2-chloropyrimidin-4-yl)-7-methylpyrazolo[1,5-a]pyridin-2-yl]phenyl}-2,6-difluoro benzamide and 3-trifluoromethylaniline in isopropanol at 150° C. for 15 min. LCMS (ESI): [M+H]$^+$ =551.

Example 157

2,6-Difluoro-N-[3-(3-{2-[(3-fluoro-4-methoxy-phenyl)amino]pyrimidin-4-yl}-7-methylpyrazolo[1,5-a]pyridin-2-yl)phenyl]benzamide

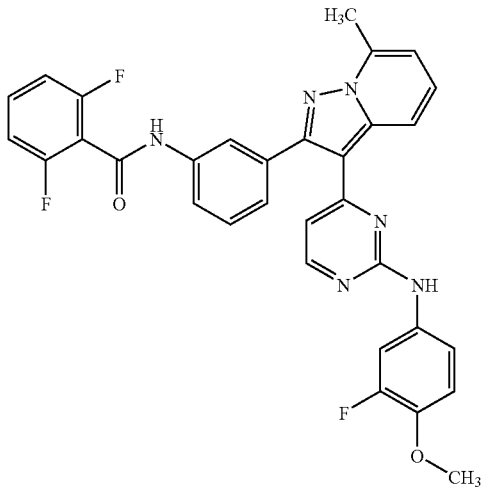

The title compound was prepared through standard displacement conditions by microwaving N-{3-[3-(2-chloropyrimidin-4-yl)-7-methylpyrazolo[1,5-a]pyridin-2-yl]phenyl}-2,6-difluorobenzamide and 3-trifluoromethylaniline in isopropanol at 150° C. for 15 min. $^1$H NMR (400 MHz, DMSO d-6) 2.73 (s, 3H), 3.76 (s, 3H), 6.50 (s, 1H), 7.02 (m, 2H), 7.22 (m, 2H), 7.33 (m, 2H), 7.43 (m, 2H), 7.57 (m, 1H), 7.70 (m, 1H), 7.83 (d, J=8.8 Hz, 1H), 7.95 (s, 1H), 8.23 (d, J=5.6 Hz, 1H), 8.35 (d, J=8.4 Hz, 1H), 9.52 (s, 1H), 10.9 (s, 1H); LCMS (ESI): [M+H]$^+$=581.

Example 158

2,6-Difluoro-N-{3-[7-methoxy-3-(2-{[3-(trifluoromethyl)phenyl]amino}pyrimidin-4-yl)pyrazolo[1,5-a]pyridin-2-yl]phenyl}benzamide

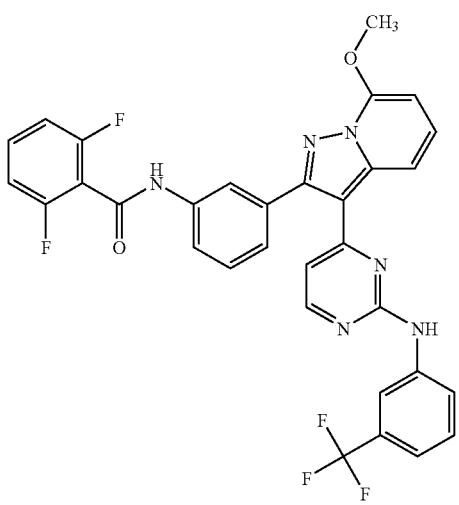

Step A: 2-Methoxy-1λ$^5$-pyridin-1-amine

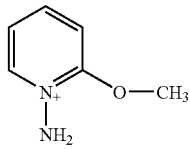

A flask was charged with 2.5 g (22.9 mmol) 2-methoxypyridine and 70 mL pH-10 Buffer. In a separate flask, HOSA (3.89 g, 34.4 mmol) was dissolved in 10 mL water. A solution of KHCO$_3$ in water (9.6 mL of a 2.4 M solution) was added dropwise to achieve pH of 7-8. This solution was added dropwise to the methoxypyridine/buffer solution and the rxn mixture heated to 70° C. After 1 h, NMR indicated 100% conversion to the aminated product. The solution was used as a 2.5 M solution in H$_2$O. $^1$H NMR (400 MHz, D$_2$O) δ 8.5 (d, J=8.0 Hz 1H), 8.23 (t, J=8.0 Hz, 1H), 7.70 (d, J=7.6 Hz, 1H), 6.46 (t, J=8.0 Hz, 1H), 4.23 (s, 3H)

Step B: N-{3-[3-(2-Chloropyrimidin-4-yl)-7-methoxypyrazolo[1,5-a]pyridin-2-yl]phenyl}-2,6-difluorobenzamide

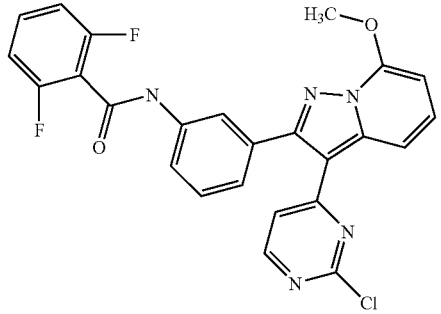

To a solution of 50 mg (0.14 mmol) of N-{3-[(2-chloropyrimidin-4-yl)ethynyl]phenyl}-2,6-difluorobenzamide in 2 mL dimethylsulfoxide was added 15 mg (0.27 mmole) KOH. The mixture was cooled to 0° C. and 0.11 mL 2-methoxy-1λ$^5$-pyridin-1-amine (0.27 mmol, 2.5 M solution in H$_2$O) was added dropwise. The ice bath was removed and the reaction stirred at rt. When all the acetylene had reacted, water was added, the mixture transferred to a separatory funnel. EtOAc was added and the organic separated. The crude was purified to give 24 mg of the title compound as a tan solid. LCMS (ESI): [M+H]$^+$=492.

Step C: 2,6-Difluoro-N-{3-[7-methoxy-3-(2-{[3-(trifluoromethyl)phenyl]amino}-pyrimidin-4-yl)pyrazolo[1,5-a]pyridin-2-yl]phenyl}benzamide (title compound)

The title compound was prepared through standard displacement conditions by microwaving N-{3-[3-(2-chloropyrimidin-4-yl)-7-methoxypyrazolo[1,5-a]pyridin-2-yl]phenyl}-2,6-difluorobenzamide and 3-trifluoromethylaniline in isopropanol at 150° C. for 15 min. $^1$H (400 MHz, DMSO d-6) 4.15 (s, 3H), 6.59 (d, J=5.2 Hz, 1H), 6.62 (d, J=7.6 Hz, 1H), 7.24 (m, 3H), 7.33 (d, J=8.0 Hz, 1H), 7.46 (m, 2H), 7.58 (m, 2H), 7.80 (d, J=8.4 Hz, 1H), 7.92 (d, J=7.6 Hz, 1H), 8.00 (s, 1H), 8.05 (d, J=8.8 Hz, 1H), 8.27 (s, 1H), 8.31 (d, J=5.2 Hz, 1H), 9.91 (s, 1H), 10.9 (s, 1H); LCMS (APCI): [M+H]$^+$=617.

Example 159

2,6-Difluoro-N-(2-(methyloxy)-5-{3-[2-(1,2,3,4-tetrahydro-7-isoquinolinylamino)-4-pyrimidinyl]pyrazolo[1,5-a]pyridin-2-yl}phenyl)benzamide

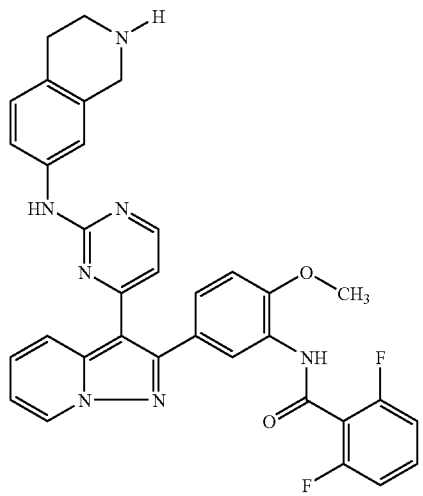

Step A: N-[5-Bromo-2-(methyloxy)phenyl]-2,2,2-trifluoroacetamide

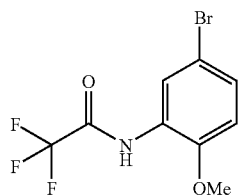

To a solution of 4-bromo-2-nitroanisole (2.0 g, 0.009 mol) in absolute ethanol (100 mL) was added SnCl$_2$.2H$_2$O (11.68 g, 0.051 mol) and the resulting mixture was allowed to stir overnight at ambient temperature. The solvent was removed under reduced pressure, the residue was suspended in EtOAc (100 mL), washed with 1M NaOH (100 mL) and filtered through a celite pad. The organic layer was removed, concentrated by rotary evaporation, and dried under high vacuum. The resulting residue was then dissolved in DCM (150 mL) followed by the addition of triethylamine (5.19 g, 0.051 mol) and trifluoroacetic anhydride (4.52 g, 22 mmol). After overnight stirring, the reaction was washed with 1M HCl (50 mL), organic layer concentrated and purified by column chromatography (1-10% gradient of EtOAc in hexanes) to yield the title compound (1.53 g, 60%) as a white solid. ESIMS (M−H)−=297.

Step B: 2,2,2-Trifluoro-N-{2-(methyloxy)-5[(trimethylsilyl)ethynyl]phenyl}-acetamide

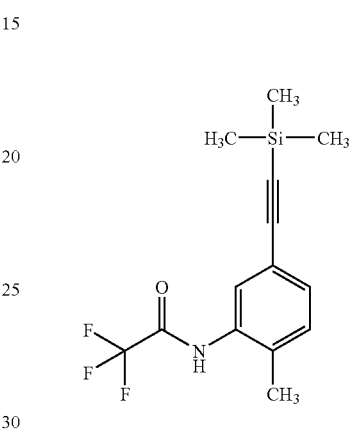

To an oven-dried flask under N$_2$ was added N-[5-bromo-2-(methyloxy)phenyl]-2,2,2-trifluoroacetamide (1.53 g, 0.005 mol), anhydrous degassed THF (100 mL), dichlorobis(triphenylphosphine)palladium(II) (0.45 g, 0.6 mmol), copper(I) iodide (73 mg, 0.38 mmol), and trimethylsilylacetylene (1.26 g, 13 mmol). Next, triethylamine (5.19 g, 50 mmol) was added dropwise and the resulting mixture was heated at 60° C. overnight. The crude reaction mixture was adsorbed to silica gel and purified by column chromatography (0-10% EtOAc in hexanes) to afford the desired product (0.68 g, 42%) as an off white solid. ESIMS (M−H)−=314.

Step C: N-[5-Ethynyl-2-(methyloxy)phenyl]-2,2,2-trifluoroacetamide

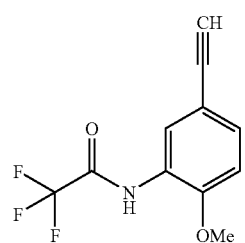

To a solution of 2,2,2-trifluoro-N-{2-(methyloxy)-5-[(trimethylsilyl)ethynyl]phenyl}acetamide (680 mg, 2.16 mmol) in THF (50 mL) was added dropwise 1.0 M TBAF in THF (2.59 ml, 2.59 mmol) and the resulting mixture was stirred for 30 min at ambient temperature. The reaction was quenched with H₂O (50 mL), concentrated under reduced pressure, and the aqueous layer was extracted with DCM (2×50 mL). The organic layers were combined, solvent removed under reduced pressure, and purified by column chromatography (5-25% EtOAc in hexanes) to give the title compound (500 mg, 96%) as an off white solid. ¹H NMR (400 MHz, CDCl₃) δ 3.00 (s, 1H), 3.93 (s, 3H), 6.86 (d, 1H, J=8.42 Hz), 7.31 (dd, 1H, J=8.42 Hz, 2.01 Hz), 8.46 (d, 1H, J=2.01 Hz).

Step D: N-[5-[(2-Chloro-4-pyrimidinyl)ethynyl]-2-(methyloxy)phenyl]-2,2,2-trifluoroacetamide

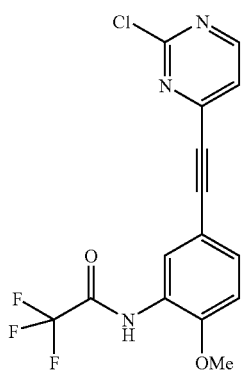

To an oven-dried flask under N₂ was added 2,4-dichloropyrimidine (860 mg, 5.76 mmol), anhydrous degassed THF (100 mL), dichlorobis(triphenylphosphine)-palladium(II) (81 mg, 0.12 mmol), copper(I) iodide (13 mg, 0.07 mmol), and triethylamine (1.26 g, 13 mmol). After heating the reaction at 60° C. for 30 min, N-[5-ethynyl-2-(methyloxy)phenyl]-2,2,2-trifluoroacetamide (560 mg, 2.30 mmol) was added dropwise as a solution in THF (10 mL) and the resulting mixture was allowed to heat overnight. The crude reaction mixture was adsorbed to silica gel and purified by column chromatography (0-10% EtOAc in hexanes) to afford the desired product (0.68 g, 42%) as an off white solid. ESIMS (M+H)+=356.

Step E: N-[5-[3-(2-Chloro-4-pyrimidinyl)pyrazolo[1,5-a]pyridin-2-yl]-2-(methyloxy)phenyl]-2,2,2-trifluoroacetamide

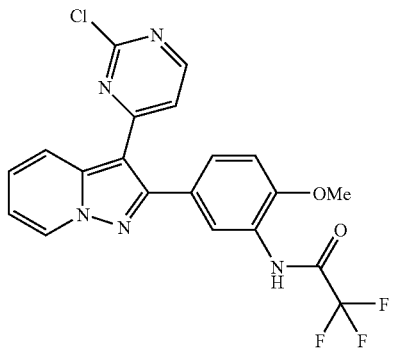

A solution of N-[5-[(2-chloro-4-pyrimidinyl)ethynyl]-2-(methyloxy)phenyl]-2,2,2-trifluoroacetamide (534 mg, 1.50 mmol), aminopyridinium iodide (670 mg, 3.01 mmol), and potassium carbonate (620 mg, 4.51 mmol) in DMF (10 mL) was stirred at ambient temperature for 3 h, followed by solvent removal. The residue was redissolved in DCM (50 mL) and washed with H₂O (50 mL). The organic layer was adsorbed to silica gel and purified by column chromatography (5-50% EtOAc in hexanes) to afford the pyrazolopyridine (370 mg, 55%) as a tan solid. ESIMS (M+H)+=448.

Step F: N-[5-[3-(2-Chloro-4-pyrimidinyl)pyrazolo[1,5-a]pyridin-2-yl]-2-(methyloxy)phenyl]-2,6-difluorobenzamide

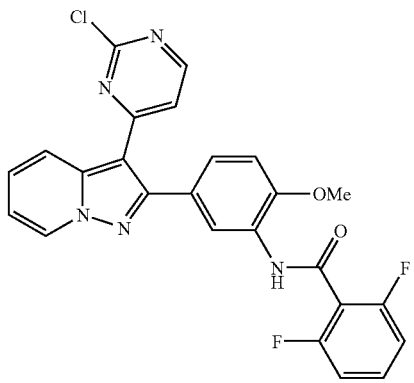

A solution of N-[5-[3-(2-chloro-4-pyrimidinyl)pyrazolo[1,5-a]pyridin-2-yl]-2-(methyloxy)phenyl]-2,2,2-trifluoroacetamide (370 mg, 0.83 mmol) and 1M LiOH (4.97 mL, 4.97 mmol) in 10:1 THF:H₂O (10 mL) was heated at 50° C. overnight. The reaction was washed with brine (25 mL), the aqueous layer was extracted with EtOAc (25 mL) and the organic layers were combined, filtered through a cotton plug, and solvent removed by rotary evaporation. After high vacuum removal of residual solvent, the crude mixture was dissolved in THF (25 mL) and to this was added 2,6-difluorobenzoyl chloride (920 mg, 5.25 mmol). After stirring 3 h at ambient temperature, DMF (25 mL) was added to dissolve any suspended solids followed by the addition of excess polymer-bound trisamine resin. Upon overnight stirring, the amine resin was removed by vacuum filtration, rinsed with MeOH (50 mL) and filtrate concentrated under reduced pressure to afford the desired amide (410 mg, 79%) as an off-white solid. ESIMS (M+H)+=492.

Step G: 2,6-Difluoro-N-{2-(methyloxy)-5-[3-(2-{[2-(trifluoroacetyl)-1,2,3,4-tetrahydro-7-isoquinolinyl]amino}-4-pyrimidinyl)pyrazolo[1,5-a]pyridin-2-yl]phenyl}benzamide

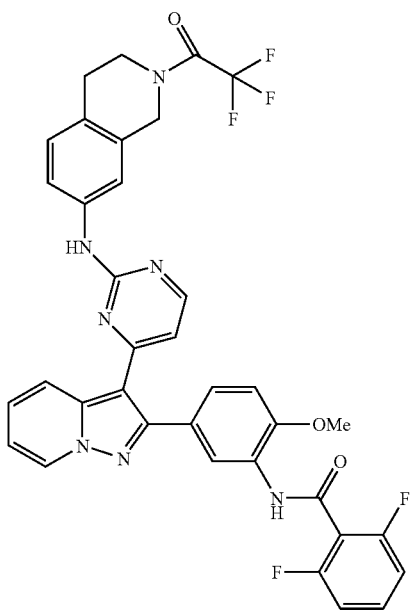

To a solution of N-[5-[3-(2-chloro-4-pyrimidinyl)pyrazolo[1,5-a]pyridin-2-yl]-2-(methyloxy)phenyl]-2,6-difluorobenzamide (158 mg, 0.32 mmol) in 1,4-dioxane (6 mL) and 2-propanol (2 mL) was added 7-amino-N-trifluoroacetyl tetrahydroisoquinoline (158 mg, 0.64 mmol) followed by catalytic 12M HCl. After heating overnight at 80° C., reaction was quenched with saturated NaHCO₃ (25 mL), solvent removed by rotary evaporation, aqueous layer extracted with DCM (25 mL), the organic layer was concentrated and purified by column chromatography (5-50% EtOAc in hexanes) to provide the product (100 mg, 44%) as an off-white solid. ESIMS (M+H)+=700.

Step H: 2,6-Difluoro-N-(2-(methyloxy)-5-{3-[2-(1,2,3,4-tetrahydro-7-isoquinolinylamino)-4-pyrimidinyl]pyrazolo[1,5-a]pyridin-2-yl}phenyl)benzamide (title compound)

To a solution of 2,6-difluoro-N-{2-(methyloxy)-5-[3-(2-{[2-(trifluoroacetyl)-1,2,3,4-tetrahydro-7-isoquinolinyl]amino}-4-pyrimidinyl)pyrazolo[1,5-a]pyridin-2-yl]phenyl}benzamide (50 mg, 0.072 mmol) in 10:1 THF:H2O (10 mL) was added 1M LiOH (0.43 ml, 0.43 mmol) and the reaction mixture was heated at 50° C. overnight. The reaction was washed with brine (10 mL), organic layer removed, adsorbed to silica gel and purified by column chromatography (0-10% MeOH/DCM+1% NH4OH) to afford the title compound (32 mg, 74%) as an off-white solid. ¹H NMR (400 MHz, CDCl₃) δ 2.75 (t, 2H, J=5.86 Hz), 3.13 (t, 2H, J=5.86 Hz), 3.93 (s, 3H), 3.97 (s, 2H), 6.64 (d, 1H, J=5.31 Hz), 6.86-6.89 (m, 1H), 6.94-7.03 (m, 4H), 7.24-7.44 (m, 5H), 8.16 (d, 1H, J=5.31 Hz), 8.32-8.38 (m, 2H), 8.50 (d, 1H, J=6.96 Hz), 8.98 (m, 1H); ESIMS (M+H)+=604.

Example 160

2,6-Difluoro-N-(2-fluoro-5-{3-[2-(1,2,3,4-tetrahydro-7-isoquinolinylamino)-4-pyrimidinyl]pyrazolo[1,5-a]pyridin-2-yl}phenyl)benzamide

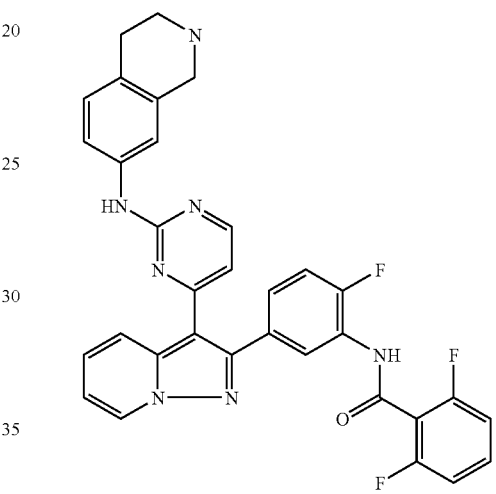

Step A: N-(5-Bromo-2-fluorophenyl)-2,2,2-trifluoroacetamide

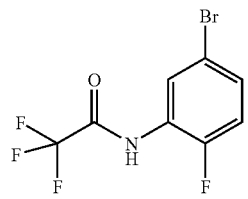

To a solution of 4-fluoro-3-nitrobromobenzene (1.0 g, 5 mmol) in absolute ethanol (100 mL) was added SnCl₂.2H₂O (6.15 g, 27 mmol) and the resulting mixture was allowed to stir overnight at ambient temperature. The solvent was removed under reduced pressure, residue suspended in EtOAc (100 mL), washed with 1M NaOH (100 mL), and filtered through a celite pad. The organic layer was removed, concentrated by rotary evaporation, and dried under high vacuum. The resulting residue was then dissolved in DCM (150 mL) followed by the addition of triethylamine (3.68 g, 0.036 mols) and trifluoroacetic anhydride (1.90 g, 9 mmol). After overnight stirring, the reaction was washed with 1M HCl (50 mL), organic layer concentrated and purified by column chromatography (1-10% gradient of EtOAc in hexanes) to yield the title compound (0.75 g, 58%) as a white solid. ESIMS (M–H)–=284.

Step B: 2,2,2-Trifluoro-N-{2-fluoro-5-[(trimethylsilyl)ethynyl]phenyl}acetamide

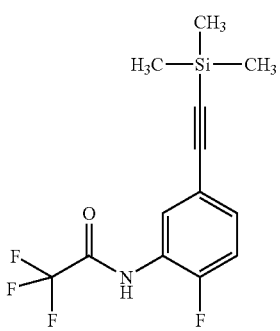

To an oven-dried flask under $N_2$ was added N-(5-bromo-2-fluorophenyl)-2,2,2-trifluoroacetamide (750 mg, 2.62 mmol), anhydrous degassed THF (100 mL), dichlorobis(triphenylphosphine)palladium(II) (230 mg, 0.33 mmol), copper(I) iodide (38 mg, 0.20 mmol), and trimethylsilylacetylene (640 mg, 6.53 mmol). Next, triethylamine (2.64 g, 26 mmol) was added dropwise and the resulting mixture was heated at 60° C. overnight. The crude reaction mixture was adsorbed to silica gel and purified by column chromatography (0-10% EtOAc in hexanes) to afford the desired product (0.67 g, 84%) as an off white solid. ESIMS (M–H)–=302.

Step C: N-(5-Ethynyl-2-fluorophenyl)-2,2,2-trifluoroacetamide

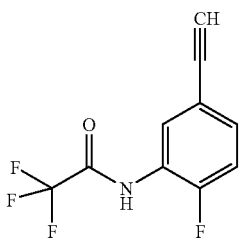

To a solution of 2,2,2-trifluoro-N-{2-fluoro-5-[(trimethylsilyl)ethynyl]phenyl}-acetamide (670 mg, 2.21 mmol) in THF (50 mL) was added dropwise 1.0 M TBAF in THF (2.61 ml, 2.65 mmol) and the resulting mixture was stirred for 30 min at ambient temperature. The reaction was quenched with $H_2O$ (50 mL), concentrated under reduced pressure, and the aqueous layer was extracted with DCM (2×50 mL). The organic layers were combined, solvent removed under reduced pressure, and purified by column chromatography (5-25% EtOAc in hexanes) to give the title compound (410 mg, 80%) as an off white solid. ESIMS (M–H)–=230.

Step D: N-{5-[(2-Chloro-4-pyrimidinyl)ethynyl]-2-fluorophenyl}-2,2,2-trifluoroacetamide

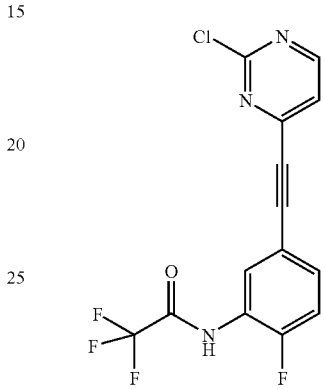

To an oven-dried flask under $N_2$ was added 2,4-dichloropyrimidine (520 mg, 3.49 mmol), anhydrous degassed THF (100 mL), dichlorobis(triphenylphosphine)-palladium(II) (62 mg, 0.09 mmol), copper(I) iodide (10 mg, 0.05 mmol), and triethylamine (718 mg, 7.10 mmol). After heating the reaction at 60° C. for 30 min, N-(5-ethynyl-2-fluorophenyl)-2,2,2-trifluoroacetamide (410 mg, 1.77 mmol) was added dropwise as a solution in THF (10 mL) and the resulting mixture was allowed to heat overnight. The crude reaction mixture was adsorbed to silica gel and purified by column chromatography (5-50% EtOAc in hexanes) to afford the desired product (300 mg, 49%) as an off white solid. ESIMS (M+H)+=344.

Step E: N-{5-[3-(2-Chloro-4-pyrimidinyl)pyrazolo[1,5-a]pyridin-2-yl]-2-fluorophenyl}-2,2,2-trifluoroacetamide

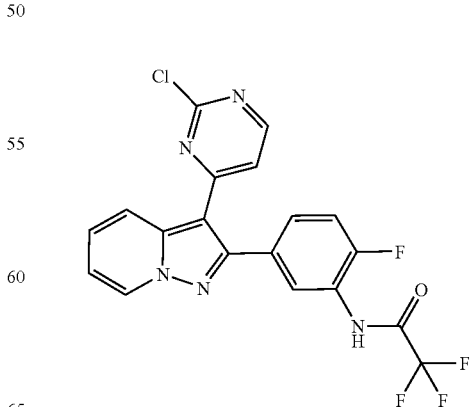

A solution of N-{5-[(2-chloro-4-pyrimidinyl)ethynyl]-2-fluorophenyl}-2,2,2-trifluoroacetamide (300 mg, 0.87 mmol), aminopyridinium iodide (390 mg, 1.74 mmol), and potassium carbonate (360 mg, 2.62 mmol) in DMF (10 mL) was stirred at ambient temperature for 3 h followed by solvent removal. The residue was redissolved in DCM (50 mL) and washed with H$_2$O (50 mL). The organic layer was adsorbed to silica gel and purified by column chromatography (5-50% EtOAc in hexanes) to afford the pyrazolopyridine (300 mg, 79%) as a tan solid. ESIMS (M+H)+=436.

Step F: N-{5-[3-(2-Chloro-4-pyrimidinyl)pyrazolo[1,5-a]pyridin-2-yl]-2-fluorophenyl}-2,6-difluorobenzamide

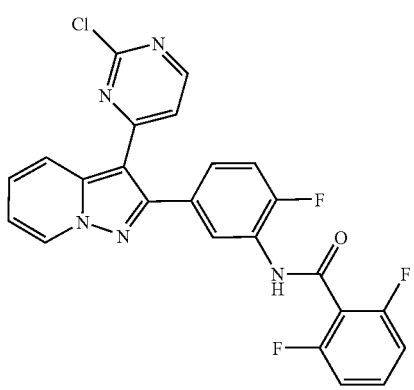

A solution of N-{5-[3-(2-chloro-4-pyrimidinyl)pyrazolo[1,5-a]pyridin-2-yl]-2-fluorophenyl}-2,2,2-trifluoroacetamide (300 mg, 0.69 mmol) and 1M LiOH (4.13 ml, 4.13 mmol) in 10:1 THF:H$_2$O (15 mL) was heated at 50° C. overnight. The reaction was washed with brine (25 mL) and the aqueous layer was extracted with EtOAc (25 mL). The organic layers were combined, filtered through a cotton plug, and solvent removed by rotary evaporation. After high vacuum removal of residual solvent, the crude mixture was dissolved in DCM (10 mL) and to this was added 2,6-difluorobenzoyl chloride (519 mg, 2.94 mmol). After stirring 3 h at ambient temperature, DMF (25 mL) was added to dissolve any suspended solids followed by the addition of excess polymer-bound trisamine resin. Upon overnight stirring, the amine resin was removed by vacuum filtration, rinsed with MeOH (50 mL), and filtrate concentrated under reduced pressure to afford the desired amide (162 mg, 49%) as an off-white solid. ESIMS (M+H)+=480.

Step G: 2,6-Difluoro-N-{2-fluoro-5-[3-(2-{[2-(trifluoroacetyl)-1,2,3,4-tetrahydro-7-isoquinolinyl]amino}-4-pyrimidinyl)pyrazolo[1,5-a]pyridin-2-yl]phenyl}benzamide

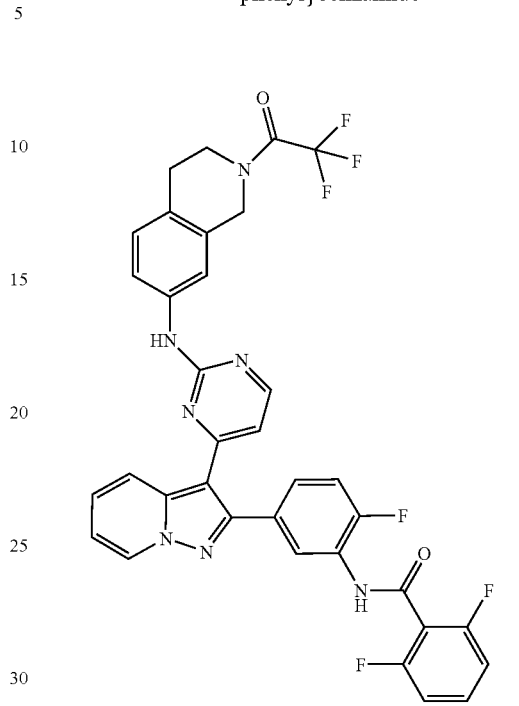

To a solution of N-{5-[3-(2-chloro-4-pyrimidinyl)pyrazolo[1,5-a]pyridin-2-yl]-2-fluorophenyl}-2,6-difluorobenzamide (162 mg, 0.34 mmol) in 1,4-dioxane (6 mL) and 2-propanol (2 mL) was added 7-amino-N-trifluoroacetyl tetrahydroisoquinoline (165 mg, 0.68 mmol) followed by catalytic 12M HCl. After heating overnight at 80° C., reaction was quenched with saturated NaHCO$_3$ (25 mL), solvent removed by rotary evaporation, aqueous layer extracted with DCM (25 mL), organic layer concentrated, and purified by column chromatography (5-50% EtOAc in hexanes) to provide the product (109 mg, 47%) as an off-white solid. ESIMS (M+H)+= 688.

Step H: 2,6-Difluoro-N-(2-Fluoro-5-{3-[2-(1,2,3,4-tetrahydro-7-isoquinolinylamino)-4-pyrimidinyl]pyrazolo[1,5-a]pyridin-2-yl}phenyl)benzamide To a solution of 2,6-difluoro-N-{2-fluoro-5-[3-(2-{[2-(trifluoroacetyl)-1,2,3,4-tetrahydro-7-isoquinolinyl]amino}-4-pyrimidinyl)pyrazolo[1,5-a]pyridin-2-yl]phenyl}benzamide (55 mg, 0.08 mmol) in 10:1 THF:H$_2$O (10 mL) was added 1M LiOH (0.48 mL, 0.48 mmol) and the reaction mixture was heated at 50° C. overnight. The reaction was washed with brine (10 mL) and the organic layer removed, adsorbed to silica gel and purified by column chromatography (0-10% MeOH/DCM+1% NH$_4$OH) to afford the title compound (39 mg, 82%) as a white solid. $^1$H NMR (400 MHz, CDCl$_3$) δ 2.72 (t, 2H, J=5.86 Hz), 3.04 (t, 2H, J=5.86 Hz), 3.86 (s, 2H), 6.55 (d, 1H, J=5.30 Hz), 6.88-6.97 (m, 4H), 7.11-7.16 (m, 1H), 7.23-7.39 (m, 5H), 8.09 (t, 1H, J=5.31 Hz), 8.28-8.29 (d, 1H, J=8.78 Hz), 8.45 (d, 1H, J=6.95 Hz), 8.61-8.63 (m, 1H); ESIMS (M+H)+=592.

Example 161

3-{[2-Chloro-4-({4-[2-(3-{[(2,6-difluorophenyl)carbonyl]amino}-phenyl)pyrazolo[1,5-a]pyridin-3-yl]-2-pyrimidinyl}amino)phenyl]oxy}-1-propanesulfonic acid

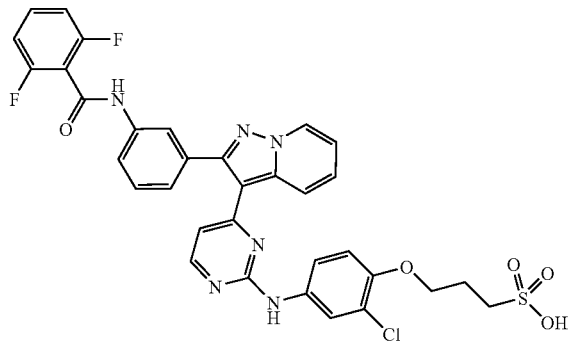

The title compound was prepared from N-[3-(3-{2-[(3-chloro-4-hydroxyphenyl)amino]-4-pyrimidinyl}pyrazolo[1,5-a]pyridin-2-yl)phenyl]-2,6-difluorobenzamide and sodium 3-bromo-1-propanesulfonate by a procedure analogous to Example 126 above. $^1$H NMR (400 MHz, DMSO-$d_6$): δ 10.95 (s, 1H), 9.76 (s, 1H), 8.86 (d, 1H), 8.43 (bs, 1H), 8.21 (d, 1H), 7.99 (s, 1H), 7.88 (s, 1H), 7.82 (d, 1H), 7.60-7.45 (m, 4H), 7.35 (d, 1H), 7.24 (m, 2H), 7.15 (t, 1H), 7.07 (d, 1H), 6.52 (d, 1H), 4.12 (t, 2H), 2.57 (t, 2H), 2.00 (m, 2H).

Example 162

Methyl 4-{[2-chloro-4-({4-[2-(3-{[(2,6-difluorophenyl)carbonyl]-amino}phenyl)pyrazolo[1,5-a]n-3-yl]-2-pyrimidinyl}amino)phenyl]oxy}-butanoate

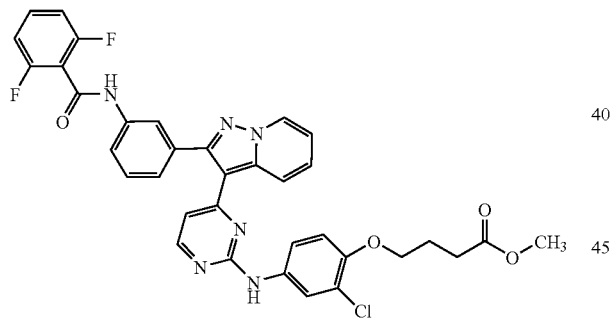

The title compound was prepared from N-[3-(3-{2-[(3-chloro-4-hydroxyphenyl)amino]-4-pyrimidinyl}pyrazolo[1,5-a]pyridin-2-yl)phenyl]-2,6-difluorobenzamide (Example 86) and methyl 4-bromobutanoate in DMF with 2.5 eq $Cs_2CO_3$, 50° C. for 24 h by a procedure similar to Example 126 above. HRMS $C_{35}H_{28}N_6O_4F_2Cl$ (M+H)$^+$ calcd 669.1823, found 669.1829

Example 163

N-{3-[3-(2-{[3-Chloro-4-({2-[(methylsulfonyl)amino]ethyl}-oxy)phenyl]amino}-4-pyrimidinyl)pyrazolo[1,5-a]pyridin-2-yl]phenyl}-2,6-difluorobenzamide

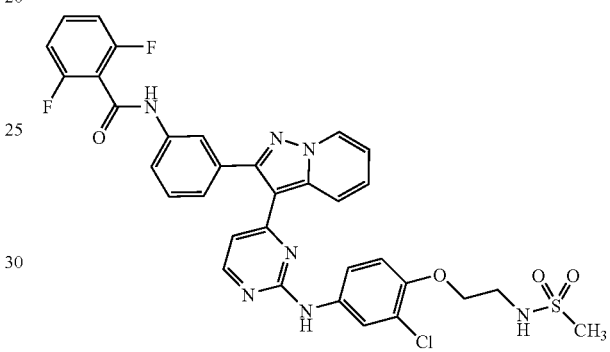

The title compound was prepared from N-[3-(3-{2-[(3-chloro-4-hydroxyphenyl)amino]-4-pyrimidinyl}pyrazolo[1,5-a]pyridin-2-yl)phenyl]-2,6-difluorobenzamide (Example 86) and N-(2-bromoethyl)methanesulfonamide in DMF with 1.5 eq $Cs_2CO_3$, 60° C. for 24 h by a procedure similar to Example 126 above. HRMS $C_{33}H_{27}N_7O_4F_2SCl$ (M+H)$^+$ calcd 690.1502, found 690.1503

Example 164

N-[3-(3-{2-[(3-chloro-4-{[3-(4-methyl-1-piperazinyl)propyl]oxy}-phenyl)amino]-4-pyrimidinyl}pyrazolo[1,5-a]pyridin-2-yl)phenyl]-2,6-difluorobenzamide

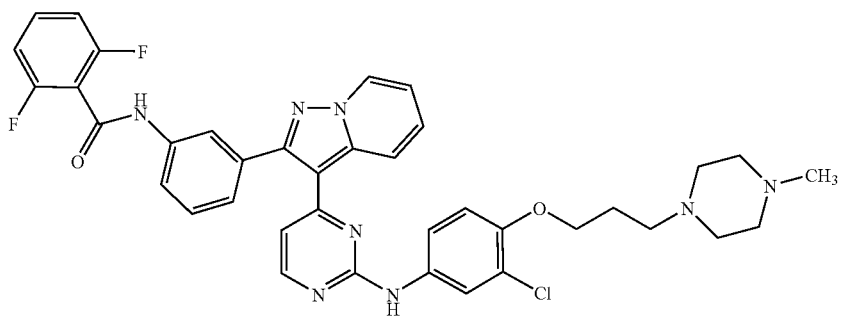

The title compound was prepared from N-[3-(3-{2-[(3-chloro-4-hydroxyphenyl)amino]-4-pyrimidinyl}pyrazolo[1,5-a]pyridin-2-yl)phenyl]-2,6-difluorobenzamide (Example 86) and 1-(3-chloropropyl)-4-methylpiperazine dihydrochloride in DMF with 2.5 eq $Cs_2CO_3$, 60° C. for 24 h by a procedure similar to Example 126 above. HRMS $C_{38}H_{36}N_8O_2F_2Cl$ (M+H)$^+$ calcd 709.2612, found 709.2607.

Example 165

N-{3-[3-(2-{[3-{[3-(Dimethylamino)propyl]oxy}-4-(methyloxy)-phenyl]amino}-4-pyrimidinyl)pyrazolo[1,5-a]pyridin-2-yl]phenyl}-2,6-difluorobenzamide formic acid salt A mixture of N-{3-[3-(2-chloro-4-pyrimidinyl)pyrazolo[1,5-a]pyridin-2-yl]phenyl}-2,6-difluorobenzamide (prepared according to a procedure similar to that described in Example 27, Step C) and 5-amino-2-(methyloxy)phenol were heated in isopropanol with catalytic conc. aq. HCl using conditions similar to those described in Example 27, Step D. HRMS $C_{31}H_{23}N_6O_3F_2$ (M+H)$^+$ calcd 565.1794, found 565.1795.

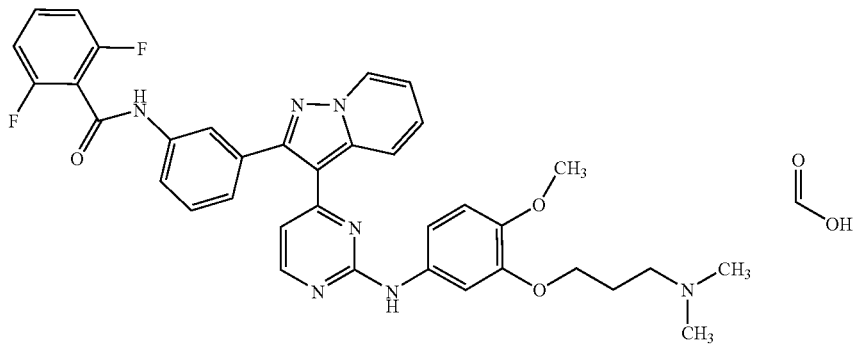

The title compound was prepared from 2,6-difluoro-N-{3-[3-(2-{[3-hydroxy-4-(methyloxy)phenyl]amino}-4-pyrimidinyl)pyrazolo[1,5-a]pyridin-2-yl]phenyl}benzamide (Example 86) and (3-chloropropyl)dimethylamine hydrochloride in DMF with 3.5 eq $Cs_2CO_3$, in a procedure similar to Example 126 above. HRMS $C_{36}H_{34}N_7O_3F_2$ (M+H)$^+$ calcd 650.2686, found 650.2680.

Example 166

2,6-Difluoro-N-{3-[3-(2-{[3-hydroxy-4-(methyloxy)phenyl]amino}-4-pyrimidinyl)pyrazolo[1,5-a]pyridin-2-yl]phenyl}benzamide

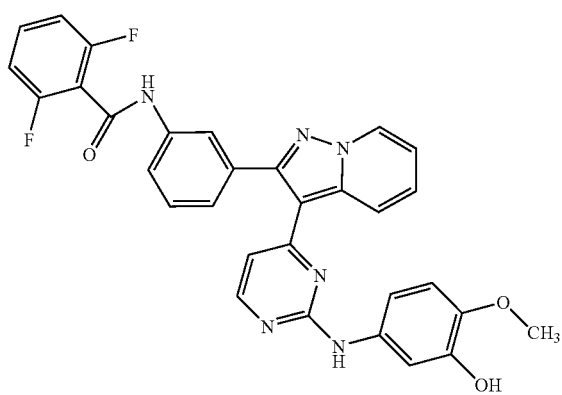

Example 167

N-{3-[3-(2-{[3-{[2-(Dimethylamino)ethyl]oxy}-4-(methyloxy)phenyl]amino}-4-pyrimidinyl)pyrazolo[1,5-a]pyridin-2-yl]phenyl}-2,6-difluorobenzamide

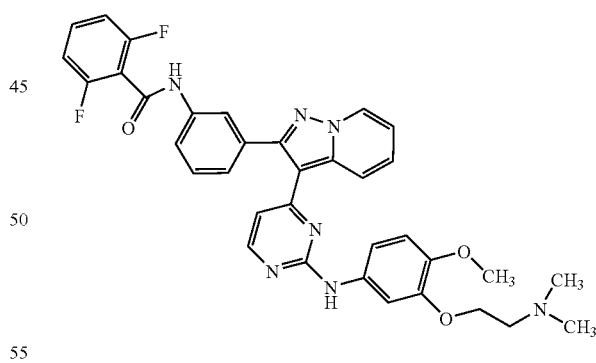

A mixture of N-{3-[3-(2-chloro-4-pyrimidinyl)pyrazolo[1,5-a]pyridin-2-yl]phenyl}-2,6-difluorobenzamide (prepared according to a procedure similar to that described in Example 27, Step C) and 3-{[2-(dimethylamino)ethyl]oxy}-4-(methyloxy)aniline were heated in isopropanol with catalytic conc. aq. HCl using conditions similar to those described in Example 27, Step D. HRMS $C_{35}H_{32}N_7O_3F_2$ (M+H)$^+$ calcd 636.2535, found 636.2527.

Example 168

N-[3-(3-{2-[(3-{[2-(Dimethylamino)ethyl]oxy}phenyl)amino]-4-pyrimidinyl}-4-fluoropyrazolo[1,5-a]pyridin-2-yl)phenyl]-2,6-difluorobenzamide

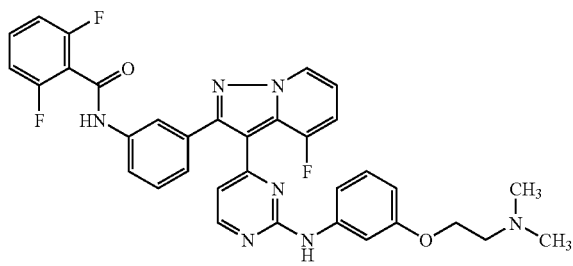

Step A: 1-Amino-3-fluoropyridinium nitrate

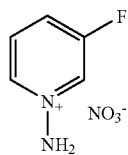

To the solution of barium oxide (7.1 g) and barium nitrate (8.1 g) in water (50 mL) was added 3-fluoropyridine (8.0 g). Hydroxylamine sulphonic acid (8.2 g) in water (20 mL) was added into the solution dropwise over 5 min. The reaction was heated to 90° C. for 12 h. Filtration removed the precipitate and the filtrate was concentrated to give a crude brown sticky solid (7.0 g, 77% yield). The crude 1-amino-3-fluoropyridinium nitrate was carried to next step without further purification.

Step B: N-{3-[3-(2-Chloro-4-pyrimidinyl)-4-fluoropyrazolo[1,5-a]pyridin-2-yl]phenyl}-2,2,2-trifluoroacetamide and N-{3-[3-(2-chloro-4-pyrimidinyl)-6-fluoropyrazolo[1,5-a]pyridin-2-yl]phenyl}-2,2,2-trifluoroacetamide

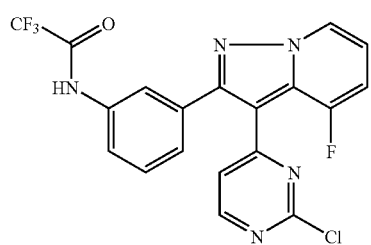

-continued

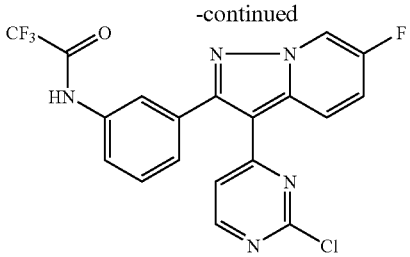

To a solution of N-[3-(2-chloro-pyrimidin-4-ylethynyl)-phenyl]-2,2,2-trifluoro-acetamide (5.0 g) in DMF (40 mL) were added 1-amino-3-fluoropyridinium nitrate (5.4 g) and potassium carbonate (6.0 g). The reaction was kept stirring at rt for 1.5 h. The DMF solution was poured into 5% LiCl solution (60 mL) and extracted with EtOAc (2×30 mL). The combined organic phase were dried (Na$_2$SO$_4$) and concentrated. The crude products were separated through silica gel column chromatography to afford two products. The first to elute was N-{3-[3-(2-chloro-4-pyrimidinyl)-6-fluoropyrazolo[1,5-a]pyridin-2-yl]phenyl}-2,2,2-trifluoroacetamide (2.0 g, 30% yield). $^1$H NMR (400 MHz, DMSO-d$_6$) δ ppm 7.08 (d, 1H, J=5.49 Hz), 7.45 (d, 1H, J=7.68 Hz), 7.55 (t, 1H, J=7.96 Hz), 7.73-7.79 (m, 1H), 7.83 (d, 1H, J=0.91 Hz), 7.95 (t, 1H, J=1.74 Hz), 8.41 (dd, 1H, J=9.97, 5.76 Hz), 8.49 (d, 1H, J=5.49 Hz), 9.27 (dd, 1H, J=4.30, 2.29 Hz); ES-LC/MS (M+H)$^+$=436.

The second to elute was N-{3-[3-(2-chloro-4-pyrimidinyl)-4-fluoropyrazolo[1,5-a]pyridin-2-yl]phenyl}-2,2,2-trifluoroacetamide (2.67 g, 40% yield). $^1$H NMR (400 MHz, DMSO-d$_6$) δ ppm 7.09-7.15 (m, 1H), 7.32-7.41 (m, 2H), 7.45 (t, 1H, J=7.96 Hz), 7.55 (dd, 1H, J=5.12, 2.56 Hz), 7.68-7.74 (m, 1H), 7.92 (t, 1H, J=1.83 Hz), 8.72 (d, 1H, J=5.12 Hz), 8.78 (d, 1H, J=6.77 Hz), 11.31 (s, 1H); ES-LC/MS (M+H)$^+$=436.

Step C: 3-[3-(2-chloro-4-pyrimidinyl)-4-fluoropyrazolo[1,5-a]pyridin-2-yl]aniline

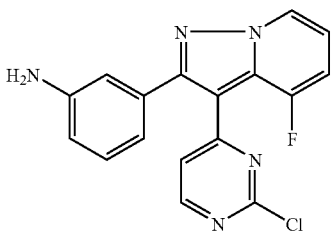

To the solution of N-{3-[3-(2-chloro-4-pyrimidinyl)-4-fluoropyrazolo[1,5-a]pyridin-2-yl]phenyl}-2,2,2-trifluoroacetamide (0.40 g) in THF (27 mL) and water (3 mL) was added 5% LiOH solution (2.3 mL). The reaction was kept stirring at rt for 15 h and was worked up with sat. NaHCO$_3$ solution (20 mL) and extracted with EtOAc (2×20 mL). The organic phase was dried (Na$_2$SO$_4$) and concentrated to afford the crude 3-[3-(2-chloro-4-pyrimidinyl)-4-fluoropyrazolo[1,5-a]pyridin-2-yl]aniline (0.30 g, 95% yield) as yellow solid. ES-LC/MS (M+H)$^+$=340.

187

Step D: N-{3-[3-(2-chloro-4-pyrimidinyl)-4-fluoro-pyrazolo[1,5-a]pyridin-2-yl]phenyl}-2,6-difluorobenzamide

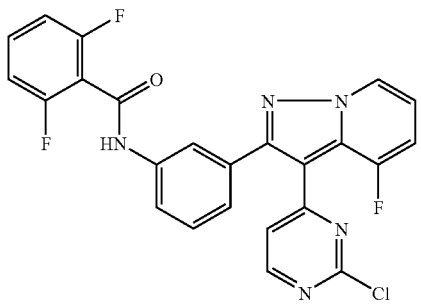

To a solution of 3-[3-(2-chloro-4-pyrimidinyl)-4-fluoropyrazolo[1,5-a]pyridin-2-yl]aniline (0.31 g) in THF (10 mL) was added 2,6-difluorobenzoyl chloride (0.18 g). The reaction was kept stirring at rt for 0.5 h and worked up with sat. NaHCO$_3$ solution (8 mL). After extraction with EtOAc (2×10 mL), drying with Na$_2$SO$_4$, and concentration, the crude mixture was purified through silica gel column chromatography to afford N-{3-[3-(2-chloro-4-pyrimidinyl)-4-fluoropyrazolo[1,5-a]pyridin-2-yl]phenyl}-2,6-difluorobenzamide as a yellow solid (0.42 g, 95%). ESIMS (M+H)$^+$=480.

Step E: N-[3-(3-{2-[(3-{[2-(dimethylamino)ethyl]oxy}phenyl)amino]-4-pyrimidinyl}-4-fluoropyrazolo[1,5-a]pyridin-2-yl)phenyl]-2,6-difluorobenzamide (title compound)

To the solution of N-{3-[3-(2-chloro-4-pyrimidinyl)-4-fluoropyrazolo[1,5-a]pyridin-2-yl]phenyl}-2,6-difluorobenzamide (0.10 g) in isopropanol (6 mL) was added 3-{[2-(dimethylamino)ethyl]oxy}aniline (0.06 g) and 3 drops of concentrated hydrochloric acid. The reaction was microwaved in a sealed tube at 180° C. for 10 min. The isopropanol was removed by rotovaporation and the residue was treated with sat. NaHCO$_3$ (5 mL), extracted with EtOAc (2×5 mL), and dried (Na$_2$SO$_4$). Concentration and purification with column chromatography afforded the title compound as a white solid (0.09 g, 70% yield). $^1$H NMR (400 MHz, CDCl$_3$) δ ppm 2.22 (s, 6H), 2.63 (t, J=5.6 Hz, 2H), 391 (t, J=5.6 Hz, 2H), 6.48 (dd, J=8.0, 1.7 Hz, 1H), 6.77 (td, J=7.2, 4.9 Hz, 1H), 6.82-6.85 (m, 1H), 6.86 (s, 1H), 6.89-6.94 (m, 3H), 7.00-7.07 (m, 1H), 7.21-7.32 (m, 4H), 7.43 (s, 1H), 7.79 (d, J=7.9 Hz, 1H), 7.90 (s, 1H), 8.33 (d, J=6.8 Hz, 1H), 8.35-8.38 (m, 1H), 8.45 (s, 1H); ESIMS (M+H)$^+$=624.

188

Example 169

2,6-Difluoro-N-[3-(4-fluoro-3-{2-[(2-methyl-1,2,3,4-tetrahydro-7-isoquinolinyl)amino]-4-pyrimidinyl}pyrazolo[1,5-a]pyridin-2-yl)phenyl]benzamide The title compound was synthesized from N-{3-[3-(2-chloro-4-pyrimidinyl)-4-fluoropyrazolo[1,5-a]pyridin-2-yl]phenyl}-2,6-difluorobenzamide (0.10 g) and 2-methyl-1,2,3,4-tetrahydro-7-isoquinolinamine (0.04 g which may be prepared according the method of Chan, Biorganic & Med. Chem., 2000, 8, 2085-2094 and references therein) using the procedure described in Example 168, step B. The title compound was isolated as a yellow solid (0.070 g, 55% yield). ESIMS (M+H)$^+$=606.

Example 170

2,6-Difluoro-N-{3-[4-fluoro-3-(2-{[3-(1-pyrrolidinylmethyl)-phenyl]amino}-4-pyrimidinyl)pyrazolo[1,5-a]pyridin-2-yl]phenyl}benzamide The title compound was synthesized from N-{3-[3-(2-chloro-4-pyrimidinyl)-4-fluoropyrazolo[1,5-a]pyridin-2-yl]phenyl}-2,6-difluorobenzamide (0.10 g) and 3-(1-pyrrolidinylmethyl)aniline (0.05 g) using the procedure described in Example 168, step B. The title compound was isolated as a yellow solid (0.084 g, 65% yield). ESIMS (M+H)$^+$=620.

Example 171

N-[3-(3-{2-[(3-{[2-(Dimethylamino)ethyl]
oxy}phenyl)amino]-4-pyrimidinyl}-6-fluoropyrazolo
[1,5-a]pyridin-2-yl)phenyl]-2,6-difluorobenzamide

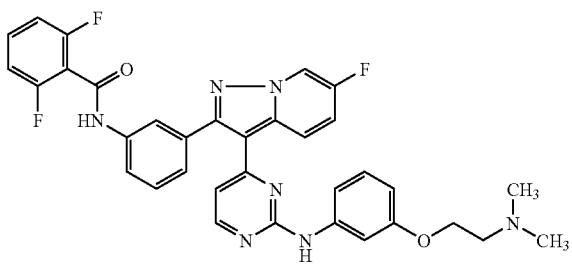

Step A: N-{3-[3-(2-Chloro-4-pyrimidinyl)-6-fluoro-
pyrazolo[1,5-a]pyridin-2-yl]phenyl}-2,6-difluo-
robenzamide

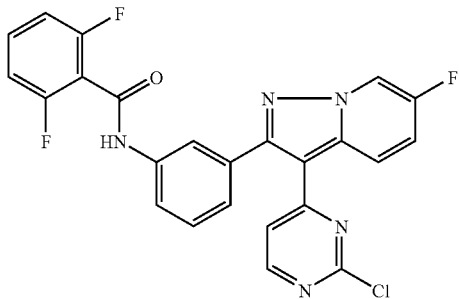

To the solution of 3-[3-(2-chloro-4-pyrimidinyl)-6-fluoro-
pyrazolo[1,5-a]pyridin-2-yl]aniline (0.31 g) (prepared from
N-{3-[3-(2-chloro-4-pyrimidinyl)-4-fluoropyrazolo[1,5-a]
pyridin-2-yl]phenyl}-2,2,2-trifluoroacetamide obtained
Example 168, Step B using a protocol similar to that
described in Example 168, Step C) in THF (10 mL) was added
2,6-difluorobenzoyl chloride (0.19 g). The reaction was kept
stirring at rt for 0.5 h and worked up with sat. NaHCO₃
solution (8 mL). After extraction with EtOAc (2×10 mL),
drying with Na₂SO₄, and concentration, the crude mixture
was purified through silica gel column chromatography to
afford N-{3-[3-(2-chloro-4-pyrimidinyl)-6-fluoropyrazolo
[1,5-a]pyridin-2-yl]phenyl}-2,6-difluorobenzamide as a yel-
low solid (0.43 g, 96%). ESIMS (M+H)⁺=480.

Step B: N-[3-(3-{2-[(3-{[2-(Dimethylamino)ethyl]
oxy}phenyl)amino]-4-pyrimidinyl}-6-fluoropyrazolo
[1,5-a]pyridin-2-yl)phenyl]-2,6-difluorobenzamide

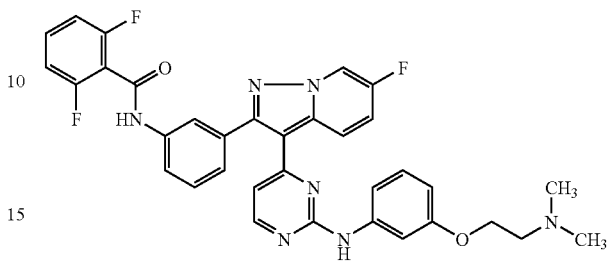

To the solution of N-{3-[3-(2-chloro-4-pyrimidinyl)-6-
fluoropyrazolo[1,5-a]pyridin-2-yl]phenyl}-2,6-difluoroben-
zamide (0.09 g) in isopropanol (5 mL) was added 3-{[2-
(dimethylamino)ethyl]oxy}aniline (0.07 g) and 3 drops of
concentrated hydrochloric acid. The reaction was micro-
waved in a sealed tube at 180° C. for 10 min. The isopropanol
was removed by rotaevaporation and the residue was treated
with sat. NaHCO₃ (5 mL), extracted with EtOAc (2×5 mL),
and dried (Na₂SO₄). Concentration and purification with col-
umn chromatography afforded the title compound as a yellow
solid (0.11 g, 93% yield). ¹H NMR (400 MHz, CDCl₃) δ ppm
2.30 (d, J=2.7 Hz, 6H), 2.70 (t, J=5.7 Hz, 2H), 4.01-4.07 (m,
2H), 6.58-6.68 (m, 2H), 6.95-7.03 (m, 2H), 7.10 (d, J=7.9 Hz,
1H), 7.17-7.30 (m, 4H), 7.37-7.50 (m, 4H), 7.80 (s, 1H), 7.93
(d, J=7.9 Hz, 1H), 8.20 (dd, J=5.2, 2.8 Hz, 1H), 8.39-8.48 (m,
2H); ESIMS (M+H)⁺=624.

Example 172

2,6-Difluoro-N-{3-[6-fluoro-3-(2-{[3-(1-pyrrolidi-
nylmethyl)phenyl]amino}-4-pyrimidinyl)pyrazolo[1,
5-a]pyridin-2-yl]phenyl}benzamide

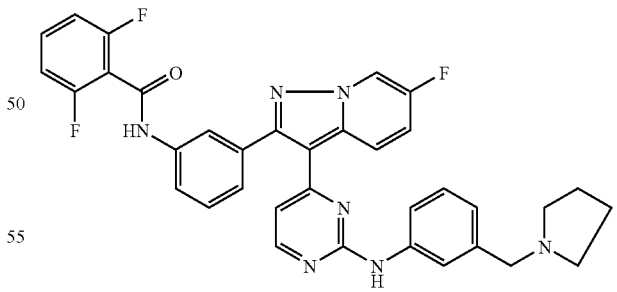

The title compound was synthesized from N-{3-[3-(2-
chloro-4-pyrimidinyl)-6-fluoropyrazolo[1,5-a]pyridin-2-yl]
phenyl}-2,6-difluorobenzamide (0.08 g) (obtained according
to the procedure of Example 168, Step B) and 3-(1-pyrrolidi-
nylmethyl)aniline (0.04 g) using a procedure analogous to
that described in Example 171, step B. The title compound
was isolated as a yellow solid (0.084 g, 80% yield). ESIMS
(M+H)⁺=620.

Example 173

2,6-Difluoro-N-[3-(6-fluoro-3-{2-[(2-methyl-1,2,3,4-tetrahydro-7-isoquinolinyl)amino]-4-pyrimidinyl}pyrazolo[1,5-a]pyridin-2-yl)phenyl]benzamide

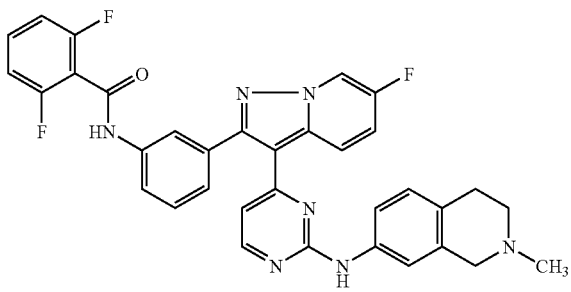

The title compound was synthesized from N-{3-[3-(2-chloro-4-pyrimidinyl)-6-fluoropyrazolo[1,5-a]pyridin-2-yl]phenyl}-2,6-difluorobenzamide (0.09 g) (obtained according to the procedure of Example 168, Step B) and 2-methyl-1,2,3,4-tetrahydro-7-isoquinolinamine (0.05 g) using a procedure analogous to that described in Example 171, step B. The title compound was isolated as a yellow solid (0.063 g, 55% yield). ESIMS (M+H)$^+$=606.

Example 174

N-[3-(3-{2-[(7-Amino-5,6,7,8-tetrahydro-2-naphthalenyl)amino]-4-pyrimidinyl}pyrazolo[1,5-g]pyridin-2-yl)phenyl]-2,6-difluorobenzamidedifluorobenzamide

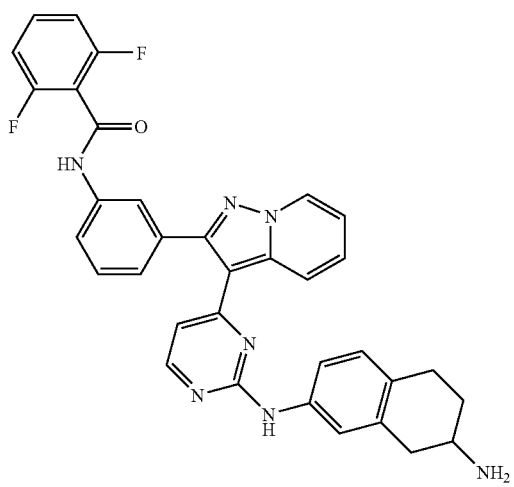

Step A: 7-Nitro-1,2,3,4-tetrahydro-1-naphthalenol

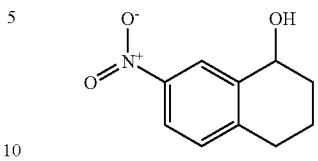

7-Nitro-3,4-dihydro-1(2H)-naphthalenone (5.0 g, 26.1 mmol) was stirred with 2M borane-dimethylsulfide in THF (14.4 mL, 28.8 mmol) in THF (200 mL) at rt for 15 h. The reaction was cooled to 0° C. and quenched with MeOH. The solvent and reaction byproducts were removed under vacuum and afforded 5.0 g (99%) of the desired alcohol as a brown powder. $^1$H NMR (400 MHz, DMSO-d$_6$) δ 8.25 (d, J=2.6 Hz, 1 H), 7.98 (dd, J=8.5, 2.6 Hz, 1H), 7.34 (d, J=8.5 Hz, 1H), 5.55 (d, J=5.7 Hz, 1H), 4.63 (m, 1H), 2.87-2.73 (m, 2H), 2.00-1.83 (m, 2H), 1.75-1.60 (m, 2H).

Step B: 6-Nitro-1a,2,3,7b-tetrahydronaphtho[1,2-b]oxirene

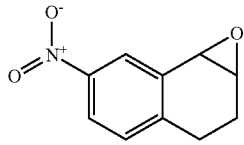

7-Nitro-1,2,3,4-tetrahydro-1-naphthalenol (4.0 g, 20.9 mmol) was treated with Amberlyst-15 (5.0 g) in toluene (100 mL) at 100° C. for 15 h. The reaction was cooled and the Amberlyst was removed by filtration. The filtrate was concentrated under vacuum to afford 3.33 g (92%) of the desired alkene as a brown oil. The 6-nitro-1,2-dihydronaphthalene (3.3 g, 18.9 mmol) was combined with 3-chloroperoxybenzoic acid (5.1 g, 22.6 mmol) in chloroform (60 mL) and heated to reflux for 15 h. The reaction was cooled, diluted with EtOAc and washed three times with 5% aqueous potassium carbonate. The organic was dried with Na$_2$SO$_4$, concentrated to a residue and purified by silica gel flash column chromatography (0-50% EtOAc/hexanes). Purification yielded 1.3 g (36%) of the epoxide as a white solid. $^1$H NMR (400 MHz, DMSO-d$_6$) δ 8.44 (d, J=2.6 Hz, 1H), 8.12 (dd, J=8.1, 2.4 Hz, 1H), 7.41 (d, J=8.5 Hz, 1H), 4.16 (d, J=4.4 Hz, 1H), 3.78 (m, 1H), 2.75-2.55 (m, 2H), 2.39-2.33 (m, 1H), 1.75-1.67 (m, 1H).

Step C: 7-Nitro-3,4-dihydro-2(1h-naphthalenone

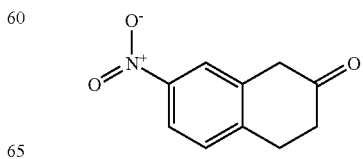

6-Nitro-1a,2,3,7b-tetrahydronaphtho[1,2-b]oxirene (1.3 g, 6.8 mmol) was combined with anhydrous zinc iodide powder (1.0 g, 3.1 mmol) in benzene and stirred at rt under nitrogen in a dark vessel for 15 h. The reaction mixture was filtered and the filtrate concentrated under vacuum. The crude residue was purified by silica gel flash column chromatography (10-50% EtOAc/hexanes) to yield 750 mg (58%) of the desired ketone as a yellow powder. $^1$H NMR (400 MHz, DMSO-d$_6$) δ 8.09 (d, J=2.1 Hz, 1H), 8.06 (dd, J=8.2, 2.4 Hz, 1H), 7.55 (d, J=8.3 Hz, 1H), 3.75 (s, 2H), 3.15 (t, J=6.7 Hz, 2H), 2.50-2.43 (m, 4H).

Step D:
7-Nitro-1,2,3,4-tetrahydro-2-naphthalenamine

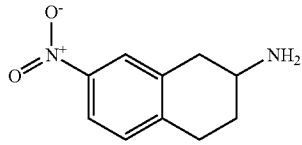

7-Nitro-3,4-dihydro-2(1H)-naphthalenone (200 mg, 1.1 mmol) was combined with ammonium acetate (807 mg, 10.5 mmol), sodium cyanoborohydride (86 mg, 1.4 mmol) and MeOH (5 mL) and heated to 50° C. for 15 h. The reaction was cooled and concentrated under vacuum and the residue was partitioned between EtOAc and water. The organic layer was washed with 5% aqueous potassium carbonate, brine and dried over Na$_2$SO$_4$. The crude was concentrated under vacuum and purified by silica gel flash column chromatography (0-100% (90% DCM/9% MeOH/1% NH$_4$OH)/DCM). Purification provided 130 mg (65%) of the desired amine as a brown oil. $^1$H NMR (400 MHz, DMSO-d$_6$) δ 7.90-7.89 (m, 2H), 7.31 (d, J=8.5 Hz, 1H), 3.06-2.88 (m, 3H), 2.84-2.72 (m, 1H), 2.54-2.44 (m, 2H), 1.81 (d, J=35.2 Hz, 2H), 1.51-1.42 (m, 1H).

Step E: N-(7-Amino-1,2,3,4-tetrahydro-2-naphthalenyl)-2,2,2-trifluoroacetamide

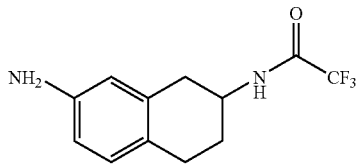

7-Nitro-1,2,3,4-tetrahydro-2-naphthalenamine (130 mg, 0.68 mmol) was acylated with TFAA (191 μL, 1.4 mmol) in a manner similar to that described in Example 54, Step A in 90% yield, and subsequently reduced to the corresponding aniline as described in Example 54, Step B in 99% yield. $^1$H NMR (400 MHz, DMSO-d$_6$) δ 9.39 (d, J=7.7 Hz, 1H), 6.70 (d, J=7.8 Hz, 1H), 6.33 (dd, J=8.1, 2.4 Hz, 1H), 6.23 (s, 1H), 4.78 (s, 2H), 3.97-3.87 (m, 1H), 2.79-2.58 (m, 4H), 1.91-1.84 (m, 1H), 1.69-1.59 (m, 1H); ES-LC/MS (M+H)$^+$=259.16.

Step F: 2,6-Difluoro-N-(3-{3-[2-({7-[(trifluoroacetyl)amino]-5,6,7,8-tetrahydro-2-naphthalenyl}amino)-4-pyrimidinyl]pyrazolo[1,5-a]pyridin-2-yl}phenyl)benzamide

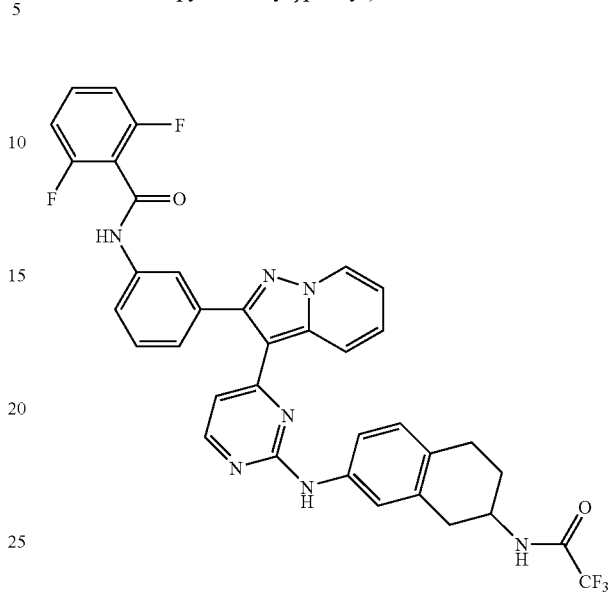

The title compound was synthesized by combining N-{3-[3-(2-chloro-4-pyrimidinyl)pyrazolo[1,5-a]pyridin-2-yl]phenyl}-2,6-difluorobenzamide (119 mg, 0.26 mmol), N-(7-amino-1,2,3,4-tetrahydro-2-naphthalenyl)-2,2,2-trifluoroacetamide (80 mg, 0.31 mmol), hydrochloric acid (0.026 mmol, 26 uL 1M HCl/diethylether) and 3 mL isopropanol in a sealed vessel. The vial and contents were heated at 180° C. for 30 mins. The reaction was cooled and concentrated. The residue was partitioned between EtOAc and saturated aqueous Na$_2$CO$_3$. The organic was washed with brine, dried with magnesium sulfate and concentrated. The crude material was purified by silica gel column chromatography (0-100% gradient; (90% DCM:9% MeOH:1% NH$_4$OH/DCM)) Purification provided 161 mg (91%) of the coupled adduct. ESIMS (M+H)+=684.20.

Step G: N-[3-(3-{2-[(7-Amino-5,6,7,8-tetrahydro-2-naphthalenyl)amino]-4-pyrimidinyl}pyrazolo[1,5-a]pyridin-2-yl)phenyl]-2,6-difluorobenzamide-difluorobenzamide (title compound)

The title compound was prepared by treating 2,6-difluoro-N-(3-{3-[2-({7-[(trifluoroacetyl)amino]-5,6,7,8-tetrahydro-2-naphthalenyl}amino)-4-pyrimidinyl]pyrazolo[1,5-a]pyridin-2-yl}phenyl)benzamide (161 mg, 0.24 mmol) with excess LiOH (200 mg) in MeOH. After stirring for 15 h at rt, the reaction was concentrated. The crude was partitioned between CHCl$_3$ and saturated aqueous NaHCO$_3$. The organic was washed with brine, dried over Na$_2$SO$_4$ and concentrated to a brown powder. Yield: 97 mg (70%). $^1$H NMR (400 MHz, DMSO-d$_6$) δ 10.91 (s, 1H), 9.34 (d, 1H), 8.82 (d, 1H), 8.45 (d, 1H), 8.21 (d, 1H), 7.98 (s, 1H), 7.79 (d, 1H), 7.54 (m, 1H), 7.46 (s, 3H), 7.33 (m, 2H), 7.23 (m, 2H), 7.10 (s, 1H), 6.90 (d, 1H), 6.46 (d, 1H), 2.96 (brs, 1H), 2.85-2.55 (m, 3H), 2.40-2.33 (m, 1H), 1.82 (m, 1H), 1.66 (m, 2H), 1.41 (m, 1H); ESIMS (M+H)+=588.27.

Example 175

N-[3-(7-(Dimethylamino)-3-{2-[(3-fluorophenyl)amino]-4-pyrimidinyl}pyrazolo[1,5-a]pyridin-2-yl)phenyl]-2,6-difluorobenzamide trifluoroacetate

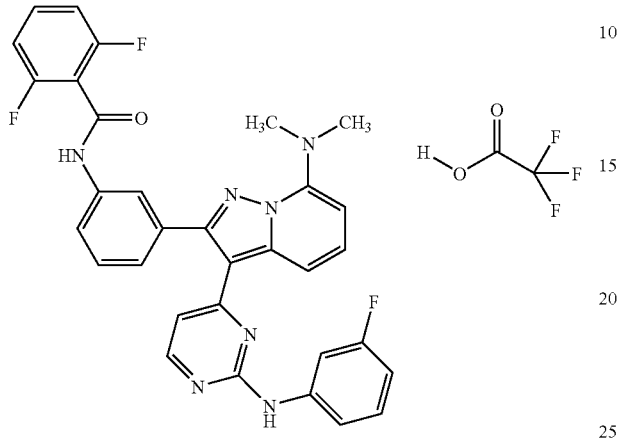

Step A: N-(3-Fluorophenyl)urea nitrate

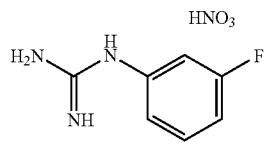

Cyanamide (1.3 mL, 16.8 mmol, 50% by wt. in water), 3-fluoroaniline (1.34 mL, 14 mmol), and 14 M nitric acid (1 mL, 14 mmol) were refluxed in EtOH (14 mL) for 15 h. The reaction was cooled and poured into diethylether. The resulting white suspension was filtered and dried under vacuum. Yield: 1.17 g (38%) of a white powder. $^1$H NMR (400 MHz, DMSO-$d_6$) δ 9.65 (brs, 1H), 7.43 (m, 5H), 7.16-6.90 (m, 3H).

Step B: 2-(3-Bromophenyl)-3-{2-[(3-fluorophenyl)amino]-4-pyrimidinyl}-N,N-dimethylpyrazolo[1,5-a]pyridin-7-amine

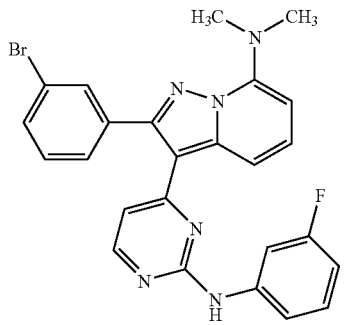

A mixture of (2E)-1-[2-(3-bromophenyl)-7-chloropyrazolo[1,5-a]pyridin-3-yl]-3-(dimethylamino)-2-propen-1-one (500 mg, 1.23 mmol—prepared according to WO 02072581 example 1, p. 77) and N-(3-fluorophenyl)urea nitrate (600 mg, 2.8 mmol) were stirred with $K_2CO_3$ (1 g, 6.9 mmol) and DMF (5 mL) at 100° C. for 15 h. The reaction was then stirred at rt for 7 days. The resulting brown solution was concentrated under vacuum, partitioned between EtOAc and water. The organic fraction was washed with brine and dried over $MgSO_4$. The crude solution was concentrated and purified by silica gel column chromatography (20-100% gradient EtOAc/hexanes). The purification yielded 254 mg (42%) of an orange powder. ESIMS (M+H)+=505.13

Step C: N-[3-(7-(Dimethylamino)-3-{2-[(3-fluorophenyl)amino]-4-pyrimidinyl}pyrazolo[1,5-a]pyridin-2-yl)phenyl]-2,6-difluorobenzamide trifluoroacetate (title compound)

The title compound was prepared by heating in a sealed vessel the product of step a) (130 mg, 0.26 mmol), with 2,6-dichlorobenzamide (50 mg, 0.32 mmol), Xantphos (24 mg, 0.04 mmol), $Pd_2(dba)_3$ (8 mg, 0.02 mmol), $CsCO_3$ (120 mg, 0.37 mmol) and 1,4-dioxane (2 mL) under a nitrogen atmosphere. The reaction stirred at 100° C. for 16 h. The reaction product was purified by silica gel column chromatography (0-100% (90% DCM: 9% $CH_3OH$: 1% $NH_4OH$)/DCM) followed by reverse phase preparative HPLC (10-90% $CH_3CN$ (0.5% trifluoroacetic acid)/$H_2O$). Purification yielded 17 mg (11%) of the trifluoroacetate salt, an orange powder. $^1$H NMR (400 MHz, DMSO-$d_6$) δ 10.91 (s, 1H), 9.77 (s, 1H), 8.28 (d, 1H), 8.03 (d, 1H), 7.96 (s, 1H), 7.84 (d, 1H), 7.74 (d, 1H), 7.56 (m, 1H), 7.42 (m, 3H), 7.35 (d, 1H), 7.21 (m, 3H), 6.68 (t, 1H), 6.56 (d, 1H), 6.49 (d, 1H), 3.07 (s, 6H); ESIMS (M+H)+=580.31.

Example 176

N-{3-[3-(2-{[2-(Dimethylamino)-2,3-dihydro-1H-inden-5-yl]amino}-4-pyrimidinyl)pyrazolo[1,5-a]pyridin-2-yl]phenyl}-2,6-difluorobenzamide

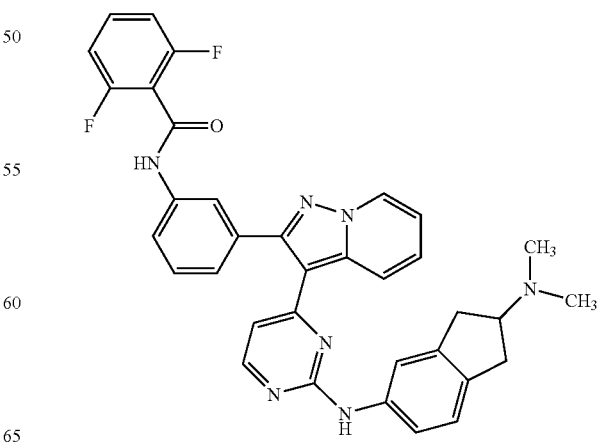

Step A:
N,N-Dimethyl-5-nitro-2,3-dihydro-1H-inden-2-amine

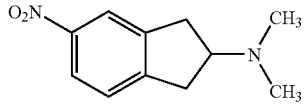

(5-Nitro-2,3-dihydro-1H-inden-2-yl)amine hydrochloride (5.52 g, 26 mmol), paraformaldehyde (4.1 g, 128 mmol), NaCNBH$_3$ (8.1 g, 128 mmol), and acetic acid (7.4 mL, 128 mmol) were combined in 1,2-dichloroethane (200 mL) and the suspension was heated to reflux for 15 h. The reaction was cooled and quenched with saturated aqueous NaHCO$_3$. The organic layer was separated, washed with brine dried with MgSO$_4$ and concentrated to an oil. The crude material was purified by silica gel flash column chromatography (0-100% (90% DCM/9% MeOH/1% NH$_4$OH)/DCM) and yielded 2.7 g (52%) of a yellow oil that crystallized while stored on the bench top. $^1$H NMR (400 MHz, CDCl$_3$) δ 8.07 (m, 2H), 7.36 (d, J=8.1 Hz, 1H), 4.13 (m, 1H), 3.34 (m, 4H), 2.74 (s, 6H).

Step B:
(5-Amino-2,3-dihydro-1-inden-2-yl)dimethylamine

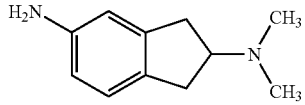

Dimethyl(5-nitro-2,3-dihydro-1H-inden-2-yl)amine (1.5 g, 7.3 mmol)) was dissolved in MeOH and stirred vigorously with of 5% Pd/C (250 mg) under a 55 psi atmosphere of hydrogen for 15 h. The reaction was filtered through Celite and the solvent was removed under vacuum. The reaction produced 1.2 g (94%) of the white powder (5-amino-2,3-dihydro-1H-inden-2-yl)dimethylamine. $^1$H NMR (400 MHz, DMSO-d$_6$) δ 6.84 (d, J=8.2 Hz, 1H), 6.41 (s, 1H), 6.38-6.36 (m, 1H), 4.88 (s, 2H), 3.86 (quint, J=8.8 Hz, 1H), 3.16-2.88 (m, 4H), 2.60 (s, 6H).

Step C: N-{3-[3-(2-{[2-(Dimethylamino)-2,3-dihydro-1H-inden-5-yl]amino}-4-pyrimidinyl)pyrazolo[1,5-a]pyridin-2-yl]phenyl}-2,6-difluorobenzamide (title compound)

The title compound was synthesized by combining N-{3-[3-(2-chloro-4-pyrimidinyl)pyrazolo[1,5-a]pyridin-2-yl]phenyl}-2,6-difluorobenzamide (152 mg, 0.33 mmol), (5-amino-2,3-dihydro-1H-inden-2-yl)dimethylamine (70 mg, 0.40 mmol), hydrochloric acid (0.033 mmol, 33 uL 1M HCl/diethylether) and 3 mL isopropanol in a sealed vessel. The vial and contents were heated at 180° C. for 30 mins. The reaction was cooled and concentrated. The residue was partitioned between EtOAc and saturated aqueous NaHCO$_3$. The organic layer was washed with brine, dried with MgSO$_4$ and concentrated. The crude material was purified by silica gel column chromatography (0-100% gradient; (90% CH$_2$Cl$_2$: 9% MeOH:1% NH$_4$OH/CH$_2$Cl$_2$)) Purification provided 28 mg (14%) of the coupled adduct. ESIMS (M+H)+=603.30.

Example 177

N-[3-(3-{2-[(2-Amino-2,3-dihydro-1H-inden-5-yl)amino]-4-pyrimidinyl}pyrazolo[1,5-a]pyridin-2-yl)phenyl]-2,6-difluorobenzamide

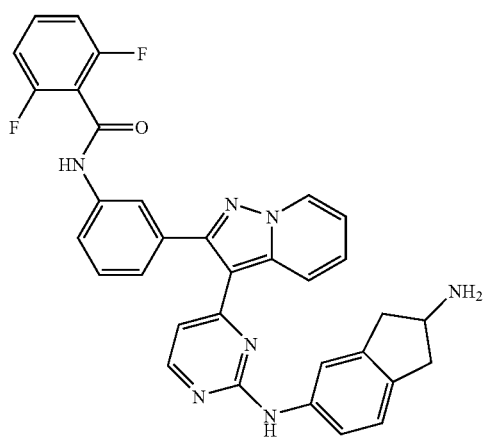

Step A: 2,2,2-Trifluoro-N-(5-nitro-2,3-dihydro-1H-inden-2-yl)acetamide

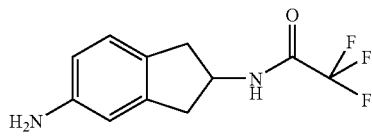

Trifluoroacetic anhydride (361 µL, 2.6 mmol) was added dropwise to a solution of (5-nitro-2,3-dihydro-1H-inden-2-yl)amine hydrochloride (500 mg, 2.3 mmol), triethylamine (327 uL, 2.3 mmol) and DCM (20 mL) stirring at 0 C. The ice bath was allowed to melt and the reaction stirred at rt for 15 h. The reaction was washed in a separatory funnel with saturated NaHCO$_3$, brine and was dried with Na$_2$SO$_4$. The solvent was removed under vacuum and the residue was purified by silica gel flash column chromatography (0-100% (90% DCM/9% MeOH/1% NH$_4$OH)/DCM). Purification yielded 476 mg (84%) of the trifluoroacetamide-protected amine, a white powder. $^1$H NMR (400 MHz, DMSO-d$_6$) δ 9.75 (d, J=6.8 Hz, 1H), 8.10 (s, 1H), 8.06 (dd, J=8.3, 2.2 Hz, 1H), 7.49 (d, J=8.2 Hz, 1H), 4.67-4.58 (m, 1H), 3.35 (dd, J=16.8, 8.1 Hz, 2H), 3.01 (dd, J=16.5, 5.7 Hz, 2H).

Step B: N-(5-Amino-2,3-dihydro-1-inden-2-yl)-2,2,2-trifluoroacetamide

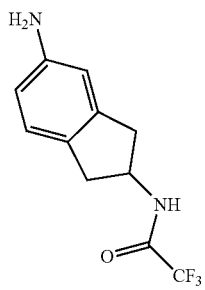

2,2,2-Trifluoro-N-(5-nitro-2,3-dihydro-1H-inden-2-yl)acetamide (245 mg, 0.89 mmol) was dissolved in EtOAc and stirred vigorously for 15 h with 5% palladium on carbon (70 mg) under hydrogen atmosphere (1 atm). The reaction was filtered through Celite and the solvent was removed under vacuum. Filtration yielded 214 mg (98%) of the title compound, a brown powder. $^1$H NMR (400 MHz, DMSO-$d_6$) δ 9.60 (d, J=7.1 Hz, 1H), 6.81 (d, J=8.0 Hz, 1H), 6.39 (s, 1H), 6.34 (d, J=8.1 Hz, 1H), 4.83 (s, 2H), 4.43 (m, 1H), 3.01 (m, 2H), 2.71 (m, 2H); ESIMS (M+H)+=245.11.

Step C: 2,6-Difluoro-N-(3-{3-[2-({2-[(trifluoroacetyl)amino]-2,3-dihydro-1H-inden-5-yl}amino)-4-pyrimidinyl]pyrazolo[1,5-a]pyridin-2-yl}phenyl)benzamide

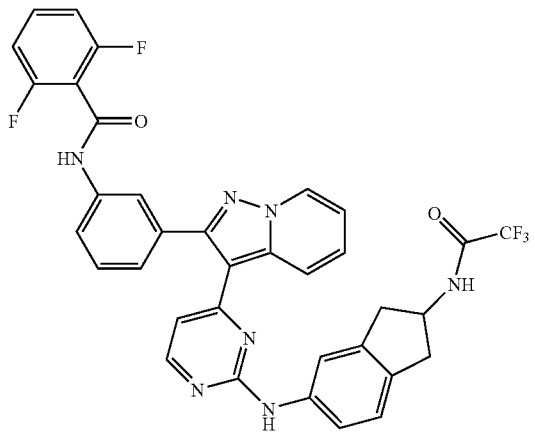

The title compound was synthesized by combining N-{3-[3-(2-chloro-4-pyrimidinyl)pyrazolo[1,5-a]pyridin-2-yl]phenyl}-2,6-difluorobenzamide (200 mg, 0.43 mmol) (prepared according to a procedure similar to that described in Example 27, Step C), N-(5-amino-2,3-dihydro-1H-inden-2-yl)-2,2,2-trifluoroacetamide (127 mg, 0.52 mmol), hydrochloric acid (0.043 mmol, 43 µL 1M HCl/diethylether) and 2 mL isopropanol in a sealed vessel. The vial and contents were heated in a microwave synthesizer at 180° C. for 30 min. The reaction was cooled and concentrated. The residue was partitioned between EtOAc and saturated NaHCO$_3$. The organic was washed with brine, dried with MgSO$_4$ and concentrated. The crude material was purified by silica gel column chromatography (0-100% gradient; (90% DCM:9% MeOH:1% NH$_4$OH/DCM)). Purification provided 278 mg (95%) of the coupled adduct. ESIMS (M+H)+=684.20.

Step D: N-[3-(3-{2-[(2-Amino-2,3-dihydro-1H-inden-5-yl)amino]-4-pyrimidinyl}pyrazolo[1,5-a]pyridin-2-yl)phenyl]-2,6-difluorobenzamide (title compound)

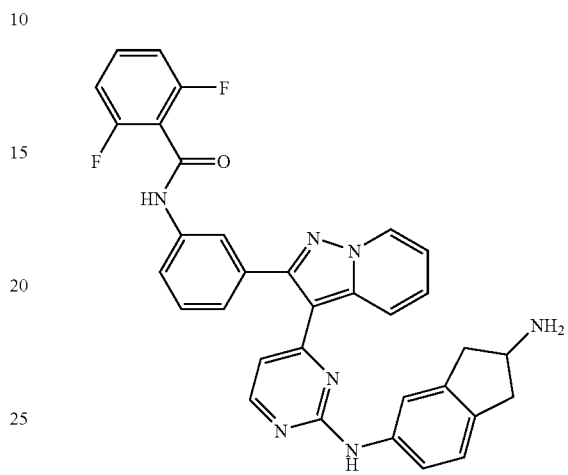

The purified product of Step D (100 mg, 0.15 mmol)) was combined with LiOH (31 mg, 0.75 mmol) and stirred in MeOH for 2 h at rt. The reaction was concentrated under vacuum and partitioned between EtOAc and water. The organic fraction was washed with brine and dried over MgSO$_4$. The crude solution was concentrated and purified by silica gel column chromatography (0-100% gradient; (90% DCM:9% MeOH:1% NH$_4$OH/DCM)). Purification yielded 50 mg (58%) of a tan powder. ESIMS (M+H)+=574.17.

Example 178

2,6-Difluoro-N-{3-[3-(2-{[3-(4-methyl-1,3-oxazol-5-yl)phenyl]amino}-4-pyrimidinyl)pyrazolo[1,5-a]pyridin-2-yl]phenyl}benzamide

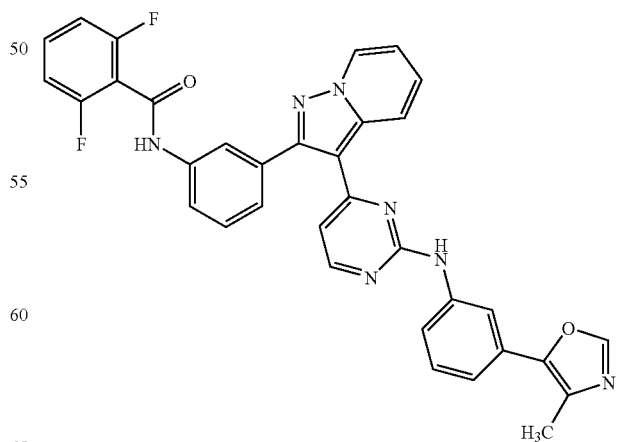

Step A: {1-[(4-Methylphenyl)sulfonyl]ethyl}formamide

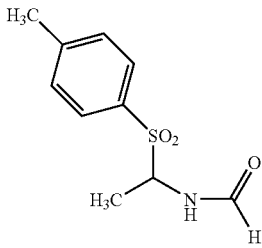

A stirred mixture of dry acetonitrile (500 mL) and dry toluene (500 mL) was cooled to −30° C., followed by the addition of formamide (50.7 g, 1.1 mol), acetaldehyde (37 g, 0.85 mol) and TMSCl (106.4 g, 0.98 mol) at −30° C. under $N_2$ atmosphere. The reaction mixture was stirred at rt for 1 h and warmed to 55° C., then p-toluene sulphonic acid was added and stirred the reaction mixture at this temperature overnight. The reaction mixture was cooled to 0° C. and followed by the addition of 300 mL of tert-butyl ether and stirred for 1 h. The white precipitate formed was filtered off and dried. The crude product was taken into next step without further purification. Yield (crude): 110 g.

Step B: 1-Isocyanoethyl 4-methylphenyl sulfone

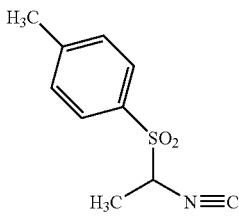

To a cooled (0° C.) solution of the formamide (110 g, 0.484 mol) from the previous step A) in dry THF (1000 mL), $POCl_3$ (148.4 g, 0.968 mol) was added slowly and stirred for 30 min. Then TEA (293.8 g, 2.9 mol) was added dropwise over 30 min and the reaction stirred for 2 h at 0° C. The reaction mixture was quenched with water and extracted with EtOAc (3×350 mL). The combined organic layer was washed with brine, water, dried over anhydrous $Na_2SO_4$ and concentrated. The crude product was taken to next step without further purification. Yield (crude): 60 g.

Step C: 4-Methyl-5-(3-nitrophenyl)-1,3-oxazole

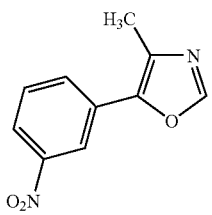

To a cooled (0° C.) solution of the isonitrile (60 g, 0.287 mol) from the previous step in dry MeOH (800 mL), dry powdered $K_2CO_3$ was added and stirred at rt for 1 h. The mixture was recooled to 0° C., and 3-nitro benzaldehyde was added. The reaction mixture was warmed to rt, followed by heating at 55° C. overnight with stirring. The excess solvent was removed under reduced pressure and the residue was dissolved in water (100 mL). The mixture was extracted with EtOAc (3×350 mL). The combined organic layer was washed with brine, water, dried over anhydrous $Na_2SO_4$ and concentrated. The crude product was purified by silica gel (60-120 mesh) column chromatograph using 15% EtOAc in pet.ether to obtain product as yellow solid. Yield 50 g (86%).

Step D: 3-(4-Methyl-1,3-oxazol-5-yl)aniline

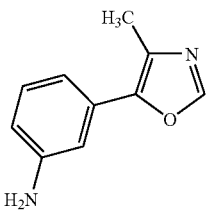

A solution of the nitrobenzene adduct (50 g) produced in the previous step C in MeOH (600 mL) was prepared in parr-shaker bottle; Pd/C (5 g) was transferred carefully and hydrogenated at 3.5 kg pressure for 20 h. The reaction mixture was filtered over celite bed and the filtrate was concentrated. The residue was purified by silica gel column chromatograph using 40% EtOAc in pet.ether to get yellow color solid. Yield 18 g (42%). $^1$H NMR (400 MHz, DMSO-$d_6$) δ 8.23 (s, 1H), 7.08 (t, J=8.0 Hz, 1H), 6.82 (s, 1H), 6.71 (d, J=7.9 Hz, 1H), 6.52 (d, J=8.2 Hz, 1H), 5.24 (s, 2H), 2.29 (s, 3H).

Step E: 2,6-Difluoro-N-{3-[3-(2-{[3-(4-methyl-1,3-oxazol-5-yl)phenyl]amino}-4-pyrimidinyl)pyrazolo[1,5-a]pyridin-2-yl]phenyl}benzamide

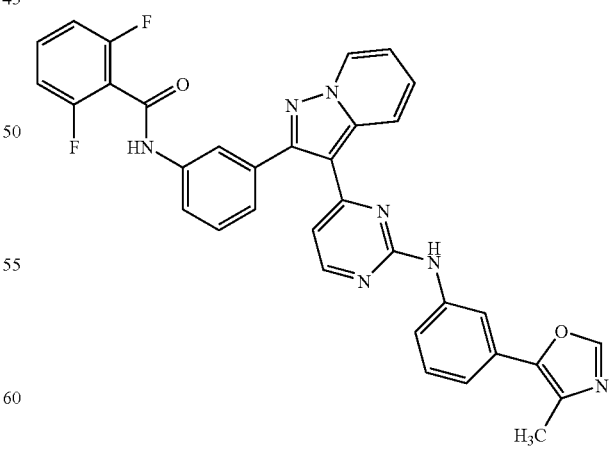

The title compound was prepared by heating N-{3-[3-(2-chloro-4-pyrimidinyl)pyrazolo[1,5-a]pyridin-2-yl]phenyl}-2,6-difluorobenzamide (180 mg, 0.39 mmol) (prepared according to a procedure similar to that described in Example 27, Step C), 3-(4-methyl-1,3-oxazol-5-yl)aniline (75 mg, 0.43 mmol), hydrochloric acid (40 µL, 0.040 mmol, 1M HCl/Et₂O) and isopropanol (2 mL) at 160° C. for 15 min in a microwave synthesizer. The reaction was cooled and concentrated and purified by silica gel column chromatography (20-100% gradient EtOAc (0.5% TEA)/hexanes (0.5% TEA)). Purification yielded 60 mg (25%) of a yellow powder. ESIMS (M+H)+=601.17.

Step F: 2,6-Difluoro-N-[3-(3-{2-[(2,4,4-trimethyl-1,2,3,4-tetrahydro-7-isoquinolinyl)amino]-4-pyrimidinyl}pyrazolo[1,5-a]pyridin-2-yl)phenyl]benzamide

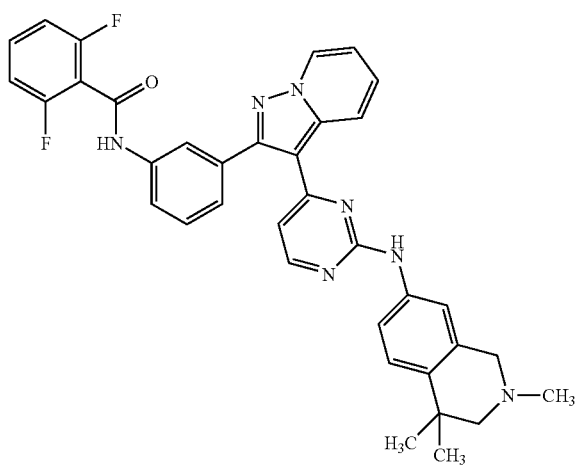

The title compound was prepared following a procedure similar to the Example 177, Step C, from 2,4,4-trimethyl-1,2,3,4-tetrahydro-7-isoquinolinamine (50 mg, 0.26 mmol) (synthesized as described in patent WO 0009486, p. 18) and N-{3-[3-(2-chloro-4-pyrimidinyl)pyrazolo[1,5-a]pyridin-2-yl]phenyl}-2,6-difluorobenzamide (101 mg, 0.22 mmol, prepared according to a procedure similar to that described in Example 27, Step C). ESIMS (M+H)+=616.32.

Example 179

2,6-Difluoro-N-[3-(3-{2-[(2-methyl-1,2,3,4-tetrahydro-7-isoquinolinyl)amino]-4-pyrimidinyl}pyrazolo[1,5-a]pyridin-2-yl)phenyl]benzamide

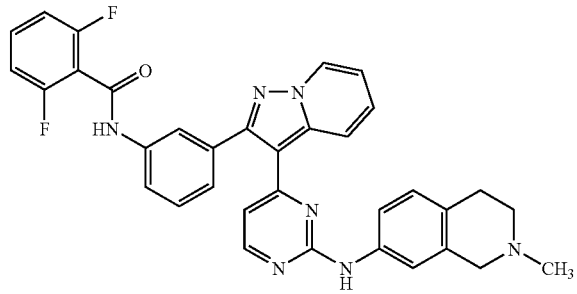

To a suspension of N-{3-[3-(2-chloro-4-pyrimidinyl)pyrazolo[1,5-a]pyridin-2-yl]phenyl}-2,6-difluorobenzamide (100 mg, 0.22 mmol) (prepared according to a procedure similar to that described in Example 27, Step C) and 2-methyl-1,2,3,4-tetrahydro-7-isoquinolinamine (44 mg, 0.27 mmol) in 2-propanol (3 mL) was added 2 drops of concentrated HCl. The mixture was stirred at 90° C. overnight, and the reaction mixture was partitioned between saturated aqueous NaHCO₃ and 4:1 CHCl₃/MeOH. The organic layer was dried over MgSO₄, filtered, and purified by flash chromatography to give the title compound as a yellow oil (76 mg, 59% yield). ¹H NMR (400 MHz, d₆-DMSO): δ 10.95 (s, 1H), 9.44 (s, 1H), 8.85 (d, J=7.0 Hz, 1H), 8.46 (d, J=9.0 Hz, 1H), 8.26 (d, J=5.3 Hz, 1H), 8.02 (s, 1H), 7.83 (d, J=9.2 Hz, 1H), 7.55-7.65 (m, 1H), 7.45-7.49 (m, 2H), 7.35-7.39 (m, 1H), 7.26 (t, J=8.1 Hz, 2H), 7.14 (t, J=6.8 Hz, 1H), 6.97 (d, J=8.4 Hz, 1H), 6.72 (d, J=8.0 Hz, 1H), 6.52 (d, J=5.3 Hz, 1H), 6.35 (d, J=8.0 Hz, 1H), 6.21 (s, 1H), 3.30 (s, 2H) 2.75 (t, J=5.5 Hz, 2H), 2.52-2.63 (m, 2H), 2.26 (s, 3H). MS (ESI) m/z=588 [M+H]⁺.

Example 180

N-{3-[3-(2-{[3-(Aminomethyl)phenyl]amino}-4-pyrimidinyl)pyrazolo[1,5-a]pyridin-2-yl]phenyl}-2,6-difluorobenzamide

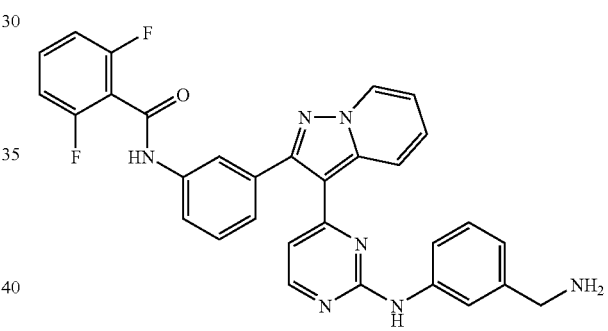

Step A:
2,2,2-trifluoro-N-[(3-nitrophenyl)methyl]acetamide

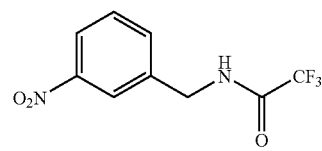

To a solution of 3-nitrobenzylammonium chloride (10.2 g, 54 mmol) and triethylamine (37.6 mL, 270 mmol) in DCM (500 mL) was added TFAA (11.4 mL, 81 mmol) over 30 min. After 16 h at rt, the reaction was washed with 200 mL 1 N HCl, dried over Na₂SO₄, filtered, and concentrated. The crude product was purified by flash chromatography to yield the title compound (12.3 g, 50 mmol, 92%). ¹H NMR (400 MHz, CDCl₃): δ 8.15-8.19 (m, 2H), 7.65 (d, J=7.7 Hz, 1H), 7.56 (t, J=7.9 Hz, 1H), 6.7 (bs, 1H), 4.64 (d, J=6.0 Hz, 2H). MS (ESI) m/z=249 [M+H]⁺.

Step B: N-[(3-aminophenyl)methyl]-2,2,2-trifluoroacetamide

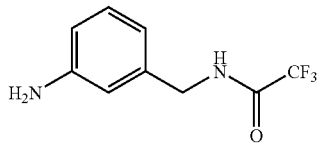

To a solution of 2,2,2-trifluoro-N-[(3-nitrophenyl)methyl]acetamide (0.5 g, 2.0 mmol) in 2-propanol (30 mL) was added 10% palladium on carbon (40 mg). The reaction was stirred at rt under a hydrogen atmosphere (1 atm) for 15 hours. The reaction mixture was filtered through Celite, adsorbed to silica, and purified by column chromatography to yield the title compound (0.37 g, 1.7 mmol, 85% yield). $^1$H NMR (400 MHz, CDCl$_3$): δ 7.14-7.27 (m, 1H), 6.59-6.68 (m, 3H), 4.44 (d, J=7.9 Hz, 2H), 3.74 (s, 2H). MS (ESI) m/z=219 [M+H]$^+$.

Step C: 2,6-Difluoro-N-[3-(3-{2-[(3-{[(trifluoroacetyl)amino]methyl}phenyl)amino]-4-pyrimidinyl}pyrazolo[1,5-a]pyridin-2-yl)phenyl]benzamide

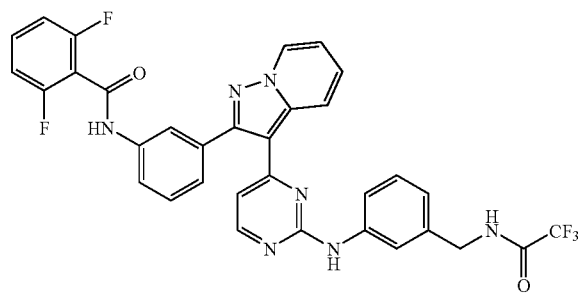

To a suspension of N-{3-[3-(2-chloro-4-pyrimidinyl)pyrazolo[1,5-a]pyridin-2-yl]phenyl}-2,6-difluorobenzamide (100 mg, 0.22 mmol) (prepared according to a procedure similar to that described in Example 27, Step C) and N-[(3-aminophenyl)methyl]-2,2,2-trifluoroacetamide (59 mg, 0.27 mmol) in 2-propanol (3 mL) was added 2 drops of concentrated HCl. The mixture was heated to 180° C. in a microwave for 10 min. The reaction mixture was diluted with 25 mL DCM and washed with saturated aqueous NaHCO$_3$. The organic layer was dried over MgSO$_4$, filtered, and purified by flash chromatography to give the title compound as a glassy solid (110 mg, 78% yield). MS (ESI) m/z=644 [M+H]$^+$.

Step D: N-{3-[3-(2-{[3-(Aminomethyl)phenyl]amino}-4-pyrimidinyl)pyrazolo[1,5-a]pyridin-2-yl]phenyl}-2,6-difluorobenzamide (title compound)

To a solution of 2,6-difluoro-N-[3-(3-{2-[(3-{[(trifluoroacetyl)amino]methyl}phenyl)-amino]-4-pyrimidinyl}pyrazolo[1,5-a]pyridin-2-yl]phenyl]benzamide (110 mg, 0.17 mmol) in THF (3 mL) and water (0.5 mL) was added LiOH.H$_2$O (14 mg, 0.34 mmol). The solution was stirred at 50° C. for two hours, then diluted with 25 mL DCM and washed with 1 M aqueous Na$_2$CO$_3$. The aqueous layer was extracted with DCM, and the combined organic layers were dried over Na$_2$SO$_4$, filtered, and concentrated. The residue was redissolved in MeOH and lyophilized to generate 96 mg of the title compound as a yellow solid (0.17 mmol, quantative yield). $^1$H NMR (400 MHz, d$_6$-DMSO): δ 10.95 (s, 1H), 9.51 (s, 1H), 8.85 (d, J=6.7 Hz, 1H), 8.53 (d, J=9.0 Hz, 1H), 8.27 (d, J=5.3 Hz, 1H), 8.02 (s, 1H), 7.83 (d, J=7.8 Hz, 1H), 7.73 (s, 1H), 7.46-7.63 (m, 4H), 7.37 (d, J=7.5 Hz, 1H), 7.26 (t, J=8.0 Hz, 2H), 7.12-7.21 (m, 2H), 6.95 (d, J=7.5 Hz, 1H), 6.52 (d, J=5.1 Hz, 1H), 3.67 (s, 2H). MS (ESI) m/z=548 [M+H]$^+$.

Example 181

N-{5-[3-(2-{[2-(Dimethylamino)-2,3-dihydro-1H-inden-5-yl]amino}-4-pyrimidinyl)pyrazolo[1,5-a]pyridin-2-yl]-2-fluorophenyl}-2,6-difluorobenzamide

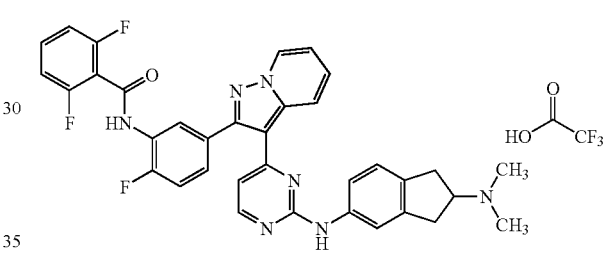

Step A: N-(5-Bromo-2-fluorophenyl)-2,2,2-trifluoroacetamide

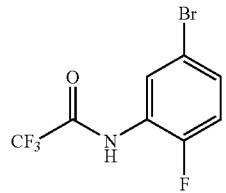

To a solution of 4-fluoro-3-nitrobromobenzene (5.0 g, 23 mmol) in absolute EtOH (500 mL) was added SnCl$_2$ dihydrate (31 g, 136 mmol) and the resulting mixture was allowed to stir overnight at rt. The solvent was removed under reduced pressure, and the residue was suspended in EtOAc, washed with 1 N NaOH, and filtered through a celite pad. The organic layer was concentrated by rotary evaporation, and dissolved in DCM (500 mL). To this solution were added TEA (26 mL, 184 mmol) and TFAA (6.5 mL, 46 mmol). After overnight stirring, the reaction was washed with 1 N HCl, dried over Na$_2$SO$_4$, concentrated and purified by column chromatography to yield the title compound (5.6 g, 87%) as a white solid. ES-LC/MS m/z=287 [M+H]$^+$.

Step B: 2,2,2-Trifluoro-N-{2-fluoro-5-[(trimethylsilyl)ethynyl]phenyl}acetamide

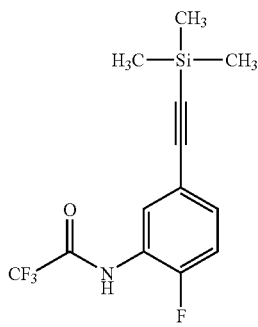

To an oven-dried flask under N₂ was added N-(5-bromo-2-fluorophenyl)-2,2,2-trifluoroacetamide (5.6 g, 20 mmol), anhydrous degassed THF (200 mL), dichlorobis(triphenylphosphine)palladium(II) (1.7 g, 2.5 mmol), copper(I) iodide (0.28 g, 1.5 mmol), and trimethylsilylacetylene (7.0 mL, 50 mmol). Next, TEA (27 mL, 197 mmol) was added dropwise and the resulting mixture was heated at 60° C. overnight. The crude reaction mixture was adsorbed to silica gel and purified by column chromatography to afford the desired product (5.3 g, 89%) as an off white solid. ES-LC/MS m/z=302 [M–H]⁻.

Step C: N-(5-Ethynyl-2-fluorophenyl)-2,2,2-trifluoroacetamide

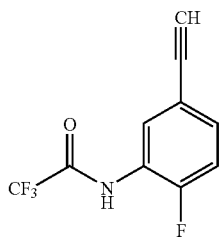

A solution of 2,2,2-trifluoro-N-{2-fluoro-5-[(trimethylsilyl)ethynyl]phenyl}acetamide (5.3 g, 17 mmol) in THF (400 mL) was cooled to 0° C., and a 1.0 M solution of TBAF in THF (17 mL, 17 mmol) was added dropwise. The resulting mixture was stirred for 10 min. at 0° C. The reaction was quenched with H₂O (150 mL), concentrated under reduced pressure, and extracted with DCM. The combined organic layers were concentrated under reduced pressure, and the crude solid was used in the next reaction without further purification. ES-LC/MS m/z=230 [M–H]⁻.

Step D: N-{5-[(2-Chloro-4-pyrimidinyl)ethynyl]-2-fluorophenyl}-2,2,2-trifluoroacetamide

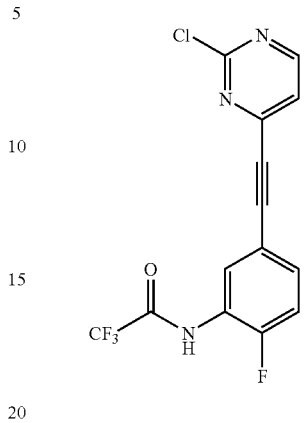

To an oven-dried flask under N₂ was added 2,4-dichloropyrimidine (5.1 g, 34 mmol), anhydrous degassed THF (250 mL), dichlorobis(triphenylphosphine)-palladium(II) (595 mg, 0.85 mmol), copper(I) iodide (97 mg, 0.5 mmol), and TEA (9.5 mL, 68 mmol), and the resulting suspension was heated to 60° C. A solution of N-(5-ethynyl-2-fluorophenyl)-2,2,2-trifluoroacetamide (3.9 g, 17 mmol) in THF (100 mL) was added dropwise, and the resulting mixture stirred overnight at 60° C. After 16 h, the crude reaction mixture was filtered through celite, adsorbed to silica gel, and purified by column chromatography to afford the desired product (4.6 g, 78%) as an off white solid. ¹H NMR (400 MHz, CDCl₃): δ 8.65 (d, J=5.1 Hz, 1H), 8.58 (d, J=7.3 Hz, 1H), 7.49 (m, 1H), 7.41 (d, J=5.0 Hz, 1H), 7.24 (m, 1H). ES-LC/MS m/z=344 [M+H]⁺.

Step E: N-{5-[3-(2-Chloro-4-pyrimidinyl)pyrazolo[1,5-a]pyridin-2-yl]-2-fluorophenyl}-2,2,2-trifluoroacetamide

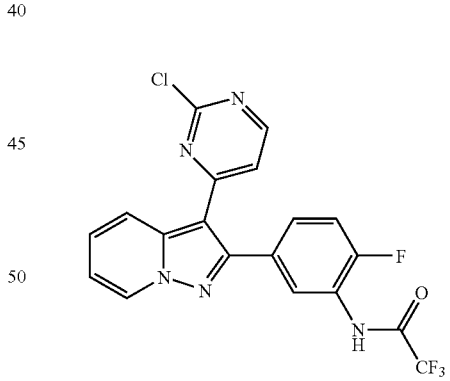

To a solution of N-{5-[(2-chloro-4-pyrimidinyl)ethynyl]-2-fluorophenyl}-2,2,2-trifluoroacetamide (4.6 g, 13 mmol) in DMF (100 mL) was added aminopyridinium iodide (5.9 g, 27 mmol) and potassium carbonate (5.5 g, 40 mmol). After stirring 2 h at rt, the reaction mixture was diluted with diethyl ether (250 mL) and EtOAc (250 mL), and washed with water. The organic layer was adsorbed to silica gel and purified by column chromatography to afford the desired product (3.2 g, 55%) as a tan solid. ¹H NMR (400 MHz, CDCl₃): δ 8.57 (m, 2H), 8.31 (d, J=5.5 Hz, 1H), 8.14 (s, 1H), 7.47 (m, 2H), 7.31 (t, J=9.4 Hz, 1H), 7.04 (t, J=6.8 Hz), 6.99 (d, J=5.3 Hz, 1H). ES-LC/MS m/z=436 [M+H]⁺.

Step F: N-{5-[3-(2-{[2-(Dimethylamino)-2,3-dihydro-1H-inden-5-yl]amino}-4-pyrimidinyl)pyrazolo[1,5-a]pyridin-2-yl]-2-fluorophenyl}-2,2,2-trifluoroacetamide

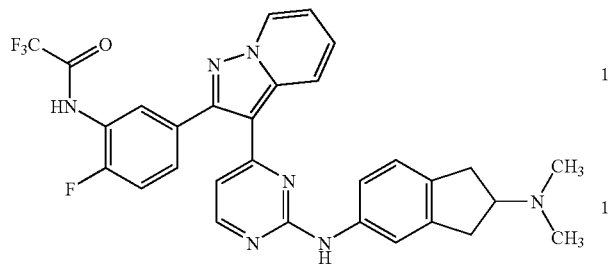

The title compound was prepared from N-{5-[3-(2-chloro-4-pyrimidinyl)pyrazolo-[1,5-a]pyridin-2-yl]-2-fluorophenyl}-2,2,2-trifluoroacetamide (from Step E) (200 mg, 0.46 mmol) and N2,N2-dimethyl-2,3-dihydro-1H-indene-2,5-diamine (101 mg, 0.46 mmol) (prepared according to the method described in Example 176) using displacement conditions described in Example 176 to generate the title compound in 83% yield. MS (ESI) m/z=576 [M+H]+.

Step G: {4-[2-(3-Amino-4-fluorophenyl)pyrazolo[1,5-a]pyridin-3-yl]-2-pyrimidinyl}[2-(dimethylamino)-2,3-dihydro-1H-inden-5-yl]amine

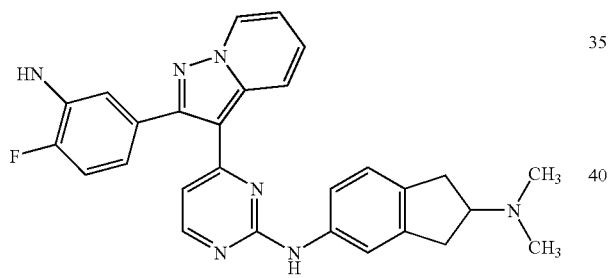

The title compound was prepared from N-{5-[3-(2-{[2-(dimethylamino)-2,3-dihydro-1H-inden-5-yl]amino}-4-pyrimidinyl)pyrazolo[1,5-a]pyridin-2-yl]-2-fluorophenyl}-2,2,2-trifluoroacetamide (161 mg, 315 mmol) and LiOH.H$_2$O using hydrolysis conditions as described above in Example 11, Step E to generate the desired product in 88% yield. $^1$H NMR (400 MHz, d$_6$-DMSO): δ 9.40 (s, 1H), 8.79 (d, J=7.0 Hz, 1H), 8.48 (d, J=9.0 Hz, 1H), 8.23 (d, J=5.4 Hz, 1H), 7.66 (s, 1H), 7.39-7.46 (m, 2H), 7.01-7.11 (m, 4H), 6.70-6.72 (m, 1H), 6.48 (d, J=5.4 Hz, 1H), 5.31 (s, 2H), 2.91-2.98 (m, 3H), 2.68-2.72 (m, 2H), 2.20 (s, 6H). ES-LC/MS m/z=480 [M+H]+.

Step H: N-{5-[3-(2-{[2-(dimethylamino)-2,3-dihydro-1H-inden-5-yl]amino}-4-pyrimidinyl)pyrazolo[1,5-a]pyridin-2-yl]-2-fluorophenyl}-2,6-difluorobenzamide (title compound)

To a solution of {4-[2-(3-amino-4-fluorophenyl)pyrazolo[1,5-a]pyridin-3-yl]-2-pyrimidinyl}[2-(dimethylamino)-2,3-dihydro-1H-inden-5-yl]amine (80 mg, 0.17 mmol) in THF (3 mL) was added TEA (25 μL, 0.25 mmol) and 2,6-difluorobenzoyl chloride (22 μL, 0.18 mmol). The reaction was stirred at rt for 2 h, and the reaction was diluted with 30 mL DCM and adsorbed onto silica. The crude product was purified by flash chromatography and reversed-phase HPLC to generate, after lyophilization, the title compound as a TFA salt (38 mg, 37% yield). $^1$H NMR (400 MHz, d$_6$-DMSO): δ 10.84 (s, 1H), 9.59 (s, 1H), 8.88 (d, J=6.7 Hz, 1H), 8.44 (d, J=8.4 Hz, 1H), 8.30 (d, J=5.3 Hz, 1H), 8.24 (d, J=7.0 Hz, 1H), 7.75 (s, 1H), 7.58-7.62 (m, 1H), 7.41-7.52 (m, 4H), 7.24 (t, J=8.0 Hz, 2H), 7.13-7.16 (m, 2H), 6.61 (d, J=5.3 Hz, 1H), 4.04-4.12 (m, 1H), 3.22-3.28 (m, 2H), 3.06-3.12 (m, 2H), 2.82 (s, 6H). MS (ESI) m/z=620 [M+H]+.

Example 182

N-[5-(3-{2-[(3-{[2-(Dimethylamino)ethyl]oxy}phenyl)amino]-4-pyrimidinyl}pyrazolo[1,5-a]pyridin-2-yl)-2-fluorophenyl]-2,6-difluorobenzamide

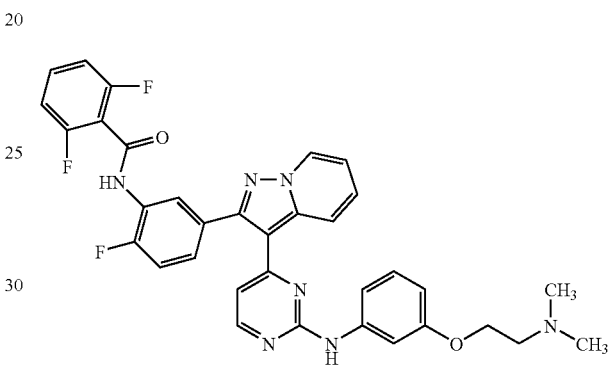

Step A: N-[5-(3-{2-[(3-{[2-(Dimethylamino)ethyl]oxy}phenyl)amino]-4-pyrimidinyl}pyrazolo[1,5-a]pyridin-2-yl)-2-fluorophenyl]-2,2,2-trifluoroacetamide

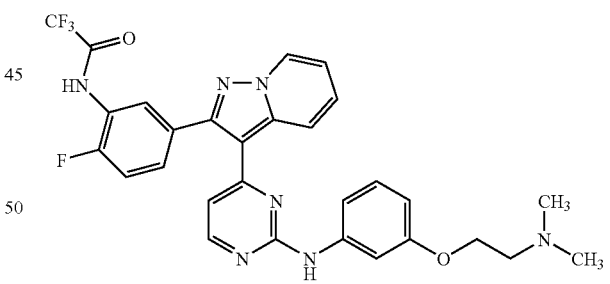

The title compound was prepared from N-{5-[3-(2-chloro-4-pyrimidinyl)pyrazolo[1,5-a]pyridin-2-yl]-2-fluorophenyl}-2,2,2-trifluoroacetamide (200 mg, 0.46 mmol) (Example 160, Step E) and 3-{[2-(dimethylamino)ethyl]oxy}aniline (123 mg, 0.57 mmol) using displacement conditions as described in Example 36, Step F to generate the title compound in 77% yield (204 mg, 0.35 mmol). $^1$H NMR (400 MHz, d$_6$-DMSO): δ 11.3 (bs, 1H), 9.58 (s, 1H), 8.84 (d, J=6.9 Hz, 1H), 8.49 (d, J=9.0 Hz, 1H), 8.30 (d, J=5.3 Hz, 1H), 7.82 (dd, J=7.3, 2.2 Hz, 1H), 7.44-7.52 (m, 4H), 7.28 (d, J=8.9 Hz, 1H), 7.14 (t, J=7.9 Hz, 1H), 6.52-6.55 (m, 2H), 4.00 (t, J=5.7 Hz, 2H), 2.63 (t, J=5.7 Hz, 2H), 2.21 (s, 6H). ES-LC/MS m/z=580 [M+H]+.

211

Step B: 4-[2-(3-Amino-4-fluorophenyl)pyrazolo[1,5-a]pyridin-3-yl]-N-(3-{[2-(dimethylamino)ethyl]oxy}phenyl)-2-pyrimidinamine

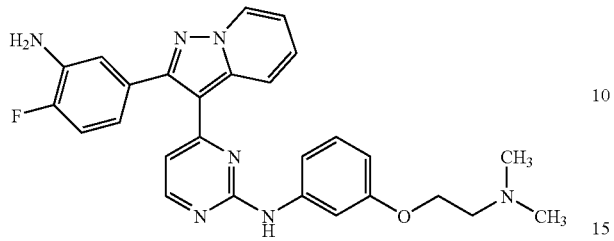

The title compound was prepared from N-[5-(3-{2-[(3-{[2-(dimethylamino)ethyl]oxy}phenyl)amino]-4-pyrimidinyl}pyrazolo[1,5-a]pyridin-2-yl)-2-fluorophenyl]-2,2,2-trifluoroacetamide (204 mg, 0.35 mmol) and LiOH using the hydrolysis conditions similar to those described in (Example 11, Step E) to generate the desired product in 97% yield (164 mg, 0.34 mmol). $^1$H NMR (400 MHz, $d_6$-DMSO): δ 9.53 (s, 1H), 8.80 (d, J=6.9 Hz, 1H), 8.52 (d, J=9.2 Hz, 1H), 8.27 (d, J=5.3 Hz, 1H), 7.53 (s, 1H), 7.46 (t, J=7.9 Hz, 1H), 7.29 (d, J=9.1 Hz, 1H), 7.07-7.18 (m, 3H), 7.02 (dd, J=8.8, 2.0 Hz, 1H), 6.70-6.72 (m, 1H), 6.54 (dd, J=8.1, 2.4 Hz, 1H), 6.50 (d, J=5.3 Hz, 1H), 5.31 (s, 2H), 4.02 (t, J=5.9 Hz, 2H), 2.61 (t, J=5.9 Hz, 2H), 2.22 (s, 6H). ES-LC/MS m/z=484 [M+H]$^+$.

Step C: N-[5-(3-{2-[(3-{[2-(dimethylamino)ethyl]oxy}phenyl)amino]-4-pyrimidinyl}pyrazolo[1,5-a]pyridin-2-yl)-2-fluorophenyl]-2,6-difluorobenzamide (title compound)

The title compound was obtained by treatment 4-[2-(3-amino-4-fluorophenyl)pyrazolo[1,5-a]pyridin-3-yl]-N-(3-{[2-(dimethylamino)ethyl]oxy}-phenyl)-2-pyrimidinamine (82 mg, 0.17 mmol) with 2,6-difluorobenzoyl chloride (22 μL, 0.18 mmol) and triethylamine (35 mL, 0.26 mmol) in THF (3 mL), using conditions described in Example 11, Step F. MS (ESI) m/z=624 [M+H]+.

Example 183

2,6-Difluoro-N-(3-{3-[2-({3-[(methylamino)methyl]phenyl}amino)-4-pyrimidinyl]pyrazolo[1,5-a]pyridin-2-yl}phenyl)benzamide

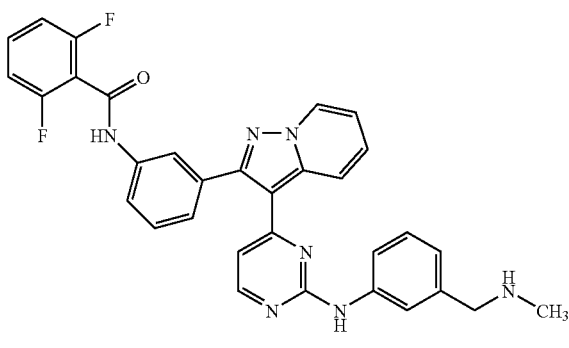

212

Step A: 2,2,2-Trifluoro-N-methyl-N-[(3-nitrophenyl)methyl]acetamide

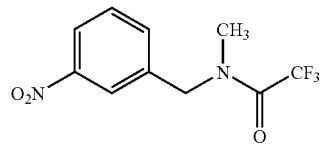

To a suspension of a 60% dispersion of sodium hydride in mineral oil (96 mg, 2.4 mmol) in dry tetrahydrofuran (5 mL), cooled to 0° C., was added a solution of 2,2,2-trifluoro-N-[(3-nitrophenyl)methyl]acetamide (500 mg, 2.0 mmol) in 5 mL dry teterahydrofuran. After stirring for 1 hour at 0° C., methyl iodide (132 μL, 2.2 mmol) was added in one portion. The reaction was stirred for 1 hour at 0° C., and warmed to rt overnight. After 16 h, the reaction mixture was concentrated, and the residue was partitioned between saturated aqueous NaHCO$_3$ and EtOAc. The organic layer was dried over Na$_2$SO$_4$, filtered, adsorbed onto silica, and purified by column chromatography to yield the desired compound (0.36 g, 1.4 mmol, 69% yield). $^1$H NMR (400 MHz, CDCl$_3$): δ 8.13-8.22 (m, 2H), 7.56-7.64 (m, 2H), 4.74 (s, 2H), 3.14 (s, 3H). MS (ESI) m/z=263 [M+H]$^+$.

Step B: N-[(3-aminophenyl)methyl]-2,2,2-trifluoro-N-methylacetamide

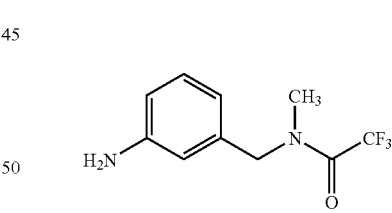

To a solution of 2,2,2-trifluoro-N-methyl-N-[(3-nitrophenyl)methyl]acetamide (0.36 g, 1.4 mmol) in 2-propanol (25 mL) was added 10% Pd/C (30 mg). The reaction was stirred at rt under a hydrogen atmosphere (1 atm) for 15 hours. The reaction mixture was filtered through Celite, adsorbed to silica, and purified by column chromatography to yield the title compound (0.23 g, 1.0 mmol, 71% yield). $^1$H NMR (400 MHz, CDCl$_3$): δ 7.11-7.17 (m, 1H), 6.49-6.63 (m, 3H), 4.53 (s, 2H), 3.71 (bs, 2H), 3.04 (s, 3H). MS (ESI) m/z=233 [M+H]$^+$.

Step C: 2,6-Difluoro-N-[3-(3-{2-[(3-{[methyl(trifluoroacetyl)amino]methyl}-phenyl)amino]-4-pyrimidinyl}pyrazol[1,5-a]pyridin-2-yl)phenyl]benzamide

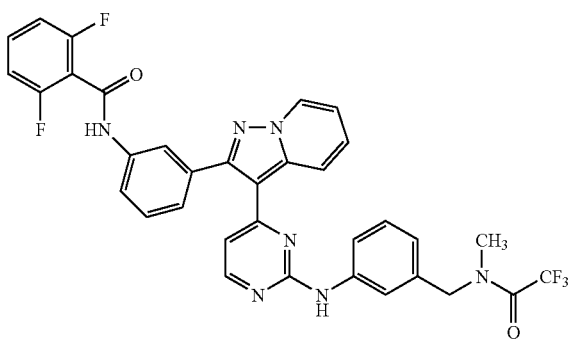

To a suspension of N-{3-[3-(2-chloro-4-pyrimidinyl)pyrazolo[1,5-a]pyridin-2-yl]phenyl}-2,6-difluorobenzamide (75 mg, 0.16 mmol) (prepared according to a procedure similar to that described in Example 27, Step C) and N-[(3-aminophenyl)methyl]-2,2,2-trifluoro-N-methylacetamide (47 mg, 0.20 mmol) in 2-propanol (3 mL) was added 2 drops of concentrated HCl. The mixture was heated to 180° C. in a microwave for 15 min. The reaction mixture was diluted with 25 mL DCM and washed with saturated aqueous NaHCO$_3$. The organic layer was dried over MgSO$_4$, filtered, and purified by flash chromatography to give the title compound (70 mg, 67% yield). MS (ESI) m/z=658 [M+H]$^+$.

Step D: 2,6-Difluoro-N-(3-{3-[2-({3-[(methylamino)methyl]phenyl}amino)-4-pyrimidinyl]pyrazolo[1,5-a]pyridin-2-yl}phenyl)benzamide (title compound)

To a solution of 2,6-difluoro-N-[3-(3-{2-[(3-{[methyl(trifluoroacetyl)amino]-methyl}phenyl)amino]-4-pyrimidinyl}pyrazolo[1,5-a]pyridin-2-yl)phenyl]benzamide (70 mg, 0.11 mmol) in THF (3 mL) and water (0.5 mL) was added LiOH.H$_2$O (10 mg, 0.21 mmol). The solution was stirred at 50° C. for two h, then diluted with 25 mL DCM and washed with 1 M aqueous Na$_2$CO$_3$. The aqueous layer was extracted with DCM, and the combined organic layers were dried over Na$_2$SO$_4$, filtered, and concentrated. The crude product was purified by flash chromatography to generate 26 mg of the title compound as a yellow solid (0.05 mmol, 42% yield). $^1$H NMR (400 MHz, d$_6$-DMSO): δ 10.95 (s, 1H), 9.52 (s, 1H), 8.86 (d, J=7.0 Hz, 1H), 8.52 (d, J=8.8 Hz, 1H), 8.27 (d, J=5.1 Hz, 1H), 8.02 (s, 1H), 7.83 (d, J=8.2 Hz, 1H), 7.73 (s, 1H), 7.46-7.62 (m, 4H), 7.36 (d, J=7.5 Hz, 1H), 7.12-7.28 (m, 4H), 6.92 (d, J=7.3 Hz, 1H), 6.53 (d, J=5.3 Hz, 1H), 3.59 (s, 2H), 2.26 (s, 3H). MS (ESI) m/z=562 [M+H]$^+$.

Example 184

N-{3-[3-(2-{[3-(Aminomethyl)phenyl]amino}-4-pyrimidinyl)pyrazolo[1,5-a]pyridin-2-yl]phenyl}-2,5-difluorobenzamide

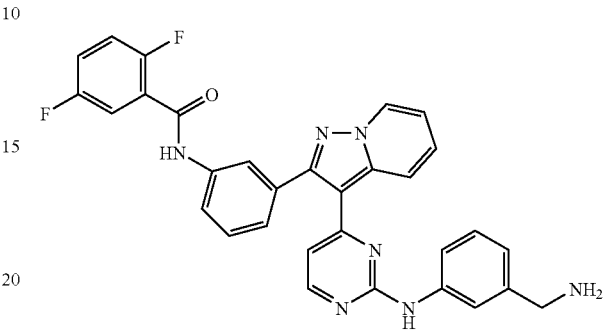

Step A: 2,5-Difluoro-N-[3-(3-{2-[(3-{[(trifluoroacetyl)amino]methyl}phenyl)amino]-4-pyrimidinyl}pyrazolo[1,5-a]pyridin-2-yl)phenyl]benzamide

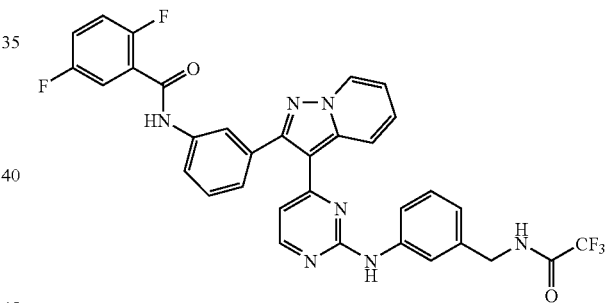

To a suspension of N-{3-[3-(2-chloro-4-pyrimidinyl)pyrazolo[1,5-a]pyridin-2-yl]phenyl}-2,5-difluorobenzamide (100 mg, 0.22 mmol) (prepared according to a procedure similar to that described in Example 43, Step A) and N-[(3-aminophenyl)methyl]-2,2,2-trifluoroacetamide (59 mg, 0.27 mmol) (prepared as described in Example 180) in 2-propanol (3 mL) was added 2 drops of concentrated HCl. The mixture was heated to 180° C. in a microwave for 15 min. The reaction mixture was diluted with 25 mL EtOAc and washed with saturated aqueous NaHCO$_3$. The organic layer was dried over MgSO$_4$, filtered, and purified by flash chromatography to give the title compound (90 mg, 64% yield). $^1$H NMR (400 MHz, d$_6$-DMSO): δ 10.64 (s, 1H), 9.99 (t, J=5.7 Hz, 1H), 9.63 (s, 1H), 8.85 (d, J=7.0 Hz, 1H), 8.53 (d, J=8.8 Hz, 1H), 8.27 (d, J=5.3 Hz, 1H), 8.04 (s, 1H), 7.86 (d, J=8.1 Hz, 1H), 7.71 (s, 1H), 7.67 (d, J=8.3 Hz, 1H), 7.42-7.55 (m, 5H), 7.35 (d, J=7.5 Hz, 1H), 7.24 (t, J=7.9 Hz, 1H), 7.14 (t, J=6.8 Hz, 4H), 6.85 (d, J=7.3 Hz, 1H), 6.54 (d, J=5.1 Hz, 1H), 4.35 (d, J=5.8 Hz, 2H). MS (ESI) m/z=645 [M+H]$^+$.

Step B: N-{3-[3-(2-{[3-(Aminomethyl)phenyl]amino}-4-pyrimidinyl)pyrazolo[1,5-a]pyridin-2-yl]phenyl}-2,5-difluorobenzamide (title compound)

To a solution of 2,5-difluoro-N-[3-(3-{2-[(3-{[(trifluoro-acetyl)amino]methyl}phenyl)-amino]-4-pyrimidinyl}pyrazolo[1,5-a]pyridin-2-yl)phenyl]benzamide (90 mg, 0.14 mmol) in THF (3 mL) and water (0.5 mL) was added LiOH.H$_2$O (12 mg, 0.28 mmol). The solution was stirred at 50° C. for 2 h, then diluted with 25 mL EtOAc and washed with 1 M aqueous Na$_2$CO$_3$. The aqueous layer was extracted with EtOAc, and the combined organic layers were dried over Na$_2$SO$_4$, filtered, and concentrated. The crude product was purified by flash chromatography to generate 42 mg of the title compound as a yellow solid (0.08 mmol, 55% yield). $^1$H NMR (400 MHz, d$_6$-DMSO): δ 10.66 (s, 1H), 9.55 (s, 1H), 8.85 (d, J=7.0 Hz, 1H), 8.54 (d, J=8.8 Hz, 1H), 8.27 (d, J=5.1 Hz, 1H), 8.05 (s, 1H), 7.87 (d, J=7.7 Hz, 1H), 7.77 (s, 1H), 7.35-7.59 (m, 7H), 7.11-7.23 (m, 2H), 6.97 (d, J=7.5 Hz, 1H), 6.51 (d, J=4.9 Hz, 1H), 3.72 (s, 2H). MS (ESI) m/z=548 [M+H]$^+$.

Example 185

N-{3-[3-(2-{[3-({[2-(Dimethylamino)ethyl]amino}methyl)phenyl]-amino}-4-pyrimidinyl)pyrazolo[1,5-a]pyridin-2-yl]phenyl}-2,6-difluorobenzamide

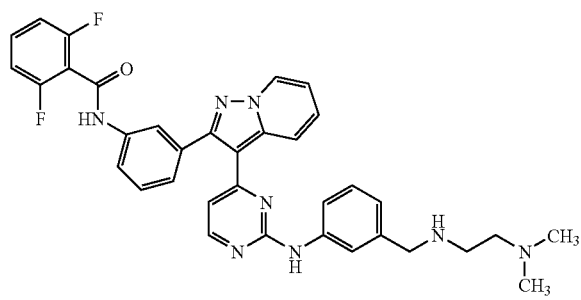

Step A: N-[2-(Dimethylamino)ethyl]-2,2,2-trifluoro-N-[(3-nitrophenyl)methyl]acetamide

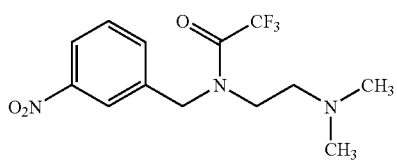

A solution of 3-nitrobenzaldehyde (127 mg, 0.84 mmol), N,N-dimethylethylenediamine (184 μL, 1.7 mmol), and acetic acid (5 drops) in DCM (10 mL) was stirred for 6 h at rt and 1 h at 40° C. The solution was cooled to 0° C., sodium triacetoxyborohydride (360 mg, 1.7 mmol) was added in one portion, and the reaction was stirred overnight at rt. After 16 h, the reaction was extracted with 4 N NaOH, dried over Na$_2$SO$_4$, filtered, and concentrated. The crude product was redissolved in DCM (10 mL), and TEA (167 μL, 1.2 mmol) and TFAA (135 μL, 0.96 mmol) were added. After 3 h at rt, the reaction mixture was diluted with DCM, washed with 2 N NaOH, dried over Na$_2$SO$_4$, filtered, and adsorbed onto silica. The crude product was purified by column chromatography to generate the title compound in 76% yield over two step (204 mg, 0.64 mmol). $^1$H NMR (400 MHz, CDCl$_3$): δ 8.18 (s, 1H), 8.12 (d, J=8.2 Hz, 1H), 7.74 (d, J=7.5 Hz, 1H), 7.52 (t, J=7.9 Hz, 1H), 3.95 (s, 2H), 3.13 (t, J=6.0 Hz, 2H), 3.00 (t, J=6.0 Hz, 2H), 2.78 (s, 6H). MS (ESI) m/z=320 [M+H]$^+$.

Step B: N-[(3-Aminophenyl)methyl]-N-[2-(dimethylamino)ethyl]-2,2,2-trifluoroacetamide

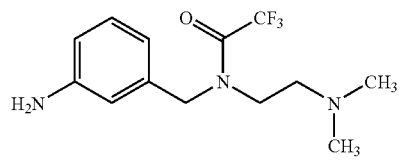

To a solution of N-[2-(dimethylamino)ethyl]-2,2,2-trifluoro-N-[(3-nitrophenyl)methyl]acetamide (204 mg, 0.64 mmol) in 2-propanol (15 mL) was added 10% palladium on carbon (20 mg). The reaction was stirred at rt under a hydrogen atmosphere (1 atm) for 17 h. The reaction mixture was filtered through Celite, adsorbed to silica, and purified by column chromatography to generate the title compound in 62% yield (115 mg, 0.40 mmol). $^1$H NMR (400 MHz, CDCl$_3$): δ 7.10 (t, J=7.6 Hz, 1H), 6.68-6.70 (m, 2H), 6.58 (d, J=7.9 Hz, 1H), 3.76 (s, 2H), 2.75 (t, J=6.0 Hz, 2H), 2.49 (t, J=6.0 Hz, 2H), 2.24 (s, 6H). MS (ESI) m/z=290 [M+H]$^+$.

Step C: N-{3-[3-(2-{[3-({[2-(Dimethylamino)ethyl]amino}methyl)phenyl]-amino}-4-pyrimidinyl)pyrazolo[1,5-a]pyridin-2-yl]phenyl}-2,6-difluorobenzamide (title compound)

To a suspension of N-{3-[3-(2-chloro-4-pyrimidinyl)pyrazolo[1,5-a]pyridin-2-yl]phenyl}-2,6-difluorobenzamide (75 mg, 0.16 mmol) (prepared according to a procedure similar to that described in Example 27, Step C) and N-[(3-aminophenyl)methyl]-N-[2-(dimethylamino)ethyl]-2,2,2-trifluoroacetamide (58 mg, 0.20 mmol) in 2-propanol (3 mL) was added 2 drops of concentrated HCl. The mixture was heated to 180° C. in a microwave for 25 min. The reaction mixture was diluted with 20 mL DCM and 5 mL MeOH, and washed with saturated aqueous NaHCO$_3$. The aqueous layer was extracted with DCM, and the combined organic layers were dried over Na$_2$SO$_4$, filtered, and purified by flash chromatography to give the title compound (24 mg, 24% yield). $^1$H NMR (400 MHz, d$_6$-DMSO): δ 10.94 (s, 1H), 9.52 (s, 1H), 8.85 (d, J=7.0 Hz, 1H), 8.51 (d, J=9.2 Hz, 1H), 8.27 (d, J=5.1 Hz, 1H), 8.02 (s, 1H), 7.83 (d, J=7.8 Hz, 1H), 7.74 (s, 1H), 7.46-7.60 (m, 4H), 7.36 (d, J=7.9 Hz, 1H), 7.26 (t, J=8.1 Hz, 2H), 7.12-7.21 (m, 2H), 6.92 (d, J=7.7 Hz, 1H), 6.53 (d, J=5.2 Hz, 1H), 3.66 (s, 2H), 2.54-2.57 (m, 2H), 2.27-2.33 (m, 2H), 2.08 (s, 6H). MS (ESI) m/z=620 [M+H]$^+$.

Example 186

N-[3-(3-{2-[(3-chloro-4-{[2-(dimethylamino)ethyl]oxy}phenyl)-amino]-4-pyrimidinyl}pyrazolo[1,5-a]pyridin-2-yl)phenyl]-2,6-difluoro-3-methylbenzamide-TFA

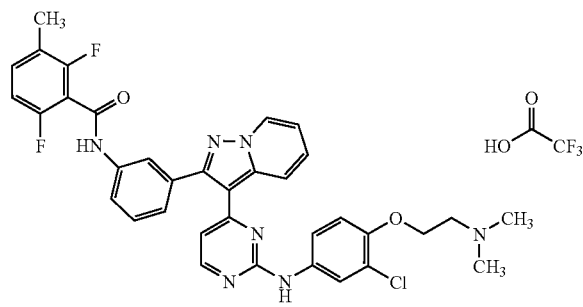

To a suspension of N-{3-[3-(2-chloro-4-pyrimidinyl)pyrazolo[1,5-a]pyridin-2-yl]phenyl}-2,6-difluoro-3-methylbenzamide (100 mg, 0.21 mmol) (this may be prepared by treating {3-[3-(2-chloro-4-pyrimidinyl)pyrazolo[1,5-a]pyridin-2-yl]phenyl}amine with 2,6-difluoro-3-methylbenzoyl chloride in a procedure similar to that described in Example 37) and {2-[(4-amino-2-chlorophenyl)oxy]ethyl}-dimethylammoniumchloride (75 mg, 0.26 mmol) (which may be prepared according to the procedure described in Example 128) in 2-propanol (3 mL) was added 2 drops of concentrated HCl. The reaction was heated at 80° C. for 22 h, and then heated at 180° C. in a microwave for 20 min. The reaction mixture was diluted with 25 mL DCM, washed with saturated aqueous NaHCO$_3$, and adsorbed onto silica. The crude product was purified by flash chromatography and reversed-phase HPLC to generate, after lyophilization, the title compound as a TFA salt (57 mg, 41% yield). $^1$H NMR (400 MHz, d$_6$-DMSO): δ 10.90 (s, 1H), 9.63 (s, 1H), 8.87 (d, J=6.8 Hz, 1H), 8.46 (d, J=9.7 Hz, 1H), 8.29 (d, J=5.1 Hz, 1H), 8.03-8.05 (m, 2H), 7.79 (d, J=8.3 Hz, 1H), 7.59 (d, J=9.2 Hz, 1H), 7.46-7.51 (m, 3H), 7.35 (d, J=7.8 Hz, 1H), 7.13-7.17 (m, 3H), 6.57 (d, J=5.3 Hz, 1H), 4.34-4.36 (m, 2H), 3.54-3.58 (m, 2H), 2.94 (d, J=4.8 Hz, 6H), 2.26 (s, 3H). MS (ESI) m/z=654 [M+H]$^+$.

Example 187

2,5-Difluoro-N-{3-[3-(2-{[3-({[2-(methylsulfonyl)ethyl]amino}-methyl)phenyl]amino}-4-pyrimidinyl)pyrazolo[1,5-a]pyridin-2-yl]phenyl}benzamide

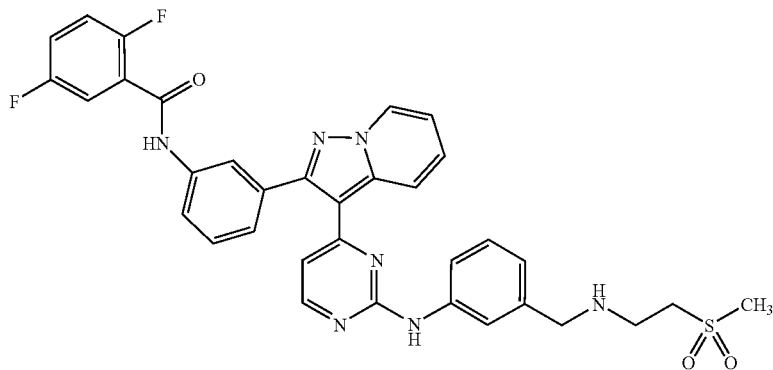

Step A: [2-(Methylsulfonyl)ethyl][(3-nitrophenyl)methyl]amine

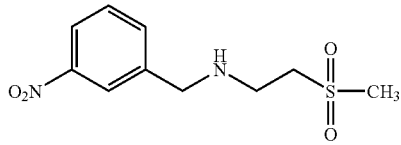

To a solution of 3-nitrobenzylamine (1.0 g, 5.3 mmol) in MeOH (10 mL) was added methylvinylsulfone (232 µL, 2.6 mmol). After 5 hours, the reaction mixture was absorbed onto silica and purified by column chromatography to yield the title compound (0.7 g, 2.7 mmol, 100% yield. $^1$H NMR (400 MHz, CDCl$_3$): δ 8.21 (s, 1H), 8.13 (d, J=8.2 Hz, 1H), 7.67 (d, J=7.5 Hz, 1H), 7.51 (t, J=7.9 Hz, 1H), 3.93 (s, 2H), 3.16-3.29 (m, 4H), 3.01 (s, 3H). MS (ESI) m/z=258 [M+H]$^+$.

Step B: 2,2,2-Trifluoro-N-[2-(methylsulfonyl)ethyl]-N-[(3-nitrophenyl)methyl]-acetamide

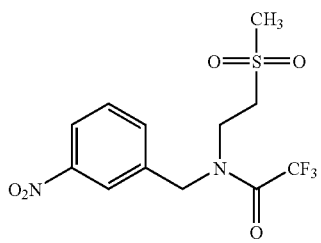

To a solution of [2-(methylsulfonyl)ethyl][(3-nitrophenyl)methyl]amine (0.70 g, 2.7 mmol) in DCM (25 mL) was added diisopropylethylamine (710 µL, 4.0 mmol) and TFAA (424 µL, 3.0 mmol). The reaction was stirred at rt for 1 h, then diluted with 25 mL DCM, washed with saturated aqueous NaHCO$_3$, dried over Na$_2$SO$_4$, filtered, and adsorbed onto silica. The crude product was purified by column chromatography to generate the title compound in 92% yield (0.88 g, 2.5 mmol). $^1$H NMR (400 MHz, CDCl$_3$): δ 8.11-8.25 (m, 2H), 7.58-7.63 (m, 2H), 4.91 (s, 2H), 3.78 (t, J=6.4 Hz, 2H), 3.36 (t, J=6.3 Hz, 2H), 2.99 (s, 3H). MS (ESI) m/z=355 [M+H]$^+$.

Step C: N-[(3-Aminophenyl)methyl]-2,2,2-trifluoro-N-[2-(methylsulfonyl)ethyl]-acetamide

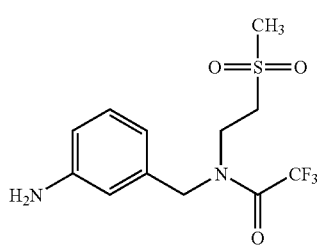

To a solution of 2,2,2-trifluoro-N-[2-(methylsulfonyl)ethyl]-N-[(3-nitrophenyl)methyl]acetamide (0.88 g, 2.5 mmol) in 2-propanol (75 mL) was added 10% Pd/C (80 mg). The reaction was stirred at rt under a hydrogen atmosphere (1 atm) for 72 h. The reaction mixture was filtered through Celite, adsorbed to silica, and purified by column chromatography to generate the title compound in 93% yield (0.75 g, 2.3 mmol). $^1$H NMR (400 MHz, CDCl$_3$): δ 7.17 (t, J=7.9 Hz, 1H), 6.66 (d, J=6.9 Hz, 1H), 6.61 (d, J=7.7 Hz, 1H), 6.53 (s, 1H), 4.62 (s, 2H), 3.72-3.77 (m, 4H), 3.18 (t, J=6.8 Hz, 2H), 3.01 (s, 3H). MS (ESI) m/z=324 [M+H]$^+$.

Step D: 2,5-Difluoro-N-[3-(3-{2-[(3-{[[2-(methylsulfonyl)ethyl](trifluoroacetyl)-amino]methyl}phenyl)amino]-4-pyrimidinyl}pyrazolo[1,5-a]pyridin-2-yl)phenyl]-benzamide

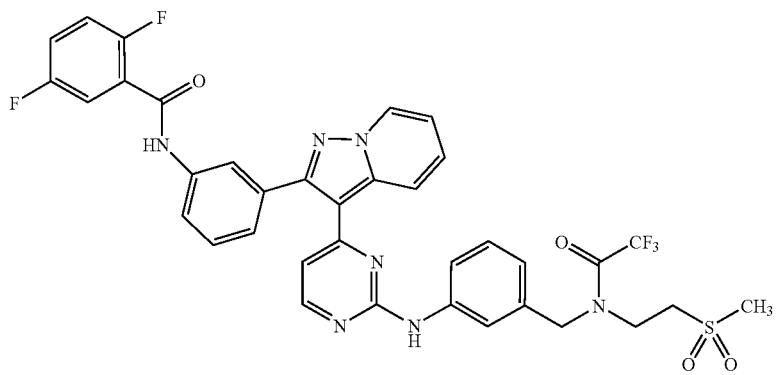

To a suspension of N-{3-[3-(2-chloro-4-pyrimidinyl)pyrazolo[1,5-a]pyridin-2-yl]phenyl}-2,5-difluorobenzamide (75 mg, 0.16 mmol) (prepared according to a procedure similar to Example 43, Step A) and N-[(3-aminophenyl)methyl]-2,2,2-trifluoro-N-[2-(methylsulfonyl)ethyl]acetamide (65 mg, 0.20 mmol) in 2-propanol (3 mL) was added 2 drops of concentrated HCl. The mixture was heated to 180° C. in a microwave apparatus for 15 min. The reaction mixture was diluted with 25 mL EtOAc and washed with saturated aqueous NaHCO$_3$. The organic layer was dried over MgSO$_4$, filtered, and purified by flash chromatography to give the title compound (104 mg, 87% yield). MS (ESI) m/z=750 [M+H]$^+$.

Step E: 2,5-Difluoro-N-{3-[3-(2-{[3-({[2-(methyl-sulfonyl)ethyl]amino}methyl)-phenyl]amino}-4-pyrimidinyl)pyrazolo[1,5-a]pyridin-2-yl]phenyl}benzamide (title compound)

To a solution of 2,5-difluoro-N-[3-(3-{2-[(3-{[[2-(methyl-sulfonyl)ethyl]-(trifluoroacetyl)amino]methyl}phenyl)amino]-4-pyrimidinyl}pyrazolo[1,5-a]pyridin-2-yl)phenyl]benzamide (104 mg, 0.14 mmol) in THF (3 mL), MeOH (0.5 mL), and water (0.5 mL) was added LiOH.H$_2$O (12 mg, 0.28 mmol). The solution was stirred at 50° C. for 4 h, then diluted with 25 mL EtOAc and washed with 1 M aqueous Na$_2$CO$_3$. The aqueous layer was extracted with EtOAc, and the combined organic layers were dried over Na$_2$SO$_4$, filtered, and concentrated. The crude product was purified by flash chromatography to generate 42 mg of the title compound as a yellow solid (67 mg, 73% yield). $^1$H NMR (400 MHz, d$_6$-DMSO): δ 10.65 (s, 1H), 9.55 (s, 1H), 8.85 (d, J=6.7 Hz, 1H), 8.54 (d, J=8.8 Hz, 1H), 8.26 (d, J=5.2 Hz, 1H), 8.04 (s, 1H), 7.87 (d, J=8.0 Hz, 1H), 7.76 (s, 1H), 7.60 (d, J=7.9 Hz, 1H), 7.42-7.55 (m, 5H), 7.36 (d, J=7.8 Hz, 1H), 7.20 (t, J=7.9 Hz, 1H), 7.14 (t, J=6.8 Hz, 1H), 6.93 (d, J=7.6 Hz, 1H), 6.51 (d, J=5.3 Hz, 1H), 3.67 (s, 2H), 3.23 (t, J=6.6 Hz, 2H), 3.01 (s, 3H), 2.91 (t, J=6.6 Hz, 2H). MS (ESI) m/z=654 [M+H]$^+$.

Example 188

2,6-Difluoro-N-{3-[3-(2-{[3-({[2-(methylsulfonyl)ethyl]amino}-methyl)phenyl]amino}-4-pyrimidinyl)pyrazolo[1,5-a]pyridin-2-yl]phenyl}benzamide

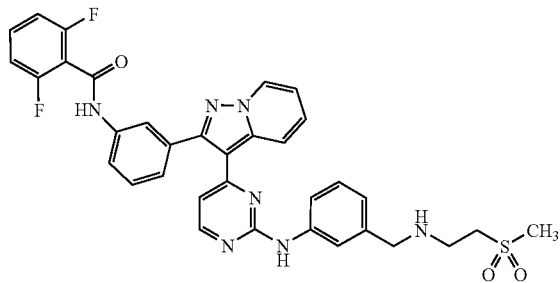

Step A: 2,6-Difluoro-N-[3-(3-{2-[(3-{[[2-(methyl-sulfonyl)ethyl](trifluoroacetyl)-amino]methyl}phenyl)amino]-4-pyrimidinyl}pyrazolo[1,5-a]pyridin-2-yl)phenyl]benzamide

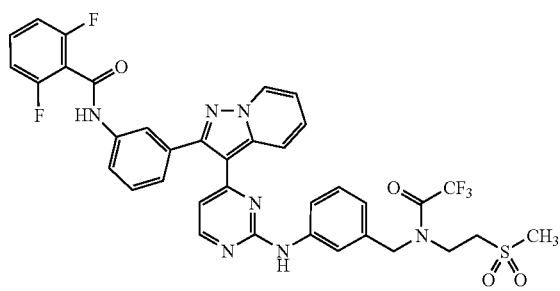

To a suspension of N-{3-[3-(2-chloro-4-pyrimidinyl)pyrazolo[1,5-a]pyridin-2-yl]phenyl}-2,6-difluorobenzamide (75 mg, 0.16 mmol) (prepared according to a procedure similar to that described in Example 27, Step C) and N-[(3-aminophenyl)methyl]-2,2,2-trifluoro-N-[2-(methylsulfonyl)ethyl]acetamide (65 mg, 0.20 mmol) (prepared according to the procedure described in Example 187) in 2-propanol (3 mL) was added 2 drops of concentrated HCl. The mixture was heated to 180° C. in a microwave for 15 min. The reaction mixture was diluted with 25 mL EtOAc and washed with saturated aqueous NaHCO$_3$. The organic layer was dried over MgSO$_4$, filtered, and purified by flash chromatography to give the title compound (102 mg, 87% yield). MS (ESI) m/z=750 [M+H]$^+$.

Step B: 2,6-Difluoro-N-{3-[3-(2-{[3-({[2-(methyl-sulfonyl)ethyl]amino}methyl)-phenyl]amino}-4-pyrimidinyl)pyrazolo[1,5-a]pyridin-2-yl]phenyl}benzamide (title compound)

To a solution of 2,6-difluoro-N-[3-(3-{2-[(3-{[[2-(methyl-sulfonyl)ethyl](trifluoro-acetyl)amino]methyl}phenyl)amino]-4-pyrimidinyl}pyrazolo[1,5-a]pyridin-2-yl)phenyl]benzamide (102 mg, 0.14 mmol) in THF (3 mL) and water (0.5 mL) was added LiOH.H$_2$O (12 mg, 0.28 mmol). The solution was stirred at 50° C. for 1 h, then diluted with 25 mL EtOAc and washed with 1 M aqueous Na$_2$CO$_3$. The aqueous layer was extracted with EtOAc, and the combined organic layers were dried over Na$_2$SO$_4$, filtered, and lyophilized to generate 42 mg of the title compound as a yellow powder (77 mg, 84% yield). $^1$H NMR (400 MHz, d$_6$-DMSO): δ 10.95 (s, 1H), 9.55 (s, 1H), 8.86 (d, J=6.6 Hz, 1H), 8.52 (d, J=8.2 Hz, 1H), 8.27 (d, J=5.0 Hz, 1H), 8.02 (s, 1H), 7.83 (d, J=7.9 Hz, 1H), 7.75 (s, 1H), 7.59 (d, J=7.3 Hz, 1H), 7.50 (bs, 2H), 7.37 (d, J=7.5 Hz, 1H), 7.27 (d, J=7.7 Hz, 1H), 7.22 (t, J=8.1 Hz, 1H), 7.13-7.18 (m, 4H), 6.93 (d, J=6.9 Hz, 1H), 6.53 (d, J=5.5 Hz, 1H), 3.67 (s, 2H), 3.23 (bs, 2H), 3.01 (s, 3H), 2.87-2.91 (m, 2H). MS (ESI) m/z=654 [M+H]$^+$.

Example 189

2,5-Difluoro-N-[3-(3-{2-[(2-methyl-1,2,3,4-tetrahydro-7-isoquinolinyl)amino]-4-pyrimidinyl}pyrazolo[1,5-a]pyridin-2-yl)phenyl]benzamide

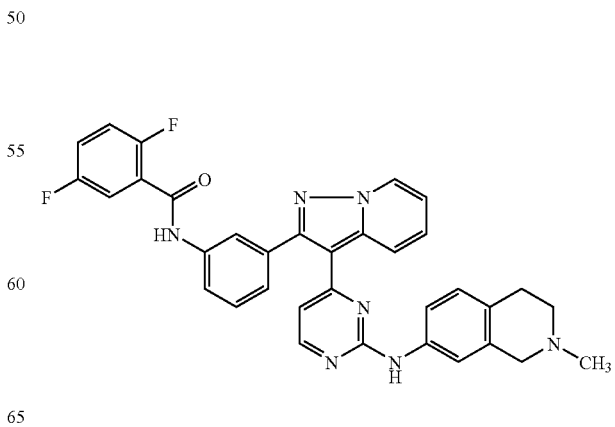

Step A: 2,2,2-Trifluoro-N-[3-(3-{2-[(2-methyl-1,2,3,4-tetrahydro-7-isoquinolinyl)amino]-4-pyrimidinyl}pyrazolo[1,5-a]pyridin-2-yl)phenyl]acetamide

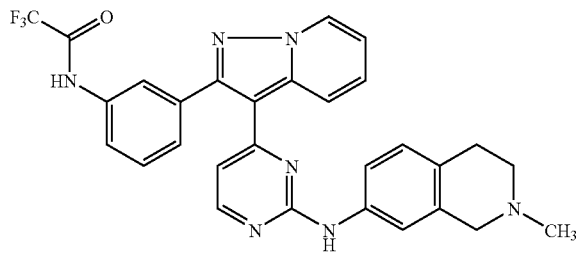

To a suspension of N-{3-[3-(2-chloro-4-pyrimidinyl)pyrazolo[1,5-a]pyridin-2-yl]phenyl}-2,2,2-trifluoroacetamide (310 mg, 0.74 mmol, which may be prepared according to Example 11, Step C) and 2-methyl-1,2,3,4-tetrahydro-7-isoquinolinamine (150 mg, 0.92 mmol) in 2-propanol (10 mL) was added 6 drops concentrated HCl. The reaction was stirred for 18 h at 80° C., then partitioned between saturated aqueous NaHCO$_3$ and 20% (v/v) MeOH in EtOAc. The aqueous layer was extracted with 20% (v/v) MeOH in EtOAc, and the combined organic layers were dried over Na$_2$SO$_4$, filtered, and adsorbed onto silica. The crude product was purified by column chromatography to generate the title compound in 72% yield (290 mg, 0.53 mmol). $^1$H NMR (400 MHz, d$_6$-DMSO) δ 11.39 (s, 1H), 9.45 (s, 1H), 8.85 (d, J=7.0 Hz, 1H), 8.44 (d, J=8.6 Hz, 1H), 8.27 (d, J=5.1 Hz, 1H), 8.02 (s, 1H), 7.83 (d, J=8.6 Hz, 1H), 7.44-7.55 (m, 4H), 7.38 (d, J=8.2 Hz, 1H), 7.14 (t, J=6.9 Hz, 1H), 6.97 (d, J=8.4 Hz, 1H), 6.50 (d, J=5.3 Hz, 1H), 3.39 (s, 2H), 2.75 (t, J=5.7 Hz, 2H), 2.59 (t, J=5.7 Hz, 2H), 2.32 (s, 3H). MS (ESI) m/z=544 [M+H]$^+$.

Step B: N-{4-[2-(3-Aminophenyl)pyrazolo[1,5-a]pyridin-3-yl]-2-pyrimidinyl}-2-methyl-1,2,3,4-tetrahydro-7-isoquinolinamine

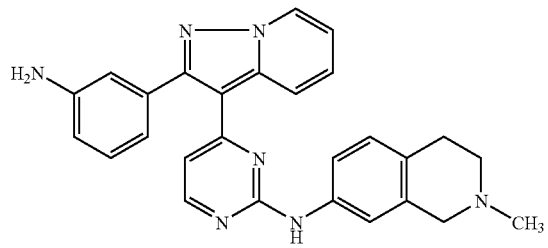

To a solution of 2,2,2-trifluoro-N-[3-(3-{2-[(2-methyl-1,2,3,4-tetrahydro-7-isoquinolinyl)amino]-4-pyrimidinyl}pyrazolo[1,5-a]pyridin-2-yl)phenyl]acetamide (290 mg, 0.53 mmol) in tetrahydrofuran (2 mL) and deionized water (2 mL) was added LiOH.H$_2$O (34 mg, 0.80 mmol). The reaction was heated to 50° C. for 3 h, and then diluted with 10 mL DCM. The aqueous layer was extracted with EtOAc, and the combined organic layers were dried over Na$_2$SO$_4$, filtered, and concentrated to generate the title compound in 92% yield (219 mg, 0.49 mmol). $^1$H NMR (400 MHz, d$_6$-DMSO) δ 9.41 (s, 1H), 8.79 (d, J=6.8 Hz, 1H), 8.52 (bd, 1H), 8.21 (d, J=5.3 Hz, 1H), 7.53 (s, 1H), 7.41-7.46 (m, 2H), 7.08-7.15 (m, 2H), 7.00 (d, J=8.2 Hz, 1H), 6.80 (s, 1H), 6.67 (t, J=7.7 Hz, 1H), 6.49 (d, J=5.3 Hz, 1H), 5.25 (s, 2H), 3.42 (s, 2H), 2.76 (t, J=5.7 Hz, 2H), 2.58 (t, J=5.7 Hz, 2H), 2.32 (s, 3H). MS (ESI) m/z=448 [M+H]$^+$.

Step C: 2,5-Difluoro-N-[3-(3-{2-[(2-methyl-1,2,3,4-tetrahydro-7-isoquinolinyl)amino]-4-pyrimidinyl}pyrazolo[1,5-a]pyridin-2-yl)phenyl]benzamide

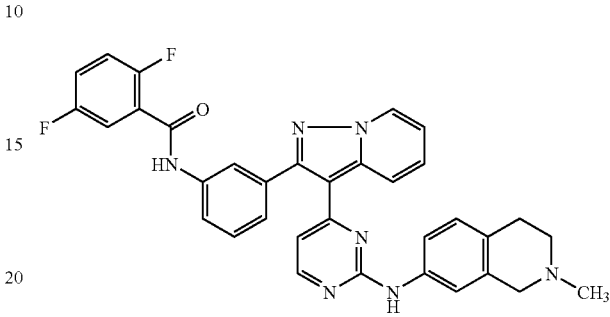

To a solution of N-{4-[2-(3-aminophenyl)pyrazolo[1,5-a]pyridin-3-yl]-2-pyrimidinyl}-2-methyl-1,2,3,4-tetrahydro-7-isoquinolinamine (96 mg, 0.21 mmol) and TEA (45 µL, 0.32 mmol) in DCM (2 mL) was added 2,5-difluorobenzoyl chloride (28 µL, 0.23 mmol). After 16 h at rt, the reaction mixture was adsorbed onto silica and purified by column chromatography to generate the title compound in 51% yield (63 mg, 0.11 mmol). $^1$H NMR (400 MHz, d$_6$-DMSO) δ 10.65 (s, 1H), 9.44 (s, 1H), 8.87 (d, J=6.9 Hz, 1H), 8.47 (d, J=9.3 Hz, 1H), 8.26 (d, J=5.7 Hz, 1H), 8.05 (s, 1H), 7.86 (d, J=8.4 Hz, 1H), 7.34-7.55 (m, 8H), 7.13 (t, J=6.9 Hz, 1H), 6.99 (d, J=8.4 Hz, 1H), 6.51 (d, J=5.3 Hz, 1H), 3.41 (s, 2H), 2.76 (t, J=5.7 Hz, 2H), 2.58-2.60 (m, 2H), 2.33 (s, 3H). HRMS=588.23178 (calculated for C$_{34}$H$_{27}$F$_2$N$_7$O=587.6313).

Example 190

N-[3-(3-{2-[(3-{[2-(Dimethylamino)ethyl]oxy}phenyl)amino]-4-pyrimidinyl}pyrazolo[1,5-a]pyridin-2-yl)phenyl]-2,6-difluoro-3-methylbenzamide

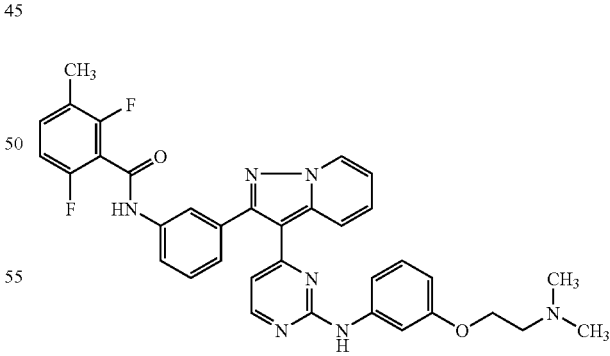

To a suspension of N-{3-[3-(2-chloro-4-pyrimidinyl)pyrazolo[1,5-a]pyridin-2-yl]phenyl}-2,6-difluoro-3-methylbenzamide (100 mg, 0.21 mmol) (prepared in a manner similar to that described in Example 186) and {2-[(3-aminophenyl)oxy]ethyl}dimethylamine (47 mg, 0.26 mmol) in 2-propanol (3 mL) was added 2 drops of concentrated HCl. The reaction was stirred at 80° C. overnight. After 16 h, the mixture was diluted with DCM, washed with saturated aqueous NaHCO$_3$, dried over Na₂SO₄, filtered, and adsorbed onto silica. The crude product was purified by column chromatography to generate the title compound in 86% yield (112 mg, 0.18 mmol). ¹H NMR (400 MHz, d₆-DMSO) δ 10.90 (s, 1H), 9.55 (s, 1H), 8.86 (d, J=6.7 Hz, 1H), 8.51 (d, J=8.6 Hz, 1H), 8.28 (d, J=5.2 Hz, 1H), 8.01 (s, 1H), 7.83 (d, J=7.9 Hz, 1H), 7.45-7.52 (m, 4H), 7.36 (d, J=7.3 Hz, 1H), 7.27 (d, J=8.1 Hz, 1H), 7.12-7.16 (m, 3H), 6.53 (d, J=5.1 Hz, 1H), 3.97 (t, J=5.6 Hz, 2H), 2.58 (t, J=5.8 Hz, 2H), 2.26 (s, 3H), 2.17 (s, 6H). MS (ESI) m/z=620 [M+H]+.

Example 191

2,6-Difluoro-N-{3-[3-{2-[(3-fluorophenyl)amino]-4-pyrimidinyl}-6-(trifluoromethyl)pyrazolo[1,5-a]pyridin-2-yl]phenyl}benzamide

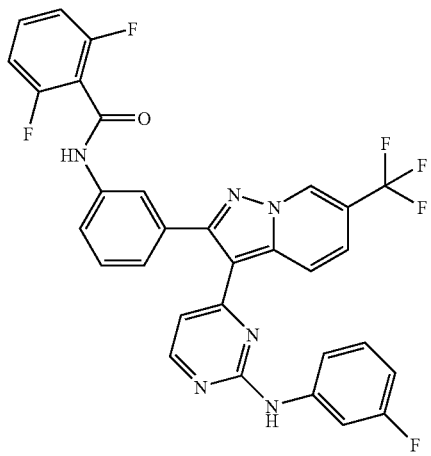

Step A: 1-(3-Bromophenyl)-2-[5-(trifluoromethyl)-2-pyridinyl]ethanone

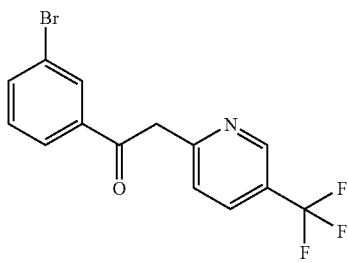

To NaH (4.4 g, 110 mmol) was added hexanes (2×100 mL) and then decanted. 1-(3-Bromophenyl)ethanone (10 g, 50 mmol) was then added to the washed NaH as a solution in THF (200 mL). 2-Chloro-5-trifluoromethylpyridine (8.3 g, 46 mmol) was then added and the reaction mixture stirred at 60° C. for 12 h. When TLC showed the reaction to be complete, the solution was diluted with EtOAc and brine. The layers were separated. The organic phase was washed with water and brine, dried over MgSO₄ and concentrated to an oil which was purified by silica gel chromatography (0-30% EtOAc/Hex) to give the title compound as an off-white solid (12 g, 69%). ESIMS (M+H)⁺=345.

Step B: (1Z)-1-(3-Bromophenyl)-2-[5-(trifluoromethyl)-2-pyridinyl]ethanone oxime

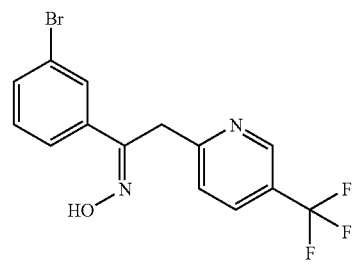

To a solution of 1-(3-bromophenyl)-2-[5-(trifluoromethyl)-2-pyridinyl]ethanone (10 g, 29 mmol) in MeOH (100 mL) was added 10% aqueous NaOH (50 mL). Hydroxylamine hydrochloride (10 g, 146 mmol) was added portionwise over 10 min and the mixture was then heated to reflux for 1 h. After cooling to rt and concentration by rotary evaporation, the solid was collected and dried on a vacuum line (1 torr) at 50° C. overnight to give the title compound (10.4 g, crude) which was used crude in the next reaction. ESIMS (M+H)⁺=360.

Step C: 2-[3-(3-Bromophenyl)-2H-azirin-2-yl]-5-(trifluoromethyl)pyridine

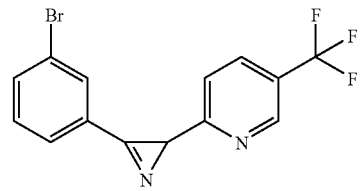

To a solution of (1Z)-1-(3-bromophenyl)-2-[5-(trifluoromethyl)-2-pyridinyl]ethanone oxime (10.4 g, 29 mmol) in DCM (100 mL) at 0° C. was added TEA (16 mL, 116 mmol). Trifluoroacetic anhydride (4.7 mL, 33 mmol) was then added dropwise over 15 min. The reaction mixture was allowed to warm to rt. After 1 h, water (100 mL) was added followed by saturated, aqueous NaHCO₃ until pH was 7.0. The organic layer was separated and dried (over MgSO₄) followed by addition of SiO₂ and concentration in vacuuo. The mixture, adsorbed on silica gel, was purified by column chromatography (0-20% Ea/Hex) to provide the title compound (~8 g, 81%) as an orange semi-solid. ESIMS (M+H)⁺=342.

Step D: 2-(3-Bromophenyl)-6-(trifluoromethyl)pyrazolo[1,5-a]pyridine

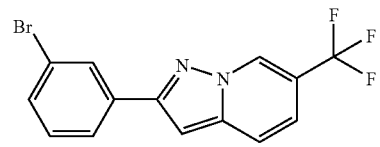

To a solution of 2-[3-(3-bromophenyl)-2H-azirin-2-yl]-5-(trifluoromethyl)pyridine (~8 g, 23 mmol) in dichloroethane (20 mL) was applied microwave irradiation (Personal Chemistry Optimizer, 175° C., 25 min). After cooling to rt, the solvent was removed in vacuuo and the material purified by silica gel column chromatography (0-15% EA/Hex) to provide the title compound (6.8 g, 86%) as an orange semi-solid. ESIMS (M+H)⁺=342.

Step E: 1-[2-(3-Bromophenyl)-6-(trifluoromethyl)pyrazolo[1,5-a]pyridin-3-yl]ethanone

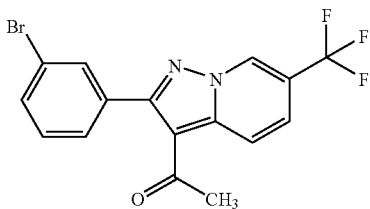

To a solution of 2-(3-bromophenyl)-6-(trifluoromethyl)pyrazolo[1,5-a]pyridine (3.4 g, 10 mmol) in acetic anhydride (10 mL, 100 mmol) was added 2 drops H₂SO₄ followed by heating at 10° C. for 3 h. The reaction was cooled to rt followed by the addition of ice (100 g), DCM (300 mL) and then solid NaOH until pH 7 was obtained. The organic layer was separated and dried (over MgSO₄) followed by addition of SiO₂ and concentration in vacuuo. The mixture, adsorbed on silica gel, was purified by column chromatography (0-20% Ea/Hex) to provide the title compound (2.2 g, 57%) as an orange solid. ESIMS (M+H)⁺=384.

Step F: (2E)-1-[2-(3-Bromophenyl)-6-(trifluoromethyl)pyrazolo[1,5-a]pyridin-3-yl]-3-(dimethylamino)-2-propen-1-one

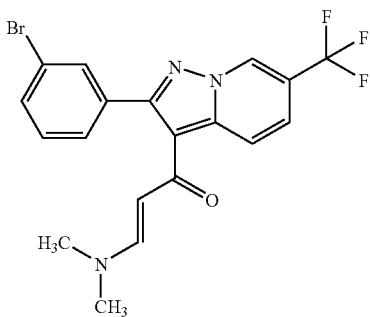

To a solution of 1-[2-(3-bromophenyl)-6-(trifluoromethyl)pyrazolo[1,5-a]pyridin-3-yl]ethanone (500 mg, 1.3 mmol) in DMF (5 mL) was added dimethylformamide di-t-butylacetal (0.5 mL, 2 mmol) followed by heating at 100° C. for 30 min. The reaction was cooled to rt followed by concentration in vacuuo to provide the title compound (500 mg, 88%) as an brown solid. ESIMS (M+H)⁺=439.

Step G: 4-[2-(3-Bromophenyl)-6-(trifluoromethyl)pyrazolo[1,5-a]pyridin-3-yl]-N-(3-fluorophenyl)-2-pyrimidinamine

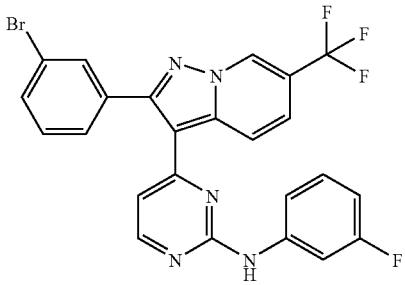

To a solution of (2E)-1-[2-(3-bromophenyl)-6-(trifluoromethyl)pyrazolo[1,5-a]pyridin-3-yl]-3-(dimethylamino)-2-propen-1-one (370 mg, 0.84 mmol) in dioxane (4 mL) was added N-(3-fluorophenyl)guanidine (278 mg, 1.3 mmol), TEA (0.58 mL, 4.2 mmol), and K₂CO₃ (115 mg, 0.84 mmol). The reaction mixture was then subjected to microwave irradiation (Personal Chemistry Optimizer, 160° C., 2 pulses of 15 min each). The reaction was cooled to rt followed by addition of saturated aqueous NaHCO₃ (20 mL) and EtOAc (40 mL). The organic layer was separated, dried (over MgSO₄) and concentrated in vacuuo to provide crude material which was re-submitted to conditions described above. After an additional 30 min in the microwave, the reaction was cooled and partitioned in EtOAc and water. The organic layer was separated, dried (over MgSO₄) and concentrated. The crude material was purified by silica gel column chromatography (20-50% EA/Hex) to provide the title compound (250 mg, 56%) as a beige solid. ESIMS (M+H)⁺=529.

Step H: 2,6-Difluoro-N-{3-[3-{2-[(3-fluorophenyl)amino]-4-pyrimidinyl}-6-(trifluoromethyl)pyrazolo[1,5-a]pyridin-2-yl]phenyl}benzamide (title compound)

To a solution of 4-[2-(3-bromophenyl)-6-(trifluoromethyl)pyrazolo[1,5-a]pyridin-3-yl]-N-(3-fluorophenyl)-2-pyrimidinamine (125 mg, 0.24 mmol) in dioxane (10 mL) was added Pd₂dba₃ (7 mg, 0.007 mmol), Cs₂CO₃ (94 mg, 0.34 mmol), Xantphos (7 mg, 0.011 mmol), and 2,6-difluorobenzamide (44 mg, 0.28 mmol). The reaction mixture was then subjected to microwave irradiation (Personal Chemistry Optimizer, 170° C., 15 min). The reaction was then cooled and the mixture partitioned in EtOAc (100 mL) and water (25 mL). The organic layer was separated, dried (over MgSO₄) and concentrated. The crude material was purified by silica gel column chromatography (20-50% EA/Hex) to provide the title compound (43 mg, 30%) as an beige solid. ¹H NMR (400 MHz, d₆-DMSO): δ 10.95 (s, 1H), 9.88 (s, 1H), 9.54 (s, 1H), 8.54 (d, J=9.3 Hz, 1H), 8.38 (d, J=5.3 Hz, 1H), 8.07 (s, 1H), 7.80 (d, J=8.8 Hz, 1H), 7.71 (m, 2H), 7.59 (m, 1H), 7.49 (t, J=8.0 Hz, 1H), 7.43 (d, J=9.3 Hz, 1H), 7.35 (d, J=7.7 Hz, 1H), 7.25 (m, 3H), 6.71 (dt, J=2.3, 8.4 Hz, 1H), 6.65 (d, J=5.1 Hz, 1H) ppm. ESIMS (M+H)⁺=605.

Example 192

N-[5-{3-[2-({3-[(Dimethylamino)methyl]phenyl}amino)-4-pyrimidinyl]pyrazolo[1,5-a]pyridin-2-yl}-2-(methyloxy)phenyl]-2,6-difluorobenzamide

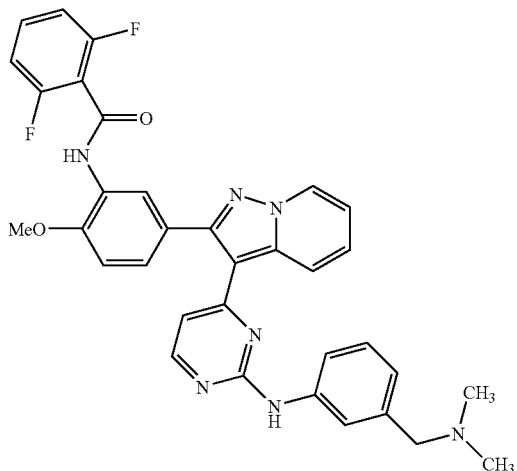

Step A: N-[5-Bromo-2-(methyloxy)phenyl]-2,2,2-trifluoroacetamide

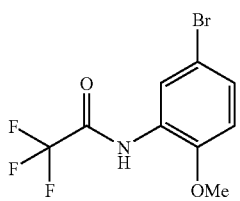

To a solution of 4-bromo-2-nitroanisole (2.0 g, 0.009 mol) in absolute EtOH (100 mL) was added $SnCl_2 \times 2H_2O$ (11.68 g, 0.051 mol) and the resulting mixture was allowed to stir overnight at rt. The solvent was removed under reduced pressure, residue suspended in EtOAc (100 mL), washed with 1M NaOH (100 mL), and filtered through a celite pad. The organic layer was removed, concentrated by rotary evaporation, and dried under high vacuum. The resulting residue was then dissolved in DCM (150 mL) followed by the addition of TEA (5.19 g, 0.051 mol) and trifluoroacetic anhydride (4.52 g, 0.022 mol). After overnight stirring, the reaction was washed with 1M HCl (50 mL), organic layer concentrated and purified by column chromatography (1-10% gradient of EtOAc in hexanes) to yield the title compound (1.53 g, 60%) as a white solid. ESIMS (M–H)–=297.

Step B: 2,2,2-Trifluoro-N-{2-(methyloxy)-5-[(trimethylsilyl)ethynyl]phenyl}-acetamide

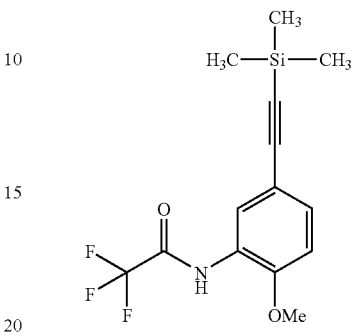

To an oven-dried flask under $N_2$ was added N-[5-bromo-2-(methyloxy)phenyl]-2,2,2-trifluoroacetamide (1.53 g, 0.005 mol), anhydrous degassed THF (100 mL), dichlorobis(triphenylphosphine)palladium(II) (0.45 g, 0.0006 mol), Cu(I)I (73 mg, 0.38 mmol), and trimethylsilylacetylene (1.26 g, 0.013 mol). Next, TEA (5.19 g, 0.05 mol) was added dropwise and the resulting mixture was heated at 60° C. overnight. The crude reaction mixture was adsorbed to silica gel and purified by column chromatography (0-10% EtOAc in hexanes) to afford the desired product (0.68 g, 42%) as an off white solid. ESIMS (M–H)–=314.

Step C: N-[5-Ethynyl-2-(methyloxy)phenyl]-2,2,2-trifluoroacetamide

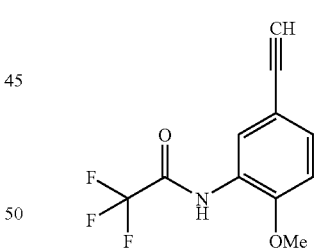

To a solution of 2,2,2-trifluoro-N-{2-(methyloxy)-5-[(trimethylsilyl)ethynyl]-phenyl}acetamide (680 mg, 2.16 mmol) in THF (50 mL) was added dropwise 1.0 M TBAF in THF (2.59 ml, 2.59 mmol) and the resulting mixture was stirred for 30 min at rt. The reaction was quenched with $H_2O$ (50 mL), concentrated under reduced pressure, and the aqueous layer was extracted with DCM (2×50 mL). The organic layers were combined, solvent removed under reduced pressure, and purified by column chromatography (5-25% EtOAc in hexanes) to give the title compound (500 mg, 96%) as an off white solid. $^1$H NMR (400 MHz, $CDCl_3$) δ 3.00 (s, 1H), 3.93 (s, 3H), 6.86 (d, 1H, J=8.42 Hz), 7.31 (dd, 1H, J=8.42 Hz, 2.01 Hz), 8.46 (d, 1H, J=2.01 Hz).

231

Step D: N-[5-[(2-Chloro-4-pyrimidinyl)ethynyl]-2-(methyloxy)phenyl]-2,2,2-trifluoroacetamide

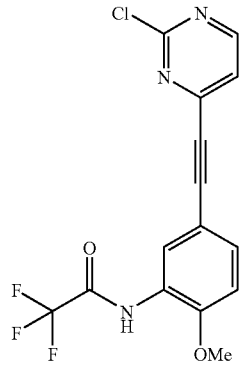

To an oven-dried flask under N₂ was added 2,4-dichloropyrimidine (860 mg, 5.76 mmol), anhydrous degassed THF (100 mL), dichlorobis(triphenylphosphine)palladium(II) (81 mg, 0.12 mmol), copper(I) iodide (13 mg, 0.07 mmol), and TEA (1.26 g, 0.013 mol). After heating the reaction at 60° C. for 30 min, N-[5-ethynyl-2-(methyloxy)phenyl]-2,2,2-trifluoroacetamide (560 mg, 2.30 mmol, obtained from composite batches) was added dropwise as a solution in THF (10 mL) and the resulting mixture was allowed to heat overnight at 60° C. The crude reaction mixture was adsorbed to silica gel and purified by column chromatography (0-10% EtOAc in hexanes) to afford the desired product (0.68 g, 42%) as an off white solid. ESIMS (M+H)+=356.

Step E: N-[5-[3-(2-Chloro-4-pyrimidinyl)pyrazolo[1,5-a]pyridin-2-yl]-2-(methyloxy)phenyl]-2,2,2-trifluoroacetamide

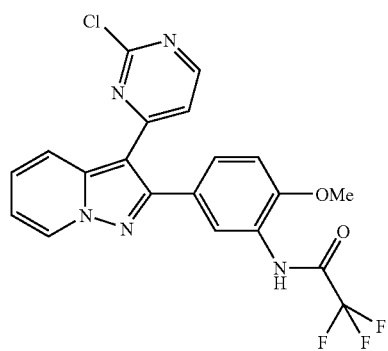

A solution of N-[5-[(2-chloro-4-pyrimidinyl)ethynyl]-2-(methyloxy)phenyl]-2,2,2-trifluoroacetamide (534 mg, 1.50 mmol), aminopyridinium iodide (670 mg, 3.01 mmol), and K₂CO₃ (620 mg, 4.51 mmol) in DMF (10 mL) was stirred at rt for 3 h followed by solvent removal. The residue was redissolved in DCM (50 mL) and washed with H₂O (50 mL). The organic layer was adsorbed to silica gel and purified by column chromatography (5-50% EtOAc in hexanes) to afford the pyrazolopyridine (370 mg, 55%) as a tan solid. ESIMS (M+H)+=448.

232

Step F: N-[5-[3-(2-Chloro-4-pyrimidinyl)pyrazolo[1,5-a]pyridin-2-yl]-2-(methyloxy)phenyl]-2,6-difluorobenzamide

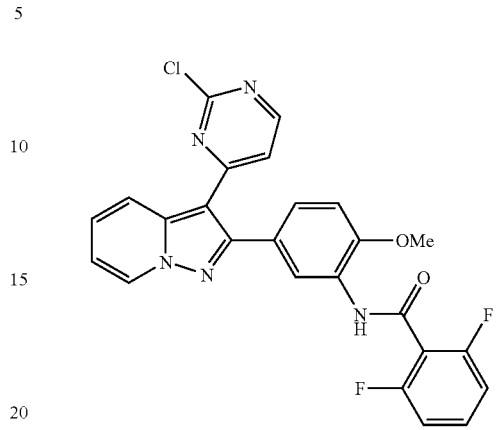

A solution of N-[5-[3-(2-chloro-4-pyrimidinyl)pyrazolo[1,5-a]pyridin-2-yl]-2-(methyloxy)phenyl]-2,2,2-trifluoroacetamide (370 mg, 0.83 mmol) and 1M LiOH (4.97 ml, 4.97 mmol) in 10:1 THF:H₂O (10 mL) was heated at 50° C. overnight. The reaction was washed with brine (25 mL), aqueous layer extracted with EtOAc (25 mL), organic layers combined, filtered through a cotton plug, and solvent removed by rotary evaporation. After high vacuum removal of residual solvent, the crude mixture was dissolved in THF (25 mL) and to this was added 2,6-difluorobenzoyl chloride (920 mg, 5.25 mmol). After stirring 3 h at rt, DMF (25 mL) was added to dissolve any suspended solids followed by the addition of excess polymer-bound trisamine resin. Upon overnight stirring, the amine resin was removed by vacuum filtration, rinsed with MeOH (50 mL), and filtrate concentrated under reduced pressure to afford the desired amide (410 mg, 79%) as an off-white solid. ESIMS (M+H)+=492.

Step G: N-[5-{3-[2-({3-[(dimethylamino)methyl]phenyl}amino)-4-pyrimidinyl]pyrazolo[1,5-a]pyridin-2-yl}-2-(methyloxy)phenyl]-2,6-difluorobenzamide (title compound)

To a solution of N-[5-[3-(2-chloro-4-pyrimidinyl)pyrazolo[1,5-a]pyridin-2-yl]-2-(methyloxy)phenyl]-2,6-difluorobenzamide (30 mg, 0.06 mmol) in 1,4-dioxane (6 mL) and 2-propanol (3 mL) was added 3-[(dimethylamino)methyl]aniline (27 mg, 0.18 mmol) followed by 4M HCl in dioxane (0.076 ml, 0.31 mmol). After heating overnight at 80° C., the reaction was quenched with saturated NaHCO₃ (25 mL), solvent removed by rotary evaporation, the aqueous layer extracted with DCM (25 mL), organic layer concentrated, and purified by column chromatography (5-50% EtOAc in hexanes) to provide the product (12.8 mg, 35%) as an off-white solid. ESIMS (M+H)+=606. $^1$H NMR (400 MHz, DMSO-d₆) δ 2.12 (s, 6H), 3.33 (bs, 2H), 3.86 (s, 3H), 6.57 (d, 1H, J=5.49 Hz), 6.85 (d, 1H, J=7.14 Hz), 7.07-7.10 (t, J=6.78 Hz, 1H), 7.15-7.19 (m, 4H), 7.35-7.38 (m, 1H), 7.41-7.45 (m, 1H), 7.50-7.54 (m, 1H), 7.63 (d, 1H, J=6.78 Hz), 7.69 (s, 1H), 8.23 (d, 1H, J=5.49 Hz), 8.32 (s, 1H), 8.49-8.50 (m, 1H), 8.80-8.82 (m, 1H), 9.50 (s, 1H), 10.19 (s, 1H).

Example 193

2,6-Difluoro-N-[3-[3-{5-fluoro-2-[(3-fluorophenyl)amino]-4-pyrimidinyl]-6-(trifluoromethyl)pyrazolo[1,5-a]pyridin-2-yl]phenyl}benzamide

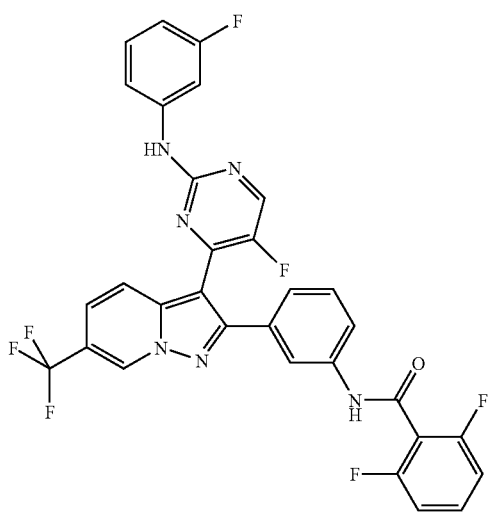

Step A: 2-Bromo-1-[2-(3-bromophenyl)-6-(trifluoromethyl)pyrazolo[1,5-a]pyridin-3-yl]ethanone

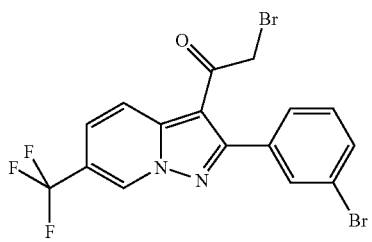

To a solution of 1-[2-(3-bromophenyl)-6-(trifluoromethyl)pyrazolo[1,5-a]pyridin-3-yl]ethanone (89 mg, 0.23 mmol) in glacial acetic acid was added bromine (15 mg, 0.30 mmol) in glacial acetic acid (0.5 mL). After overnight stirring, reaction was diluted with water, pH adjusted to 8 with saturated NaHCO₃, and extracted with EtOAc (25 mL). The organic layer was adsorbed to silica gel and purified by LC (2-10% EtOAc in hexanes) to afford the bromoketone (70 mg, 70%). ESIMS (M+H)+=460.

Step B: 1-[2-(3-Bromophenyl)-6-(trifluoromethyl)pyrazolo[1,5-a]pyridin-3-yl]-2-fluoroethanone

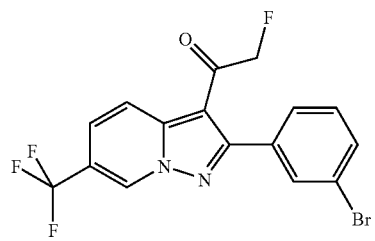

A solution of 2-bromo-1-[2-(3-bromophenyl)-6-(trifluoromethyl)pyrazolo[1,5-a]pyridin-3-yl]ethanone (300 mg, 0.65 mmol, obtained from composite batches), KF (190 mg, 3.27 mmol) in DMA (10 mL) was heated for 3 h at 80° C. Water (25 mL) was added and the aqueous layer was extracted with EtOAc (2×50 mL). The organic layers were combined and purified by LC (2-10% EtOAc in hexanes) to yield the desired product (130 mg, 42%) as a pale yellow glass. ESIMS (M+H)+=401.

Step C: (2Z)-1-[2-(3-Bromophenyl)-6-(trifluoromethyl)pyrazolo[1,5-a]pyridin-3-yl]-3-(dimethylamino)-2-fluoro-2-propen-1-one

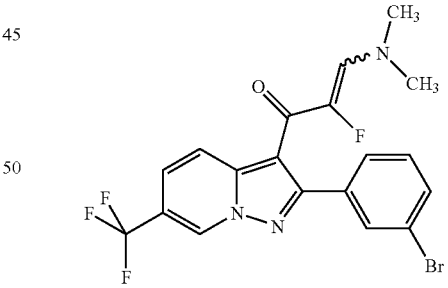

To a solution of 1-[2-(3-bromophenyl)-6-(trifluoromethyl)pyrazolo[1,5-a]pyridin-3-yl]-2-fluoroethanone (10 mg, 0.025 mmol) in DMF (2 mL) was added DMF di-tert-butyl acetal (0.85 g, 4.2 mmol) and the reaction was heated at 80° C. for 15 min. The crude reaction mixture was adsorbed to silica gel and purified by LC (5-50% EtOAc in hexanes) to give the title compound (10 mg, 88%). ESIMS (M+H)+=456.

235

Step D: 4-[2-(3-Bromophenyl)-6-(trifluoromethyl)pyrazolo[1,5-a]pyridin-3-yl]-5-fluoro-N-(3-fluorophenyl)-2-pyrimidinamine

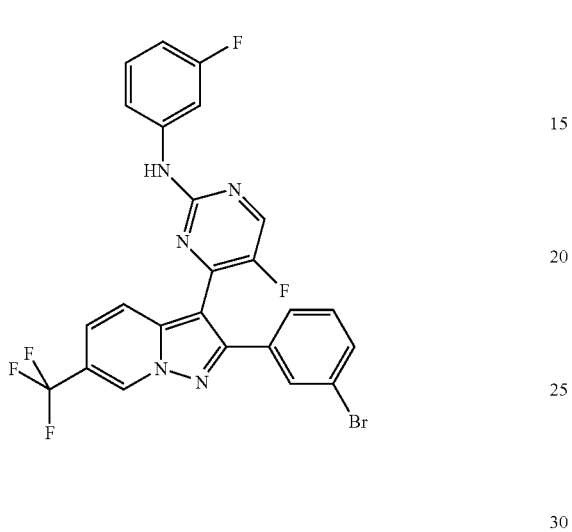

To a solution of (2Z)-1-[2-(3-bromophenyl)-6-(trifluoromethyl)pyrazolo[1,5-a]pyridin-3-yl]-3-(dimethylamino)-2-fluoro-2-propen-1-one (100 mg, 0.22 mmol, obtained from composite batches) in DMA (5 mL) was added the requisite guanidine HCl salt (141 mg, 0.65 mmol) and $K_2CO_3$ (152 mg, 1.10 mmol). After heating overnight at 130° C., the mixture was diluted with EtOAc (50 mL) and washed with water (25 mL). The organic layer was separated, concentrated under reduced pressure, and purified by LC (10-50% EtOAc in hexanes) to give the pyrimidine (60 mg, 60%). ESIMS (M+H)+=546.

Step E: 2,6-Difluoro-N-{3-[3-{5-fluoro-2-[(3-fluorophenyl)amino]-4-pyrimidinyl}-6-(trifluoromethyl)pyrazolo[1,5-a]pyridin-2-yl]phenyl}benzamide (title compound)

To an oven-dried flask under $N_2$ was added 4-[2-(3-bromophenyl)-6-(trifluoromethyl)pyrazolo[1,5-a]pyridin-3-yl]-5-fluoro-N-(3-fluorophenyl)-2-pyrimidinamine (40 mg, 0.08 mmol), anhydrous degassed 1,4-dioxane (10 mL), $Pd_2(dba)_3$ (13.4 mg, 0.01 mmol), Xantphos (12.7 mg, 0.02 mmol), 2,6-difluorobenzamide (34.5 mg, 0.2 mmol), and $Cs_2CO_3$ (83 mg, 0.26 mmol). The reaction was heated in the microwave at 160° C. for 15 min, adsorbed to silica gel, and purified by LC (DCM to 5% MeOH/DCM) to afford the desired product (30 mg, 66%) as a tan solid. $^1H$ NMR (400 MHz, DMSO-$d_6$) δ 6.63-6.67 (m, 1H), 7.10-7.25 (m, 4H), 7.29-7.34 (m, 2H), 7.39-7.47 (m, 1H), 7.53-7.59 (m, 1H), 7.68-7.70 (m, 2H), 8.04-8.10 (m, 2H), 8.60 (s, 1H), 9.57 (s, 1H), 9.97 (s, 1H), 10.87 (s, 1H); ESIMS (M+H)+=623.

236

Example 194

N-{3-[3-{2-[(3-{[2-(Dimethylamino)ethyl]oxy}phenyl)amino]-4-pyrimidinyl}-6-(trifluoromethyl)pyrazolo[1,5-a]pyridin-2-yl]phenyl}-2,6-difluorobenzamide

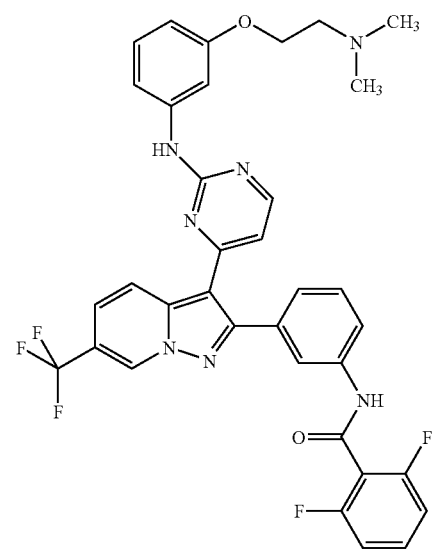

Step A: N-{3-[3-Acetyl-6-(trifluoromethyl)pyrazolo[1,5-a]pyridin-2-yl]phenyl}-2,6-difluorobenzamide

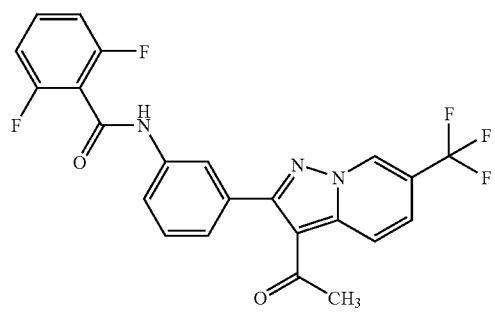

This intermediate may be prepared using procedures similar to that described in Example 191, Step E to afford a product which may be taken into the next step as a crude product.

Step B: N-{3-[3-[(2E)-3-(Dimethylamino)-2-propenoyl]-6-(trifluoromethyl)pyrazolo[1,5-a]pyridin-2-yl]phenyl}-2,6-difluorobenzamide

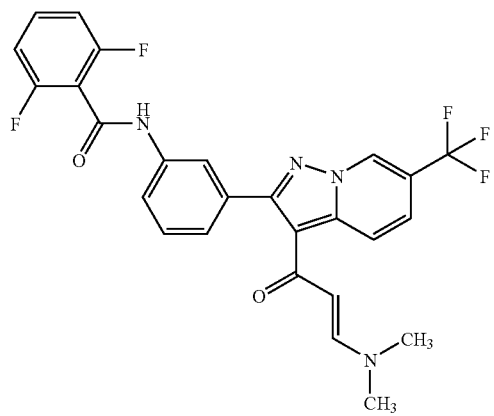

The title compound may be prepared by treating N-{3-[3-acetyl-6-(trifluoromethyl)pyrazolo[1,5-a]pyridin-2-yl]phenyl}-2,6-difluorobenzamide with dimethylformamide di-t-butylacetal followed by heating at 100° C. for 30 min. The reaction can then be cooled to rt followed by concentration in vacuuo to provide the title compound that can be used crude in the next reaction.

Step C: N-{3-[3-{2-[(3-{[2-(Dimethylamino)ethyl]oxy}phenyl)amino]-4-pyrimidinyl}-6-(trifluoromethyl)pyrazolo[1,5-a]pyridin-2-yl]phenyl}-2,6-difluorobenzamide (title compound)

The title compound may be prepared by treating N-{3-[3-[(2E)-3-(dimethylamino)-2-propenoyl]-6-(trifluoromethyl)pyrazolo[1,5-a]pyridin-2-yl]phenyl}-2,6-difluorobenzamide with N-(3-{[2-(dimethylamino)ethyl]oxy}phenyl)guanidine HCl (which in turn can be prepared by treatment of 3-{[2-(dimethylamino)ethyl]oxy}aniline with cyanamide in the presence of 12 M HCl using standard methods) to give the product. ESIMS (M+H)+=674.

Example 195

2,6-Difluoro-N-{3-[3-(2-{[3-({2-[methyl(2-propen-1-yl)amino]ethyl}oxy)phenyl]amino}-4-pyrimidinyl)pyrazolo[1,5-a]pyridin-2-yl]phenyl}benzamide

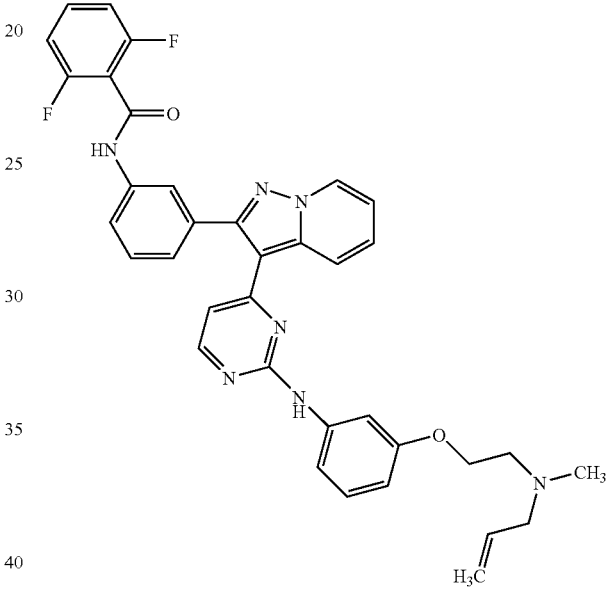

The title compound can be prepared from N-(3-{3-[2-({3-[(2-chloroethyl)oxy]phenyl}amino)-4-pyrimidinyl]pyrazolo[1,5-a]pyridin-2-yl}phenyl)-2,2,2-trifluoroacetamide (obtained according to the procedure described in Example 136, Step C) through a two step process consisting of treatment of N-(3-{3-[2-({3-[(2-chloroethyl)oxy]phenyl}amino)-4-pyrimidinyl]pyrazolo[1,5-a]pyridin-2-yl}phenyl)-2,2,2-trifluoroacetamide with N-methyl-2-propen-1-amine to give 4-[2-(3-aminophenyl)pyrazolo[1,5-a]pyridin-3-yl]-N-[3-({2-[methyl(2-propen-1-yl)amino]ethyl}oxy)phenyl]-2-pyrimidinamine, which in turn can be treated with 2,6-difluorobenzoyl chloride in THF and TEA to give the product as a solid. ES-LCMS m/z 632 (M+H).

Example 196

2,5-Difluoro-N-{3-[3-(2-{[3-({2-[methyl(2-propen-1-yl)amino]ethyl}oxy)phenyl]amino}-4-pyrimidinyl)pyrazolo[1,5-a]pyridin-2-yl]phenyl}benzamide

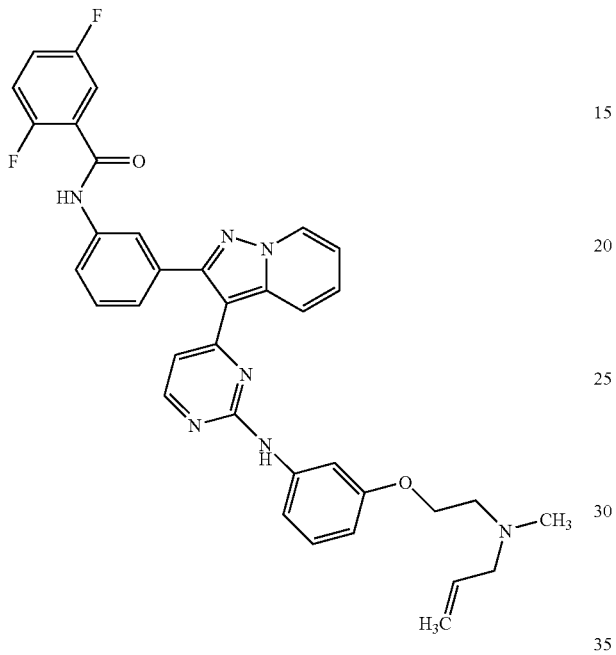

Step A: 4-[2-(3-Aminophenyl)pyrazolo[1,5-a]pyridin-3-yl]-N-[3-({2-[methyl(2-propen-1-yl)amino]ethyl}oxy)phenyl]-2-pyrimidinamine

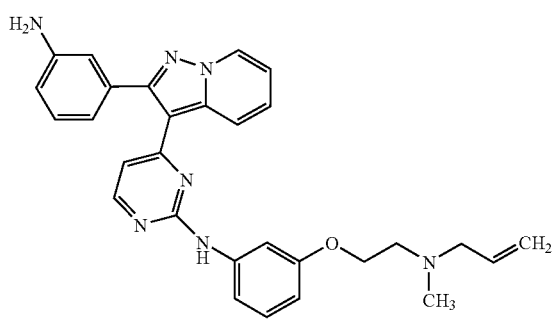

The title compound was obtained by treating N-(3-{3-[2-({3-[(2-chloroethyl)oxy]phenyl}amino)-4-pyrimidinyl]pyrazolo[1,5-a]pyridin-2-yl}phenyl)-2,2,2-trifluoroacetamide with N-methyl-2-propen-1-amine in a manner similar to Example 136 to give the product, ES-LCMS m/z 492 (M+H).

Step B: 2,5-Difluoro-N-{3-[3-(2-{[3-({2-[methyl(2-propen-1-yl)amino]ethyl}oxy)phenyl]amino}-4-pyrimidinyl)pyrazolo[1,5-a]pyridin-2-yl]phenyl}benzamide (title compound)

The title compound was obtained by treating 4-[2-(3-aminophenyl)pyrazolo[1,5-a]pyridin-3-yl]-N-[3-({2-[methyl(2-propen-1-yl)amino]ethyl}oxy)phenyl]-2-pyrimidinamine with 2-5 difluorobenzoyl chloride in a manner similar to Example 195 to give the product, $^1$H NMR (400 MHz, DMSO-D$_6$) δ ppm 2.2 (s, 3H), 2.7 (m, 2H), 3.0 (d, J=6.4 Hz, 2H), 4.0 (t, J=6.2 Hz, 2H), 5.1 (m, 2H), 5.8 (m, 1H), 6.5 (m, 2H), 7.1 (m, 2H), 7.3 (dd, J=8.0, 1.4 Hz, 1H), 7.4 (dd, J=8.0, 1.2 Hz, 1H), 7.4 (m, 2H), 7.5 (m, 4H), 7.9 (m, 1H), 8.0 (t, J=2.6 Hz, 1H), 8.3 (d, J=5.3 Hz, 1H), 8.5 (dd, J=8.9, 1.0 Hz, 1H), 8.8 (d, J=7.3 Hz, 1H), 9.5 (s, 1H) 10.6 (s, 1H). ES-LCMS m/z 632 (M+H).

Example 197

2,6-Difluoro-N-[3-(3-{2-[(3-oxo-3,4-dihydro-2H-1,4-benzoxazin-6-yl)amino]-4-pyrimidinyl}pyrazolo[1,5-a]pyridin-2-yl)phenyl]benzaide

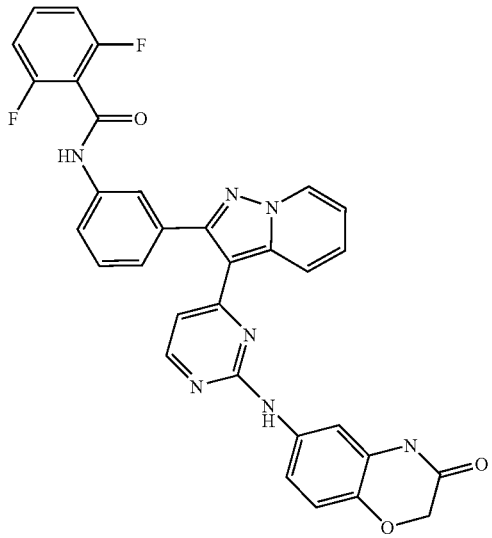

The title compound was prepared from N-{3-[3-(2-chloro-4-pyrimidinyl)pyrazolo[1,5-a]pyridin-2-yl]phenyl}-2,6-difluorobenzamide (prepared according to a procedure similar to Example 27, Step C) and 6-amino-2H-1,4-benzoxazin-3(4H)-one by heating in a microwave apparatus in a manner similar to Example 1, Step G to afford the product. ES-LCMS m/z 590 (M+H).

Example 198

N-[3-(3-{2-[(3-{[(3-(Dimethylamino)propyl]oxy}phenyl)amino]-4-pyrimidinyl}pyrazolo[1,5-a]pyridin-2-yl)phenyl]-2,6-difluorobenzamide

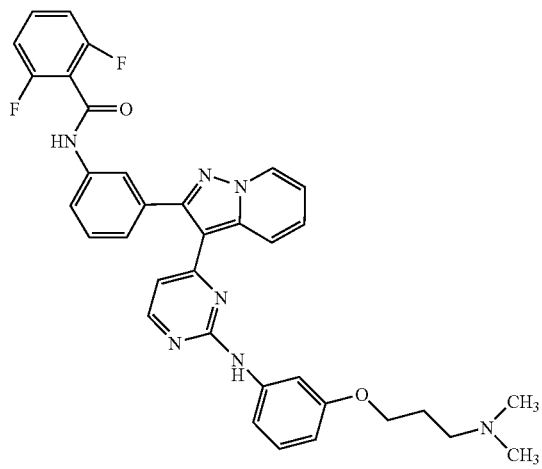

Step A: N-(3-{3-[2-({3-[(3-chloropropyl)oxy]phenyl}amino)-4-pyrimidinyl]pyrazolo[1,5-a]pyridin-2-yl}phenyl)-2,2,2-trifluoroacetamide

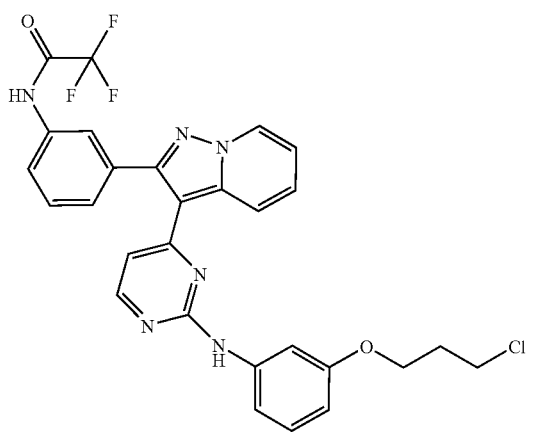

The title compound may be obtained by displacement of N-{3-[3-(2-chloro-4-pyrimidinyl)pyrazolo[1,5-a]pyridin-2-yl]phenyl}-2,2,2-trifluoroacetamide (which may be prepared according to Example 11, Step C) with 3-[(3-chloropropyl)oxy]aniline. The requisite aniline may in turn be prepared by heating a mixture of 3-nitrophenol, K₂CO₃ and 1-bromo-3-chloropropane in 2-butanone at 85° C. to afford the product. ES-LCMS m/z 567 (M+H).

Step B: 4-[2-(3-Aminophenyl)pyrazolo[1,5-a]pyridin-3-yl]-N-(3-{[3-(dimethylamino)propyl]oxy}phenyl)-2-pyrimidinamine

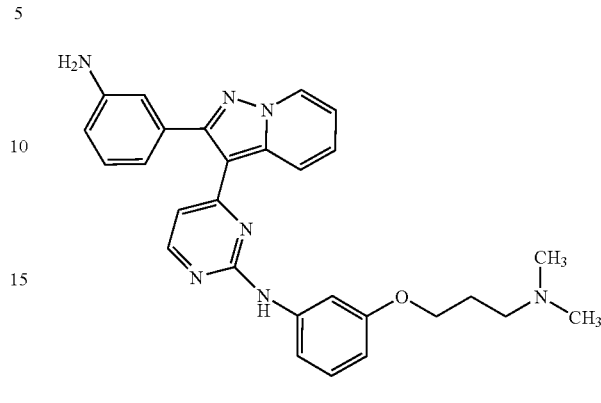

The title compound may be prepared by treating N-(3-{3-[2-({3-[(3-chloropropyl)oxy]phenyl}amino)-4-pyrimidinyl]pyrazolo[1,5-a]pyridin-2-yl}phenyl)-2,2,2-trifluoroacetamide with dimethylamine to give product.

Step C: N-[3-(3-{2-[(3-{[3-(dimethylamino)propyl]oxy}phenyl)amino]-4-pyrimidinyl}pyrazolo[1,5-a]pyridin-2-yl)phenyl]-2,6-difluorobenzamide (title compound)

The title compound may be prepared by treating 4-[2-(3-aminophenyl)pyrazolo[1,5-a]pyridin-3-yl]-N-(3-{[3-(dimethylamino)propyl]oxy}phenyl)-2-pyrimidinamine with 2,6-difluorobenzoyl chloride in a manner similar to Example 168, Step D to give the title compound.
ES-LCMS m/z 620 (M+H).

Example 199

2,6-Difluoro-N-[3-(3-{2-[(2-methyl-1,3-benzothiazol-5-yl)amino]-4-pyrimidinyl}pyrazolo[1,5-a]pyridin-2-yl)phenyl]benzamide

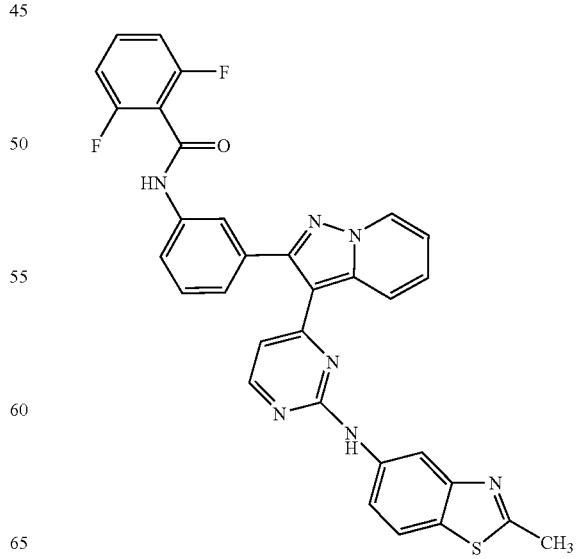

A mixture of N-{3-[3-(2-chloro-4-pyrimidinyl)pyrazolo[1,5-a]pyridin-2-yl]phenyl}-2,6-difluorobenzamide (which may be prepared according to a procedure similar to Example 27, Step C) and 2-methyl-1,3-benzothiazol-5-amine are heated in isopropanol with catalytic conc. HCl at approximately 85° C. to afford the product. ES-LCMS m/z 590 (M+H).

Example 200

2,6-Difluoro-N-[3-(3-{2-[(3-oxo-3,4-dihydro-2H-1,4-benzoxazin-7-yl)amino]-4-pyrimidinyl}pyrazolo[1,5-a]pyridin-2-yl)phenyl]benzamide

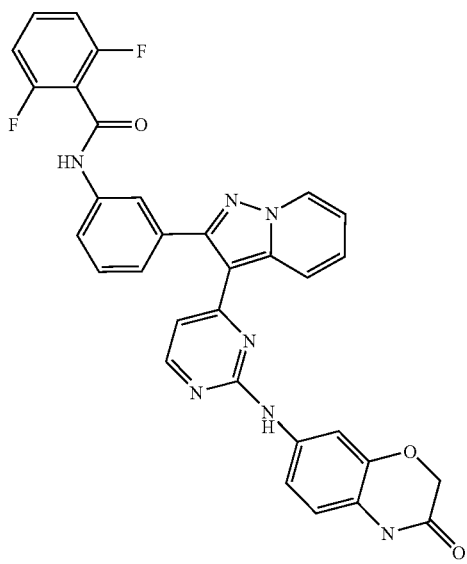

A mixture of N-{3-[3-(2-chloro-4-pyrimidinyl)pyrazolo[1,5-a]pyridin-2-yl]phenyl}-2,6-difluorobenzamide (which may be prepared according to a procedure similar to Example 27, Step C) and 7-amino-2H1,4-benzoxazin-3(4H)-one are heated in isopropanol with catalytic conc. HCl at approximately 85° C. to afford the product. ES-LCMS m/z 590 (M+H).

Example 201

2,6-Difluoro-N-{3-[3-(2-{[4-(methyloxy)-3-(4-methyl-1-piperazinyl)phenyl]amino}-4-pyrimidinyl)pyrazolo[1,5-a]pyridin-2-yl]phenyl}benzamide

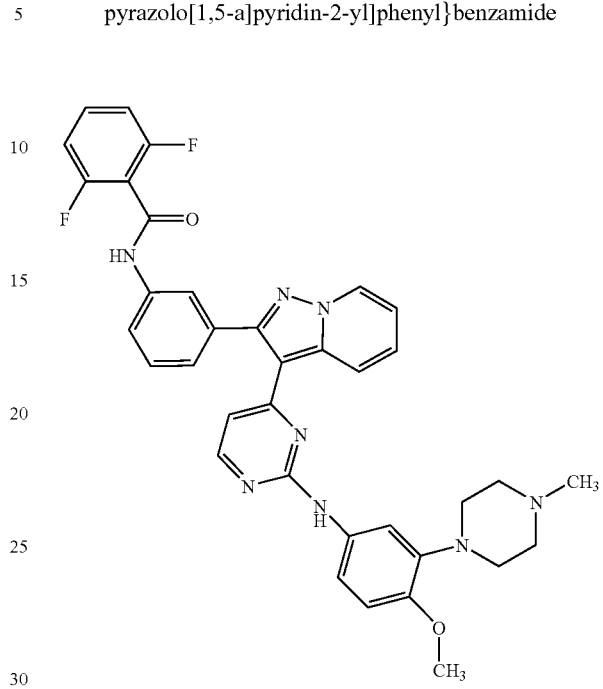

A mixture of N-{3-[3-(2-chloro-4-pyrimidinyl)pyrazolo[1,5-a]pyridin-2-yl]phenyl}-2,6-difluorobenzamide (which may be prepared according to a procedure similar to Example 11, Step C) and [4-(methyloxy)-3-(4-methyl-1-piperazinyl)phenyl]amine are heated in isopropanol with catalytic conc. HCl at approximately 85° C. to afford the product. ES-LCMS m/z 647 (M+H).

Example 202

2,6-Difluoro-N-[3-(3-{5-fluoro-2-[(3-fluorophenyl)amino]-4-pyrimidinyl}pyrazolo[1,5-d]pyridin-2-yl)phenyl]benzamide

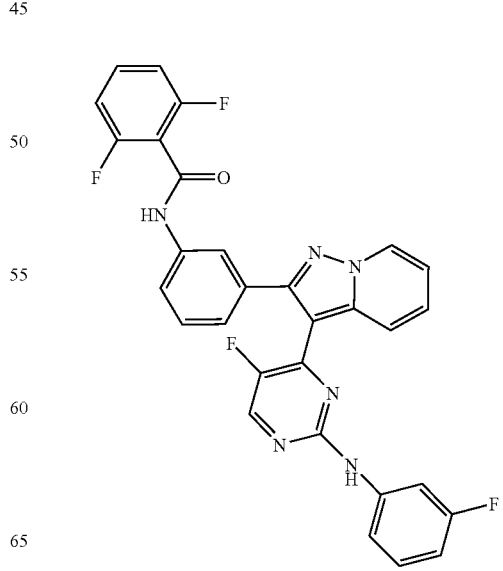

Step A: 1-Bromo-3-ethynylbenzene

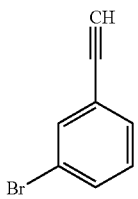

To an oven-dried flask under N₂ was added 1-bromo-3-iodobenzene (5.00 g, 17.73 mmol), anhydrous, degassed THF (100 mL), dichlorobis(triphenyl-phosphine)palladium(II) (620 mg, 0.88 mmol), copper(I) iodide (100 mg, 0.53 mmol), TEA (7.15 g, 71 mmol), and TMS acetylene (1.91 g, 20 mmol). After stirring overnight at rt, the reaction was washed with brine (100 mL), organic layer separated, concentrated under reduced pressure, adsorbed to silica gel and purified by column chromatography (5% EtOAc in hexanes) to afford the desired product (3.57 g, 80%) as a clear oil. This was dissolved in 100 ml 1:1 THF:MeOH and to this was added water (10 mL), and K₂CO₃ (5.87 g, 43 mmol). After stirring overnight at rt, the reaction was washed with brine (100 mL), adsorbed to silica gel and purified by LC (5% EtOAc in hexanes) to afford the alkyne (1.92 g, 75%) as a pale yellow oil. $^1$H NMR (400 MHz, CDCl₃) δ 3.10 (s, 1H), 7.17 (t, J=7.69 Hz, 1H), 7.38-7.44 (m, 1H), 7.45-7.48 (m, 1H), 7.61-7.62 (s, 1H).

Step B: 4-[(3-Bromophenyl)ethynyl]-2-chloro-5-fluoropyrimidine

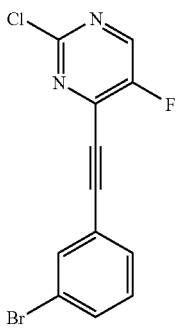

To an oven-dried flask under N₂ was added 2,4-dichloro-5-fluoropyrimidine (1.66 g, 10 mmol), anhydrous, degassed THF (100 mL), dichlorobis(triphenyl-phosphine)palladium (II) (180 mg, 0.26 mmol), copper(I) iodide (29 mg, 0.15 mmol), and TEA (2.02 g, 20 mmol). After heating the reaction at 60° C. for 30 min, 1-bromo-3-ethynylbenzene (0.9 g, 5.0 mmol) was added dropwise as a solution in THF (25 mL) and the resulting mixture was allowed to heat overnight. The crude reaction mixture was adsorbed to silica gel and purified by column chromatography (2-10% EtOAc in hexanes) to afford the desired product (1.25 g, 78%) as an off white solid. ESIMS (M+H)+=311.

Step C: 2-(3-Bromophenyl)-3-(2-chloro-5-fluoro-4-pyrimidinyl)pyrazolo[1,5-a]pyridine

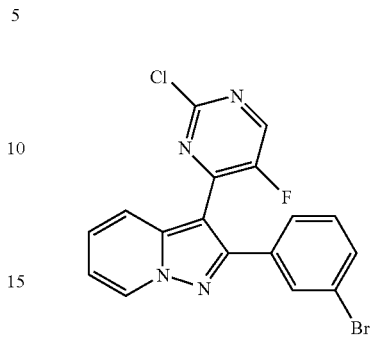

A solution of 4-[(3-bromophenyl)ethynyl]-2-chloro-5-fluoropyrimidine (25 mg, 0.08 mmol), aminopyridinium iodide (36 mg, 0.16 mmol), and potassium carbonate (33 mg, 0.23 mmol) in DMF (1 mL) was stirred at rt for 2 h followed by solvent removal. The residue was suspended in water (50 mL) and extracted with EtOAc (2×100 mL). The organic layer was adsorbed to silica gel and purified by column chromatography (2-20% EtOAc in hexanes) to afford the pyrazolopyridine (27 mg, 85%) as an off-white solid. ESIMS (M+H)+=403.

Step D: 4-[2-(3-Bromophenyl)pyrazolo[1,5-a]pyridin-3-yl]-5-fluoro-N-(3-fluorophenyl)-2-pyrimidinamine

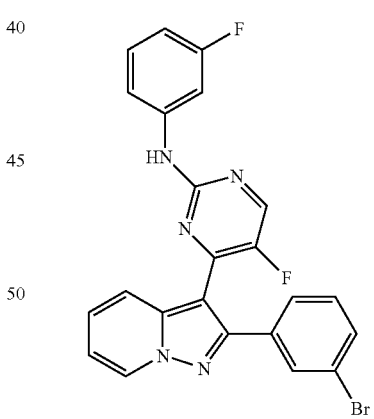

A solution 2-(3-bromophenyl)-3-(2-chloro-5-fluoro-4-pyrimidinyl)pyrazolo[1,5-a]pyridine (100 mg, 0.25 mmol, obtained from composite batches) in 2-propanol (5 mL) was added 3-fluoroaniline (166 mg, 1.4 mmol) followed by 4M HCl/dioxane (0.4 ml, 1.6 mmol). The reaction mixture was heated at 180° C. in the microwave for 1 h. The solvent was removed under reduced pressure and the solids were recrystallized from EtOAc/hexanes to afford the desired product (92 mg, 77%) as a brown solid. ESIMS (M+H)+=478.

247

Step E: 2,6-difluoro-N-[3-(3-{5-fluoro-2-[(3-fluorophenyl)amino]-4-pyrimidinyl}pyrazolo[1,5-a]pyridin-2-yl)phenyl]benzamide (title compound)

A solution 4-[2-(3-bromophenyl)pyrazolo[1,5-a]pyridin-3-yl]-5-fluoro-N-(3-fluorophenyl)-2-pyrimidinamine (40 mg, 84 mmol), Pd$_2$(dba)$_3$ (15.3 mg, 0.016 mmol), xantphos (14.5 mg, 0.025 mmol), Cs$_2$CO$_3$ (95 mg, 0.29 mmol), and 2,6-difluorobenzamide (39 mg, 0.25 mmol) in anhydrous 1,4-dioxane, that had been previously degassed with nitrogen, was heated at 160° C. in the microwave for 15 min. At this time, the crude reaction was adsorbed to silica gel and purified by LC (DCM to 5% MeOH/DCM) to afford the product (28.3 mg, 61%) as a white solid. ESIMS (M+H)+=555. $^1$H NMR (400 MHz, DMSO-d$_6$) δ 6.63-6.67 (m, 1H), 7.09-7.24 (m, 4H), 7.29-7.49 (m, 3H), 7.54-7.61 (m, 1H), 7.68-7.72 (m, 1H), 7.81 (s, 1H), 7.90-7.94 (m, 1H), 8.04 (m, 1H), 8.09 (m, 1H), 8.53-8.54 (m, 1H), 8.87-8.89 (m, 1H), 9.91 (s, 1H), 10.84 (s, 1H); ESIMS (M+H)+=555.

Example 203

N-{4-[2-(3-Aminophenyl)pyrazolo[1,5-a]pyridin-3-yl]-5-fluoro-2-pyrimidinyl}-2-methyl-1,2,3,4-tetrahydro-7-isoquinolinamine

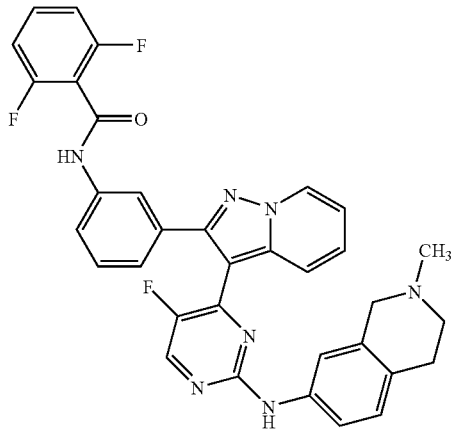

Step A: N-{3-[(2-Chloro-5-fluoro-4-pyrimidinyl)ethynyl]phenyl}-2,2,2-trifluoroacetamide

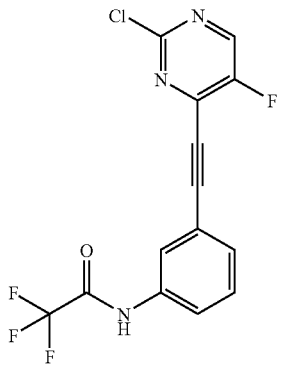

248

To an oven-dried flask under N$_2$ was added 2,4-dichloro-5-fluoropyrimidine (1.56 g, 9.4 mmol), anhydrous, degassed THF (100 mL), dichlorobis(triphenyl-phosphine)palladium (II) (62 mg, 0.09 mmol), copper(I) iodide (10 mg, 0.05 mmol), and triethylamine (0.164 g, 0.23 mmol). After heating the reaction at 60° C. for 30 min, N-(3-ethynylphenyl)-2,2,2-trifluoroacetamide (1.0, 4.69 mmol) was added dropwise as a solution in THF (25 mL) and the resulting mixture was allowed to heat overnight. The crude reaction mixture was adsorbed to silica gel and purified by column chromatography (2-10% EtOAc in hexanes) to afford the desired product (1.25 g, 78%) as an off-white solid. ESIMS (M+H)+=344.

Step B: N N-{3-[3-(2-Chloro-5-fluoro-4-pyrimidinyl)pyrazolo[1,5-a]pyridin-2-yl]phenyl}-2,2,2-trifluoroacetamide A solution of N-{3-[(2-chloro-5-fluoro-4-pyrimidinyl)ethynyl]phenyl}-2,2,2-trifluoroacetamide (1.25 g, 3.64 mmol), aminopyridinium iodide (1.63 g, 7.34 mmol), and potassium carbonate (1.52 g, 11 mmol) in DMF (50 mL) was stirred at rt for 2 h followed by solvent removal. The residue was suspended in water (50 mL) and extracted with EtOAc (2×100 mL). The organic layer was adsorbed to silica gel and purified by column chromatography (10-50% EtOAc in hexanes) to afford the pyrazolopyridine (1.34 g, 85%) as an off-white solid. ESIMS (M+H)+=436.

Step C: 2,2,2-Trifluoro-N-[3-(3-{5-fluoro-2-[(2-methyl-1,2,3,4-tetrahydro-7-isoquinolinyl)amino]-4-pyrimidinyl}pyrazolo[1,5-a]pyridin-2-yl)phenyl]acetamide

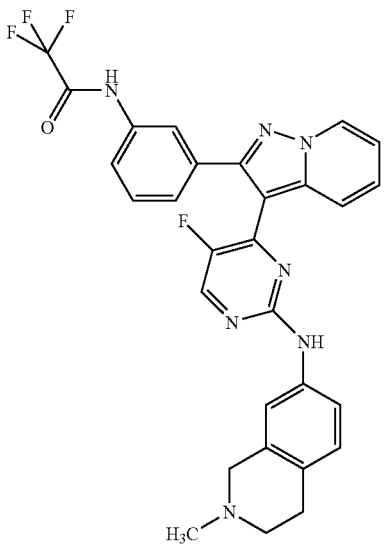

A solution N, N-{3-[3-(2-chloro-5-fluoro-4-pyrimidinyl)pyrazolo[1,5-a]pyridin-2-yl]phenyl}-2,2,2-trifluoroacetamide (20 mg, 0.05 mmol), Pd$_2$(dba)$_3$ (8.4 mg, 0.009 mmol), xantphos (8.0 mg, 0.013 mmol), cesium carbonate (67 mg, 0.21 mmol), and 2-methyl-1,2,3,4-tetrahydro-6-isoquinolinamine (22.3 mg, 0.14 mmol) in anhydrous 1,4-dioxane, that had been previously degassed with nitrogen, was heated at 100° C. for 48 h. At this time, the crude reaction was adsorbed to silica gel and purified by LC (DCM to 10% MeOH/DCM) to afford the product (13 mg, 50%) as a tan solid. ESIMS (M+H)+=562.

Step D: N-{4-[2-(3-Aminophenyl)pyrazolo[1,5-a]pyridin-3-yl]-5-fluoro-2-pyrimidinyl}-2-methyl-1,2,3,4-tetrahydro-7-isoquinolinamine

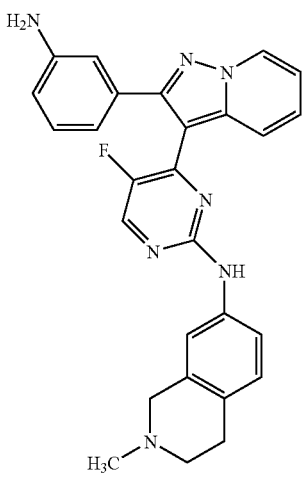

To a solution of 2,2,2-trifluoro-N-[3-(3-{5-fluoro-2-[(2-methyl-1,2,3,4-tetrahydro-7-isoquinolinyl)amino]-4-pyrimidinyl}pyrazolo[1,5-a]pyridin-2-yl)phenyl]acetamide (13 mg, 0.023 mmol) in 5:1 THF:H$_2$O (6 mL) was added 1M LiOH (0.14 ml, 0.14 mmol) and the reaction mixture was stirred overnight at rt. The reaction was washed with brine (10 mL), organic layer removed, adsorbed to silica gel and purified by column chromatography (0-10% MeOH/DCM+1% NH$_4$OH) to afford the title compound (8.6 mg, 80%) as an off-white solid. ESIMS (M+H)+=466.

Step E: 2,6-Difluoro-N-[3-(3-{5-fluoro-2-[(2-methyl-1,2,3,4-tetrahydro-7-isoquinolinyl)amino]-4-pyrimidinyl}pyrazolo[1,5-a]pyridin-2-yl)phenyl]benzamide (title compound)

To a solution of N-{4-[2-(3-aminophenyl)pyrazolo[1,5-a]pyridin-3-yl]-5-fluoro-2-pyrimidinyl}-2-methyl-1,2,3,4-tetrahydro-7-isoquinolinamine (50 mg, 0.11 mmol) in THF (5 mL) was added 2,6-difluorobenzoyl chloride (20 mg, 0.11 mmol) and the reaction mixture stirred at rt for 20 min. The reaction was diluted with MeOH, adsorbed to silica gel, and purified by column chromatography (0-10% MeOH/DCM+ 1% NH$_4$OH) to afford the title compound (15.4 mg, 24%) as a pale yellow solid. $^1$H NMR (400 MHz, DMSO-d$_6$) δ 10.86 (s, 1H), 9.52 (s, 1H), 8.86 (d, J=7.69 Hz, 1H), 8.45-8.46 (m, 1H), 8.06 (s, 1H), 7.89 (d, J=8.61 Hz, 1H), 7.71-7.73 (m, 1H), 7.54-7.58 (m, 1H), 7.30-7.47 (m, 4H), 7.20-7.24 (m, 3H), 7.08-7.12 (m, 1H), 6.86 (d, J=8.42 Hz, 1H), 3.26 (s, 2H), 2.66-2.69 (m, 2H), 2.49-2.51 (m, 2H), 2.26 (s, 3H); ESIMS (M+H)+=606.

Biological Example

Compounds of the present invention were tested for ErbB family protein tyrosine kinase inhibitory activity in substrate phosphorylation assays and cell proliferation assays.

A. Enzyme Assays:

Compounds of the present invention were tested for EGFR, ErbB-2, and ErbB-4 protein tyrosine kinase inhibitory activity in substrate phosphorylation assays using enzymes purified from a baculovirus expression system. Reagent production was conducted essentially as described in Brignola, P. S., et al, (2002) J. Biol. Chem. 277(2): 1576-1585.

The method measures the ability of the isolated enzyme to catalyse the transfer of the gamma-phosphate from ATP onto the tyrosine residue of a biotinylated synthetic peptide referenced "Peptide C" in Brignola, P. S., et al, (2002) J. Biol. Chem. 277(2):1576-1585. The extent of tyrosine phosphorylation was measured using an anti-phosphotyrosine antibody, and quantified by homogenous time-resolved fluorescence (HTRF).

Reactions were performed in black 384-well polystyrene flat-bottom plates in a final volume of 20 ul. Assays were performed by adding 10 μl of each of the following solutions, substrate Mix and enzyme mix: The Substrate mix contained 100 mM 3-[N-morpholino]propanesulfonic acid (MOPS) (pH 7.5), 2 mM MnCl$_2$, 20 μM ATP, 0.01% Tween-20, 0.1 mg/mL (BSA), 0.8 uM peptide substrate, and 1 mM dithiothreitol. The enzyme mix contained 100 mM MOPS (pH7.5); 0.01% Tween-20; 0.1 mg/mL BSA, and either 0.8 nM EGFR, 10 nM ErbB2, or 1 nM ErbB4

During the course of these studies, two separate methods have been used to measure the potency of compounds. In Method A, the substrate mix was added to the compound plates first, then the reaction was started by adding the enzyme mix. In Method B, the enzyme mix was added to the compound plates and the plates were incubated at 20° C. for 1 hour. The reactions were then started by adding the substrate mix.

After initiating the reaction with either method describe above, the reactions were allowed to proceed for 90 minutes at 20° C. The reactions were then terminated by the addition of 20 µl 100 mM EDTA to each well. 40 µl/well of HTRF detection mix were added to the assay plates. The final concentrations of the detection reagents were: 100 mM HEPES (pH7.5), 0.1 mg/mL BSA, 15 nM streptavidin-labeled allophycocyanin (PerkinElmer), and 1 nM europium-labeled anti-phosphotyrosine antibody (PerkinElmer). Assay plates were left unsealed and were counted in a Wallac Multilabel Counter 1420 (PerkinElmer).

Compounds under analysis were dissolved in Me$_2$SO to 1.0 mM and serially diluted 1 to 3 with Me$_2$SO through twelve dilutions. 1 µl of each concentration was transferred to the corresponding well of an assay plate. This creates a final compound concentration range from 0.00027 to 47.6 µM.

The data for dose responses were plotted as % Inhibition calculated with the data reduction formula 100*(1−(U1−C2)/(C1−C2)) versus concentration of compound where U is the unknown value, C1 is the average control value obtained for 4.76% DMSO, and C2 is the average control value obtained for 0.035 M EDTA. Data were fitted with a curve described by:

$$y=((V\text{max}*x)/(K+x))+Y^2$$

where Vmax is the upper asymptote, Y2 is the Y intercept, and K is the IC50. The results for each compound were recorded as pIC50s, calculated as follows:

$$pIC50=-\text{Log }10(K)$$

Many of the exemplified compounds Examples 1-203 were run in the recited assay and the results are reported in the following Table 1. In the following table:

"+" indicates no pIC50 measurement greater than 6 against either ErbB2 or EGFR;

"++" indicates at least one pIC50 measurement greater than 6 against either ErbB2 or EGFR but no measurement greater than pIC50 of 7; and "+++" indicates at least one pIC50 measurement of greater than 7 against either ErbB2 or EGFR.

TABLE 1

| Example | Activity (Method) |
|---|---|
| 1 | ++ (A) |
| 2 | ++ (A) |
| 3 | +++ (A) |
| 4 | +++ (A) |
| 5 | +++ (A) |
| 6 | +++ (A) |
| 7 | ++ (A) |
| 8 | ++ (A) |
| 9 | ++ (A) |
| 10 | ++ (A) |
| 11 | +++ (B) |
| 12 | ++ (B) |
| 13 | +++ (B) |
| 14 | +++ (B) |
| 15 | +++ (B) |
| 16 | +++ (B) |
| 17 | +++ (B) |
| 18 | ++ (B) |
| 19 | +++ (B) |
| 20 | ++ (B) |
| 21 | +++ (B) |

TABLE 1-continued

| Example | Activity (Method) |
|---|---|
| 22 | +++ (B) |
| 23 | ++ (B) |
| 24 | + (B) |
| 25 | +++ (B) |
| 26 | ++ (B) |
| 27 | ++ (B) |
| 28 | +++ (B) |
| 29 | ++ (A) |
| 30 | +++ (A) |
| 31 | +++ (B) |
| 32 | +++ (B) |
| 33 | +++ (A) |
| 34 | +++ (B) |
| 35 | +++ (B) |
| 36 | +++ (A) |
| 37 | +++ (B) |
| 38 | +++ (B) |
| 39 | +++ (B) |
| 40 | +++ (A) |
| 41 | +++ (B) |
| 42 | +++ (B) |
| 43 | +++ (A) |
| 44 | +++ (A) |
| 45 | +++ (A) |
| 46 | + (B) |
| 47 | +++ (A) |
| 48 | +++ (A) |
| 49 | +++ (A) |
| 50 | +++ (A) |
| 51 | +++ (A) |
| 52 | +++ (A) |
| 53 | ++ (A) |
| 54 | +++ (A) |
| 55 | +++ (B) |
| 56 | +++ (B) |
| 57 | +++ (B) |
| 58 | +++ (B) |
| 59 | +++ (B) |
| 60 | +++ (B) |
| 61 | +++ (B) |
| 62 | +++ (B) |
| 63 | +++ (B) |
| 64 | +++ (B) |
| 65 | ++ (B) |
| 66 | ++ (B) |
| 67 | +++ (B) |
| 68 | ++ (B) |
| 69 | +++ (B) |
| 70 | ++ (B) |
| 71 | ++ (B) |
| 72 | ++ (B) |
| 73 | ++ (B) |
| 74 | ++ (B) |
| 75 | +++ (B) |
| 76 | +++ |
| 77 | +++ (B) |
| 78 | +++ (B) |
| 79 | ++ (B) |
| 80 | ++ (B) |
| 81 | ++ (B) |
| 82 | +++ (B) |
| 83 | ++ (A) |
| 84 | +++ (B) |
| 85 | +++ (A) |
| 86 | +++ (A) |
| 87 | +++ (A) |
| 88 | +++ (A) |
| 89 | ++ (A) |
| 90 | ++ (A) |
| 91 | +++ (B) |
| 92 | ++ (A) |
| 93 | ++ (A) |
| 94 | +++ (A) |
| 95 | +++ (B) |
| 96 | ++ (A) |
| 97 | +++ (A) |
| 98 | ++ (A) |

TABLE 1-continued

| Example | Activity (Method) |
|---|---|
| 99 | +++ (A) |
| 100 | +++ (A) |
| 101 | +++ (A) |
| 102 | +++ (A) |
| 103 | +++ (B) |
| 104 | +++ (B) |
| 105 | +++ (B) |
| 106 | +++ (A) |
| 107 | +++ (B) |
| 108 | +++ (B) |
| 109 | +++ (B) |
| 110 | +++ (B) |
| 111 | +++ (B) |
| 112 | +++ (B) |
| 113 | +++ (B) |
| 114 | +++ (A) |
| 115 | ++ (B) |
| 116 | +++ (B) |
| 117 | ++ (A) |
| 118 | +++ (B) |
| 119 | +++ (B) |
| 120 | +++ (B) |
| 121 | +++ (A) |
| 122 | +++ (B) |
| 123 | — |
| 124 | — |
| 125 | +++ (A) |
| 126 | +++ (B) |
| 127 | +++ (B) |
| 128 | +++ (B) |
| 129 | +++ (B) |
| 130 | ++ (A) |
| 131 | +++ (B) |
| 132 | +++ (B) |
| 133 | +++ (B) |
| 134 | +++ (A) |
| 135 | +++ (B) |
| 136 | +++ (B) |
| 137 | +++ (A) |
| 138 | +++ (A) |
| 139 | ++ (A) |
| 140 | ++ (A) |
| 141 | ++ (A) |
| 142 | ++ (A) |
| 143 | +++ (A) |
| 144 | +++ (A) |
| 145 | +++ (A) |
| 146 | +++ (B) |
| 147 | +++ (A) |
| 148 | +++ (A) |
| 149 | ++ (A) |
| 150 | +++ (B) |
| 151 | ++ (A) |
| 152 | ++ (B) |
| 153 | +++ (B) |
| 154 | ++ (A) |
| 155 | ++ (A) |
| 156 | ++ (A) |
| 157 | ++ (A) |
| 158 | ++ (A) |
| 159 | + (B) |
| 160 | +++ (B) |
| 161 | +++ (B) |
| 162 | ++ (B) |
| 163 | +++ (B) |
| 164 | +++ (B) |
| 165 | +++ (B) |
| 166 | +++ (B) |
| 167 | +++ (B) |
| 168 | +++ (B) |
| 169 | +++ (B) |
| 170 | +++ (B) |
| 171 | +++ (B) |
| 172 | +++ (B) |
| 173 | +++ (B) |
| 174 | +++ (B) |
| 175 | +++ (B) |
| 176 | +++ (B) |
| 177 | +++ (B) |
| 178 | +++ (B) |
| 179 | +++ (B) |
| 180 | +++ (B) |
| 181 | +++ (B) |
| 182 | +++ (B) |
| 183 | +++ (B) |
| 184 | +++ B) |
| 185 | +++ (B) |
| 186 | +++ (B) |
| 187 | +++ (B) |
| 188 | +++ (B) |
| 189 | +++ (B) |
| 190 | +++ (B) |
| 191 | ++ (B) |
| 192 | + (B) |
| 193 | + (B) |
| 194 | +++ (B) |
| 195 | +++ (B) |
| 196 | +++ (B) |
| 197 | +++ (B) |
| 198 | +++ (B) |
| 199 | +++ (B) |
| 200 | +++ (B) |
| 201 | +++ (B) |
| 202 | ++ (B) |
| 203 | +++ (B) |

B. Cellular Assays

Method A: Methylene Blue Growth Inhibition Assay

Human breast (BT474) and head and neck (HN5) were cultured in low glucose DMEM (Life Technologies 12320-032) containing 10% fetal bovine serum (FBS). Human colon tumor cells (Colo205) were cultured in DMEM (Invitrogen, 10564) containing 10% FBS. The SV40 transformed human mammary epithelial cell line HB4a was transfected with either human H-ras cDNA (HB4a r4.2) or the human c-ErbB2 cDNA (HB4a c5.2). The HB4a clones were cultured in RPMI containing 10% FBS, insulin (5 g/mL), hydrocortisone (5 g/mL), supplemented with the selection agent hygromycin B (50 g/mL). All lines were grown in a humidified incubator at 37° C. in 95% air, 5% $CO_2$. Cells were harvested using trypsin/EDTA, counted using a haemocytometer, and plated in 100 microliters of the appropriate media, at the following densities, in a 96-well tissue culture plate (Falcon 3075): BT474 10,000 cells/well, HN5 3,000 cells/well. The next day, compounds were diluted in DMEM containing 100 mg/mL gentamicin, at twice the final required concentration, from 10 mM stock solutions in DMSO. 100 microliters/well of these dilutions were added to the 100 microliters of media currently on the cell plates. Medium containing 0.6% DMSO was added to control wells. Compounds diluted in DMEM were added to all cell lines. The final concentration of DMSO in all wells was 0.3%. Cells were returned to the incubator (37° C., 10% $CO_2$) for 3 days. Medium was then removed by aspiration. Cell biomass was estimated by staining cells with 90 microliters per well methylene blue (Sigma M9140, 0.5% in 1:1 ethanol:water), and incubation at rt for at least 30 minutes. Stain was removed, and the plates rinsed by immersion in deionized water and air-dried. To release stain from the cells 100 microliters of solubilization solution was added (1% N-lauroyl sarcosine, Sodium salt, Sigma L5125, in PBS), and plates were shaken gently for about 30 minutes. Optical density at 620 nM was measured on a microplate reader. Percent inhibition of cell growth was calculated relative to vehicle treated control wells. Concentration of compound that inhibits 50% of control cell growth (IC$_{50}$) was interpolated using nonlinear regression (Levenberg-Marquardt) and the equation, $$y=V\max*(1-(x/(K+x)))+Y2, \text{ where "K" was equal to the IC}_{50}.$$

Method B: Celltiter Glo® Growth Inhibition Assays

Human breast tumor cells (BT474) were cultured in RPMI, (Invitrogen, 22400) containing 10% fetal bovine serum (FBS). Human head and neck tumor cells (HN5) were cultured in low glucose DMEM (Invitrogen, 12320) containing 10% FBS. Human colon tumor cells (Colo205) were cultured in DMEM (Invitrogen, 10564) containing 10% FBS. All cell lines were maintained at 37° C. in a humidified 5% CO$_2$, 95% air incubator. Cells were harvested using trypsin/EDTA, counted using a haemocytometer, and plated in 30 microliters of the appropriate media described above, at the following densities, in a half area, black-walled, 96-well tissue culture plate (Corning 3882): BT474 3,000 cells/well, HN5 500 cells/well and Colo205 cells, 3,000 cells/well. The next day, compounds were diluted in DMEM containing 100 mg/mL gentamicin, from 10 mM stock solutions in DMSO. 30 microliters/well of these dilutions were added to the 30 microliters/well of media currently on the cell plates. Medium containing 0.6% DMSO was added to control wells. The final concentration of DMSO in all wells was 0.3%. Cells were incubated at 37° C., 5% CO$_2$ for 3 days. Cell biomass was estimated using Celltiter Glo (Promega G7571). Briefly, plates were removed from the incubator and allowed to equilibrate to rt for 30 minutes. 60 microliters of Celltiter Glo reagent were added to each well of the treated cells and plates were shaken on an orbital plate shaker for 2 min. Plates were incubated without shaking for 30 more min and read in a luminometer with an integration time of 0.5 seconds per well. Percent inhibition of cell growth was calculated relative to vehicle treated control wells. Concentration of compound that inhibits 50% of vehicle control cell growth (IC50) was interpolated using nonlinear regression (Levenberg-Marquardt) and the equation, y=Vmax*(1−(x/(K+x)))+Y2, where "K" was equal to the IC50.

The compounds of Examples 1-203 were run in the recited assay and the results are reported in the following Table 2. In the following table:

"+" indicates that the compound showed activity of >1 µM in both BT474 and HN5 tumor cell lines;

"++" indicates that the compound showed activity of between 100 nM and 1 µM in at least one of BT474 and HN5 tumor cell lines; and "+++" indicates that the compound showed activity of less than 100 nM in at least one one of BT474 and HN5 tumor cell lines.

TABLE 2

| Example | Activity (Method) |
|---|---|
| 1 | + (A) |
| 2 | + (A) |
| 3 | ++ (A) |
| 4 | +++ (A) |
| 5 | ++ (A) |
| 6 | +++ (A) |
| 7 | ++ (A) |
| 8 | ++ (A) |
| 9 | ++ (A) |
| 10 | ++ (A) |
| 11 | ++ (A) |
| 12 | +++ (A) |
| 13 | +++ (A) |
| 14 | +++ (A) |
| 15 | ++ (A) |
| 16 | +++ (A) |
| 17 | ++ (A) |
| 18 | ++ (A) |
| 19 | ++ (A) |
| 20 | ++ (A) |
| 21 | ++ (A) |
| 22 | ++ (A) |
| 23 | + (A) |
| 24 | + (A) |
| 25 | ++ (A) |
| 26 | + (A) |
| 27 | +++ (A) |
| 28 | +++ (A) |
| 29 | +++ (A) |
| 30 | +++ (A) |
| 31 | +++ (A) |
| 32 | +++ (A) |
| 33 | ++ (A) |
| 34 | +++ (A) |
| 35 | +++ (A) |
| 36 | +++ (A) |
| 37 | +++ (A) |
| 38 | ++ (A) |
| 39 | ++ (A) |
| 40 | ++ (A) |
| 41 | +++ (A) |
| 42 | +++ (A) |
| 43 | ++ (A) |
| 44 | +++ (A) |
| 45 | +++ (A) |
| 46 | + (A) |
| 47 | ++ (A) |
| 48 | +++ (A) |
| 49 | ++ (A) |
| 50 | ++ (A) |
| 51 | ++ (A) |
| 52 | ++ (A) |
| 53 | ++ (A) |
| 54 | +++ (A) |
| 55 | +++ (A) |
| 56 | +++ (A) |
| 57 | +++ (A) |
| 58 | +++ (A) |
| 59 | +++ (A) |
| 60 | +++ (A) |
| 61 | +++ (A) |
| 62 | +++ (A) |
| 63 | +++ (A) |
| 64 | +++ (A) |
| 65 | + (A) |
| 66 | ++ (A) |
| 67 | ++ (A) |
| 68 | ++ (A) |
| 69 | ++ (A) |
| 70 | ++ (A) |
| 71 | ++ (A) |
| 72 | ++ (A) |
| 73 | + (A) |
| 74 | ++ (A) |
| 75 | ++ (A) |
| 76 | ++ (A) |
| 77 | ++ (A) |
| 78 | ++ (A) |
| 79 | ++ (A) |
| 80 | ++ (A) |
| 81 | ++ (A) |
| 82 | ++ (A) |
| 83 | ++ (A) |
| 84 | + (A) |
| 85 | ++ (A) |
| 86 | +++ (A) |
| 87 | +++ (A) |
| 88 | +++ (A) |
| 89 | ++ (A) |
| 90 | ++ (A) |

TABLE 2-continued

| Example | Activity (Method) |
|---------|-------------------|
| 91 | +++ (A) |
| 92 | ++ (A) |
| 93 | ++ (A) |
| 94 | +++ (A) |
| 95 | +++ (A) |
| 96 | ++ (A) |
| 97 | ++ (A) |
| 98 | ++ (A) |
| 99 | +++ (A) |
| 100 | +++ (A) |
| 101 | ++ (A) |
| 102 | ++ (A) |
| 103 | +++ (A) |
| 104 | +++ (A) |
| 105 | +++ (A) |
| 106 | +++ (A) |
| 107 | +++ (A) |
| 108 | +++ (A) |
| 109 | +++ (A) |
| 110 | ++ (A) |
| 111 | +++ (A) |
| 112 | +++ (A) |
| 113 | +++ (A) |
| 114 | +++ (A) |
| 115 | +++ (B) |
| 116 | +++ (A) |
| 117 | +++ (A) |
| 118 | +++ (A) |
| 119 | +++ (A) |
| 120 | ++ (A) |
| 121 | ++ (A) |
| 122 | ++ (A) |
| 123 | +++ (A) |
| 124 | +++ (A) |
| 125 | +++ (A) |
| 126 | +++ (A) |
| 127 | +++ (A) |
| 128 | +++ (B) |
| 129 | +++ (A) |
| 130 | + (A) |
| 131 | +++ (A) |
| 132 | +++ (A) |
| 133 | +++ (A) |
| 134 | +++ (A) |
| 135 | +++ (B) |
| 136 | +++ (A) |
| 137 | ++ (A) |
| 138 | ++ (A) |
| 139 | ++ (A) |
| 140 | ++ (A) |
| 141 | ++ (A) |
| 142 | + (A) |
| 143 | ++ (A) |
| 144 | ++ (A) |
| 145 | +++ (A) |
| 146 | ++ (A) |
| 147 | ++ (A) |
| 148 | +++ (A) |
| 149 | ++ (A) |
| 150 | +++ (A) |
| 151 | ++ (A) |
| 152 | ++ (A) |
| 153 | ++ (A) |
| 154 | ++ (A) |
| 155 | ++ (A) |
| 156 | ++ (A) |
| 157 | ++ (A) |
| 158 | ++ (A) |
| 159 | + (A) |
| 160 | +++ (A) |
| 161 | + (A) |
| 162 | ++ (A) |
| 163 | +++ (B) |
| 164 | +++ (B) |
| 165 | +++ (B) |
| 166 | +++ (A) |
| 167 | +++ (A) |
| 168 | +++ (B) |
| 169 | +++ (B) |
| 170 | ++ (B) |
| 171 | +++ (B) |
| 172 | +++ (B) |
| 173 | +++ B) |
| 174 | +++ (A) |
| 175 | ++ (B) |
| 176 | +++ (A) |
| 177 | +++ (A) |
| 178 | +++ (A) |
| 179 | +++ (A) |
| 180 | +++ (B) |
| 181 | +++ (B) |
| 182 | +++ (B) |
| 183 | +++ (B) |
| 184 | +++ (B) |
| 185 | +++ (B) |
| 186 | +++ (B) |
| 187 | +++ (B) |
| 188 | +++ (B) |
| 189 | +++ (A) |
| 190 | +++ (A) |
| 191 | + (B) |
| 192 | + (A) |
| 193 | + (B) |
| 194 | ++ (B) |
| 195 | ++ (A) |
| 196 | +++ (A) |
| 197 | +++ (A) |
| 198 | +++ (A) |
| 199 | +++ (A) |
| 200 | +++ (A) |
| 201 | +++ (A) |
| 202 | ++ (B) |
| 203 | +++ (B) |

The compounds of Selected Examples were run in the recited assay using Colo205 cell lines and the results are reported in the following Table 3. In the following table:

"+" indicates that the compound showed activity of >1 µM in Colo205 tumor cell lines;

"++" indicates that the compound showed activity of between 100 nM and 1 µM in Colo205 tumor cell lines; and "+++" indicates that the compound showed activity of less than 100 nM in Colo205 tumor cell lines.

TABLE 3

| Example | Activity (Method) |
|---------|-------------------|
| 1 | + (A) |
| 2 | + (A) |
| 4 | ++ (A) |
| 5 | + (A) |
| 11 | + (A) |
| 25 | + (A) |
| 28 | ++ (A) |
| 29 | + (A) |
| 31 | ++ (A) |
| 41 | ++ (A) |
| 42 | + (A) |
| 43 | + (A) |
| 44 | ++ (A) |
| 45 | ++ (A) |
| 46 | + (A) |
| 47 | + (A) |
| 50 | + (A) |
| 54 | ++ (A) |
| 55 | ++ (A) |
| 56 | ++ (A) |
| 57 | ++ (A) |
| 58 | + (A) |

TABLE 3-continued

| Example | Activity (Method) |
|---|---|
| 59 | + (A) |
| 60 | ++ (A) |
| 61 | ++ (A) |
| 62 | + (A) |
| 83 | + (A) |
| 84 | + (A) |
| 86 | + (A) |
| 87 | ++ (A) |
| 91 | ++ (A) |
| 94 | + (A) |
| 101 | + (A) |
| 103 | ++ (A) |
| 104 | ++ (A) |
| 105 | +++ (A) |
| 106 | ++ (A) |
| 107 | +++ (A) |
| 108 | +++ (A) |
| 109 | ++ (A) |
| 110 | ++ (A) |
| 115 | + (B) |
| 116 | ++ (A) |
| 117 | ++ (A) |
| 118 | ++ (A) |
| 119 | ++ (A) |
| 120 | ++ (A) |
| 121 | + (A) |
| 122 | ++ (A) |
| 126 | ++ (A) |
| 127 | ++ (A) |
| 128 | + (B) |
| 129 | ++ (A) |
| 131 | ++ (A) |
| 132 | +++ (A) |
| 133 | ++ (A) |
| 134 | + (A) |
| 135 | + (B) |
| 136 | ++ (A) |
| 142 | + (A) |
| 150 | + (A) |
| 156 | + (A) |
| 159 | + (A) |
| 160 | +++ (A) |
| 161 | + (A) |
| 162 | ++ (A) |
| 163 | +++ (B) |
| 164 | + (B) |
| 165 | + (B) |
| 166 | + (A) |
| 167 | ++ (A) |
| 168 | + (B) |
| 169 | + (B) |
| 170 | + (B) |
| 171 | + (B) |
| 172 | + (B) |
| 173 | + (B) |
| 174 | ++ (A) |
| 175 | + (B) |
| 176 | ++ (A) |
| 177 | ++ (A) |
| 178 | ++ (B) |
| 179 | ++ (A) |
| 180 | + (B) |
| 181 | ++ (B) |
| 182 | ++ (B) |
| 183 | + (B) |
| 184 | + (B) |
| 185 | + (B) |
| 186 | + (B) |
| 187 | ++ (B) |
| 188 | + (B) |
| 189 | + (A) |
| 190 | ++ (A) |
| 191 | + (B) |
| 192 | + (A) |
| 193 | + (B) |
| 194 | + (B) |
| 195 | + (A) |
| 196 | ++ (A) |
| 197 | ++ (A) |
| 198 | ++ (A) |
| 199 | + (A) |
| 200 | ++ (A) |
| 201 | ++ (A) |
| 202 | + (B) |
| 203 | ++ (B) |

That which is claimed is:

1. A compound of formula (I):

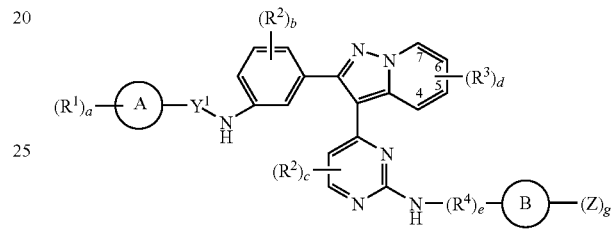

wherein:

a is 0, 1, 2 or 3;

each $R^1$ is the same or different and is independently selected from halo, alkyl, alkenyl, alkynyl, cycloalkyl, cycloalkenyl, Ay, Het, —$OR^6$, —$R^4OR^6$, —$OC(O)R^6$, —$C(O)R^6$, —$R^4C(O)R^6$, —$C(O)NR^6R^7$, —$R^4C(O)NR^6R^7$, —$CO_2R^6$, —$C(S)R^6$, —$C(S)NR^6R^7$, —$S(O)_fR^6$, —$R^4S(O)_fR^6$, —$S(O)_2NR^6R^7$, —$NR^6R^7$, —$R^4NR^6R^7$, —$N(R^6)$—$R^4R^7$, —$N(R^6)$—$R^4$—$OR^7$, —$N(R^6)$—$R^4$—$S(O)_fR^7$, —$N(R^6)$—$R^4$—CN, —$C(NH)NR^6R^7$, —$N(R^6)C(O)R^6$, —$N(R^6)S(O)_2R^6$, —$N(R^6)$—$C(O)$—$NR^6R^7$, —$N(R^6)$—$S(O)_2$—$NR^6R^7$, —CN, and —$NO_2$;

f is 0, 1 or 2;

Ay is aryl optionally substituted 1, 2 or 3 times with a substituent selected from halo, $C_{1-3}$alkyl, $C_{1-3}$alkoxy, $NH_2$, $N(H)C_{1-3}$alkyl, $N(C_{1-3}$alkyl$)_2$, CN and $NO_2$;

Het is a 5-6 membered heterocycle or heteroaryl having 1 or 2 heteroatoms selected from N, O and S and optionally substituted 1, 2 or 3 times with a substituent selected from halo, $C_{1-3}$alkyl, $C_{1-3}$alkoxy, hydroxyl, oxo, $NH_2$, $N(H)C_{1-3}$alkyl, $N(C_{1-3}$alkyl$)_2$, CN and $NO_2$;

Ring A is selected from aryl, heterocycle and heteroaryl;

$Y^1$ is —C(O)—, —N(H)C(O)—, —C(S)— or —N(H)C(S)—;

b and c are the same or different and are each independently is 0, 1 or 2;

each $R^2$ is the same or different and is independently selected from halo, alkyl, —$OR^6$, —$S(O)_fR^6$, —$NR^6R^7$, —CN and —$NO_2$;

d is 0, 1 or 2;

each R³ is the same or different and is independently selected from halo, alkyl, alkenyl, alkynyl, cycloalkyl, cycloalkenyl, Ay, Het, —OR⁶, —R⁴OR⁶, —OAy, —R⁴OAy,
—OC(O)R⁶, —COR⁶, —R⁴C(O)R⁶, —C(O)Ay, —C(O)NR⁶R⁷, —R⁴C(O)NR⁶R⁷, —C(O)N(H)Ay, —C(O)N(H)Het, —CO₂R⁶, —CO₂Ay, —C(S)R⁶, —C(S)NR⁶R⁷, —S(O)ᵢR⁶,
—R⁴S(O)ᵢR⁶, —S(O)ᵢAy, —S(O)₂NR⁶R⁷, —NR⁶R⁷, —R⁴NR⁶R⁷, —N(H)Ay, —R⁴N(H)Ay, —N(H)Het, —N(H)R⁴Het, —N(R⁶)—R⁴R⁷, —N(R⁶)—R⁴—OR⁷, —N(R⁶)—R⁴—S(O)ᵢR⁷, —N(R⁶)—R⁴—CN, —C(NH)NR⁶R⁷, —N(H)C(O)R⁶, —N(H)C(O)Ay, —N(H)SO₂R⁶, —N(R⁶)—C(O)—NR⁶R⁷, —N(R⁶)—S(O)₂—NR⁶R⁷, —CN and —NO₂;

e is 0 or 1;

each R⁴ is the same or different and is independently C₁₋₄alkylene or C₃₋₄alkenylene;

Ring B is selected from aryl and heteroaryl;

g is 0, 1, 2, 3 or 4;

each Z is the same or different and is independently a moiety of formula ii:

(ii)

wherein:
m, n and p are the same or different and are each independently 0 or 1;
each Alk is the same or different and is independently selected from C₁₋₄alkylene and C₃₋₄alkenylene;
Y² is —O—, —C(O)—, —S(O)ᵢ—, —N(H)— or —N(Alk)—;
q is 1 or 2;
each R⁵ is the same or different and is independently selected from H, halo, alkyl, alkenyl, cycloalkyl, cycloalkenyl, Ay, Het, oxo, —OR⁶, —OAy, —C(O)R⁶,
—OC(O)R⁶, —C(O)Ay, —OC(O)Ay, —C(O)NR⁶R⁷, —CO₂R⁶, —CO₂Ay, —S(O)ᵢR⁶, —S(O)ᵢAy, —S(O)₂NR⁶R⁷, —C(S)R⁶, —C(S)NR⁶R⁷, —C(S)N(H)Ay, —NR⁶R⁷,
—N(H)Ay, —N(H)Het, —N(R⁶)—R⁴R⁷, —N(R⁶)—R⁴—OR⁷, —N(R⁶)—R⁴—S(O)ᵢR⁷, —N(R⁶)—R⁴—CN, —NHC(O)R⁶, —N(H)S(O)₂R⁶, —C(NH)NR⁶R⁷, —N(R⁶)—C(O)—NR⁶R⁷, —N(R⁶)—S(O)₂—NR⁶R⁷, —N(R⁶)—C(O)—R⁴NR⁶R⁷, —N(R⁶)—S(O)₂—R⁴NR⁶R⁷, —CN and —NO₂; and each R⁶ and R⁷ are the same or different and are each independently selected from H, alkyl, alkenyl, alkynyl, C₃₋₆cycloalkyl and C₃₋₆cycloalkenyl;

or a pharmaceutically acceptable salt thereof.

2. The compound according to claim 1, wherein a is 1 or 2.

3. The compound according to claim 1, wherein each R¹ is the same or different and is independently selected from halo, alkyl, alkenyl, alkynyl, cycloalkyl, cycloalkenyl, Ay, Het, —OR⁶, —R⁴OR⁶, —OC(O)R⁶, —C(O)R⁶, —R⁴C(O)R⁶, —C(O)NR⁶R⁷, —CO₂R⁶, C(S)R⁶, C(S)NR⁶R⁷, —S(O)ᵢR⁶, —R⁴S(O)ᵢR⁶, —S(O)₂NR⁶R⁷, —NR⁶R⁷, —R⁴NR⁶R⁷, —N(R⁶)—C(O)—NR⁶R⁷, —N(R⁶)—S(O)₂—NR⁶R⁷, —CN and —NO₂.

4. The compound according to claim 1, wherein Ring A is aryl or heteroaryl.

5. The compound according to claim 1, wherein Y¹ is —C(O)—, —N(H)C(O)— or —N(H)C(S)—.

6. The compound according to claim 1, wherein Ring B is aryl.

7. The compound according to claim 1, wherein g is 0, 1, 2 or 3.

8. The compound according to claim 1, wherein each Alk the same or different and is independently C₁₋₃alkylene.

9. The compound according to claim 1, wherein n is 1 and Y² is —O—, —C(O)— or —N(H)—.

10. The compound according to claim 1, wherein n is 0.

11. The compound according to claim 1, wherein q is 1 and each R⁵ is the same or different and is independently selected from H, halo, alkyl, alkenyl, cycloalkyl, Ay, Het, oxo, —OW, —OAy, —C(O)R⁶, —OC(O)R⁶, —C(O)Ay, —C(O)NR⁶R⁷, —CO₂R⁶, —S(O)ᵢR⁶, —S(O)₂NR⁶R⁷, —C(S)NR⁶R⁷, —NR⁶R⁷, —N(H)Ay,
—N(H)Het, —N(R⁶)—R⁴R⁷, —N(R⁶)—R⁴—OR⁷, —N(R⁶)—R⁴—S(O)ᵢR⁷, —N(R⁶)—R⁴—CN, —NHC(O)R⁶,
—N(H)S(O)₂R⁶, —C(NH)NR⁶R⁷, —N(R⁶)—C(O)—NR⁶R⁷, —N(R⁶)—S(O)₂—NR⁶R⁷, —N(R⁶)—C(O)—R⁴NR⁶R⁷, —CN and —NO₂.

12. A compound according to claim 1 selected from:
2,6-Difluoro-N-[3-(3-{2-[(3-oxo-3,4-dihydro-2H-1,4-benzoxazin-7-yl)amino]-4-pyrimidinyl}pyrazolo[1,5-a]pyridin-2-yl)phenyl]benzamide;
2,5-Difluoro-N-{3-[3-(2-{[3-({2-[methyl(2-propen-1-yl)amino]ethyl}oxy)phenyl]-amino}-4-pyrimidinyl)pyrazolo[1,5-a]pyridin-2-yl]phenyl}benzamide;
N-{3-[3-(2-{[2-(Dimethylamino)-2,3-dihydro-1H-inden-5-yl]amino}-4-pyrimidinyl)pyrazolo[1,5-a]pyridin-2-yl]phenyl}-2,6-difluorobenzamide;
N-[3-(3-{2-[(3-Chloro-4-{[2-(4-morpholinyl)ethyl]-oxy}phenyl)amino]-4-pyrimidinyl}pyrazolo[1,5-a]pyridin-2-yl)phenyl]-2,6-difluorobenzamide;
N-[3-(3-{2-[(3-Chloro-4-{[3-(dimethylamino)propyl]-oxy}phenyl)amino]-4-pyrimidinyl}pyrazolo[1,5-a]pyridin-2-yl)phenyl]-2,6-difluorobenzamide;
2,6-Difluoro-N-{3-[3-(2-{[3-fluoro-4-({[(2S)-1-methyl-2-pyrrolidinyl]methyl}oxy)-phenyl]amino}-4-pyrimidinyl)pyrazolo[1,5-a]pyridin-2-yl]phenyl}benzamide;
2,6-Difluoro-N-(3-{3-[2-({4-[(methylsulfonyl)methyl]-phenyl}amino)-4-pyrimidinyl]pyrazolo[1,5-a]pyridin-2-yl}phenyl)benzamide;
2,6-Difluoro-N-(3-{3-[2-({2-(methyloxy)-4-[(methylsulfonyl)methyl]phenyl}amino)-4-pyrimidinyl]pyrazolo[1,5-a]pyridin-2-yl}phenyl)benzamide;
2,6-Difluoro-N-(3-{3-[2-(1,2,3,4-tetrahydro-7-isoquinolinylamino)-4-pyrimidinyl]pyrazolo[1,5-a]pyridin-2-yl}phenyl)benzamide;
N-[3-(3-{2-[(3-{[2-(Dimethylamino)ethyl]oxy}-phenyl)amino]-4-pyrimidinyl}pyrazolo[1,5-a]pyridin-2-yl)phenyl]-2,6-difluorobenzamide;
N-[3-(3-{2-[(3-Chloro-4-{[2-(dimethylamino)ethyl]-oxy}phenyl)amino]-4-pyrimidinyl}pyrazolo[1,5-a]pyridin-2-yl)phenyl]-2,6-difluorobenzamide;
N-[3-(3-{2-[4-(4-methyl-1-piperazinyl)phenylamino]-4-pyrimidinyl}-7-trifluoropyrazolo[1,5-b]pyridin-2-yl)phenyl]-2,6-difluorobenzamide;
2,6-Difluoro-N-{3-[3-(2-{[4-(methyloxy)-3-(4-methyl-1-piperazinyl)phenyl]amino}-4-pyrimidinyl)pyrazolo[1,5-a]pyridin-2-yl]phenyl}benzamide;
2,6-Difluoro-N-[3-(3-{2-[(3-oxo-3,4-dihydro-2H-1,4-benzoxazin-6-yl)amino]-4-pyrimidinyl}pyrazolo[1,5-a]pyridin-2-yl)phenyl]benzamide;
N-[3-(3-{2-[(3-{[2-(Dimethylamino)ethyl]oxy}phenyl)amino]-4-pyrimidinyl}pyrazolo[1,5-a]pyridin-2-yl)phenyl]-2,6-difluoro-3-methylbenzamide;

N-{3-[3-(2-{[3-Chloro-4-({2-[(methylsulfonyl)amino]ethyl}-oxy)phenyl]amino}-4-pyrimidinyl)pyrazolo[1,5-a]pyridin-2-yl]phenyl}-2,6-difluorobenzamide;

2,6-Difluoro-N-(2-(methyloxy)-5-{3-[2-(1,2,3,4-tetrahydro-7-isoquinolinylamino)-4-pyrimidinyl]pyrazolo[1,5-a]pyridin-2-yl}phenyl)benzamide;

N-{4-[2-(3-Aminophenyl)pyrazolo[1,5-a]pyridin-3-yl]-5-fluoro-2-pyrimidinyl}-2-methyl-1,2,3,4-tetrahydro-7-isoquinolinamine;

2,5-Difluoro-N-[3-(3-{2-[(2-methyl-1,2,3,4-tetrahydro-7-isoquinolinyl)amino]-4-pyrimidinyl}pyrazolo[1,5-a]pyridin-2-yl)phenyl]benzamide; and N-[3-(3-{2-[(3-chloro-4-{[2-(dimethylamino)ethyl]oxy}phenyl)-amino]-4-pyrimidinyl}pyrazolo[1,5-a]pyridin-2-yl)phenyl]-2,6-difluoro-3-methylbenzamide-TFA;

and pharmaceutically acceptable salts thereof.

13. A pharmaceutical composition comprising a compound according to claim 1 and a pharmaceutically acceptable carrier, diluent or excipient.

14. A method for treating breast cancer in a mammal in need thereof, said method comprising administering to the mammal a therapeutically effective amount of a compound according to claim 1.

15. A process for preparing a compound according to claim 1, said process comprising the steps of:

a) reacting a compound of formula (VII):

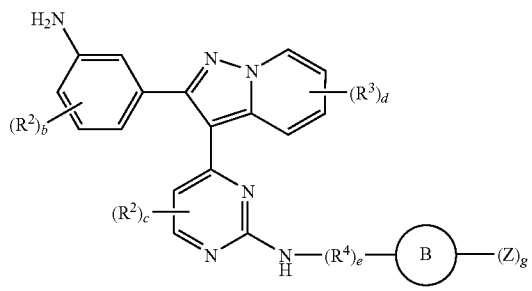

VII with a compound of formula (VIII):

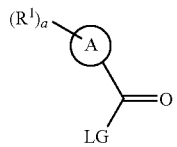

VIII wherein LG is a leaving group;
or a compound of formula (X):

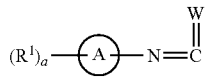

X wherein W is O or S;
to prepare a compound of formula (I).

* * * * *